(12) United States Patent
Miller et al.

(10) Patent No.: US 7,691,850 B2
(45) Date of Patent: Apr. 6, 2010

(54) ANTIBACTERIAL AGENTS

(75) Inventors: William Henry Miller, Collegeville, PA (US); Israil Pendrak, Collegeville, PA (US); Mark Andrew Seefeld, Collegeville, PA (US)

(73) Assignee: Glaxo Group Limited, Brentford, Middlesex (GB)

( * ) Notice: Subject to any disclaimer, the term of this patent is extended or adjusted under 35 U.S.C. 154(b) by 405 days.

(21) Appl. No.: 11/628,705

(22) PCT Filed: Jun. 15, 2005

(86) PCT No.: PCT/US2005/020950

§ 371 (c)(1),
(2), (4) Date: Dec. 5, 2006

(87) PCT Pub. No.: WO2006/002047

PCT Pub. Date: Jan. 5, 2006

(65) Prior Publication Data

US 2007/0287701 A1    Dec. 13, 2007

Related U.S. Application Data

(60) Provisional application No. 60/579,873, filed on Jun. 15, 2004.

(51) Int. Cl.
*A61K 31/542*    (2006.01)
(52) U.S. Cl. .............. 514/224.2; 544/48; 544/105; 546/122; 548/518
(58) Field of Classification Search .............. 544/48, 544/105
See application file for complete search history.

(56) References Cited

U.S. PATENT DOCUMENTS

| | | | |
|---|---|---|---|
| 5,208,243 A | 5/1993 | Peglion et al. ............ 514/309 |
| 6,194,413 B1 | 2/2001 | Bhatnagar et al. ....... 514/252.11 |
| 6,410,566 B1 | 6/2002 | Endo et al. .............. 514/329 |
| 6,962,917 B2 | 11/2005 | Davies et al. ........... 514/264.1 |
| 7,001,913 B1 | 2/2006 | Davies et al. ........... 514/300 |
| 2004/0138219 A1 | 7/2004 | Davies et al. ............ 514/243 |
| 2004/0224946 A1 | 11/2004 | Bigot et al. ............. 514/227.8 |
| 2005/0032800 A1 | 2/2005 | Bigot et al. ............. 514/243 |
| 2005/0085494 A1 | 4/2005 | Daines et al. ........... 514/266.22 |
| 2005/0159411 A1 | 7/2005 | Daines et al. ........... 514/224.8 |
| 2006/0014749 A1 | 1/2006 | Davies et al. ........... 514/249 |
| 2006/0040925 A1 | 2/2006 | Davies et al. ........... 514/222.8 |
| 2006/0041123 A1 | 2/2006 | Axten et al. ............ 544/48 |
| 2006/0058287 A1 | 3/2006 | Axten et al. ............ 514/224.2 |
| 2006/0116512 A1 | 6/2006 | Axten et al. ............ 540/553 |
| 2006/0166977 A1 | 7/2006 | Axten et al. ............ 514/224.2 |
| 2006/0189601 A1 | 8/2006 | Hennessy et al. ....... 514/222.8 |
| 2006/0189604 A1 | 8/2006 | Axten et al. ............ 514/224.2 |
| 2006/0205719 A1 | 9/2006 | Hubschwerlen et al. .. 514/230.5 |
| 2007/0004710 A1 | 1/2007 | Axten et al. ............ 514/224.2 |

FOREIGN PATENT DOCUMENTS

| | | |
|---|---|---|
| CA | 2571668 A1 | 2/2006 |
| EP | 0526342 | 2/1993 |
| JP | 2002047272 | 2/2002 |
| WO | WO 97/17973 | 5/1997 |
| WO | WO 00/51609 | 9/2000 |
| WO | WO 01/07432 A2 | 2/2001 |
| WO | WO 02/08224 A1 | 1/2002 |
| WO | WO 02/056882 A1 | 7/2002 |
| WO | WO 03/064421 A1 | 8/2003 |
| WO | WO 03/064431 A2 | 8/2003 |
| WO | WO 2004/002490 A2 | 1/2004 |
| WO | WO 2004/002992 A1 | 1/2004 |
| WO | WO 2004/014361 A1 | 2/2004 |
| WO | WO 2004/035569 | 4/2004 |
| WO | WO 2004/041210 A2 | 5/2004 |
| WO | WO 2004/050036 A2 | 6/2004 |
| WO | WO 2004/058144 A2 | 7/2004 |
| WO | WO 2004/087145 A2 | 10/2004 |
| WO | WO 2004/087647 | 10/2004 |
| WO | WO 2004/089947 A2 | 10/2004 |

(Continued)

OTHER PUBLICATIONS

West, Anthony R., Solid State Chemistry and its Applications, Wiley, New York, 1988, pp. 358 and 365.*
U.S. Appl. No. 11/570,441, Date to be assigned, Miller et al., PCT Jul. 8, 2005.
U.S. Appl. No. 11/570,443, Date to be assigned, Miller et al., PCT Jul. 8, 2005.

(Continued)

*Primary Examiner*—James O Wilson
*Assistant Examiner*—Brian McDowell
(74) *Attorney, Agent, or Firm*—Reid S. Willis; John Lemanowicz

(57) ABSTRACT

Compounds of formula (I) and derivatives thereof:

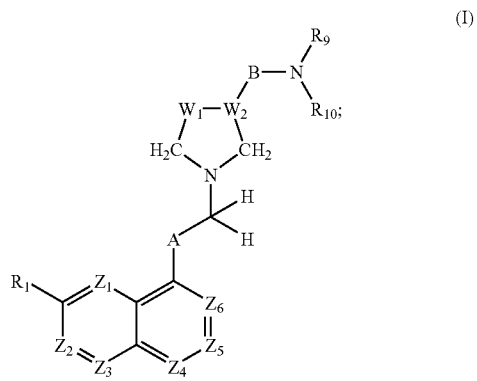

compositions containing them, their preparation and their use as antibacterials.

17 Claims, No Drawings

FOREIGN PATENT DOCUMENTS

| WO | WO 2004/096982 A2 | | 11/2004 |
|---|---|---|---|
| WO | WO 2005/016916 | | 2/2005 |
| WO | WO 2006/010831 | | 2/2006 |
| WO | WO 2006/014580 | * | 2/2006 |
| WO | WO 2006/021448 | | 3/2006 |
| WO | WO 2006/046552 | | 5/2006 |
| WO | WO 2006/105289 | | 10/2006 |

OTHER PUBLICATIONS

U.S. Appl. No. 11/570,600, Date to be assigned, Miller et al., PCT Jul. 13, 2005.

U.S. Appl. No. 11,570,777, Date to be assigned, Miller et al., PCT Jul. 21, 2005.

U.S. Appl. No. 11/572,929, Date to be assigned, Miller et al., PCT Aug. 2, 2005.

U.S. Appl. No. 11/573,270, Date to be assigned, Miller et al., PCT Aug. 9, 2005.

U.S. Appl. No. 10/937,468, Erskine et al., Sep. 9, 2004, Compounds and Methods for the Treatment of Disease.

* cited by examiner

ANTIBACTERIAL AGENTS

This application is a 371 of International Application No. PCT/US2005/020950, filed 15 Jun. 2005, which claims the benefit of U.S. Provisional Application No. 60/579,873 filed 15 Jun. 2004.

FIELD OF THE INVENTION

This invention relates to novel compounds, compositions containing them and their use as antibacterials.

BACKGROUND OF THE INVENTION

The emergence of pathogens resistant to known antibiotic therapy is becoming a serious global healthcare problem (Chu, et al., (1996) *J. Med. Chem.,* 39: 3853-3874). Thus, there is a need to discover new broad spectrum antibiotics useful in combating multidrug-resistant organisms. Importantly, it has now been discovered that certain compounds have antibacterial activity, and, therefore, may be useful for the treatment of bacterial infections in mammals, particularly in humans.

SUMMARY OF THE INVENTION

This invention comprises compounds of the formula (I), as described hereinafter, which are useful in the treatment of bacterial infections. This invention is also a pharmaceutical composition comprising a compound according to formula (I) and a pharmaceutically acceptable carrier. This invention is also processes for the preparation of compounds of formula (I), as well as processes for the preparation of intermediates useful in the synthesis of compounds of formula (I). This invention is also a method of treating bacterial infections in mammals, particularly in humans.

DETAILED DESCRIPTION OF THE INVENTION

This invention provides a compound of formula (I) or a pharmaceutically acceptable salt, solvate or derivative thereof:

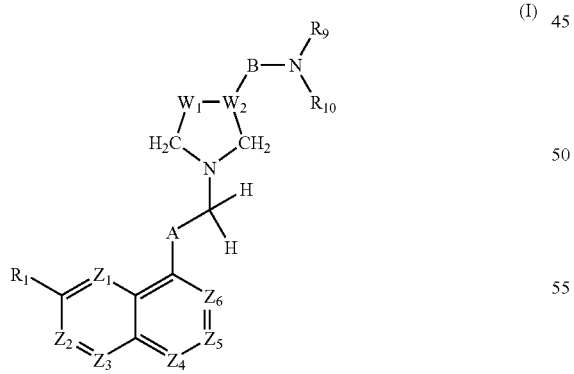

(I)

wherein:
$Z_1$, $Z_3$, and $Z_4$ are each independently N or $CR^{1a}$;
$Z_2$, $Z_5$ and $Z_6$ are each $CR^{1a}$;
$R_1$ and $R^{1a}$ are independently at each occurrence hydrogen; cyano; halogen; hydroxy; $(C_{1-6})$alkoxy unsubstituted or substituted by $(C_{1-6})$alkoxy, hydroxy, amino, piperidyl, guanidino or amidino any of which is unsubstituted or N-substituted by one or two $(C_{1-6})$alkyl, acyl, $(C_{1-6})$alkylsulphonyl, $CONH_2$, hydroxy, $(C_{1-6})$alkylthio, heterocyclylthio, heterocyclyloxy, arylthio, aryloxy, acylthio, acyloxy or $(C_{1-6})$alkylsulphonyloxy; $(C_{1-6})$alkyl; $(C_{1-6})$alkylthio; trifluoromethyl; trifluoromethoxy; nitro; azido; acyl; acyloxy; acylthio; $(C_{1-6})$alkylsulphonyl; $(C_{1-6})$alkylsulphoxide; arylsulphonyl; arylsulphoxide; or an amino, piperidyl, guanidino or amidino group unsubstituted or N-substituted by one or two $(C_{1-6})$alkyl, acyl or $(C_{1-6})$alkylsulphonyl groups; or $R_1$ and $R^{1a}$ of $Z_2$ or $R_1$ and $R^{1a}$ of $Z_1$ together form ethylenedioxy;

A is $CR_2R_3$;
$R_2$ is hydrogen; halogen; hydroxy; acyloxy; or $(C_{1-6})$alkoxy; and $R_3$ is hydrogen;
$W_1$ is $CR_4R_5$;
$R_4$ is hydrogen; halogen; hydroxy; $(C_{1-6})$alkyl; $(C_{1-6})$hydroxyalkyl; $C(=O)-NR^{1d}R1^{d'}$; $(C_{1-6})$alkoxy; $NR^{1b}R^{1b'}$ or acyloxy; and $R_5$ is hydrogen or $(C_{1-6})$alkyl; or $R_4$ and $R_5$ together are $=N-OH$;
$R^{1b}$ and $R^{1b'}$ are each independently hydrogen; acyl; $(C_{1-6})$alkyl; aryl; heteroaryl; or together with the nitrogen they are attached form an aziridine, azetidine, pyrrolidine, piperidine or hexamethyleneimine ring (wherein said aziridine, azetidine, pyrrolidine, piperidine or hexamethyleneimine ring is optionally substituted with 1 to 3 substitutents selected from halogen, $(C_{1-6})$alkyl, hydroxy or aryl);
$W_2$ is $CR_6$;
$R_6$ is hydrogen; halogen; hydroxy; $(C_{1-6})$alkyl; $NR^{1c}R^{1c'}$; acyloxy; or $(C_{1-6})$alkoxy;
$R^{1c}$ and $R^{1c'}$ are each independently hydrogen; $(C_{1-6})$alkyl; aryl; heteroaryl; or together with the nitrogen they are attached form an aziridine, azetidine, pyrrolidine, piperidine or hexamethyleneimine ring (wherein said aziridine, azetidine, pyrrolidine, piperidine or hexamethyleneimine ring is optionally substituted with 1 to 3 substitutents selected from halogen, $(C_{1-6})$alkyl, hydroxy or aryl);
$R^{1d}$ and $R^{1d'}$ are each independently hydrogen or $(C_{1-6})$alkyl;
B is $CR_7R_8$ or a bond;
$R_7$ and $R_8$ are each independently hydrogen or $(C_{1-6})$alkyl;
$R_9$ is hydrogen; aryl; heteroaryl; $(C_{1-6})$alkyl unsubstituted or substituted by one or two $(C_{1-6})$alkoxy, acyloxy, carboxy, hydroxy, amino, piperidyl, piperazinyl, morpholino, guanidino, or amidino, any of which is unsubstituted or N-substituted by one or two aryl, heteroaryl, halogen, unsubstituted $(C_{1-6})$alkyl, acyl, $(C_{1-6})$alkylsulphonyl, arylsulphonyl, hydroxy, $(C_{1-6})$alkylthio, heterocyclylthio, heterocyclyloxy, arylthio, aryloxy, acylthio, acyloxy, or $(C_{1-6})$alkylsulphonyloxy, so long as the substitution does not lead to an unstable compound; $(C_{1-6})$alkylcarbonyl; or $(C_{2-6})$alkenylcarbonyl;
$R_{10}$ is a group $-U-R_{11}$ where $R_{11}$ is a substituted or unsubstituted bicyclic carbocyclic or heterocyclic ring system (A):

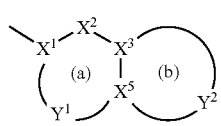

(A)

containing up to four heteroatoms in each ring in which at least one of rings (a) and (b) is aromatic;
$X^1$ is C or N when part of an aromatic ring or $CR_{12}$ when part of a non aromatic ring;

X² is N, NR₁₃, O, S(O)ₓ; CO or CR₁₂ when part of an aromatic or non-aromatic ring or may in addition be CR₁₄R₁₅ when part of a non aromatic ring;

X³ and X⁵ are independently N or C;

Y¹ is a 0 to 4 atom linker group each atom of which is independently selected from N, NR₁₃, O, S(O)ₓ, CO and CR₁₂ when part of an aromatic or non-aromatic ring or may additionally be CR₁₄R₁₅ when part of a non aromatic ring, Y² is a 2 to 6 atom linker group, each atom of Y² being independently selected from N, NR₁₃, O, S(O)ₓ, CO and CR₁₂ when part of an aromatic or non-aromatic ring or may additionally be CR₁₄R₁₅ when part of a non aromatic ring; R₁₂, R₁₄ and R₁₅ are at each occurrence independently selected from: H; $(C_{1-4})$alkylthio; halo; $(C_{1-4})$alkyl; $(C_{2-4})$alkenyl; hydroxy; hydroxy$(C_{1-4})$alkyl; mercapto$(C_{1-4})$alkyl; $(C_{1-4})$alkoxy; trifluoromethoxy; nitro; cyano; carboxy; amino or aminocarbonyl unsubstituted or substituted by $(C_{1-4})$alkyl;

R₁₃ is at each occurrence independently hydrogen; trifluoromethyl; $(C_{1-4})$alkyl unsubstituted or substituted by hydroxy, carboxy, $(C_{1-4})$alkoxy, $(C_{1-6})$alkylthio, halo or trifluoromethyl; $(C_{2-4})$alkenyl; or aminocarbonyl wherein the amino group is optionally substituted with $(C_{1-4})$alkyl;

each x is independently 0, 1 or 2;

U is C(=O); SO₂; or CR₁₆R₁₇; and

R₁₆ and R₁₇ are independently selected from H; aryl; heteroaryl; $(C_{1-6})$alkyl; $(C_{1-6})$alkyl substituted by $(C_{1-6})$ alkoxy, hydroxy, amino, piperidyl, piperazinyl, morpholino, guanidino, or amidino, any of which is substituted or N-substituted by one or two hydrogen, aryl, heteroaryl, halogen, cyano, CF₃, $(C_{1-6})$alkyl, acyl, $(C_{1-6})$alkylsulphonyl, arylsulphonyl, hydroxy, $(C_{1-6})$ alkylthio, heterocyclylthio, heterocyclyloxy, arylthio, aryloxy, acylthio, acyloxy, or $(C_{1-6})$alkylsulphonyloxy, so long as the substitution does not lead to an unstable compound; $(C_{1-6})$alkoxy-substituted$(C_{1-6})$alkyl; hydroxy-substituted$(C_{1-6})$alkyl; amino-substituted $(C_{1-6})$alkyl, which is N-substituted by one or two $(C_{1-6})$ alkyl, acyl, $(C_{1-6})$alkylsulphonyl, or arylsulphonyl; $(C_{1-6})$alkylcarbonyl; $(C_{2-6})$alkenylcarbonyl; $(C_{1-6})$ alkoxycarbonyl; CO₂H; or CF₃; or a pharmaceutically acceptable salt or solvate thereof.

In some aspects, this invention describes compounds of formula I wherein Z₁, Z₃ and Z₄ are CR$^{1a}$.

In other aspects, this invention describes compounds of formula I wherein Z₁ and Z₄ are N and Z₃ is CR$^{1a}$.

In some aspects, this invention describes compounds of formula I wherein Z₁ and Z₃ are N and Z₄ is CR$^{1a}$.

In yet other embodiments, this invention describes compounds of formula I wherein Z₁ and Z₃ are CR$^{1a}$ and Z₄ is N.

In certain aspects, this invention describes a compound of formula I wherein R₁ is OCH₃.

In other aspects, this invention describes compounds of formula I wherein R$^{1a}$ is at each occurrence independently hydrogen; halogen; or cyano.

In certain embodiments, this invention describes compounds of formula I wherein Z₁ and Z₄ are N; Z₃ is CR$^{1a}$ and R$^{1a}$ of Z₂, Z₃ and Z₅ are each hydrogen; R$^{1a}$ of Z₆ is hydrogen, halogen or cyano; and R₁ is OCH₃.

In other embodiments, this invention describes compounds of formula I wherein Z₁ and Z₃ are CR$^{1a}$; Z₄ is N; R$^{1a}$ of Z₂ and Z₅ are each hydrogen; R$^{1a}$ of Z₃ is hydrogen or halogen; R$^{1a}$ of Z₆ is hydrogen, halogen or cyano; and R₁ is OCH₃.

In certain aspects, this invention describes compounds of formula I wherein R₁ and R$^{1a}$ of Z₂ together form ethylenedioxy.

In some embodiments, this invention describes compounds of formula I wherein R₁ and R$^{1a}$ of Z₁ together form ethylenedioxy.

In other aspects, this invention describes compounds of formula I wherein R₂ is hydrogen or hydroxy.

In some aspects, this invention describes compounds of formula I wherein R₂ is hydrogen.

In some embodiments, this invention describes compounds of formula I wherein R₄ is hydrogen; halogen; hydroxy; $(C_{1-6})$alkyl; $(C_{1-6})$hydroxyalkyl; C(=O)—NR$^{1a}$R1$^{a'}$; and R₅ is hydrogen or $(C_{1-6})$alkyl or R₄ and R₅ together are =N—OH.

In other embodiments, this invention describes compounds of formula I wherein R₄ is hydroxy; and R₅ is hydrogen.

In some embodiments, this invention describes a compound of formula I wherein R₄ is C(=O)—NH₂ and R₅ is hydrogen.

In certain embodiments, this invention describes compounds of formula I wherein R₆ is hydrogen; hydroxy; halogen; or $(C_{1-6})$alkyl.

In some embodiments, this invention describes a compound of formula I wherein B is CH₂.

In certain other embodiments, this invention describes compounds of formula I wherein R₉ is hydrogen or $(C_{1-6})$alkyl.

In still other embodiments, this invention describes compounds of formula I wherein R₉ is hydrogen.

In further embodiments, this invention describes compounds of formula I wherein U is CH₂; SO₂; or C(=O).

In yet further embodiments, this invention describes compounds of formula I wherein U is CH₂.

In some embodiments, this invention describes compounds of formula I wherein the (a) and (b) rings of R₁₁ are both aromatic as demonstrated by the following non-limiting examples: 1H-pyrrolo[2,3-b]-pyridin-2-yl, 1H-pyrrolo[3,2-b]-pyridin-2-yl, 3H-imidazo[4,5-b]-pyrid-2-yl, 3H-quinazolin-4-one-2-yl, benzimidazol-2-yl, benzo[1,2,3]-thiadiazol-5-yl, benzo[1,2,5]-oxadiazol-5-yl, benzofur-2-yl, benzothiazol-2-yl, benzo[b]thiophen-2-yl, benzoxazol-2-yl, chromen-4-one-3-yl, imidazo[1,2-a]pyridin-2-yl, imidazo-[1,2-a]-pyrimidin-2-yl, indol-2-yl, indol-6-yl, isoquinolin-3-yl, [1,8]-naphthyridine-3-yl, oxazolo[4,5-b]-pyridin-2-yl, quinolin-2-yl, quinolin-3-yl, quinoxalin-2-yl, indan-2-yl, naphthalen-2-yl, 1,3-dioxo-isoindol-2yl, benzimidazol-2-yl, benzothiophen-2-yl, 1H-benzotriazol-5-yl, 1H-indol-5-yl, 3H-benzooxazol-2-one-6-yl, 3H-benzooxazol-2-thione-6-yl, 3H-benzothiazol-2-one-5-yl, 3H-quinazolin-4-one-2-yl, 3H-quinazolin-4-one-6-yl, 4-oxo-4H-pyrido[1,2-a]pyrimidin-3-yl, benzo[1,2,3]thiadiazol-6-yl, benzo[1,2,5]thiadiazol-5-yl, benzo[1,4]oxazin-2-one-3-yl, benzothiazol-5-yl, benzothiazol-6-yl, cinnolin-3-yl, imidazo[1,2-a]pyridazin-2-yl, imidazo[1,2-b]pyridazin-2-yl, pyrazolo[1,5-a]pyrazin-2-yl, pyrazolo[1,5-a]pyridin-2-yl, pyrazolo[1,5-a]pyrimidin-6-yl, pyrazolo[5,1-c][1,2,4]triazin-3-yl, pyrido[1,2-a]pyrimdin-4-one-2-yl, pyrido[1,2-a]pyrimidin-4-one-3-yl, quinazolin-2-yl, quinoxalin-6-yl, thiazolo[3,2-a]pyrimidin-5-one-7-yl, thiazolo[5,4-b]pyridin-2-yl, thieno[3,2-b]pyridin-6-yl, thiazolo[5,4-b]pyridin-6-yl, 4-oxo-4H-pyrido[1,2-a]pyrimidin-2-yl, 1-oxo-1,2-dihydro-isoquinolin-3-yl, thiazolo[4,5-b]pyridin-5-yl, [1,2,3]thiadiazolo[5,4-b]pyridin-6-yl, 2H-isoquinolin-1-one-3-yl.

In yet other embodiments, R₁₁ is defined by a non-aromatic (a) ring and aromatic (b) ring as illustrated by the following non-limiting examples: (2S)-2,3-dihydro-1H-indol-2-yl, (2S)-2,3-dihydro-benzo[1,4]dioxine-2-yl, 3-(R,S)-3,4-dihydro-2H-benzo[1,4]thiazin-3-yl, 3-(R)-2,3-dihydro-[1,4]dioxino[2,3-b]pyridin-3-yl, 3-(S)-2,3-dihydro-[1,4]dioxino[2,3-b]pyridin-3-yl, 2,3-dihydro-benzo[1,4]dioxan-2-yl, 3-substituted-3H-quinazolin-4-one-2-yl, 2,3-dihydro-benzo[1,4]dioxan-2-yl, 1-oxo-1,3,4,5-tetrahydrobenzo[c]azepin-2-yl.

In still other embodiments, $R_{11}$ is defined by an aromatic (a) ring and a non aromatic (b) ring as illustrated by the following non-limiting examples: 1,1,3-trioxo-1,2,3,4-tetrahydro-1/$^6$-benzo[1,4]thiazin-6-yl, benzo[1,3]dioxol-5-yl, 2,3-dihydro-benzo[1,4]dioxin-6-yl, 2-oxo-2,3-dihydro-benzooxazol-6-yl, 4H-benzo[1,4]oxazin-3-one-6-yl (3-oxo-3,4-dihydro-2H-benzo[1,4]oxazin-6-yl), 4H-benzo[1,4]thiazin-3-one-6-yl (3-oxo-3,4-dihydro-2H-benzo[1,4]thiazin-6-yl), 4H-benzo[1,4]oxazin-3-one-7-yl, 4-oxo-2,3,4,5-tetrahydrobenzo[b][1,4]thiazepine-7-yl, 5-oxo-2,3-dihydro-5H-thiazolo[3,2-a]pyrimidin-6-yl, benzo[1,3]dioxol-5-yl, 2-oxo-2,3-dihydro-1H-pyrido[2,3-b][1,4]thiazin-7-yl, 2-oxo-2,3-dihydro-1H-pyrido[3,4-b][1,4]thiazin-7-yl, 3-oxo-3,4-dihydro-2H-pyrido[3,2-b][1,4]thiazin-6-yl, 2,3-dihydro-[1,4]dioxino[2,3-b]pyridin-6-yl, 2,3-dihydro-[1,4]dioxino[2,3-c]pyridin-7-yl, 2,3-dihydro-[1,4]dioxino[2,3-b]pyridin-7-yl, 6,7-dihydro-[1,4]dioxino[2,3-d]pyrimidin-2-yl, 3-oxo-3,4-dihydro-2H-pyrido[3,2-b][1,4]oxazin-6-yl, 2-oxo-2,3-dihydro-1H-pyrido[3,4-b][1,4]oxazin-7-yl, 2-oxo-2,3-dihydro-1H-pyrido[2,3-b][1,4]oxazin-7-yl, 6-oxo-6,7-dihydro-5H-8-thia-1,2,5-triaza-naphthalen-3-yl, 3,4-dihydro-2H-benzo[1,4]oxazin-6-yl, 3-substituted-3H-benzooxazol-2-one-6-yl, 3-substituted-3H-benzooxazole-2-thione-6-yl, 3-substituted-3H-benzothiazol-2-one-6-yl, 2,3-dihydro-1H-pyrido[2,3-b][1,4]thiazin-7-yl, 3,4-dihydro-2H-benzo[1,4]thiazin-6-yl, 3,4-dihydro-1H-quinolin-2-one-7-yl, 3,4-dihydro-1H-quinoxalin-2-one-7-yl, 6,7-dihydro-4H-pyrazolo[1,5-a]pyrimidin-5-one-2-yl, 5,6,7,8-tetrahydro-[1,8]naphthyridin-2-yl, 2-oxo-3,4-dihydro-1H-[1,8]naphthyridin-6-yl, 3,4-dihydro-2H-pyrido[3,2-b][1,4]thiazin-6-yl.

In some aspects, this invention describes compounds of formula I wherein $R_{11}$ is 4H-Pyrido[3,2-b][1,4]thiazin-3-oxo-6-yl; 2,3-Dihydro-benzo[1,4]dioxin-6-yl; 4H-Pyrido[3,2-b][1,4]oxazin-3-oxo-6-yl; 4H-benzo[1,4]thiazin-3-oxo-6-yl; 2,3-Dihydro-furo[2,3-c]pyridin-5-yl; 7-Chloro-4H-pyrido[3,2-b]oxazin-3-oxo-6-yl; 2,3-Dihydro-[1,4]dioxino[2,3-c]-pyridin-6-yl; 2,3-Dihydro-benzofuran-7-carbonitrile-5-yl; 7-Methyl-4H-pyrido[3,2-b][1,4]thiazin-3-oxo-6-yl; 3-Oxa-1-thia-5-aza-indan-5-yl; 5-Methyl-2,3-dihydro-benzo[1,4]dioxin-6-yl; 6-Fluoro-2,3-dihydro[1,4]dioxin-7-yl; 2,3-Dihydro-benzofuran-5-yl; 7-Fluoro-4H-benzo[1,4]thiazin-3-oxo-6-yl; 4H-Benzo[1,4]thiazin-3-oxo-6-yl; or 8-Methyl-2,3-dihydro-benzo[1,4]dioxin-6-yl.

In other aspects, this invention describes a compound of formula I wherein $R_{11}$ is 4H-Pyrido[3,2-b][1,4]thiazin-3-oxo-6-yl.

In yet other aspects, this invention describes a compound of formula I wherein $R_{11}$ is 4H-Pyrido[3,2-b][1,4]oxazin-3-oxo-6-yl.

In some embodiments, this invention describes compounds of formula I wherein $R_1$ is OMe; $R^{1a}$ of $Z_2$ and $Z_5$ are hydrogen; $R^{1a}$ of $Z_6$ is fluoro; $R_2$ is hydrogen; $R_4$ is hydroxy; $R_5$ is hydrogen; $R_6$ is hydrogen; $R_7$ and $R_8$ are hydrogen; $R_9$ is hydrogen; U is $CH_2$; $R_{11}$ is 4H-Pyrido[3,2-b][1,4]thiazin-3-oxo-6-yl or 4H-Pyrido[3,2-b][1,4]oxazin-3-oxo-6-yl.

In some aspects, this invention describes compounds of formula I wherein $Z_1$ and $Z_4$ are N; $Z_3$ is $CR^{1a}$; $R_1$ is OMe; $R^{1a}$ of $Z_2$, $Z_3$ and $Z_5$ are hydrogen; and $R^{1a}$ of $Z_6$ is hydrogen, fluoro, chloro, or cyano.

In other aspects, this invention describes compounds of formula I wherein $Z_1$ and $Z_4$ are N; $Z_3$ is $CR^{1a}$; $R_1$ is OMe; $R^{1a}$ of $Z_2$, $Z_3$ and $Z_5$ are hydrogen; and $R^{1a}$ of $Z_6$ is fluoro or cyano.

In yet other aspects, this invention describes compounds of formula I wherein $Z_1$ and $Z_4$ are N; $Z_3$ is $CR^{1a}$; $R_1$ is OMe; $R^{1a}$ of $Z_2$, $Z_3$ and $Z_5$ are hydrogen; and $R^{1a}$ of $Z_6$ is hydrogen, fluoro, chloro, or cyano; and $R_2$ is hydrogen or hydroxy.

In some embodiments, this invention describes compounds of formula I wherein $Z_1$ and $Z_4$ are N; $Z_3$ is $CR^{1a}$; $R_1$ is OMe; $R^{1a}$ of $Z_2$, $Z_3$ and $Z_5$ are hydrogen; and $R^{1a}$ of $Z_6$ is hydrogen, fluoro, chloro, or cyano; and $R_2$ is hydrogen.

In certain aspects, this invention describes compounds of formula I wherein $Z_1$ and $Z_4$ are N; $Z_3$ is $CR^{1a}$; $R_1$ is OMe; $R^{1a}$ of $Z_2$, $Z_3$ and $Z_5$ are hydrogen; and $R^{1a}$ of $Z_6$ is hydrogen, fluoro, chloro, or cyano; $R_2$ is hydrogen or hydroxy; $R_4$ is hydrogen, hydroxy, fluoro, methyl, or methoxy; and $R_5$ is hydrogen or methyl.

In other aspects, this invention describes compounds of formula I wherein $Z_1$ and $Z_4$ are N; $Z_3$ is $CR^{1a}$; $R_1$ is OMe; $R^{1a}$ of $Z_2$, $Z_3$ and $Z_5$ are hydrogen; and $R^{1a}$ of $Z_6$ is hydrogen, fluoro, chloro, or cyano; $R_2$ is hydrogen or hydroxy; $R_4$ is hydroxy and $R_5$ is hydrogen.

In some embodiments, this invention describes compounds of formula I wherein $Z_1$ and $Z_4$ are N; $Z_3$ is $CR^{1a}$; $R_1$ is OMe; $R^{1a}$ of $Z_2$, $Z_3$ and $Z_5$ are hydrogen; and $R^{1a}$ of $Z_6$ is hydrogen, fluoro, chloro, or cyano; $R_2$ is hydrogen or hydroxy; $R_4$ is hydrogen, hydroxy, fluoro, methyl, or methoxy; $R_5$ is hydrogen or methyl; and $R_6$ is hydrogen; hydroxy; fluoro; or methyl.

In yet other embodiments, this invention describes compounds of formula I wherein $Z_1$ and $Z_4$ are N; $Z_3$ is $CR^{1a}$; $R_1$ is OMe; $R^{1a}$ of $Z_2$, $Z_3$ and $Z_5$ are hydrogen; and $R^{1a}$ of $Z_6$ is hydrogen, fluoro, chloro, or cyano; $R_2$ is hydrogen or hydroxy; $R_4$ is hydrogen, hydroxy, fluoro, methyl, or methoxy; $R_5$ is hydrogen or methyl; and $R_6$ is hydrogen.

In still yet other embodiments, this invention describes compounds of formula I wherein $Z_1$ and $Z_4$ are N; $Z_3$ is $CR^{1a}$; $R_1$ is OMe; $R^{1a}$ of $Z_2$, $Z_3$ and $Z_5$ are hydrogen; and $R^{1a}$ of $Z_6$ is hydrogen, fluoro, chloro, or; cyano; $R_2$ is hydrogen or hydroxy; $R_4$ is hydrogen, hydroxy, fluoro, methyl, or methoxy; $R_5$ is hydrogen or methyl; $R_6$ is hydrogen; hydroxy; fluoro; or methyl; and $R_7$ and $R_8$ are independently hydrogen or methyl.

In further embodiments, this invention describes compounds of formula I wherein $Z_1$ and $Z_4$ are N; $Z_3$ is $CR^{1a}$; $R_1$ is OMe; $R^{1a}$ of $Z_2$, $Z_3$ and $Z_5$ are hydrogen; and $R^{1a}$ of $Z_6$ is hydrogen, fluoro, chloro, or cyano; $R_2$ is hydrogen or hydroxy; $R_4$ is hydrogen, hydroxy, fluoro, methyl, or methoxy; $R_5$ is hydrogen or methyl; $R_6$ is hydrogen; hydroxy; fluoro; or methyl; and $R_7$ and $R_8$ are hydrogen.

In some aspects, this invention describes compounds of formula I wherein $Z_1$ and $Z_4$ are N; $Z_3$ is $CR^{1a}$; $R_1$ is OMe; $R^{1a}$ of $Z_2$, $Z_3$ and $Z_5$ are hydrogen; and $R^{1a}$ of $Z_6$ is hydrogen, fluoro, chloro, or cyano; $R_2$ is hydrogen or hydroxy; $R_4$ is hydrogen, hydroxy, fluoro, methyl, or methoxy; $R_5$ is hydrogen or methyl; $R_6$ is hydrogen; hydroxy; fluoro; or methyl; $R_7$ and $R_8$ are independently hydrogen or methyl; and $R_9$ is hydrogen or methyl.

In yet other aspects, this invention describes compounds of formula I wherein $Z_1$ and $Z_4$ are N; $Z_3$ is $CR^{1a}$; $R_1$ is OMe; $R^{1a}$ of $Z_2$, $Z_3$ and $Z_5$ are hydrogen; and $R^{1a}$ of $Z_6$ is hydrogen, fluoro, chloro, or cyano; $R_2$ is hydrogen or hydroxy; $R_4$ is hydrogen, hydroxy, fluoro, methyl, or methoxy; $R_5$ is hydrogen or methyl; $R_6$ is hydrogen; hydroxy; fluoro; or methyl; $R_7$ and $R_8$ are independently hydrogen or methyl; and $R_9$ is hydrogen.

In certain embodiments, this invention describes compounds of formula I wherein $Z_1$ and $Z_4$ are N; $Z_3$ is $CR^{1a}$; $R_1$ is OMe; $R^{1a}$ of $Z_2$, $Z_3$ and $Z_5$ are hydrogen; and $R^{1a}$ of $Z_6$ is hydrogen, fluoro, chloro, or cyano; $R_2$ is hydrogen or hydroxy; $R_4$ is hydrogen, hydroxy, fluoro, methyl, or methoxy; $R_5$ is hydrogen or methyl; $R_6$ is hydrogen; hydroxy; fluoro; or methyl; $R_7$ and $R_8$ are independently hydrogen or methyl; $R_9$ is hydrogen or methyl and U is $CH_2$; $SO_2$ or C(=O).

In still other embodiments, this invention describes compounds of formula I wherein $Z_1$ and $Z_4$ are N; $Z_3$ is $CR^{1a}$; $R_1$ is OMe; $R^{1a}$ of $Z_2$, $Z_3$ and $Z_5$ are hydrogen; and $R^{1a}$ of $Z_6$ is hydrogen, fluoro, chloro, or cyano; $R_2$ is hydrogen or hydroxy; $R_4$ is hydrogen, hydroxy, fluoro, methyl, or methoxy; $R_5$ is hydrogen or methyl; $R_6$ is hydrogen; hydroxy; fluoro; or methyl; $R_7$ and $R_8$ are independently hydrogen or methyl; $R_9$ is hydrogen or methyl and U is $CH_2$.

In some embodiments, this invention describes compounds of formula I wherein $Z_1$ and $Z_4$ are N; $Z_3$ is $CR^{1a}$; $R_1$ is OMe; $R^{1a}$ of $Z_2$, $Z_3$ and $Z_5$ are hydrogen; and $R^{1a}$ of $Z_6$ is hydrogen, fluoro, chloro, or cyano; $R_2$ is hydrogen or hydroxy; $R_4$ is hydrogen, hydroxy, fluoro, methyl, or methoxy; $R_5$ is hydrogen or methyl; $R_6$ is hydrogen; hydroxy; fluoro; or methyl; $R_7$ and $R_8$ are independently hydrogen or methyl; $R_9$ is hydrogen or methyl; U is $CH_2$; $SO_2$ or C(=O); and $R_{11}$ is 4H-Pyrido[3,2-b][1,4]thiazin-3-oxo-6-yl.

In yet other embodiments, this invention describes compounds of formula I wherein $Z_1$ and $Z_4$ are N; $Z_3$ is $CR^{1a}$; $R_1$ is OMe; $R^{1a}$ of $Z_2$, $Z_3$ and $Z_5$ are hydrogen; and $R^{1a}$ of $Z_6$ is hydrogen, fluoro, chloro, or cyano; $R_2$ is hydrogen or hydroxy; $R_4$ is hydrogen, hydroxy, fluoro, methyl, or methoxy; $R_5$ is hydrogen or methyl; $R_6$ is hydrogen; hydroxy; fluoro; or methyl; $R_7$ and $R_8$ are independently hydrogen or methyl; $R_9$ is hydrogen or methyl; U is $CH_2$; $SO_2$ or C(=O); and $R_{11}$ is 4H-Pyrido[3,2-b]oxazin-3-oxo-6-yl.

In still other embodiments, this invention describes compounds of formula I wherein $Z_1$ and $Z_4$ are N; $Z_3$ is $CR^{1a}$; $R_1$ is OMe; $R^{1a}$ of $Z_2$, $Z_3$ and $Z_5$ are hydrogen; and $R^{1a}$ of $Z_6$ is hydrogen, fluoro, chloro, or cyano; $R_2$ is hydrogen or hydroxy; $R_4$ is hydrogen, hydroxy, fluoro, methyl, or methoxy; $R_5$ is hydrogen or methyl; $R_6$ is hydrogen; hydroxy; fluoro; or methyl; $R_7$ and $R_8$ are independently hydrogen or methyl; $R_9$ is hydrogen or methyl; U is $CH_2$; $SO_2$ or C(=O); and $R_{11}$ is 2,3-Dihydro-benzo[1,4]dioxin-6-yl; 4H-benzo[1,4]thiazin-3-oxo-6-yl; 2,3-Dihydro-furo[2,3-c]pyridin-5-yl; 4H-Pyrido[3,2-b]oxazin-3-oxo-6-yl; 7-Chloro-4H-pyrido[3,2-b]oxazin-3-oxo-6-yl; 2,3-Dihydro-[1,4]dioxino[2,3-c]-pyridin-6-yl; 2,3-Dihydro-benzofuran-7-carbonitrile-5-yl; 7-Methyl-4H-pyrido[3,2-b][1,4]thiazin-3-oxo-6-yl; 3-Oxa-1-thia-5-aza-indan-5-yl; 5-Methyl-2,3-dihydro-benzo[1,4]dioxin-6-yl; 6-Fluoro-2,3-dihydro[1,4]dioxin-7-yl; 2,3-Dihydro-benzofuran-5-yl; 7-Fluoro-4H-benzo[1,4]thiazin-3-oxo-6-yl; 4H-Benzo[1,4]thiazin-3-oxo-6-yl; or 8-Methyl-2,3-dihydro-benzo[1,4]dioxin-6-yl.

In some embodiments, this invention describes compounds of formula I wherein $Z_1$ and $Z_4$ are N; $Z_3$ is $CR^{1a}$; $R_1$ is OMe; $R^{1a}$ of $Z_2$, $Z_3$ and $Z_5$ are hydrogen; $R^{1a}$ of $Z_6$ is fluoro or cyano; $R_2$ is hydrogen; $R_4$ is hydroxy; $R_5$ is hydrogen; $R_6$ is hydrogen; $R_7$ and $R_8$ are hydrogen; $R_9$ is hydrogen; $R_{11}$ is 4H-Pyrido[3,2-b][1,4]thiazin-3-oxo-6-yl or 4H-Pyrido[3,2-b]oxazin-3-oxo-6-yl.

In still other embodiments, this invention describes compounds of formula I wherein $Z_1$ and $Z_4$ are N; $Z_3$ is $CR^{1a}$; $R_1$ is OMe; $R^{1a}$ of $Z_2$, $Z_3$ and $Z_5$ are hydrogen; $R^{1a}$ of $Z_6$ is fluoro or cyano; $R_2$ is hydrogen; $R_4$ is hydroxy; $R_5$ is hydrogen; $R_9$ is hydrogen; $R_{11}$ is 4H-Pyrido[3,2-b][1,4]thiazin-3-oxo-6-yl or 4H-Pyrido[3,2-b]oxazin-3-oxo-6-yl; and $R_4$ and B are cis.

In some aspects, this invention describes compounds of formula I wherein $Z_1$ and $Z_3$ are $CR^{1a}$; $Z_4$ is N; $R_1$ is OMe; $R^{1a}$ of $Z_1$, $Z_2$ and $Z_5$ are hydrogen; $R^{1a}$ of $Z_3$ is hydrogen or fluoro; $R^{1a}$ of $Z_6$ is hydrogen, fluoro or cyano; and $R_2$ is hydrogen.

In further aspects, this invention describes compounds of formula I wherein $Z_1$ and $Z_3$ are $CR^{1a}$; $Z_4$ is N; $R_1$ is OMe; $R^{1a}$ of $Z_1$, $Z_2$ and $Z_5$ are hydrogen; $R^{1a}$ of $Z_3$ is hydrogen or fluoro; $R^{1a}$ of $Z_6$ is hydrogen, fluoro or cyano; $R_2$ is hydrogen; $R_4$ is hydrogen or hydroxy; $R_5$ is hydrogen; $R_6$ is hydrogen or methyl; $R_7$ and $R_8$ are hydrogen; $R_9$ is hydrogen; and U is $CH_2$ or $SO_2$.

In still further aspects, this invention describes compounds of formula I wherein $Z_1$ and $Z_3$ are $CR^{1a}$; $Z_4$ is N; $R_1$ is OMe; $R^{1a}$ of $Z_1$, $Z_2$ and $Z_5$ are hydrogen; $R^{1a}$ of $Z_3$ is hydrogen or fluoro; $R^{1a}$ of $Z_6$ is hydrogen, fluoro or cyano; $R_2$ is hydrogen; $R_4$ is hydrogen or hydroxy; $R_5$ is hydrogen; $R_6$ is hydrogen or methyl; $R_7$ and $R_8$ are hydrogen; $R_9$ is hydrogen; U is $CH_2$ or $SO_2$; and $R_{11}$ is 4H-Pyrido[3,2-b][1,4]thiazin-3-one-6-yl; 4H-Pyrido[3,2-b]oxazin-3-one-6-yl; 3-Oxa-1-thia-5-aza-indan-5-yl; or 4H-benzo[1,4]thiazin-3-one-6-yl.

In some embodiments, this invention describes compounds of formula I wherein $Z_1$ and $Z_3$ are $CR^{1a}$; $Z_4$ is N; $R_1$ is OMe; $R^{1a}$ of $Z_1$, $Z_2$ and $Z_5$ are hydrogen; $R^{1a}$ of $Z_3$ is hydrogen or fluoro; $R^{1a}$ of $Z_6$ is fluoro or cyano; $R_2$ is hydrogen; $R_4$ is hydroxy; $R_5$ is hydrogen; $R_6$ is hydrogen; $R_7$ and $R_8$ are hydrogen; $R_9$ is hydrogen; U is $CH_2$; and $R_{11}$ is 4H-Pyrido[3,2-b][1,4]thiazin-3-one-6-yl or 4H-Pyrido[3,2-b]oxazin-3-one-6-yl.

In still other embodiments, this invention describes compounds of formula I wherein $Z_1$ and $Z_3$ are $CR^{1a}$; $Z_4$ is N; $R_1$ is OMe; $R^{1a}$ of $Z_1$, $Z_2$ and $Z_5$ are hydrogen; $R^{1a}$ of $Z_3$ is hydrogen or fluoro; $R^{1a}$ of $Z_6$ is fluoro or cyano; $R_2$ is hydrogen; $R_4$ is hydroxy; $R_5$ is hydrogen; $R_6$ is hydrogen; $R_7$ and $R_8$ are hydrogen; $R_9$ is hydrogen; U is $CH_2$; $R_{11}$ is 4H-Pyrido[3,2-b][1,4]thiazin-3-one-6-yl or 4H-Pyrido[3,2-b]oxazin-3-one-6-yl; and $R_4$ and B are cis.

In some aspects, this invention describes compounds of formula (I) wherein the compound is 6-({[((3S)-1-{2-[6-(methyloxy)-1,5-naphthyridin-4-yl]ethyl}-3-pyrrolidinyl)methyl]amino}methyl)-2H-pyrido[3,2-b][1,4]thiazin-3(4H)-one; 6-({[((3R)-1-{2-[3-fluoro-6-(methyloxy)-1,5-naphthyridin-4-yl]ethyl}-3-pyrrolidinyl)methyl]amino}methyl)-2H-pyrido[3,2-b][1,4]thiazin-3(4H)-one; (2,3-dihydro-1-benzofuran-5-ylmethyl)[((3S)-1-{2-[3-fluoro-6-(methyloxy)-1,5-naphthyridin-4-yl]ethyl}-3-pyrrolidinyl)methyl]amine; [(7-fluoro-2,3-dihydro-1,4-benzodioxin-6-yl)methyl][((3S)-1-{2-[3-fluoro-6-(methyloxy)-1,5-naphthyridin-4-yl]ethyl}-3-pyrrolidinyl)methyl]amine; (2,3-dihydro-1,4-benzodioxin-6-ylmethyl)[((3S)-1-{2-[3-fluoro-6-(methyloxy)-1,5-naphthyridin-4-yl]ethyl}-3-pyrrolidinyl)methyl]amine; 6-({[((3R)-1-{2-[3,8-difluoro-6-(methyloxy)-4-quinolinyl]ethyl}-3-pyrrolidinyl)methyl]amino}methyl)-2H-pyrido[3,2-b][1,4]thiazin-3(4H)-one; 6-({[((3S)-1-{2-[3-fluoro-6-(methyloxy)-4-quinolinyl]ethyl}-3-pyrrolidinyl)methyl]amino}methyl)-2H-pyrido[3,2-b][1,4]thiazin-3(4H)-one; 6-({[((3S)-1-{2-[3-fluoro-6-(methyloxy)-4-quinolinyl]ethyl}-3-pyrrolidinyl)methyl]amino}methyl)-2H-pyrido[3,2-b][1,4]oxazin-3(4H)-one; 5-({[((3S)-1-{2-[3-fluoro-6-(methyloxy)-1,5-naphthyridin-4-yl]ethyl}-3-pyrrolidinyl)methyl]amino}methyl)-2,3-dihydro-1-benzofuran-7-carbonitrile; 7-chloro-6-({[((3R)-1-{2-[3-fluoro-6-(methyloxy)-1,5-naphthyridin-4-yl]ethyl}-3-pyrrolidinyl)methyl]amino}methyl)-2H-pyrido[3,2-b][1,4]oxazin-3(4H)-one; 7-fluoro-6-({[((3R)-1'-{2-[3-fluoro-6-(methyloxy)-1,5-naphthyridin-4-yl]ethyl}-3-pyrrolidinyl)methyl]amino}methyl)-2H-1,4-benzothiazin-3(4H)-one; (2,3-dihydrofuro[2,3-c]pyridin-5-ylmethyl)[((3S)-1-{2-[3- fluoro-6-(methyloxy)-1,5-naphthyridin-4-yl]ethyl}-3-pyrrolidinyl)methyl]amine; 6-(methyloxy)-4-{2-[(3S)-3-({[(3-oxo-3,4-dihydro-2H-pyrido[3,2-b][1,4]thiazin-6-yl)methyl]amino}methyl)-1-pyrrolidinyl]ethyl}-3-quinolinecarbonitrile; 6-(methyloxy)-4-[2-((3S)-3-{[([1,3]oxathiolo[5,4-c]pyridin-6-ylmethyl)amino]methyl}-1-pyrrolidinyl)ethyl]-3-quinolinecarbonitrile; 6-(methyloxy)-4-{2-[(3S)-3-({[(3-oxo-3,4-dihydro-2H-pyrido[3,2-b][1,4]oxazin-6-yl)methyl]amino}methyl)-1-pyrrolidinyl]ethyl}-3-quinolinecarbonitrile; 6-(methyloxy)-4-{2-[(3S)-3-({[(3-oxo-3,4-dihydro-2H-pyrido[3,2-b][1,4]thiazin-6-yl)methyl]amino}methyl)-1-pyrrolidinyl]ethyl}-1,5-naphthyridine-3-carbonitrile; 1-[((3S)-1-{2-[3-fluoro-6-(methyloxy)-1,5-naphthyridin-4-yl]ethyl}-3-pyrrolidinyl)methyl][(5-methyl-2,3-dihydro-1,4-benzodioxin-6-yl)methyl]amine; 1-((3S)-1-{2-[3-fluoro-6-(methyloxy)-1,5-naphthyridin-4-yl]ethyl}-3-pyrrolidinyl)-N-[(8-methyl-2,3-dihydro-1,4-benzodioxin-6-yl)methyl]methanamine; 6-({[((3S)-1-{2-[3-chloro-6-(methyloxy)-1,5-naphthyridin-4-yl]ethyl}-3-pyrrolidinyl)methyl]amino}methyl)-2H-pyrido[3,2-b][1,4]thiazin-3(4H)-one; 6-({[((3S)-1-{2-[3-chloro-6-(methyloxy)-1,5-naphthyridin-4-yl]ethyl}-3-pyrrolidinyl)methyl]amino}methyl)-2H-pyrido[3,2-b][1,4]oxazin-3(4H)-one; [((3S)-1-{2-[3-chloro-6-(methyloxy)-1,5-naphthyridin-4-yl]ethyl}-3-pyrrolidinyl)methyl]([1,3]oxathiolo[5,4-c]pyridin-6-ylmethyl)amine; 6-({[((3S)-1-{2-[3,8-difluoro-6-(methyloxy)-4-quinolinyl]ethyl}-3-pyrrolidinyl)methyl]amino}methyl)-2H-pyrido[3,2-b][1,4]oxazin-3(4H)-one; 6-({[((3S)-1-{2-[3,8-difluoro-6-(methyloxy)-4-quinolinyl]ethyl}-3-pyrrolidinyl)methyl]amino}methyl)-2H-pyrido[3,2-b][1,4]thiazin-3(4H)-one; [((3S)-1-{2-[3-fluoro-6-(methyloxy)-1,5-naphthyridin-4-yl]ethyl}-3-pyrrolidinyl)methyl]([1,3]oxathiolo[5,4-c]pyridin-6-ylmethyl)amine; 7-chloro-6-({[((3S)-1-{2-[3-fluoro-6-(methyloxy)-1,5-naphthyridin-4-yl]ethyl}-3-pyrrolidinyl)methyl]amino}methyl)-2H-pyrido[3,2-b][1,4]oxazin-3(4H)-one; 6-({[((3S)-1-{2-[3-fluoro-6-(methyloxy)-1,5-naphthyridin-4-yl]ethyl}-3-pyrrolidinyl)methyl]amino}methyl)-2H-pyrido[3,2-b][1,4]oxazin-3(4H)-one; 6-({[((3S)-1-{2-[3-fluoro-6-(methyloxy)-1,5-naphthyridin-4-yl]ethyl}-3-pyrrolidinyl)methyl]amino}methyl)-2H-pyrido[3,2-b][1,4]thiazin-3(4H)-one; (2,3-dihydro[1,4]dioxino[2,3-c]pyridin-7-ylmethyl)[((3S)-1-{2-[3-fluoro-6-(methyloxy)-1,5-naphthyridin-4-yl]ethyl}-3-pyrrolidinyl)methyl]amine; 6-({[((3S)-1-{2-[3-fluoro-6-(methyloxy)-1,5-naphthyridin-4-yl]ethyl}-3-pyrrolidinyl)methyl]amino}methyl)-7-methyl-2H-pyrido[3,2-b][1,4]thiazin-3(4H)-one; 6-({[((3S)-1-{(2S)-2-hydroxy-2-[6-(methyloxy)-1,5-naphthyridin-4-yl]ethyl}-3-pyrrolidinyl)methyl]amino}methyl)-2H-pyrido[3,2-b][1,4]thiazin-3(4H)-one; 6-({[((3S)-1-{(2S)-2-hydroxy-2-[6-(methyloxy)-1,5-naphthyridin-4-yl]ethyl}-3-pyrrolidinyl)methyl]amino}methyl)-2H-pyrido[3,2-b][1,4]oxazin-3(4H)-one; 6-({[((3R)-1-{(2S)-2-hydroxy-2-[6-(methyloxy)-1,5-naphthyridin-4-yl]ethyl}-3-pyrrolidinyl)methyl]amino}methyl)-2H-pyrido[3,2-b][1,4]oxazin-3(4H)-one; 6-({[((3R)-1-{(2S)-2-hydroxy-2-[6-(methyloxy)-1,5-naphthyridin-4-yl]ethyl}-3-pyrrolidinyl)methyl]amino}methyl)-2H-pyrido[3,2-b][1,4]thiazin-3(4H)-one; 6-({[((3S)-1-{(2R)-2-[3-fluoro-6-(methyloxy)-1,5-naphthyridin-4-yl]-2-hydroxyethyl}-3-pyrrolidinyl)methyl]amino}methyl)-2H-pyrido[3,2-b][1,4]thiazin-3(4H)-one; N-[((3S)-1-{2-[3-fluoro-6-(methyloxy)-1,5-naphthyridin-4-yl]-ethyl}-3-pyrrolidinyl)methyl]-3-oxo-3,4-dihydro-2H-1,4-benzothiazine-6-sulfonamide; N-[((3R)-1-{2-[3-fluoro-6-(methyloxy)-1,5-naphthyridin-4-yl]ethyl}-3-pyrrolidinyl)methyl]-3-oxo-3,4-dihydro-2H-1,4-benzothiazine-6-sulfonamide; N-[((3R)-1-{2-[3-fluoro-6-(methyloxy)-1,5-naphthyridin-4-yl]ethyl}-3-pyrrolidinyl)methyl]-2,3-dihydro-1,4-benzodioxin-6-sulfonamide; N-[((3R)-1-{2-[3-fluoro-6-(methyloxy)-4-quinolinyl]ethyl}-3-pyrrolidinyl)methyl]-3-oxo-3,4-dihydro-2H-1,4-benzothiazine-6-sulfonamide; N-[((3R)-1-{2-[3,8-difluoro-6-(methyloxy)-4-quinolinyl]ethyl}-3-pyrrolidinyl)methyl]-3-oxo-3,4-dihydro-2H-1,4-benzothiazine-6-sulfonamide; N-[((3R)-1-{2-[3-cyano-6-(methyloxy)-4-quinolinyl]ethyl}-3-pyrrolidinyl)methyl]-3-oxo-3,4-dihydro-2H-1,4-benzothiazine-6-sulfonamide; (±)-6-({[(1-{2-[3-fluoro-6-(methyloxy)-1,5-naphthyridin-4-yl]ethyl}-3-hydroxy-3-pyrrolidinyl)methyl]amino}methyl)-2H-pyrido[3,2-b][1,4]thiazin-3(4H)-one; (±)-6-({[(trans-3,4)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]thiazin-3(4H)-one; 6-({[(trans-3,4)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]thiazin-3(4H)-one; 6-({[(trans-3,4)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]thiazin-3(4H)-one; (±)-6-({[(trans-3,4)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]oxazin-3(4H)-one; 6-({[(trans-3,4)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]oxazin-3(4H)-one; 6-({[(trans-3,4)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]oxazin-3(4H)-one; (±)-6-({[((cis-3,4)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]thiazin-3(4H)-one; 6-({[((3S,4S)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]thiazin-3(4H)-one; 6-({[((3R,4R)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]thiazin-3(4H)-one; 6-({[((3S,4S)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]oxazin-3(4H)-one; 6-({[((3R,4R)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]oxazin-3(4H)-one; (±)-7-chloro-6-({[((cis-3,4)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]oxazin-3(4H)-one; 7-chloro-6-({[((3S,4S)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]oxazin-3(4H)-one; 7-chloro-6-({[((3R,4R)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]oxazin-3(4H)-one; (±)-(cis-3,4)-4-{[(2,3-dihydro[1,4]dioxino[2,3-c]pyridin-7-ylmethyl)amino]methyl}-1-{2-[3-fluoro-6-(methyloxy)-1,5-naphthyridin-4-yl]ethyl}-3-pyrrolidinol; (3S,4S)-4-{[(2,3-dihydro[1,4]dioxino[2,3-c]pyridin-7-ylmethyl)amino]methyl}-1-{2-[3-fluoro-6-(methyloxy)-1,5-naphthyridin-4-yl]ethyl}-3-pyrrolidinol; (3R,4R)-4-{[(2,3-dihydro[1,4]dioxino[2,3-c]pyridin-7-ylmethyl)amino]methyl}-1-{2-[3-fluoro-6-(methyloxy)-1,5-naphthyridin-4-yl]ethyl}-3-pyrrolidinol; 8-fluoro-6-({[((3S,4S)-1-{2-[3-fluoro-6-(methyloxy)-1,5-naphthyridin-4-yl]ethyl}-4-hydroxy-3-pyrrolidinyl)methyl]amino}methyl)-2H-1,4-benzoxazin-3(4H)-one; 6-({[((3S,4S)-1-{2-[3-fluoro-6-(methyloxy)-4-quinolinyl]ethyl}-4- hydroxy-3-pyrrolidinyl)methyl]amino}methyl)-2H-pyrido[3,2-b][1,4]thiazin-3(4H)-one; 6-({[((3S,4S)-1-{2-[3-fluoro-6-(methyloxy)-4-quinolinyl]ethyl}-4-hydroxy-3-pyrrolidinyl)methyl]amino}methyl)-2H-pyrido[3,2-b][1,4]oxazin-3(4H)-one; (±)-6-({[((cis-3,4)-4-hydroxy-1-{2-[6-(methyloxy)-1,5-naphthyridin-4-yl]ethyl}-3-pyrrolidinyl)methyl]amino}methyl)-2H-pyrido[3,2-b][1,4]thiazin-3(4H)-one; 6-({[((3S,4S)-4-hydroxy-1-{2-[6-(methyloxy)-1,5-naphthyridin-4-yl]ethyl}-3-pyrrolidinyl)methyl]amino}methyl)-2H-pyrido[3,2-b][1,4]thiazin-3(4H)-one; (±)-6-({[((cis-3,4)-4-hydroxy-1-{2-[6-(methyloxy)-1,5-naphthyridin-4-yl]ethyl}-3-pyrrolidinyl)methyl]amino}methyl)-2H-pyrido[3,2-b][1,4]oxazin-3(4H)-one; 6-({[((3S,4S)-1-{2-[3-chloro-6-(methyloxy)-1,5-naphthyridin-4-yl]ethyl}-4-hydroxy-3-pyrrolidinyl)methyl]amino}methyl)-2H-pyrido[3,2-b][1,4]oxazin-3(4H)-one; 6-({[((3S,4S)-1-{2-[3-chloro-6-(methyloxy)-1,5-naphthyridin-4-yl]ethyl}-4-hydroxy-3-pyrrolidinyl)methyl]amino}methyl)-2H-pyrido[3,2-b][1,4]thiazin-3(4H)-one; (3S,4S)-1-{2-[3-chloro-6-(methyloxy)-1,5-naphthyridin-4-yl]ethyl}-4-{[(2,3-dihydro[1,4]dioxino[2,3-c]pyridin-7-ylmethyl)amino]methyl}-3-pyrrolidinol; (±)-6-[({[(cis-3,4)-1-{2-[3-fluoro-6-(methyloxy)-1,5-naphthyridin-4-yl]ethyl}-4-(methyloxy)-3-pyrrolidinyl]methyl}amino)methyl]-2H-pyrido[3,2-b][1,4]thiazin-3(4H)-one; (±)-6-[({[(cis-3,4)-1-{2-[3-fluoro-6-(methyloxy)-1,5-naphthyridin-4-yl]ethyl}-4-(methyloxy)-3-pyrrolidinyl]methyl}amino)methyl]-2H-pyrido[3,2-b][1,4]oxazin-3(4H)-one; (±)-6-({[(3-fluoro-1-{2-[3-fluoro-6-(methyloxy)-1,5-naphthyridin-4-yl]ethyl}-3-pyrrolidinyl)methyl]amino}methyl)-2H-pyrido[3,2-b][1,4]thiazin-3(4H)-one; (±)-(2,3-dihydro[1,4]dioxino[2,3-c]pyridin-7-ylmethyl)[(3-fluoro-1-{2-[3-fluoro-6-(methyloxy)-1,5-naphthyridin-4-yl]ethyl}-3-pyrrolidinyl)methyl]amine; (±)-6-({[((3S,4R)-4-fluoro-1-{2-[3-fluoro-6-(methyloxy)-1,5-naphthyridin-4-yl]ethyl}-3-pyrrolidinyl)methyl]amino}methyl)-2H-pyrido[3,2-b][1,4]thiazin-3(4H)-one; (±)-6-({[((3S,4S)-4-fluoro-1-{2-[3-fluoro-6-(methyloxy)-1,5-naphthyridin-4-yl]ethyl}-3-pyrrolidinyl)methyl]amino}methyl)-2H-pyrido[3,2-b][1,4]thiazin-3(4H)-one; (±)-6-({[(1-{2-[3-fluoro-6-(methyloxy)-1,5-naphthyridin-4-yl]ethyl}-4-hydroxy-3-methyl-3-pyrrolidinyl)methyl]amino}methyl)-2H-pyrido[3,2-b][1,4]thiazin-3(4H)-one; (±)-6-({[(1-{2-[3-fluoro-6-(methyloxy)-1,5-naphthyridin-4-yl]ethyl}-4-hydroxy-3-methyl-3-pyrrolidinyl)methyl]amino}methyl)-2H-pyrido[3,2-b][1,4]thiazin-3(4H)-one; (±)-6-({[(1-{2-[3-fluoro-6-(methyloxy)-1,5-naphthyridin-4-yl]ethyl}-4-hydroxy-4-methyl-3-pyrrolidinyl)methyl]amino}methyl)-2H-pyrido[3,2-b][1,4]thiazin-3(4H)-one; (±)-6-({[(1-{2-[3-fluoro-6-(methyloxy)-1,5-naphthyridin-4-yl]ethyl}-4-hydroxy-4-methyl-3-pyrrolidinyl)methyl]amino}methyl)-2H-pyrido[3,2-b][1,4]thiazin-3(4H)-one; (±)-6-({[(1-{2-[3-fluoro-6-(methyloxy)-1,5-naphthyridin-4-yl]ethyl}-3-methyl-3-pyrrolidinyl)methyl]amino}methyl)-2H-pyrido[3,2-b][1,4]thiazin-3(4H)-one; (±)-6-({[(1-{2-[3-fluoro-6-(methyloxy)-1,5-naphthyridin-4-yl]ethyl}-3-methyl-3-pyrrolidinyl)methyl]amino}methyl)-2H-pyrido[3,2-b][1,4]oxazin-3(4H)-one; (±)-[(1-{2-[3-fluoro-6-(methyloxy)-1,5-naphthyridin-4-yl]ethyl}-3-methyl-3-pyrrolidinyl)methyl]([1,3]oxathiolo[5,4-c]pyridin-6-ylmethyl)amine; (±)-(2,3-dihydro[1,4]dioxino[2,3-c]pyridin-7-ylmethyl)[(1-{2-[3-fluoro-6-(methyloxy)-1,5-naphthyridin-4-yl]ethyl}-3-methyl-3-pyrrolidinyl)methyl]amine; (±)-4-{2-[3-methyl-3-({[(3-oxo-3,4-dihydro-2H-pyrido[3,2-b][1,4]thiazin-6-yl)methyl]amino}methyl)-1-pyrrolidinyl]ethyl}-6-(methyloxy)-3-quinolinecarbonitrile; (±)-4-[2-(3-methyl-3-{[([1,3]oxathiolo[5,4-c]pyridin-6-ylmethyl)amino]methyl}-1-pyrrolidinyl)ethyl]-6-(methyloxy)-3-quinolinecarbonitrile; 6-({[1-((3R)-1-{2-[3-fluoro-6-(methyloxy)-1,5-naphthyridin-4-yl]ethyl}-3-pyrrolidinyl)-1-methylethyl]amino}methyl)-2H-pyrido[3,2-b][1,4]thiazin-3(4H)-one; N-(2,3-dihydro[1,4]dioxino[2,3-c]pyridin-7-ylmethyl)-2-((3R)-1-{2-[3-fluoro-6-(methyloxy)-1,5-naphthyridin-4-yl]ethyl}-3-pyrrolidinyl)-2-propanamine; N-[((3S)-1-{2-[3-fluoro-6-(methyloxy)-1,5-naphthyridin-4-yl]ethyl}-3-pyrrolidinyl)methyl]-3-oxo-3,4-dihydro-2H-pyrido[3,2-b][1,4]thiazine-6-carboxamide; N-[((3S)-1-{2-[6-(methyloxy)-1,5-naphthyridin-4-yl]ethyl}-3-pyrrolidinyl)methyl]-3-oxo-3,4-dihydro-2H-pyrido[3,2-b][1,4]thiazine-6-carboxamide; N-[((3S,4S)-1-{2-[3-fluoro-6-(methyloxy)-1,5-naphthyridin-4-yl]ethyl}-4-hydroxy-3-pyrrolidinyl)methyl]-3-oxo-3,4-dihydro-2H-pyrido[3,2-b][1,4]thiazine-6-carboxamide; (±)-N-[((cis-3,4)-1-{2-[3-fluoro-6-(methyloxy)-1,5-naphthyridin-4-yl]ethyl}-4-hydroxy-3-pyrrolidinyl)methyl]-N-methyl-3-oxo-3,4-dihydro-2H-pyrido[3,2-b][1,4]thiazine-6-carboxamide; (±)-N-[(1-{2-[3-fluoro-6-(methyloxy)-1,5-naphthyridin-4-yl]ethyl}-3-pyrrolidinyl)methyl]-N-methyl-3-oxo-3,4-dihydro-2H-pyrido[3,2-b][1,4]thiazine-6-carboxamide; (3S,4S)-4-{[(2,3-dihydro[1,4]dioxino[2,3-c]pyridin-7-ylmethyl)amino]methyl}-1-{2-[6-(methyloxy)-1,5-naphthyridin-4-yl]ethyl}-3-pyrrolidinol; 6-({[((3S,4S)-1-{2-[8-fluoro-6-(methyloxy)-4-quinolinyl]ethyl}-4-hydroxy-3-pyrrolidinyl)methyl]amino}methyl)-2H-pyrido[3,2-b][1,4]thiazin-3(4H)-one; 6-({[((3S,4S)-1-{2-[8-fluoro-6-(methyloxy)-4-quinolinyl]ethyl}-4-hydroxy-3-pyrrolidinyl)methyl]amino}methyl)-2H-pyrido[3,2-b][1,4]oxazin-3(4H)-one; 6-({[((3S,4S)-1-{2-[6-fluoro-5-(methyloxy)-4-quinolinyl]ethyl}-4-hydroxy-3-pyrrolidinyl)methyl]amino}methyl)-2H-pyrido[3,2-b][1,4]oxazin-3(4H)-one; 6-({[((3S,4S)-1-{2-[6-fluoro-5-(methyloxy)-4-quinolinyl]ethyl}-4-hydroxy-3-pyrrolidinyl)methyl]amino}methyl)-2H-pyrido[3,2-b][1,4]thiazin-3(4H)-one; 6-({[((3S,4S)-1-{2-[3,8-difluoro-6-(methyloxy)-4-quinolinyl]ethyl}-4-hydroxy-3-pyrrolidinyl)methyl]amino}methyl)-2H-pyrido[3,2-b][1,4]oxazin-3(4H)-one; 6-({[((3S,4S)-1-{2-[3,8-difluoro-6-(methyloxy)-4-quinolinyl]ethyl}-4-hydroxy-3-pyrrolidinyl)methyl]amino}methyl)-2H-pyrido[3,2-b][1,4]thiazin-3(4H)-one; 6-{[({(3S,4S)-1-[2-(9-chloro-2,3-dihydro[1,4]dioxino[2,3-f]quinolin-10-yl)ethyl]-4-hydroxy-3-pyrrolidinyl}methyl)amino]methyl}-2H-pyrido[3,2-b][1,4]thiazin-3(4H)-one; 6-{[({(3S,4S)-1-[2-(9-chloro-2,3-dihydro[1,4]dioxino[2,3-f]quinolin-10-yl)ethyl]-4-hydroxy-3-pyrrolidinyl}methyl)amino]methyl}-2H-pyrido[3,2-b][1,4]oxazin-3(4H)-one; 6-{[({(3S,4S)-1-[2-(2,3-dihydro[1,4]dioxino[2,3-f]quinolin-10-yl)ethyl]-4-hydroxy-3-pyrrolidinyl}methyl)amino]methyl}-2H-pyrido[3,2-b][1,4]oxazin-3(4H)-one; 6-({[((3S,4S)-4-hydroxy-1-{2-[6-(methyloxy)-1,5-naphthyridin-4-yl]ethyl}-3-pyrrolidinyl)methyl]amino}methyl)-2H-pyrido[3,2-b][1,4]oxazin-3(4H)-one; (3S,4S)-1-{2-[6-(methyloxy)-1,5-naphthyridin-4-yl]ethyl}-4-{[([1,3]oxathiolo[5,4-c]pyridin-6-ylmethyl)amino]methyl}-3-pyrrolidinol; 7-chloro-6-({[((3S,4S)-4-hydroxy-1-{2-[6-(methyloxy)-1,5-naphthyridin-4-yl]ethyl}-3-pyrrolidinyl)methyl]amino}methyl)-2H-pyrido[3,2-b][1,4]oxazin-3(4H)-one; (3S,4S)-4-({[(7-fluoro-2,3-dihydro-1,4-benzodioxin-6-yl)methyl]amino}methyl)-1-{2-[6-(methyloxy)-1,5-naphthyridin-4-yl]ethyl}-3-pyrrolidinol; (3S,4S)-4-({[(7-fluoro-2,3-dihydro-1,4-benzodioxin-6-yl)methyl]amino}methyl)-1-{2-[3-fluoro-6-(methyloxy)-1,5-naphthyridin-4-yl]ethyl}-3-pyrrolidinol; 7-fluoro-6-({[((3S,4S)-4-hydroxy-1-{2-[6-(methyloxy)-1,5-naphthyridin-4-yl]ethyl}-3-pyrrolidinyl)methyl]amino}methyl)-2H-1,4-benzothiazin-3(4H)-one; 6-({[((3S,4S)-4-hydroxy-1-{2-[6-(methyloxy)-4-quinolinyl]ethyl}-3-pyrrolidinyl)methyl]amino}methyl)-2H-pyrido [3,2-b][1,4]thiazin-3(4H)-one; 6-({[((3S,4S)-4-hydroxy-1-{2-[6-(methyloxy)-4-quinolinyl]ethyl}-3-pyrrolidinyl) methyl]amino}methyl)-2H-pyrido[3,2-b][1,4]oxazin-3 (4H)-one; (3S,4S)-4-{[(2,3-dihydro[1,4]dioxino[2,3-c] pyridin-7-ylmethyl)amino]methyl}-1-{2-[6-(methyloxy)-4-quinolinyl]ethyl}-3-pyrrolidinol; N-[((3R,4S)-1-{2-[3-fluoro-6-(methyloxy)-1,5-naphthyridin-4-yl]ethyl}-4-hydroxy-3-pyrrolidinyl)methyl]-3-oxo-3,4-dihydro-2H-1,4-benzothiazine-6-sulfonamide; N-[((3S,4S)-1-{2-[3-fluoro-6-(methyloxy)-1,5-naphthyridin-4-yl]ethyl}-4-hydroxy-3-pyrrolidinyl)methyl]-3-oxo-3,4-dihydro-2H-pyrido[3,2-b] [1,4]oxazine-6-carboxamide; (±)-6-[({[(3R,4S)/(3S,4R)-1-{2-[3-fluoro-6-(methyloxy)-1,5-naphthyridin-4-yl]ethyl}-4-(hydroxymethyl)-3-pyrrolidinyl]methyl}amino)methyl]-2H-pyrido[3,2-b][1,4]thiazin-3(4H)-one; (±)-6-[({[(3R,4S)/ (3S,4R)-1-{2-[3-fluoro-6-(methyloxy)-1,5-naphthyridin-4-yl]ethyl}-4-(hydroxymethyl)-3-pyrrolidinyl]methyl}amino) methyl]-2H-pyrido[3,2-b][1,4]thiazin-3(4H)-one; 6-[({[(3R, 4S)-1-{2-[3-fluoro-6-(methyloxy)-1,5-naphthyridin-4-yl] ethyl}-4-(hydroxymethyl)-3-pyrrolidinyl]methyl}amino) methyl]-2H-pyrido[3,2-b][1,4]thiazin-3(4H)-one; (±)-6-[({[(3S,4R)/(3S,4R)-1-{2-[3-fluoro-6-(methyloxy)-1,5-naphthyridin-4-yl]ethyl}-4-(hydroxymethyl)-3-pyrrolidi-nyl]methyl}amino)methyl]-2H-pyrido[3,2-b][1,4]thiazin-3 (4H)-one; (±)-((3R,4S)/(3S,4R)-4-{[(2,3-dihydro[1,4] dioxino[2,3-c]pyridin-7-ylmethyl)amino]methyl}-1-{2-[3-fluoro-6-(methyloxy)-1,5-naphthyridin-4-yl]ethyl}-3-pyrrolidinyl)methanol; 6-[({[(3R,4Z)-1-{2-[3-fluoro-6-(methyloxy)-1,5-naphthyridin-4-yl]ethyl}-4-(hydroxyimino)-3-pyrrolidinyl]methyl}amino)methyl]-2H-pyrido[3,2-b][1,4]thiazin-3(4H)-one; 6-[({[(3R,4Z)-1-{2-[3-fluoro-6-(methyloxy)-1,5-naphthyridin-4-yl]ethyl}-4-(hydroxyimino)-3-pyrrolidinyl]methyl}amino)methyl]-2H-pyrido[3,2-b][1,4]oxazin-3(4H)-one; (3S,4R)-4-{[(2,3-dihydro[1,4]dioxino[2,3-c]pyridin-7-ylmethyl)amino] methyl}-1-{2-[3-fluoro-6-(methyloxy)-1,5-naphthyridin-4-yl]ethyl}-3-pyrrolidinone oxime; (±)-(3S,4S)/(3R,4R)-1-{2-[3-fluoro-6-(methyloxy)-1,5-naphthyridin-4-yl]ethyl}-4-({[(3-oxo-3,4-dihydro-2H-pyrido[3,2-b][1,4]thiazin-6-yl) methyl]amino}methyl)-3-pyrrolidinecarboxamide; (±)-(3S, 4S)/(3R,4R)-1-{2-[3-fluoro-6-(methyloxy)-1,5-naphthyridin-4-yl]ethyl}-4-({[(3-oxo-3,4-dihydro-2H-pyrido[3,2-b] [1,4]oxazin-6-yl)methyl]amino}methyl)-3-pyrrolidinecarboxamide; (±)-(3S,4S)/(3R,4R)-4-{[(2,3-dihydro[1,4]dioxino[2,3-c]pyridin-7-ylmethyl)amino] methyl}-1-{2-[3-fluoro-6-(methyloxy)-1,5-naphthyridin-4-yl]ethyl}-3-pyrrolidinecarboxamide; 4-{2-[(3S,4S)-3-hydroxy-4-({[(3-oxo-3,4-dihydro-2H-pyrido[3,2-b][1,4] thiazin-6-yl)methyl]amino}methyl)-1-pyrrolidinyl]ethyl}-6-(methyloxy)-1,5-naphthyridine-3-carbonitrile; 4-{2-[(3S, 4S)-3-hydroxy-4-({[(3-oxo-3,4-dihydro-2H-pyrido[3,2-b] [1,4]oxazin-6-yl)methyl]amino}methyl)-1-pyrrolidinyl] ethyl}-6-(methyloxy)-1,5-naphthyridine-3-carbonitrile; 4-[2-((3S,4S)-3-{[(2,3-dihydro[1,4]dioxino[2,3-c]pyridin-7-ylmethyl)amino]methyl}-4-hydroxy-1-pyrrolidinyl) ethyl]-6-(methyloxy)-1,5-naphthyridine-3-carbonitrile; (±)-6-{[((3S,4R)/(3R,4S)-4-hydroxy-1-{2-[6-(methyloxy)-1,5-naphthyridin-4-yl]ethyl}-3-pyrrolidinyl)amino]methyl}-2H-pyrido[3,2-b][1,4]thiazin-3(4H)-one; (±)-6-{[((3S,4R)/ (3R,4S)-1-{2-[3-fluoro-6-(methyloxy)-1,5-naphthyridin-4-yl]ethyl}-4-hydroxy-3-pyrrolidinyl)amino]methyl}-2H-pyrido[3,2-b][1,4]thiazin-3(4H)-one; or a pharmaceutically acceptable salt or solvate thereof.

In certain aspects, this invention describes a process for preparing an intermediate useful in the synthesis of a compound of formula (I), a compound of formula (I), or a pharmaceutically acceptable salt, solvate or derivative of a compound of formula (I), which process comprises:

(1) reacting a compound of formula (a) with a compound of formula (b) to form a compound of formula (c):

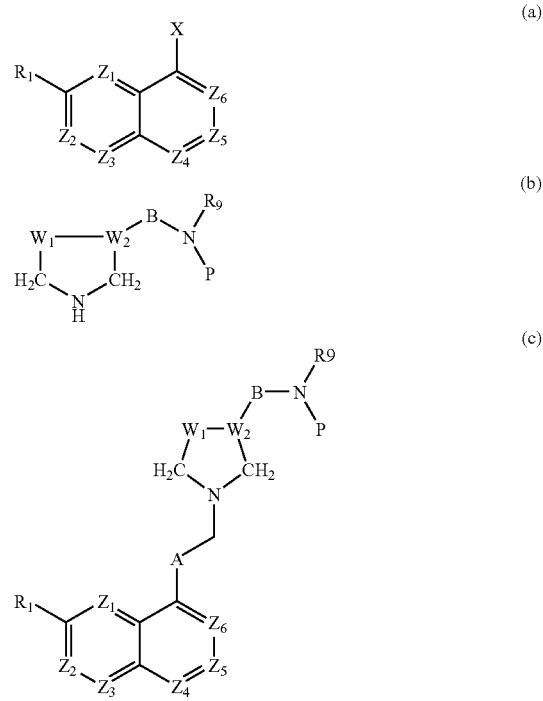

wherein:

$Z_1$, $Z_2$, $Z_3$, $Z_4$, $Z_5$, $Z_6$, $R_1$, $W_1$, $W_2$, A, B and $R_9$ are as defined in formula (I);

X is oxirane, $CH=CH_2$, or $CH_2CH_2-L$;

L is a leaving group;

P is hydrogen, a suitable protecting group or $R_{10}$; and when P is $R_{10}$;

(2) optionally forming a pharmaceutically acceptable salt, solvate or derivative thereof.

In some embodiments of the processes of this invention, $R_4$ of $W_1$ is OH and $R_5$ is H.

In some aspects, this invention describes a process for preparing intermediates useful in the preparation of compounds of formula (I), and compounds of formula (I) wherein $R_4$ of $W_1$ is OH and $R_5$ is H comprising the:

(1) reaction of a compound of formula (d) with a compound of formula (e) to form a compound of formula (f); and (2) cleavage of the N—O bond with:

(a) retention of P; or (b) cleavage of P and subsequent reintroduction of P; and (3) removal of $P_1$ to form the compound of formula (a)

-continued

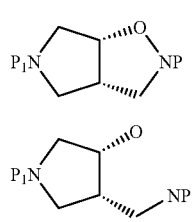
(f)

(g)

wherein P is at each occurrence an independently selected protecting group.

In other aspects of this invention, a process is described for preparing a compound of formula (I), or a pharmaceutically acceptable salt, solvate or derivative thereof, which process comprises:

(1) reacting a compound of formula (c), wherein P is hydrogen, with a compound of formula (h):

$$L_1-U-R_{11} \quad (h)$$

wherein:
U and $R_{11}$ are as previously defined;
$L_1$ is a leaving group; or
reacting a compound of formula (c), wherein P is hydrogen, with a compound of formula ($h_a$):

$$CHO-R_{11} \quad (h_a)$$

and reducing the resulting imine; and (2) optionally forming a pharmaceutically acceptable salt, solvate or derivative thereof.

In some embodiments of the immediately preceding process, $R_4$ of $W_1$ is OH and $R_5$ is H.

In some aspects, this invention describes a process for preparing a compound of formula (I) or a useful intermediate in the preparation of a compound of formula (I), said process comprising:

(1) reacting a compound of formula (i) with CN or $CH_3NO_2$ to yield a compound of formula (j):

(i)

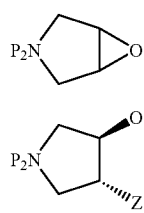
(j)

wherein:
$P_2$ is a protecting group;
Z is CN or $CH_2NO_2$; and (2) reducing Z to $CH_2NH_2$ to form a compound of formula (k); and (3) converting $CH_2NH_2$ to $CH_2NHP_3$ or $CH_2NHR_{10}$, to form a compound of formula (I); and (4) removing protecting group $P_2$ to generate a compound of formula (m); and (5) reacting said compound of formula (m) with a compound of formula (a) to generate a compound of formula (n)

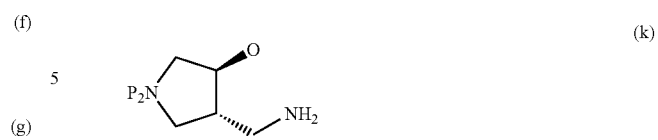
(k)

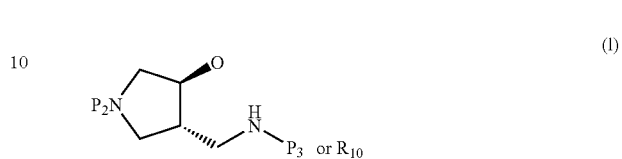
(l)

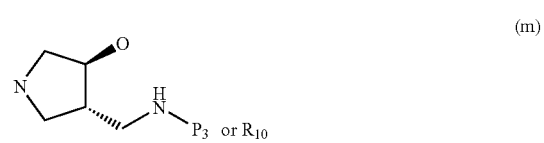
(m)

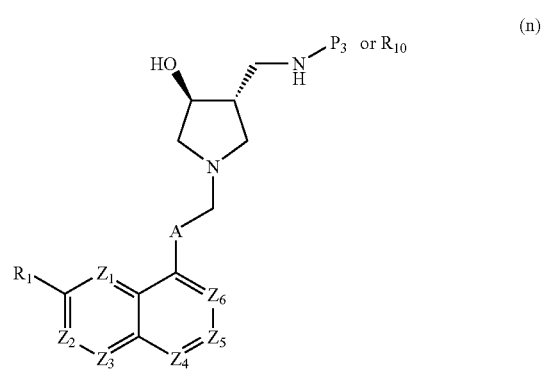
(n)

In another embodiment of this invention the compound of formula (j), (k), (l), (m) or (n) is reacted with a trialkyl- or triarylphosphine and a dialkyldiazodicarboxylate in the presence of an organic acid optionally followed by cleavage of the resultant ester to form the corresponding 3,4-(cis)-substituted compounds of formula (o), (p), (q), (r) or (s):

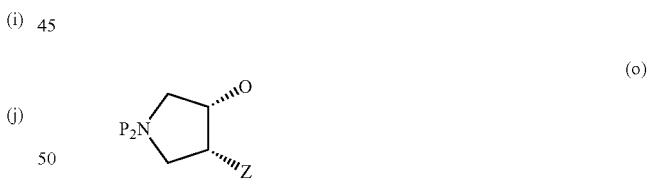
(o)

(p)

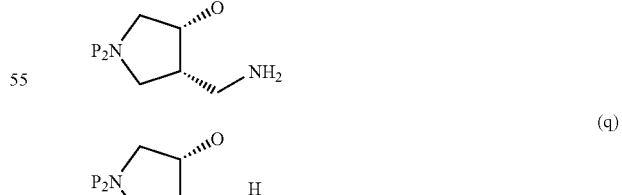
(q)

(r)

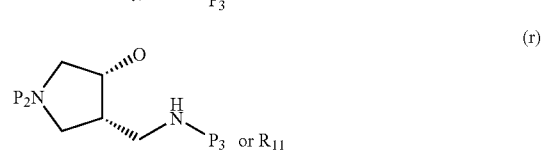

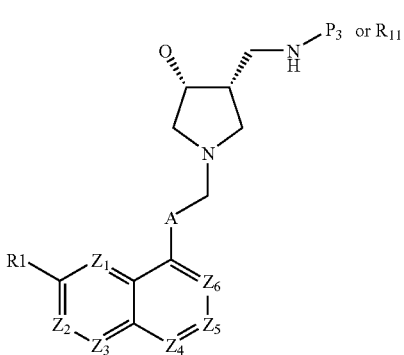

or wherein a compound of formula (j), (l), (m) or (n) is:

(1) reacted with an alkyl- or haloalkyl sulfonylhalide or an arylsulfonyl halide (said aryl group optionally substituted with from 1-3 substituents selected from halogen, CN, $NO_2$, $CF_3$, and $(C_{1-6})$alkyl); and (2) reacted with $MOP_4$ to form the compound of structural formula (t), (u), (v), or (w)

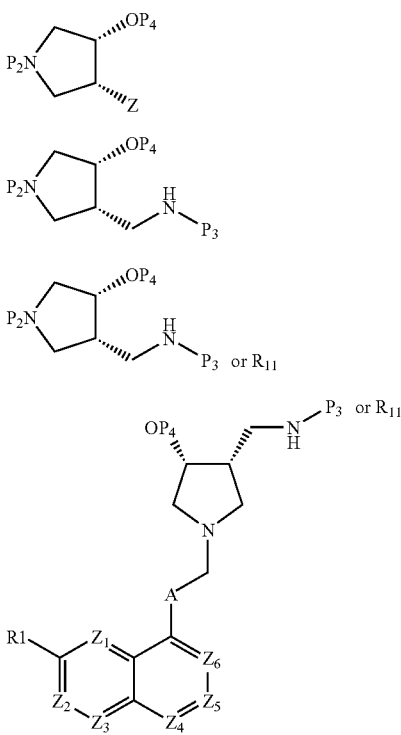

wherein M is a metal;

$P_4$ is hydrogen, $(C_{1-6})$alkyl, benzyl (wherein the phenyl group of said benzyl is optionally substituted with from 1-3 substitutents independently selected from halogen, $(C_{1-6})$ alkyl, $NO_2$, CN and $CF_3$); and (3) optionally treated under conditions suitable for removal of $P_4$; and (4) optionally forming a pharmaceutically acceptable salt, solvate or derivative thereof.

In some embodiments, this invention describes a composition comprising a compound of formula I or any of its described embodiments or aspects and a pharmaceutically acceptable excipient.

In yet other embodiments, this invention describes a method of treating bacterial infections in mammals which comprises administering to a mammal in need thereof an effective amount of a compound according to formula I.

It is to be appreciated that this invention includes all possible combinations of the described embodiments. Furthermore, this invention is not to be limited to any of the illustrated examples or any particular embodiments or aspects of the invention as described herein.

Unless otherwise defined, the term "alkyl" when used alone or when forming part of other groups (such as the 'alkoxy' group) includes substituted or unsubstituted, straight or branched chain alkyl groups containing the specified range of carbon atoms. For example, the term "$(C_{1-6})$alkyl" include methyl, ethyl, propyl, butyl, iso-propyle, sec-butyl, tert-butyl, iso-pentyl, and the like.

The term "alkenyl" means a substituted or unsubstituted alkyl group of the specified range of carbon atoms, wherein one carbon-carbon single bond is replaced by a carbon-carbon double bond. For example, the term "$(C_{2-6})$alkenyl" include ethylene, 1-propene, 2-propene, 1-butene, 2-butene, and isobutene, and the like. Both cis and trans isomers are included.

The term "cycloalkyl" refers to substituted or unsubstituted carbocyclic system of the specified range of carbon atoms, which may contain up to two unsaturated carbon-carbon bonds. For example, the term "$(C_{3-7})$cycloalkyl" include cyclopropyl, cyclobutyl, cyclopentyl, cyclopentenyl, cyclohexyl, cyclohexenyl, and cycloheptyl.

The term "alkoxy" refers to an O-alkyl radical where the alkyl group contains the specified range of carbon atoms and is as defined herein.

The term "acyl" refers to a C(=O)alkyl or a C(=O)aryl radical. In some embodiments, the alkyl group contains 13 or less carbons; in some embodiments 10 or less carbon atoms; in some embodiments 6 or less carbon atoms; and is as otherwise defined. Aryl is as defined herein.

The term "alkylsulphonyl" refers to a $SO_2$alkyl radical wherein the alkyl group contains the specified range of carbon atoms and is as defined herein.

The term "alkylthio" refers to a Salkyl the alkyl group contains the specified range of Salkyl atoms and is as defined herein.

The term "heterocyclylthio" refers to a S-heterocyclyl radical wherein the heterocyclyl moiety is as defined herein.

The term "heterocyclyloxy" refers to an O-heterocyclyl radical wherein heterocyclyl is as defined herein.

The term "arylthio" refers to an S-aryl radical wherein aryl is as defined herein.

The term "aryloxy" refers to an O-aryl radical wherein aryl is as defined herein.

The term "acylthio" refers to a S-acyl radical wherein acyl is as defined herein.

The term "acyloxy" refers to an O-acyl radical wherein acyl is as defined herein.

The term "alkoxycarbonyl" refers to a $CO_2$alkyl radical wherein the alkyl group contains the specified range of carbon atoms and is as defined herein.

The term "alkylsulphonyloxy" refers to an O—$SO_2$alkyl radical wherein the alkyl group contains the specified range of carbon atoms and is as defined herein.

The term "arylsulphonyl" refers to a $SO_2$aryl radical wherein aryl is as herein defined.

The term "arylsulphoxide" refers to a SOaryl radical wherein aryl is as defined herein.

Unless otherwise defined, suitable substituents for any alkyl, alkoxy, alkenyl, and cycloalkyl groups includes up to three substituents selected from the group consisting of hydroxy, halogen, nitro, cyano, carboxy, amino, amidino, sulphonamido, unsubstituted $(C_{1-3})$alkoxy, trifluoromethyl, and acyloxy.

Halo or halogen includes fluoro, chloro, bromo and iodo.

The term "haloalkyl" refers to an alkyl radical containing the specified range of carbon atoms and is as otherwise defined herein, which is further substituted with 1-3 halogen atoms.

The term "haloalkoxy" refers to an alkoxy radical of the specified range and as defined herein, which is further substituted with 1-3 halogen atoms.

The term "hydroxyalkyl" refers to an alkyl group as defined herein, further substituted with a hydroxy group.

Unless otherwise defined, the term "heterocyclic" as used herein includes optionally substituted aromatic and non-aromatic, single and fused, mono- or bicyclic rings suitably containing up to four hetero-atoms in each ring selected from oxygen, nitrogen and sulphur, which rings may be unsubstituted or C-substituted by, for example, up to three groups selected from $(C_{1-4})$alkylthio; halo; $(C_{1-4})$haloalkoxy; $(C_{1-4})$haloalkyl; $(C_{1-4})$alkyl; $(C_{2-4})$alkenyl; hydroxy; hydroxy, $(C_{1-4})$alkyl; $(C_{1-4})$thioalkyl; $(C_{1-4})$alkoxy; nitro; cyano, carboxy; $(C_{1-4})$alkylsulphonyl; $(C_{2-4})$alkenylsulphonyl; or aminosulphonyl wherein the amino group is optionally substituted by $(C_{1-4})$alkyl or $(C_{2-4})$alkenyl.

Each heterocyclic ring suitably has from 3 to 7, preferably 5 or 6, ring atoms. A fused heterocyclic ring system may include carbocyclic rings and need include only one heterocyclic ring.

Compounds within the invention containing a heterocyclyl group may occur in two or more tautometric forms depending on the nature of the heterocyclyl group; all such tautomeric forms are included within the scope of the invention.

Where an amino group forms part of a single or fused non-aromatic heterocyclic ring as defined above suitable optional substituents in such substituted amino groups include hydrogen; trifluoromethyl; $(C_{1-4})$alkyl optionally substituted by hydroxy, $(C_{1-4})$alkoxy, $(C_{1-4})$alkylthio, halo or trifluoromethyl; and $(C_{2-4})$alkenyl.

When used herein the term "aryl", includes optionally substituted phenyl and naphthyl.

Aryl groups may be optionally substituted with up to five, preferably up to three, groups selected from $(C_{1-4})$alkylthio; halo; $(C_{1-4})$haloalkoxy; $(C_{1-4})$haloalkyl; $(C_{1-4})$alkyl; $(C_{2-4})$alkenyl; hydroxy; $(C_{1-4})$hydroxyalkyl; $(C_{1-4})$alkylthio; $(C_{1-4})$alkoxy; nitro; cyano; carboxy; amino or aminocarbonyl optionally substituted by $(C_{1-4})$alkyl; $(C_{1-4})$alkylsulphonyl; $(C_{2-4})$alkenylsulphonyl.

Some of the compounds of this invention may be crystallised or recrystallised from solvents such as aqueous and organic solvents. In such cases solvates may be formed. This invention includes within its scope stoichiometric solvates including hydrates as well as compounds containing variable amounts of water that may be produced by processes such as lyophilisation.

Furthermore, it will be understood that phrases such as "a compound of Formula I or a pharmaceutically acceptable salt, solvate or derivative thereof" are intended to encompass the compound of Formula I, a derivative of formula (I), a pharmaceutically acceptable salt of the compound of formula (I), a solvate of formula (I), or any pharmaceutically acceptable combination of these. Thus by way of non-limiting example used here for illustrative purpose, "a compound of Formula I or a pharmaceutically acceptable salt, solvate or derivative thereof" may include a pharmaceutically acceptable salt of a compound of formula (I) that is further present as a solvate.

Since the compounds of formula (I) are intended for use in pharmaceutical compositions it will readily be understood that they are each provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the formula (I) or pharmaceutically acceptable derivative thereof.

Pharmaceutically acceptable salts of the above-mentioned compounds of formula (I) include the free base form or their acid addition or quaternary ammonium salts, for example their salts with mineral acids e.g. hydrochloric, hydrobromic, sulphuric nitric or phosphoric acids, or organic acids, e.g. acetic, fumaric, succinic, maleic, citric, benzoic, p-toluenesulphonic, methanesulphonic, naphthalenesulphonic acid or tartaric acids. Compounds of formula (I) may also be prepared as the N-oxide. Compounds of formula (I) having a free carboxy group may also be prepared as an in vivo hydrolysable ester. The invention extends to all such derivatives. One of skill in the art will recognize that where compounds of the invention contain multiple basic sites, a compound of the invention maybe present as a salt complexed with more than one equivalent of a corresponding acid or mixture of acids.

Pharmaceutically acceptable derivatives refers to compounds of formula (I) that have been covalently modified with a group that undergoes at least some in vivo cleavage to a compound of formula (I).

Examples of suitable pharmaceutically acceptable in vivo hydrolysable ester-forming groups include those forming esters which break down readily in the human body to leave the parent acid or its salt.

Suitable groups of this type include those of part formulae (i), (ii), (iii), (iv) and (v):

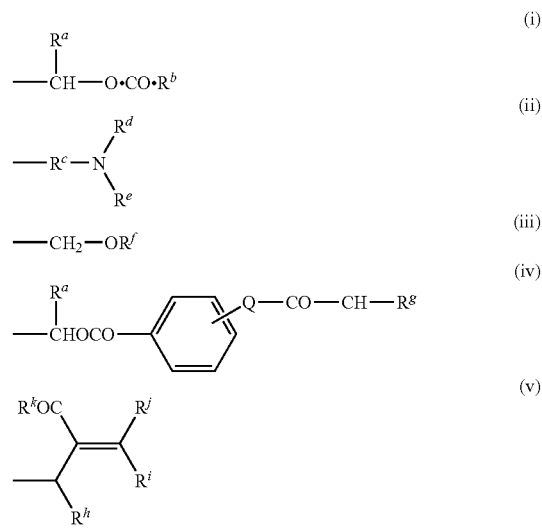

wherein $R^a$ is hydrogen, $(C_{1-6})$ alkyl, $(C_{3-7})$ cycloalkyl, methyl, or phenyl, $R^b$ is $(C_{1-6})$alkyl, $(C_{1-6})$alkoxy, phenyl, benzyl, $(C_{3-7})$cycloalkyl, $(C_{3-7})$cycloalkyloxy, $(C_{1-6})$alkyl $(C_{3-7})$cycloalkyl, 1-amino$(C_{1-6})$alkyl, or 1-$(C_{1-6}$alkyl)amino$(C_{1-6})$alkyl; or $R^a$ and $R^b$ together form a 1,2-phenylene group optionally substituted by one or two methoxy groups; $R^c$ represents $(C_{1-6})$alkylene optionally substituted with a methyl or ethyl group and $R^d$ and $R^e$ independently represent $(C_{1-6})$alkyl; $R^f$ represents $(C_{1-6})$alkyl; $R^g$ represents hydrogen or phenyl optionally substituted by up to three groups selected from halogen, $(C_{1-6})$alkyl, or $(C_{1-6})$ alkoxy; Q is oxygen or NH; $R^h$ is hydrogen or $(C_{1-6})$alkyl; $R^i$ is hydrogen, $(C_{1-6})$alkyl optionally substituted by halogen, $(C_{2-6})$ alkenyl, $(C_{1-6})$alkoxycarbonyl, aryl or heteroaryl; or $R^h$ and $R^i$ together form $(C_{1-6})$alkylene; $R^j$ represents hydrogen, $(C_{1-6})$alkyl or $(C_{1-6})$alkoxycarbonyl; and $R^k$ represents $(C_{1-6})$alkyl, $(C_{1-8})$alkoxy, $(C_{1-6})$alkoxy $(C_{1-6})$alkoxy or aryl.

Examples of suitable in vivo hydrolysable ester groups include, for example, acyloxy$(C_{1-6})$alkyl groups such as acetoxymethyl, pivaloyloxymethyl, acetoxyethyl, pivaloyloxyethyl, 1-(cyclohexylcarbonyloxy)prop-1-yl, and (1-aminoethyl)carbonyloxymethyl; $(C_{1-6})$alkoxycarbonyloxy$(C_{1-6})$ alkyl groups, such as ethoxycarbonyloxymethyl, ethoxycarbonyloxyethyl and propoxycarbonyloxyethyl; di$(C_{1-6})$alkylamino$(C_{1-6})$alkyl especially di$(C_{1-4})$alkylamino $(C_{1-4})$alkyl groups such as dimethylaminomethyl, dimethylaminoethyl, diethylaminomethyl or diethylaminoethyl; 2-$(C_{1-6})$alkoxycarbonyl)-2-$(C_{2-6})$alkenyl groups such as 2-(isobutoxycarbonyl)pent-2-enyl and 2-(ethoxycarbonyl) but-2-enyl; lactone groups such as phthalidyl and dimethoxyphthalidyl.

A further suitable pharmaceutically acceptable in vivo hydrolysable ester-forming group is that of the formula:

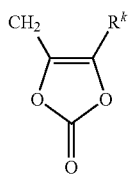

wherein $R^k$ is hydrogen, $C_{1-6}$ alkyl or phenyl.

R is preferably hydrogen.

Compounds of formula (I) may also be prepared as the corresponding N-oxides.

Certain of the compounds of formula (I) may exist in the form of optical isomers, e.g. diastereoisomers and mixtures of isomers in all ratios, e.g. racemic mixtures. The invention includes all such form, including pure isomeric forms. The different isomeric forms may be separated or resolved one from the other by conventional methods, or any given isomer may be obtained by conventional synthetic methods or by stereospecific or asymmetric syntheses.

For purposes of the processes of this invention, one of skill in the art will recognize that use of the term CN as a reagent in a reaction refers to any method of delivering a CN group. The particular CN containing reagent will, of course, depend upon the particular reaction contemplated. For example, in some embodiments of this invention, the CN maybe bonded to a triaklyl silane such as TMS-CN, and the like. In other variations, HCN itself could be used. In other embodiments, the CN maybe delivered as an inorganic salt, such as NaCN, KCN, etc. In such case, it is sometimes preferred to use a phase transfer reagent to increase the solubilty of the CN ion in an organic solvent. In such cases, for example, a quaternary ammonium salt wherein the CN functions as a counterion maybe utilized.

For purposes of the processes of this invention, one of skill in the art will recognize that the use of the reagent $CH_3NO_2$, as for example, a nucleophile, may require the coadministration of a base in order to at least partially deprotonate the $CH_3NO_2$ in order to increase its nucleophilicity. Alternatively, the reagent maybe deprotonated prior to the reaction where the reagent is introduced as a metal salt.

One of skill in the readily appreciates that optimization for a given reaction may require some routine variation in reaction parameters such as reaction time, temperature, energy source, pressure, light, pressure, solvent or solvents used, co-reagents, catalysts, and the like.

Protective groups wherever found herein maybe designated by their specific formula or alternatively, maybe referred to generically by P or $P_n$ (wherein n is an integer). It is to be appreciated that where generic descriptors are used, that such descriptors are at each occurrence independent from each other. Thus, a compound with more than one of the same generic descriptors (e.g. P) does not indicate that each P is the same protective group, they maybe the same or different, so long as the group is suitable to the chemistry being employed. Where protection or deprotection is generically referred to, one of ordinary skill in the art will understand this to mean that suitable conditions are employed that will allow for the removal of the protecting group to be removed while minimizing reaction at other positions of the molecule, unless otherwise indicated. May protective groups and protective group strategies are known to those of skill in the art in maybe found in numerous references including, Greene, et al. "Protective Groups in Organic Synthesis" (Published by Wiley-Interscience), which is herein incorporated by reference in its entirety.

Leaving groups wherever found herein maybe designated by a specific chemical formula, or alternatively, maybe generically referred to as L or Ln (wherein n is an integer). It is to be appreciated that where a generic descriptor is used, that such descriptors are at each occurrence independent from each other. Leaving groups can be single atoms such as Cl, Br, or I, or maybe a group such as $OSO_2CH_3$, $OC(=O)CH_3$, $O(C=O)CF_3$, $OSO_2CF_3$, and the like. One skilled in the art will readily ascertained that leaving groups generally refer to atoms or groups which can be eliminated, substituted or otherwise dissociate during the course of the reaction.

The antibacterial compounds according to the invention may be formulated for administration in any convenient way for use in human or veterinary medicine, by analogy with other antibacterials.

The pharmaceutical compositions of the invention include those in a form adapted for oral, topical or parenteral use and may be used for the treatment of bacterial infection in mammals including humans.

The composition may be formulated for administration by any route. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10-60% by weight, of the active material, depending on the method of administration. Where the compositions comprise dosage units, each unit will preferably contain from 50-500 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 20 mg/kg per day.

No toxicological effects are indicated when a compound of formula (I) or a pharmaceutically acceptable derivative thereof is administered in the above-mentioned dosage range.

The compound of formula (I) may be the sole therapeutic agent in the compositions of the invention or a combination with other antibacterials. If the other antibacterial is a β-lactam then a β-lactamase inhibitor may also be employed.

Compounds of formula (I) are active against a wide range of organisms including both Gram-negative and Gram-positive organisms.

All publications, including but not limited to patents and patent applications, cited in this specification are herein incorporated by reference (whether specifically stated to be so or not) as if each individual publication were specifically and individually indicated to be incorporated by reference herein as though fully set forth.

The following examples illustrate the preparation of certain compounds of formula (I) and the activity of certain compounds of formula (I) against various bacterial organisms.

The compounds of the present invention were prepared by the methods illustrated in Schemes I through XX.

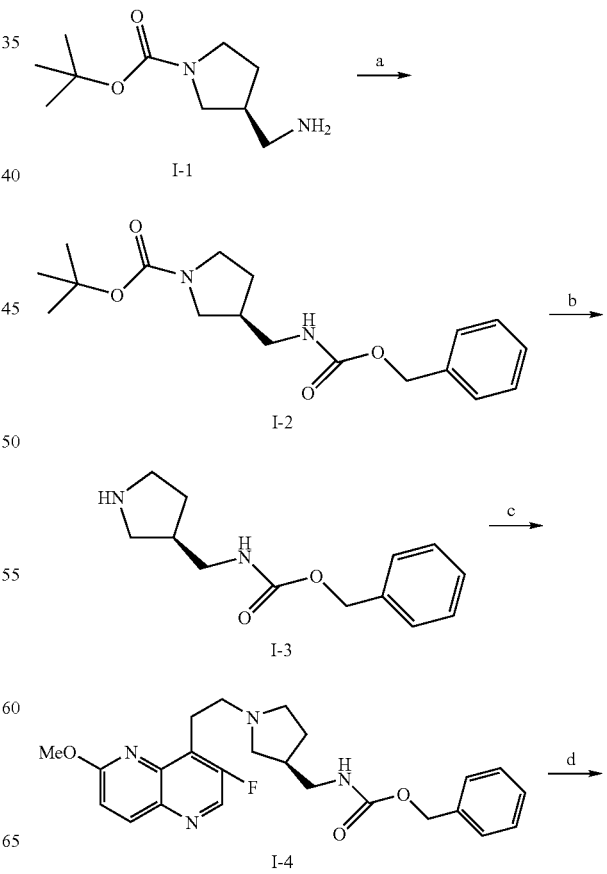

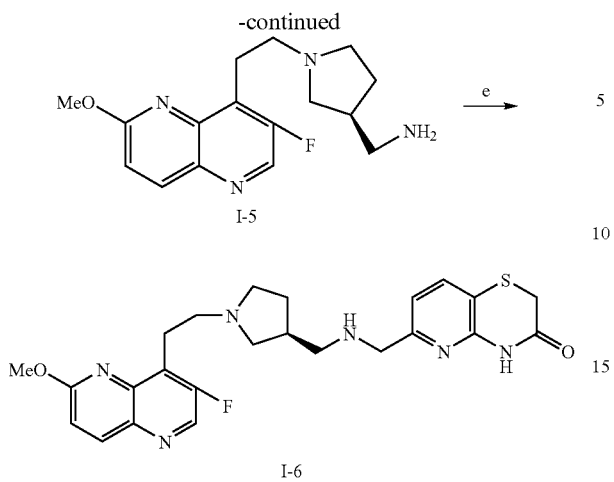

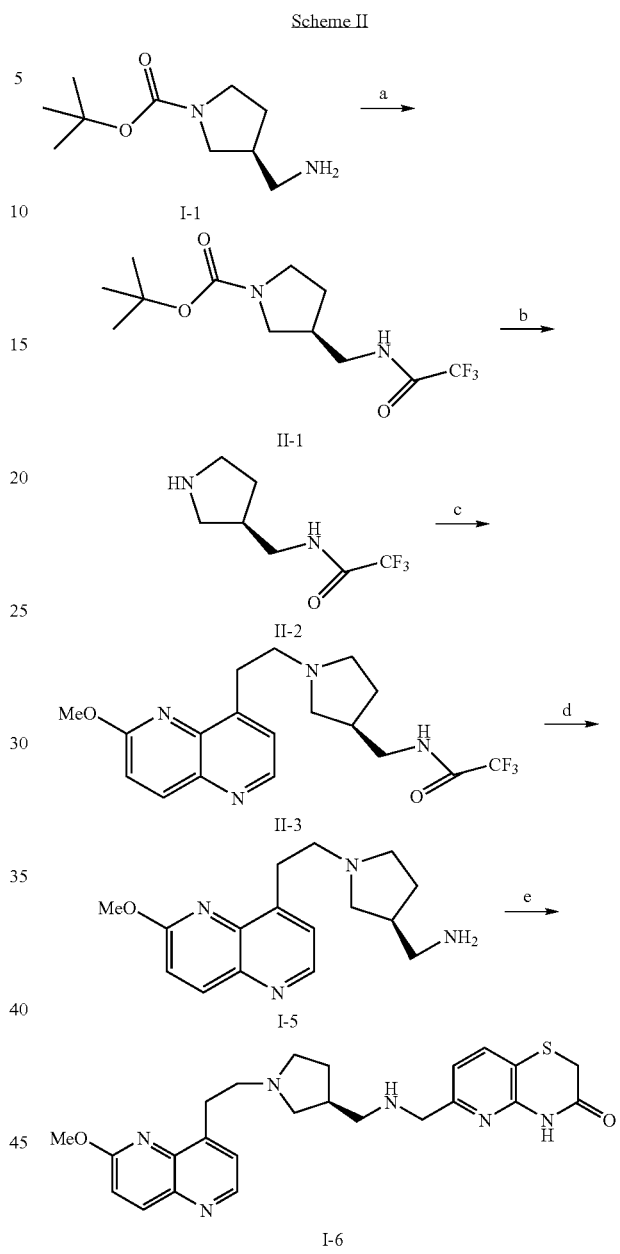

Reagents and conditions: (a) Cbz-succinimide, Et₃N, DMF, RT; (b) TFA, CH₂Cl₂, RT; (c) 8-ethenyl-7-fluoro-2-(methyloxy)-1,5-naphthyridine, EtOH, 80° C.; (d) Pd/C, H₂ (1 atm), MeOH, RT; (e) 3-oxo-3,4-dihydro-2H-pyrido[1,4]thiazine-6-carboxaldehyde, CH₂Cl₂, EtOH; then NaBH(OAc)₃.

Pyrrolidine I-1 was reacted with a suitable electrophile such as Cbz-Cl or Cbz-succinimide to afford carbamate I-2. Selective removal of the Boc group afforded I-3 and was achieved with TFA in methylene chloride. Other acids (HCl, HF, etc.) can be used to remove this protecting group. Amine I-3 was then heated with a vinyl naphthyridine either neat or in a suitable solvent (dioxane, DMF) generating the product I-4. Deprotection of the benzyl carbamate functionality was performed under hydrogenolysis conditions. The use of protecting groups to mask reactive functionality is well-known to those of skill in the art, and other protecting groups are listed in standard reference volumes and maybe used for the preparation of compounds of the present invention wherever appropriate, such as those detailed in Greene, "Protective Groups in Organic Synthesis" (published by Wiley-Interscience) citep previously, herein. The primary amine derivative I-5 is then converted to a secondary amine I-6 by reaction with an aldehyde and a suitable reducing agent. For example, [((3S)-1-{2-[3-fluoro-6-(methyloxy)-1,5-naphthyridin-4-yl]ethyl}-3-pyrrolidinyl)methyl]amine is converted to an imine by reaction with an aldehyde in protic or aprotic solvents such as DMF, CH₂Cl₂, EtOH or CH₃CN. The imine is subsequently or simultaneously reacted with a suitable reducing agent such as NaBH₄, NaBH(OAc)₃ or NaBH₃CN in solvent. Depending on whether acid neutralization is required, an added base, such as triethylamine (Et₃N), diisopropylethylamine ((i-Pr)₂NEt), or K₂CO₃, may be used. Many additional methods for reductive aminations are known and maybe used to help prepare compounds of the present invention wherever appropriate, and can be found in standard reference books, such as "Compendium of Organic Synthetic Methods", Vol. I-VI (published by Wiley-Interscience) which is herein incorporated by reference.

Reagents and conditions: (a) (CF₃CO)₂O, RT; (b) TFA, CH₂Cl₂, RT; (c) 8-ethenyl-2-(methyloxy)-1,5-naphthyridine, DMF, 100° C.; (d) K₂CO₃, H₂O, THF, RT; (e) 3-oxo-3,4-dihydro-2H-pyrido[1,4]thiazine-6-carboxaldehyde, CH₂Cl₂, EtOH; then NaBH₄, EtOH.

Pyrrolidine I-1 was reacted with a suitable electrophile such as trifluoroacetic anhydride or ethyl trifluoroacetate to afford carbamate II-1. Selective removal of the Boc group afforded II-2 and was achieved with TFA in methylene chloride. Other acids (HCl, HF, etc.) can be used to remove this protecting group. Amine II-2 was then heated with a vinyl naphthyrine either neat or in a suitable solvent (dioxane, DMF) generating the product II-3. Deprotection of the ethyl carbamate functionality was performed under basic aqueous conditions. The base used could be (KOH, NaOH, LiOH, K₂CO₃) or another similar base. The primary amine derivative II-4 is then converted to a secondary amine II-5 by reaction with an aldehyde and a suitable reducing agent. For example, 1-((3S)-1-{2-[6-(methyloxy)-1,5-naphthyridin-4-yl]ethyl}-3-pyrrolidinyl)methanamine is converted to an imine by reaction with an aldehyde in protic or aprotic solvents such as DMF, CH₂Cl₂, EtOH or CH₃CN. The imine is subsequently or simultaneously reacted with a suitable reducing agent such as NaBH₄, NaBH(OAc)₃ or NaBH₃CN in solvent. Depending on whether acid neutralization is required, an added base, such as triethylamine (Et₃N), diisopropylethylamine ((i-Pr)₂NEt), or K₂CO₃, may be used.

Scheme III

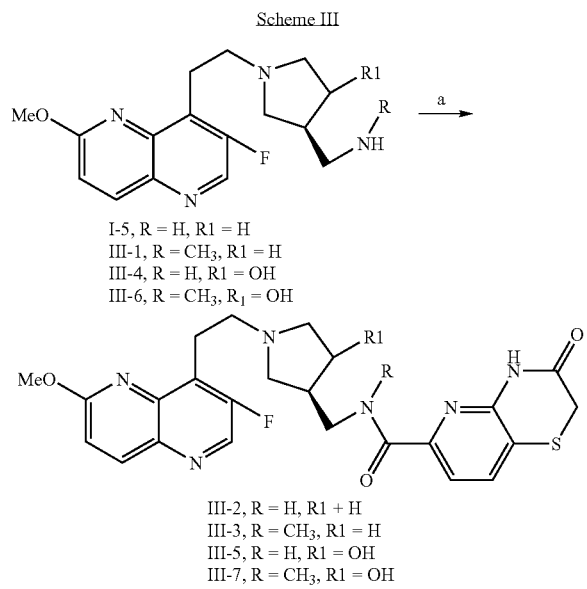

Reagents and conditions: (a) EDC, HOBt, (i-Pr)₂NEt, DMF, 3-oxo-3,4-dihydro-2H-pyrido[3,2-b][1,4]thiazine-6-carboxylic acid.

A suitable carboxylic acid, for instance 3-oxo-3,4-dihydro-2H-pyrido[3,2-b][1,4]thiazine-6-carboxylic acid, is converted to an activated form using, for example, EDC and HOBt, or SOCl₂, and the activated form is subsequently reacted with an appropriate amine, for instance amine I-5, in a suitable solvent such as DMF, CH₂Cl₂, or CH₃CN, to afford III-2. Depending on whether acid neutralization is required, an added base, such as triethylamine (Et₃N), diisopropylethylamine ((i-Pr)₂NEt), or pyridine, may be used. Many additional methods for converting a carboxylic acid to an amide are known, and can be found in standard reference books, such as "Compendium of Organic Synthetic Methods", Vol. I-VI (published by Wiley-Interscience), or Bodansky, "The Practice of Peptide Synthesis" (published by Springer-Verlag) which is herein incorporated by reference.

Scheme IV

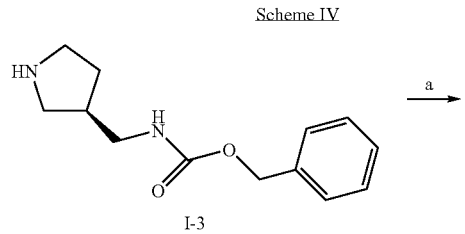

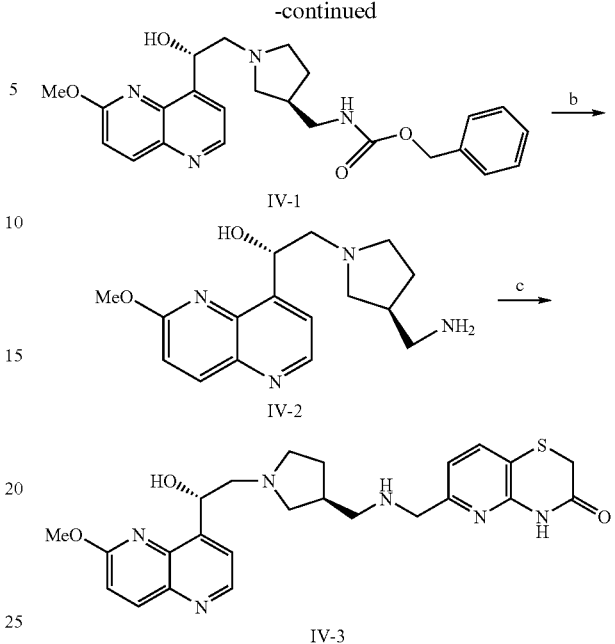

Reagents and conditions: (a) 2-(methyloxy)-8-[(2S)-2-oxiranyl]-1,5-naphthyridine, DMF, 100° C.; (b) Pd/C, H₂ (1 atm), MeOH, RT; (c) 3-oxo-3,4-dihydro-2H-pyrido[1,4]thiazine-6-carboxaldehyde, CH₂Cl₂, EtOH; then NaBH₄, EtOH.

Amine I-3 was reacted with an electrophilic epoxide such as 2-(methyloxy)-8-[(2S)-2-oxiranyl]-1,5-naphthyridine to give alcohol IV-1. Deprotection of IV-1 under hydrogenolysis conditions using Pd in an alcoholic solvent under a H₂ atmosphere provided the primary amine IV-2. The primary amine derivative IV-2 was then converted to an imine by reaction with an aldehyde in protic or aprotic solvents such as DMF, CH₂Cl₂, EtOH or CH₃CN. The imine was subsequently or simultaneously reacted with a suitable reducing agent such as NaBH₄, NaBH(OAc)₃ or NaBH₃CN in solvent to give amine IV-3. Depending on whether acid neutralization is required, an added base, such as triethylamine (Et₃N), diisopropylethylamine ((i-Pr)₂NEt), or K₂CO₃, may be used.

Scheme V

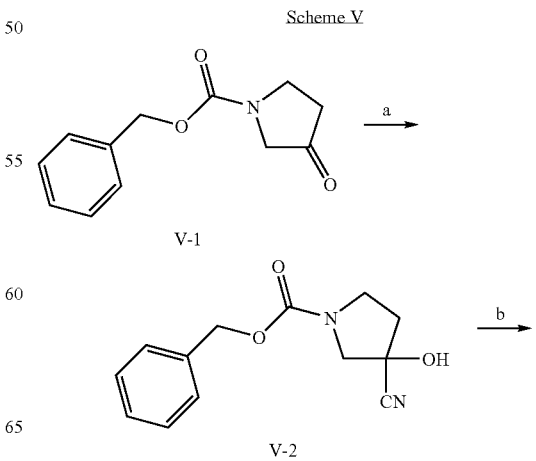

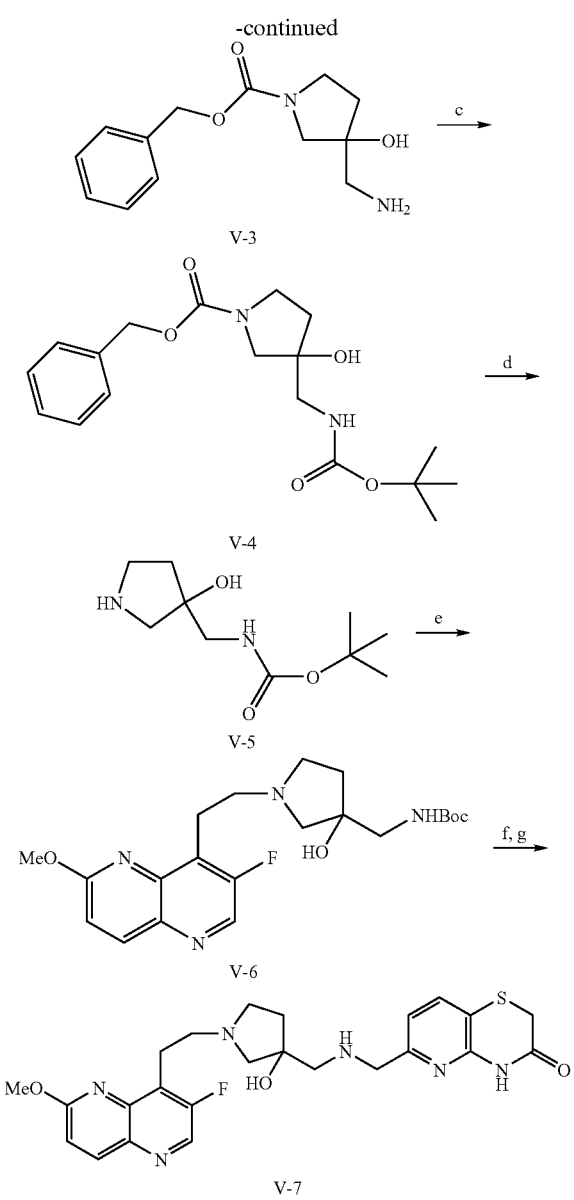

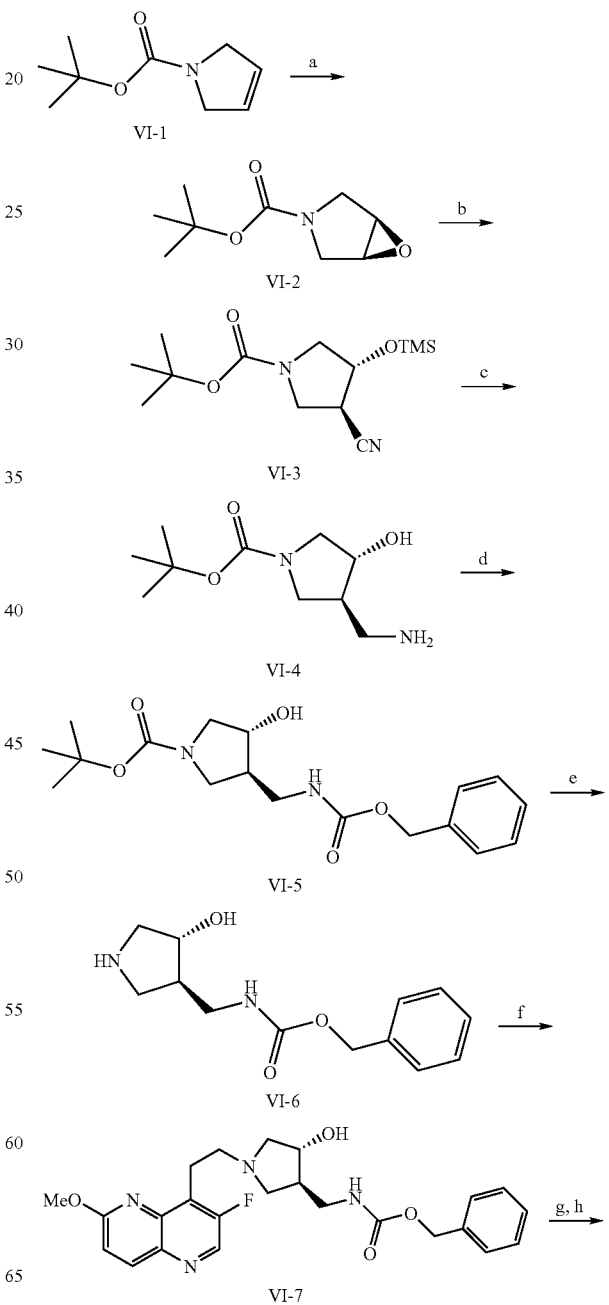

primary amine derivative was subsequently converted to a secondary amine V-7 by reaction with an aldehyde and a suitable reducing agent. For example, 3-(aminomethyl)-1-{2-[3-fluoro-6-(methyloxy)-1,5-naphthyridin-4-yl]ethyl}-3-pyrrolidinol is converted to an imine by reaction with an aldehyde in protic or aprotic solvents such as DMF, $CH_2Cl_2$, EtOH or $CH_3CN$. The imine is subsequently or simultaneously reacted with a suitable reducing agent such as $NaBH_4$, $NaBH(OAc)_3$ or $NaBH_3CN$ in solvent. Depending on whether acid neutralization is required, an added base, such as triethylamine ($Et_3N$), diisopropylethylamine ((i-Pr)$_2$NEt), or $K_2CO_3$, may be used.

Reagents and conditions: (a) $NaHSO_3$, KCN, THF, $H_2O$, 0° C.; (b) $LiAlH_4$, THF, RT, 20 h; (c) (Boc)$_2$O, MeOH, RT; (d) Pd/C, $H_2$ (1 atm), EtOH, RT; (e) 8-ethenyl-7-fluoro-2-(methyloxy)-1,5-naphthyridine, DMF, 85° C.; (f) TFA, DCM, RT; (g) 3-oxo-3,4-dihydro-2H-pyrido[1,4]thiazine-6-carboxaldehyde, $CH_2Cl_2$, EtOH; then $NaBH_4$, EtOH.

Pyrrolidinone V-1 was converted to cyanohydrin V-2 using $NaHSO_3$ in aqueous THF at 0° C. (*J. Med. Chem.* 1993, 36, 2292-2299). $LiAlH_4$ was used to reduce V-2 to the corresponding amino alcohol V-3. The amine functionality of V-3 was protected using Boc anhydride to give V-4. The benzyl carbamate protecting group was then removed under hydrogenolysis conditions using a palladium catalyst in alcohol to give the amine V-5. The secondary amine V-5 was the heated together with a vinyl electrophile either under neat conditions or in an appropriate solvent such as DMF, dioxane or DME to give the product compound V-6.

The Boc protecting group was removed under acidic conditions using TFA in methylene chloride at RT. The resulting

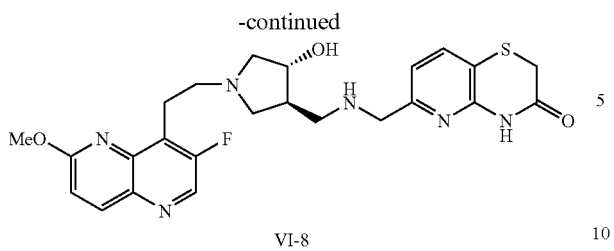

Reagents and conditions: (a) MCPBA, DCM, RT, 2 days; (b) TMSCN, Et$_2$AlCl, DCM, RT, 24 h; (c) LiAlH$_4$, THF, RT, 20 h; (d) Cbz-succinimide, Et$_3$N, DMF, RT; (e) TFA, CH$_2$Cl$_2$, RT; (f) 8-ethenyl-7-fluoro-2-(methyloxy)-1,5-naphthyridine, EtOH, 85° C.; (g) Pd/C, H$_2$ (1 atm), MeOH, RT; (h) 3-oxo-3,4-dihydro-2H-pyrido[1,4]thiazine-6-carboxaldehyde, CH$_2$Cl$_2$, EtOH; then NaBH(OAc)$_3$.

Alkene VI-1 was converted to an epoxide VI-2 using a suitable oxidizing reagent such as MCPBA or other peracids. The epoxide was opened under nucleophilic conditions aided by a Lewis acid to give the silyl protected hydroxy nitrile VI-3 in a trans relative configuration. The nitrile functionality was reduced and the TMS group cleaved simultaneously using LiAlH$_4$ as a reducing agent in a polar aprotic solvent. The resulting amino alcohol VI-4 was reacted with Cbz-succinamide to protect the primary amine and afford compound VI-5. Deprotection of the Boc-amine was achieved with TFA in DCM to give secondary amine VI-6. The amine was then reacted with a electrophilic vinyl compound either neat or in a small amount of solvent providing VI-7. Removal of the Cbz-group was achieved under hydrogenolysis conditions using a palladium catalyst in an alcoholic solvent in an atmosphere of hydrogen. The primary amine derivative was converted to an imine by reaction with an aldehyde in protic or aprotic solvents such as DMF, CH$_2$Cl$_2$, EtOH or CH$_3$CN. The imine was subsequently or simultaneously reacted with a suitable reducing agent such as NaBH$_4$, NaBH(OAc)$_3$ or NaBH$_3$CN in solvent to give the amine VI-8. Depending on whether acid neutralization is required, an added base, such as triethylamine (Et$_3$N), diisopropylethylamine ((i-Pr)$_2$NEt), or K$_2$CO$_3$, may be used.

Scheme VII

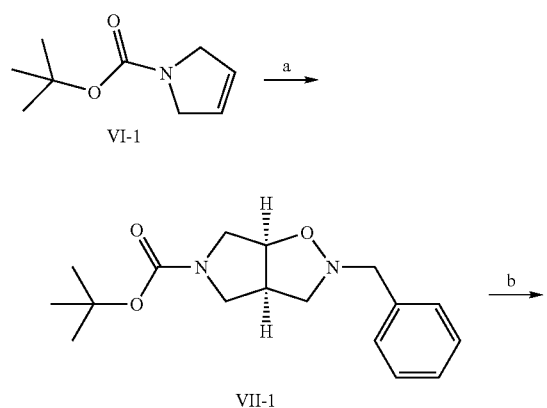

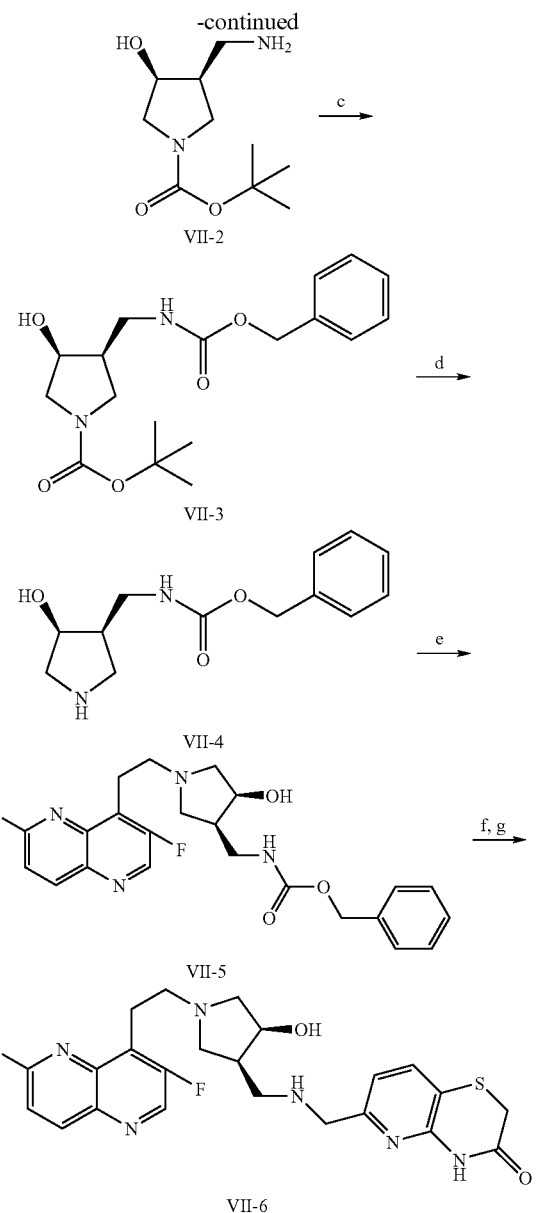

Reagents and conditions: (a) N-Hydroxybenzylamine hydrochloride, toluene, EtOH, 80° C.; (b) Pd(OH)$_2$, H$_2$ (50 psi), EtOH, RT; (c) Cbz-succinimide, Et$_3$N, DMF, RT; (d) TFA, CH$_2$Cl$_2$, RT; then MP-carbonate resin, DCM, RT; (e) 8-ethenyl-7-fluoro-2-(methyloxy)-1,5-naphthyridine, EtOH, 80° C.; (f) Pd(OH)$_2$, MeOH, H$_2$ (1 atm), RT; (g) 3-oxo-3,4-dihydro-2H-pyrido[1,4]thiazine-6-carboxaldehyde, CH$_2$Cl$_2$, EtOH; then NaBH(OAc)$_3$.

The alkene VI-1 was reacted with an appropriate electron-rich cycloaddition reagent to give the cis-adduct VII-1. The benzyl functionality was removed and the N—O bond cleaved simultaneously under hydrogenolysis conditions using Pd(OH)$_2$ in a polar protic solvent under an atmosphere of hydrogen. The resulting amino alcohol VII-2 was reacted with Cbz-succinamide to protect the primary amine and afford compound VII-3. Deprotection of the Boc-amine was achieved with TFA in DCM to give secondary amine VII-4. The secondary amine was then reacted with an electrophilic vinyl compound either neat or in a small amount of solvent providing VII-5. Removal of the Cbz-group was achieved under hydrogenolysis conditions using a palladium catalyst in an alcoholic solvent under an atmosphere of hydrogen. The primary amine derivative was converted to an imine by reaction with an aldehyde in protic or aprotic solvents such as DMF, $CH_2Cl_2$, EtOH or $CH_3CN$. The imine was subsequently or simultaneously reacted with a suitable reducing agent such as $NaBH_4$, $NaBH(OAc)_3$ or $NaBH_3CN$ in solvent to give the amine VII-6. Depending on whether acid neutralization is required, an added base, such as triethylamine ($Et_3N$), diisopropylethylamine (($i$-$Pr$)$_2NEt$), or $K_2CO_3$, may be used.

RT; (c) 8-ethenyl-7-fluoro-2-(methyloxy)-1,5-naphthyridine, EtOH, 80° C.; (d) Pd(OH)$_2$, MeOH, H$_2$ (1 atm), RT; (e) 3-oxo-3,4-dihydro-2H-pyrido[1,4]thiazine-6-carboxaldehyde, $CH_2Cl_2$, EtOH; then $NaBH(OAc)_3$.

Alcohol VII-3 was converted to an ether using dimethylsulfate as the alkylating reagent with the aid of a phase transfer catalyst in toluene. Deprotection of the Boc-amine VIII-1 was achieved with TFA in DCM to give secondary amine VIII-2. The secondary amine was then reacted with an electrophilic vinyl compound either neat or in a small amount of solvent providing VIII-3. Removal of the Cbz-group was achieved under hydrogenolysis conditions using a palladium catalyst in an alcoholic solvent under an atmosphere of hydrogen. The primary amine derivative was converted to an imine by reaction with an aldehyde in protic or aprotic solvents such as DMF, $CH_2Cl_2$, EtOH or $CH_3CN$. The imine was subsequently or simultaneously reacted with a suitable reducing agent such as $NaBH_4$, $NaBH(OAc)_3$ or $NaBH_3CN$ in solvent to give the amine VIII-4. Depending on whether acid neutralization is required, an added base, such as triethylamine ($Et_3N$), diisopropylethylamine (($i$-$Pr$)$_2NEt$), or $K_2CO_3$, may be used.

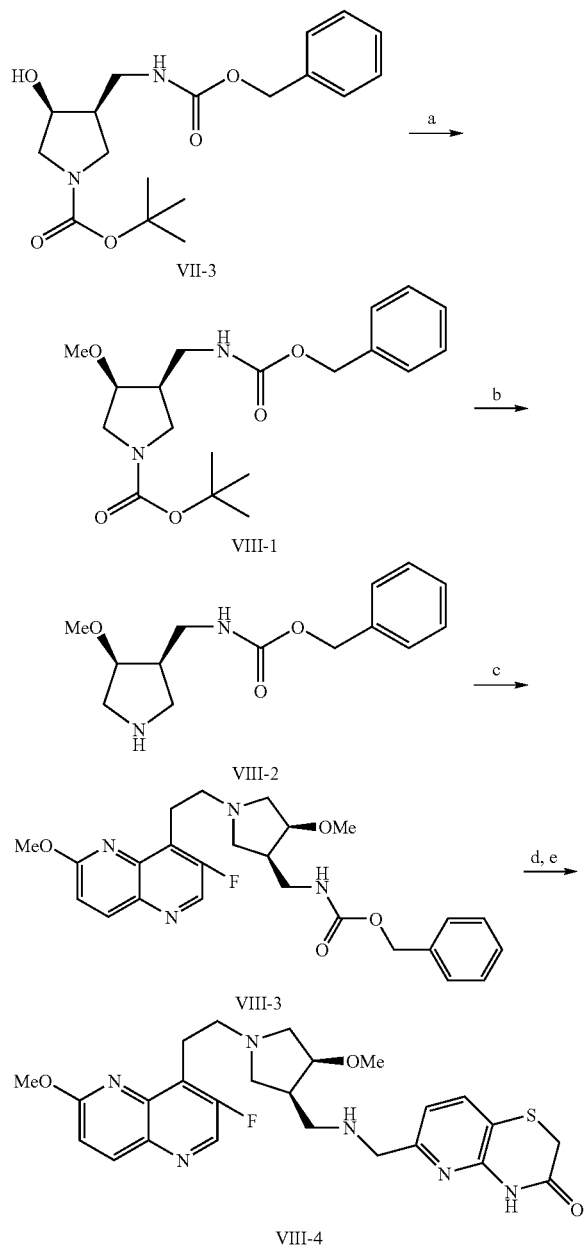

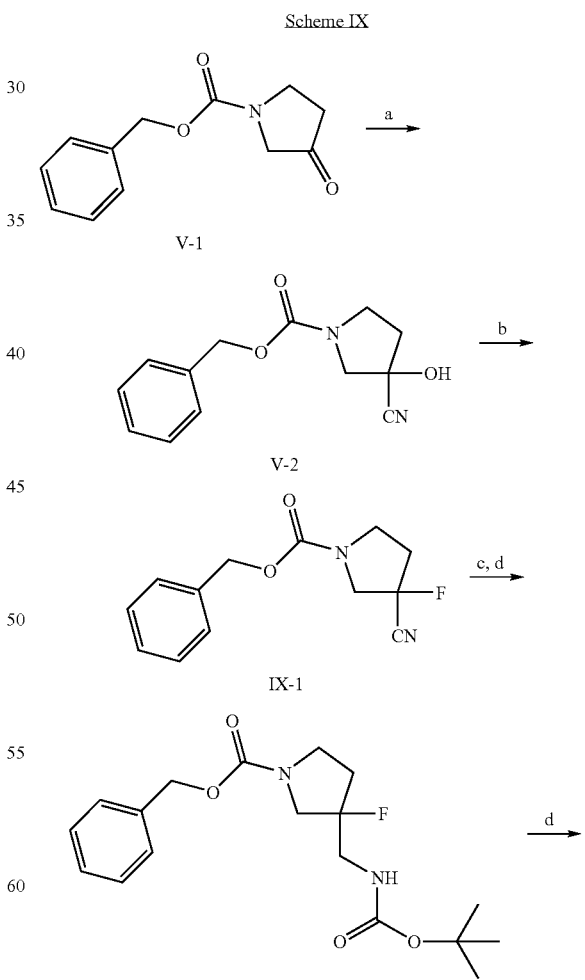

Reagents and conditions: (a) BnNEt$_3$Cl, toluene, (CH$_3$)$_2$SO$_4$, RT; (b) TFA, CH$_2$Cl$_2$, RT; then MP-carbonate resin, DCM,

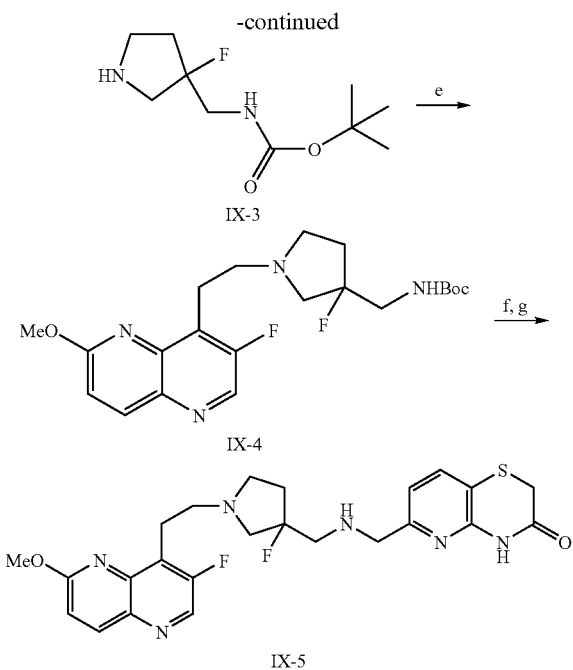
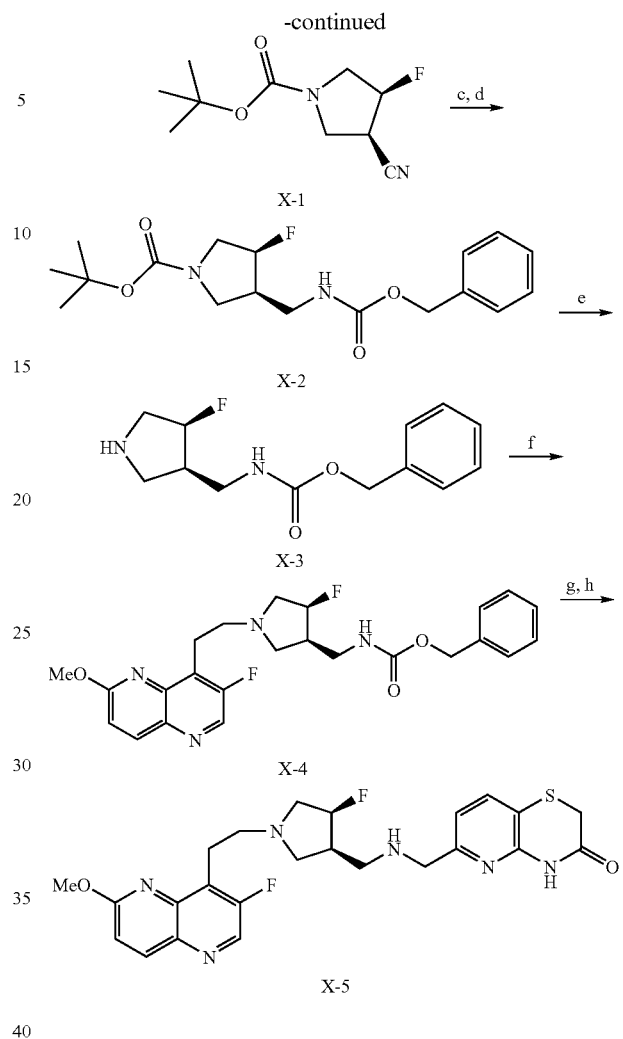

Reagents and conditions: (a) NaHSO₃, KCN, THF, H₂O, 0° C.; (b) DAST, DCM, −78° C.; (c) LiAlH₄, THF, RT, 20 h; (c) (Boc)₂O, MeOH, RT; (d) Pd/C, H₂ (1 atm), EtOH, RT; (e) 8-ethenyl-7-fluoro-2-(methyloxy)-1,5-naphthyridine, DMF, 85° C.; (f) TFA, DCM, RT; (g) 3-oxo-3,4-dihydro-2H-pyrido[1,4]thiazine-6-carboxaldehyde, CH₂Cl₂, EtOH; then NaBH(OAc)₃.

Cyanohydrin V-2 was converted to fluoride IX-1 using an DAST as a fluorinating reagent in a polar aprotic solvent such as DCM at low temperature. The nitrile functionality was subsequently reduced to the corresponding amine using LiAlH₄ in THF at 0 C and the primary amine immediately protected using Boc anhydride in THF. Removal of the Cbz-group of IX-2 was achieved under hydrogenolysis conditions using a palladium catalyst in an alcoholic solvent under an atmosphere of hydrogen. The secondary amine XI-3 was then reacted with an electrophilic vinyl compound either neat or in a small amount of solvent providing IX-4. Deprotection of the Boc-amine was achieved with TFA in DCM after which the resulting primary amine derivative was converted to an imine by reaction with an aldehyde in protic or aprotic solvent such as DMF, CH₂Cl₂, EtOH or CH₃CN. The imine was subsequently or simultaneously reacted with a suitable reducing agent such as NaBH₄, NaBH(OAc)₃ or NaBH₃CN in solvent to give the amine IX-5. Depending on whether acid neutralization is required, an added base, such as triethylamine (Et₃N), diisopropylethylamine ((i-Pr)₂NEt), or K₂CO₃, may be used.

Scheme X

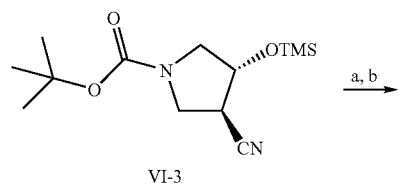

Reagents and conditions: (a) TBAF, THF, 0° C.; (b) DAST, DCM −78° C.; (c) LiAlH₄, THF, RT; (d) Cbz-succinimide, Et₃N, DMF, RT; (e) TFA, CH₂Cl₂, RT; then MP-carbonate resin, DCM, RT; (f) 8-ethenyl-7-fluoro-2-(methyloxy)-1,5-naphthyridine, EtOH, 80° C.; (g) Pd(OH)₂, MeOH, H₂ (1 atm), RT; (h) 3-oxo-3,4-dihydro-2H-pyrido[1,4]thiazine-6-carboxaldehyde, CH₂Cl₂, EtOH; then NaBH(OAc)₃.

Silyl ether VI-3 was deprotected to a secondary alcohol using TBAF in THF. The resulting alcohol was converted to fluoride X-1 using DAST as a nucleophilic fluorinating reagent in a polar aprotic solvent such as DCM at low temperature. The nitrile functionality was subsequently reduced to the corresponding amine using LiAlH₄ in THF at 0 C and the primary amine subsequently protected using Cbz succinamide in DMF to give X-2. Deprotection of the Boc-amine was achieved with TFA in DCM giving secondary amine X-3. The secondary amine was then reacted with an electrophilic vinyl compound either neat or in a small amount of solvent providing X-4. Removal of the Cbz group was achieved under hydrogenolysis conditions using a palladium catalyst in an alcoholic solvent under an atmosphere of hydrogen. The resulting primary amine derivative was converted to an imine by reaction with an aldehyde in protic or aprotic solvent such as DMF, CH₂Cl₂, EtOH or CH₃CN. The imine was subsequently or simultaneously reacted with a suitable reducing agent such as NaBH₄, NaBH(OAc)₃ or NaBH₃CN in solvent to give the amine X-5. Depending on whether acid neutralization is required, an added base, such as triethylamine (Et₃N), diisopropylethylamine ((i-Pr)₂NEt), or K₂CO₃, may be used.

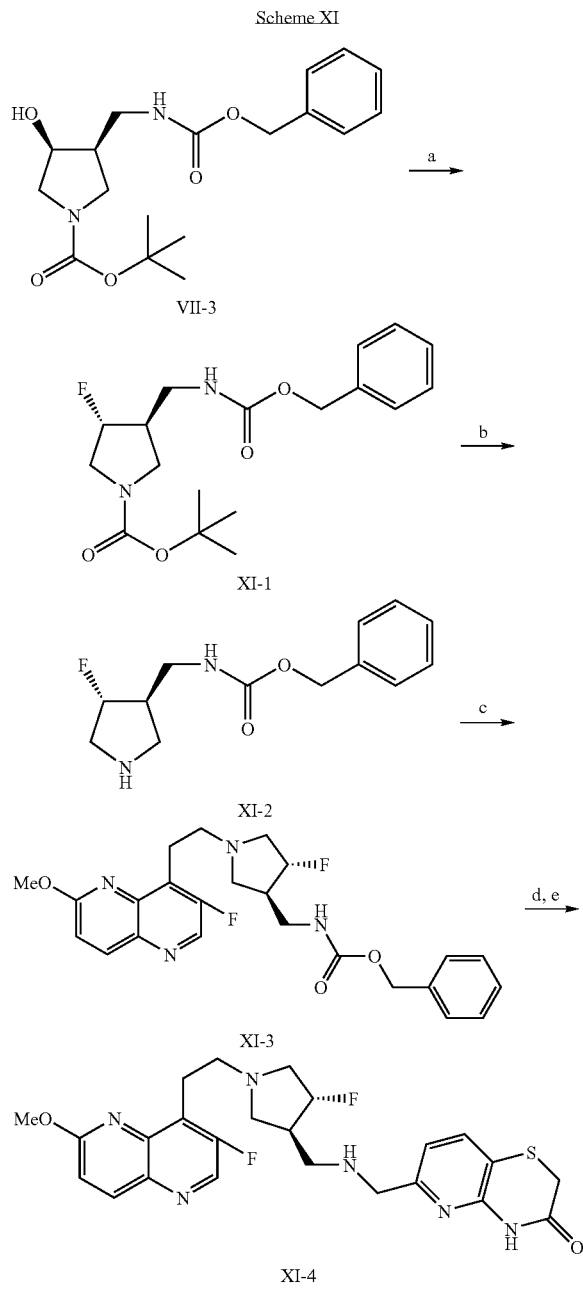

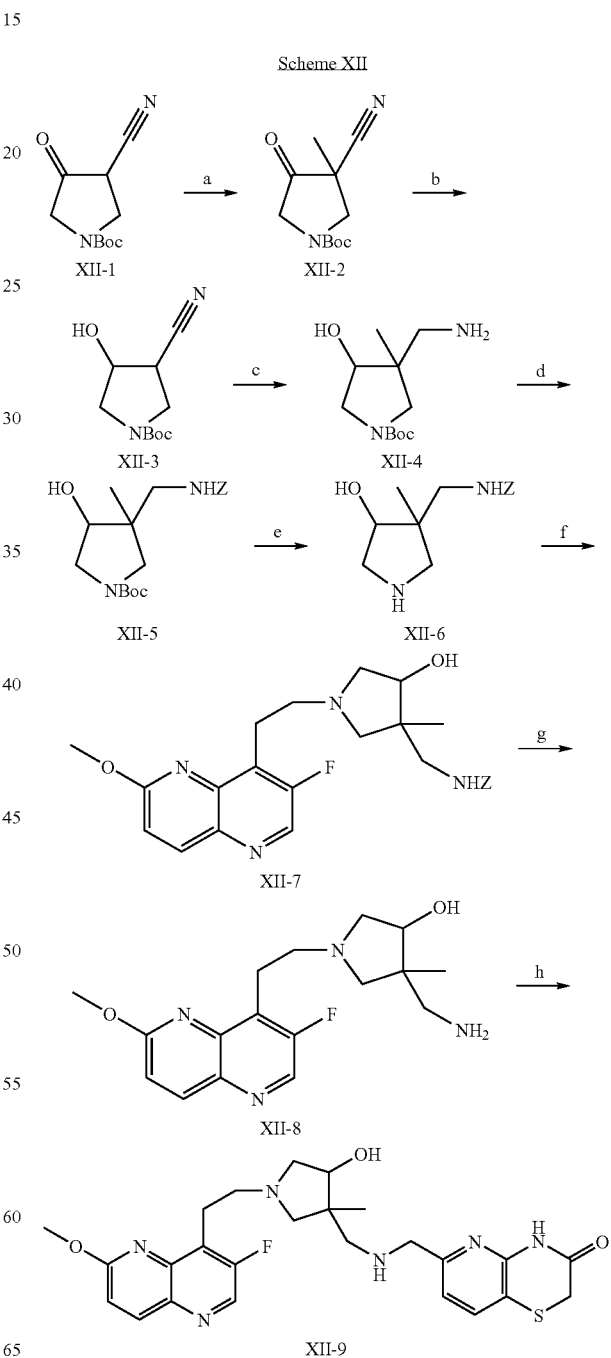

Reagents and conditions: (a) DAST, DCM −78° C.; (b) TFA, CH₂Cl₂, RT; then MP-carbonate resin, DCM, RT; (c) 8-ethenyl-7-fluoro-2-(methyloxy)-1,5-naphthyridine, EtOH, 80° C.; (d) Pd(OH)₂, MeOH, H₂ (1 atm), RT; (e) 3-oxo-3,4-dihydro-2H-pyrido[1,4]thiazine-6-carboxaldehyde, CH₂Cl₂, EtOH; then NaBH(OAc)₃.

The alcohol VII-3 was converted to fluoride XI-1 using DAST as a nucleophilic fluorinating reagent in a polar aprotic solvent such as DCM at low temperature. Deprotection of the Boc-amine was achieved with TFA in DCM giving secondary amine XI-2. The secondary amine was then reacted with an electrophilic vinyl compound either neat or in a small amount of solvent providing XI-3. Removal of the Cbz group was achieved under hydrogenolysis conditions using a palladium catalyst in an alcoholic solvent under an atmosphere of hydrogen. The resulting primary amine derivative was converted to an imine by reaction with an aldehyde in protic or aprotic solvent such as DMF, CH₂Cl₂, EtOH or CH₃CN. The imine was subsequently or simultaneously reacted with a suitable reducing agent such as NaBH₄, NaBH(OAc)₃ or NaBH₃CN in solvent to give the amine XI-4. Depending on whether acid neutralization is required, an added base, such as triethylamine (Et₃N), diisopropylethylamine ((i-Pr)₂NEt), or K₂CO₃, may be used.

Reagents and conditions: (a) K₂CO₃, MeI, acetone, reflux (b) NaBH₄, EtOH, 0° C. (c) LiAlH₄, THF, 0° C. (d) N-(benzyloxycarbonyloxy)succinimide, DCM, 0° C. (e) 4M HCl in dioxane, MeOH, 25° C. (f) 8-ethenyl-7-fluoro-2-(methyloxy)-1,5-naphthyridine, EtOH, 85° C. (g) Pd(OH)₂, EtOH, 50 psi (h) 3-oxo-3,4-dihydro-2H-pyrido[3,2-b][1,4]thiazine-6-carbaldehyde, Na₂SO₄, DCM-EtOH, 25° C. then NaBH(OAc)₃

Alkylation of commercially available cyano-ketone (XII-1) provided methylpyrrolidine (XII-2). A two step reduction, first on the ketone then the nitrile provided the amine (XII-3), which was protected as the Z-carbamate (XII-5). The Boc group was removed using the standard methods as described by references such as Kocienski and Greene, previously cited herein. The resulting amine (XII-6) underwent Michael addition into an appropriate napthyridine yielding the adduct (XII-7). The Z-carbamate was subsequently removed through standard hydrogenolysis and the primary amine underwent reductive amination with an appropriate aldehyde generating analog (XII-9).

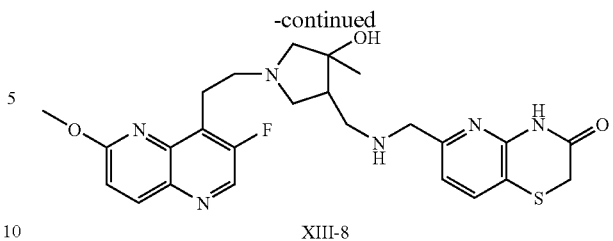

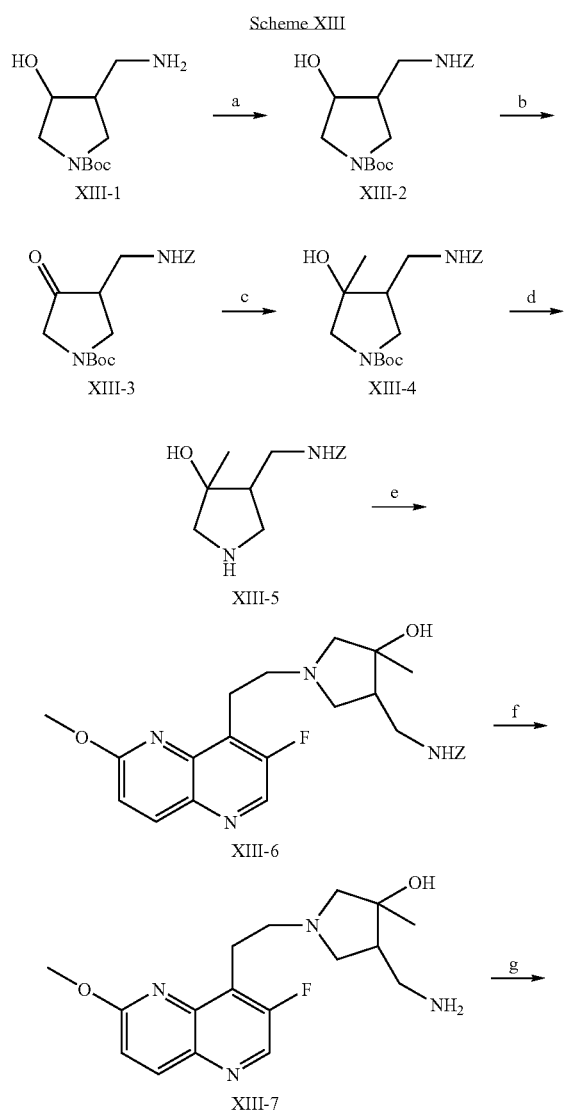

Reagents and conditions: (a) N-(benzyloxycarbonyloxy)succinimide, DCM, 0° C. (b) SO₃-pyr, DMSO, Et₃N, 0-25° C. (c) MeMgBr, THF-toluene, 0-25° C. (d) 4M HCl in dioxane, MeOH, 25° C. (e) 8-ethenyl-7-fluoro-2-(methyloxy)-1,5-naphthyridine, EtOH, 85° C. (g) Pd(OH)₂, EtOH, 50 psi (h) 3-oxo-3,4-dihydro-2H-pyrido[3,2-b][1,4]thiazine-6-carbaldehyde, Na₂SO₄, DCM-EtOH, 25° C. then NaBH(OAc)₃

The amine (XIII-1) [prepared according to Hong, C.-Y. *J. Med. Chem.* 1997, 40, 3584.] was protected as the Z-carbamate (XIII-2). The alcohol was oxidized and the resulting ketone (XIII-3) was reduced using an alkyl-Grignard to the tertiary alcohol (XIII-4). The Boc group on the pyrrolidine ring was removed using standard procedures such as those described by protecting group references like Kocienski or Greene, cited previously herein. The free amine (XIII-5) underwent Michael addition into an appropriate napthyridine generating adduct (XIII-6). The Z-carbamate was removed through hydrogenolysis and the resulting primary amine (XIII-7) underwent reductive amination with an appropriate aldehyde generating analog (XIII-8).

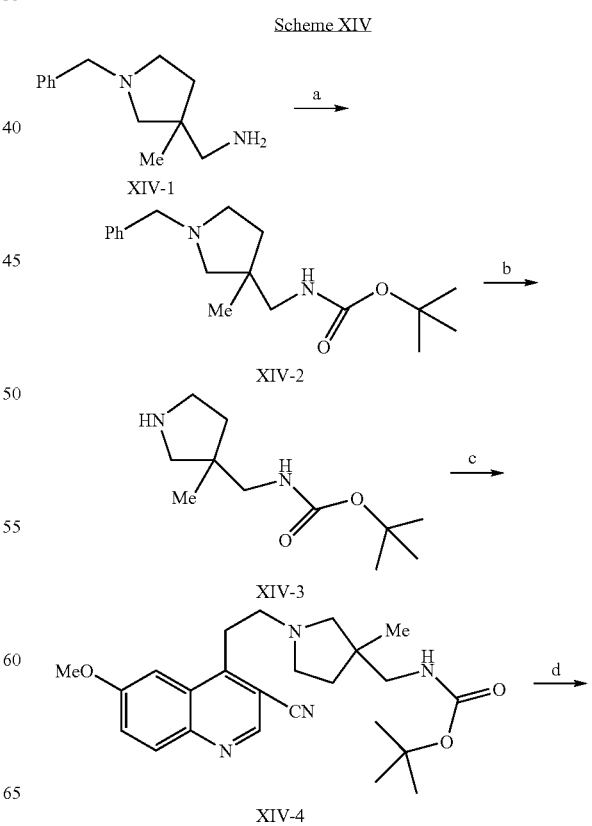

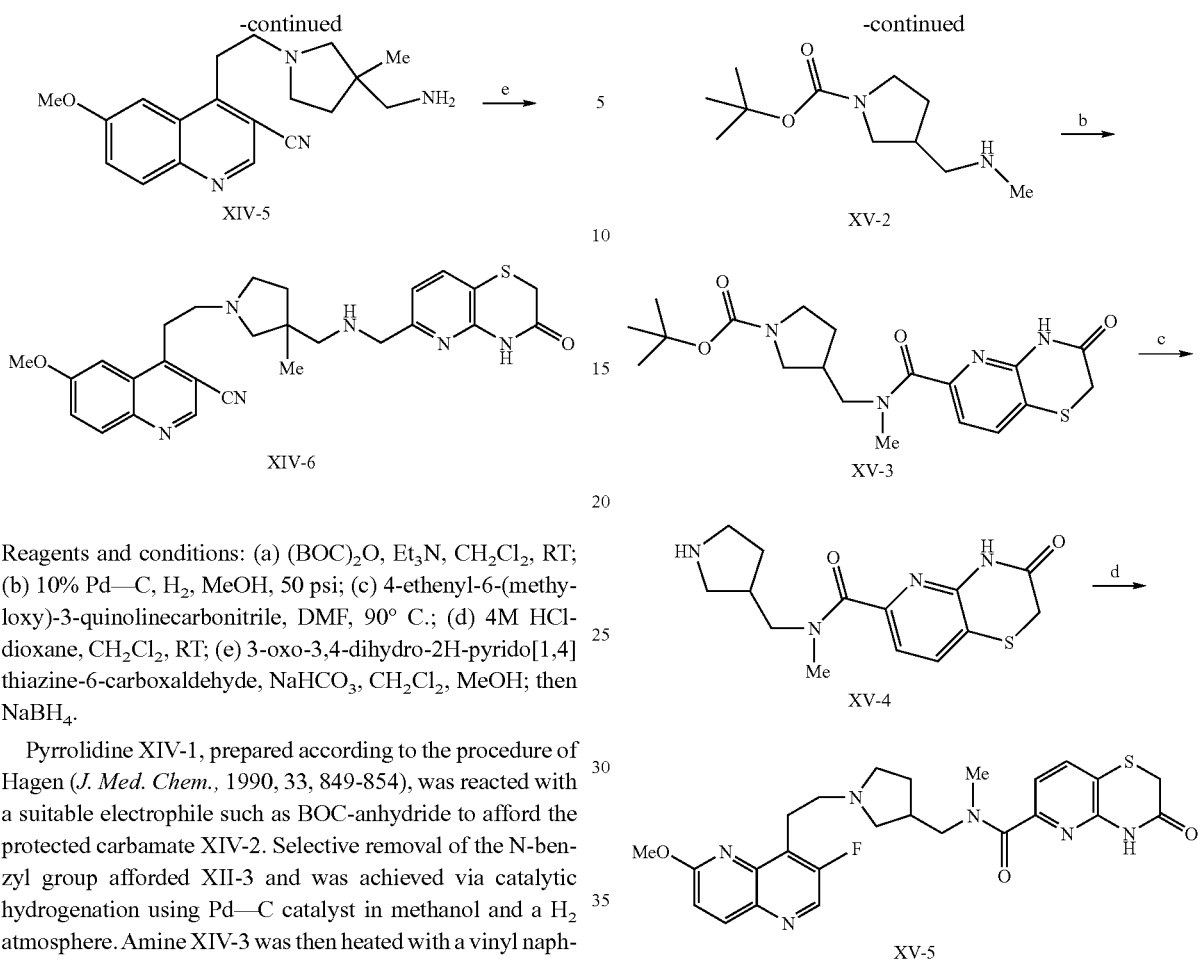

Reagents and conditions: (a) (BOC)₂O, Et₃N, CH₂Cl₂, RT; (b) 10% Pd—C, H₂, MeOH, 50 psi; (c) 4-ethenyl-6-(methyloxy)-3-quinolinecarbonitrile, DMF, 90° C.; (d) 4M HCl-dioxane, CH₂Cl₂, RT; (e) 3-oxo-3,4-dihydro-2H-pyrido[1,4]thiazine-6-carboxaldehyde, NaHCO₃, CH₂Cl₂, MeOH; then NaBH₄.

Pyrrolidine XIV-1, prepared according to the procedure of Hagen (*J. Med. Chem.*, 1990, 33, 849-854), was reacted with a suitable electrophile such as BOC-anhydride to afford the protected carbamate XIV-2. Selective removal of the N-benzyl group afforded XII-3 and was achieved via catalytic hydrogenation using Pd—C catalyst in methanol and a H₂ atmosphere. Amine XIV-3 was then heated with a vinyl naphthyrine or quinoline, either neat or in a suitable solvent (dioxane, DMF), generating the product XIV-4. In this example 4-ethenyl-6-(methyloxy)-3-quinolinecarbonitrile was utilized and the reaction was carried out at an elevated temperature. Deprotection of the t-butyl carbamate functionality was performed under acidic conditions using HCl in dioxane, however, alternative acids such as trifluoroacetic acid could be used. The primary amine derivative XIV-5, here isolated as a HCl salt, was then converted to a secondary amine XIV-6 by reaction with an aldehyde and a suitable reducing agent such as NaBH₄, NaBH(OAc)₃ or NaBH₃CN. This transformation may be carried out using the free base form of the amine or, as in this example, a salt form. If a salt-from of the amine is used, then the reaction is carried out in the presence of a base such as NaHCO₃, triethylamine (Et₃N), diisopropylethylamine ((i-Pr)₂NEt), or K₂CO₃.

Scheme XV

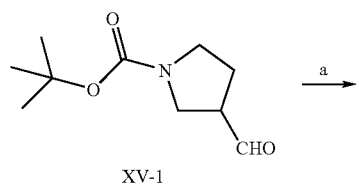

XV-1

Reagents and conditions: (a) 2M MeNH₂, DCM-MeOH, NaHCO₃, then NaBH₄, (b) 3-oxo-3,4-dihydro-2H-pyrido[3,2-b][1,4]thiazine-6-carboxylic acid, DPPA, Et₃N, DMF, RT; (c)) 4M HCl-dioxane, CH₂Cl₂, RT; (d) 8-ethenyl-7-fluoro-2-(methyloxy)-1,5-naphthyridine, diisopropylethylamine, DMF, 90° C.

The pyrrolidine aldehyde XV-1 (CB Research) was reacted with methylamine and the resulting imine was reduced with NaBH4 to provide N-methylaminomethylpyrrolidine XV-2. This reductive amination process may be carried out using any number of methods that are well known in the art. The amine XV-2 was reacted with an appropriate carboxylic acid, in this example 3-oxo-3,4-dihydro-2H-pyrido[3,2-b][1,4]thiazine-6-carboxylic acid was used, in the presence of an activating agent such as DPPA to provide the amide XV-3. The BOC protecting group was removed via standard treatment with acid, in this example HCl in dioxane was used, to provide the pyrrolidine XV-4 as an HCl salt. The secondary amine XV-4 was heated together with a vinyl electrophile such as 8-ethenyl-7-fluoro-2-(methyloxy)-1,5-naphthyridine either under neat conditions or in an appropriate solvent such as DMF, dioxane or DME to give the product XV-5. If the amine exists as a salt, the free base is generated by the addition of a suitable base such as Et₃N, diisopropylethylamine or NaHCO₃.

Scheme XVI

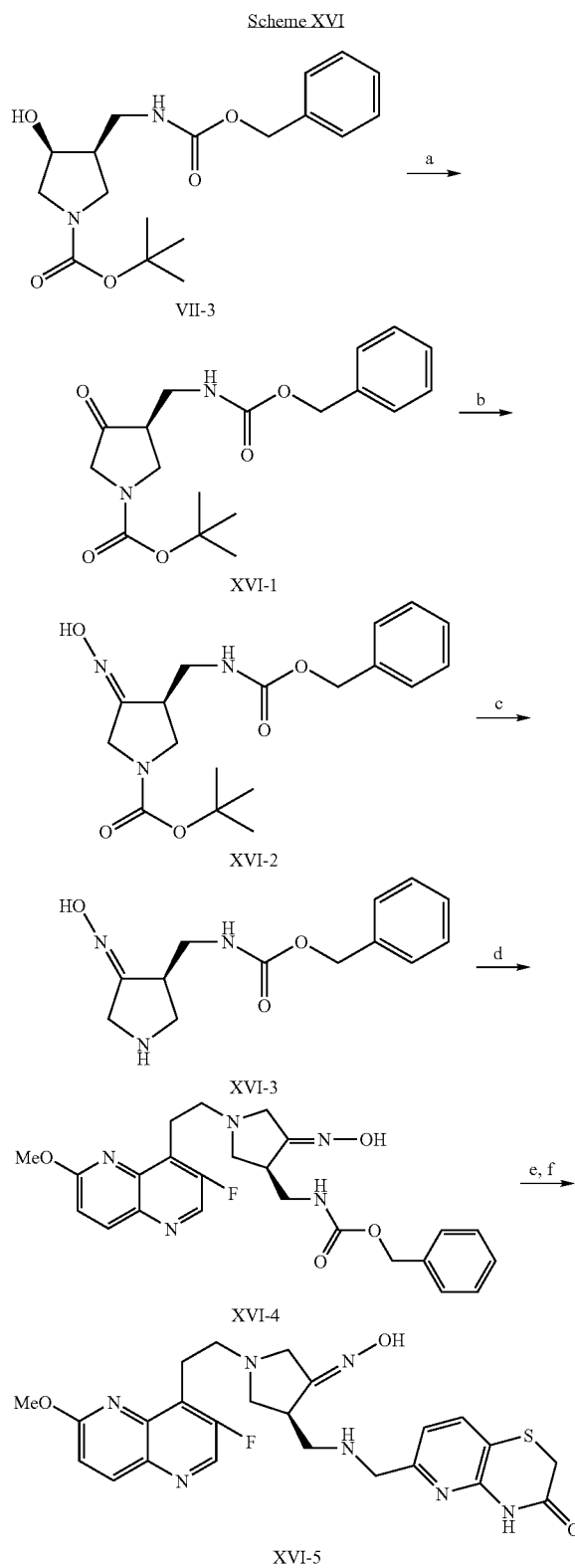

Reagents and conditions: (a) PCC, DCM, RT; (b) Hydroxlamine hydrochloride, NaOAc; (c) HCl/dioxane, RT; (d) 8-ethenyl-7-fluoro-2-(methyloxy)-1,5-naphthyridine, DMF, TEA, 90° C.; (e) 10% Pd/C, H$_2$ (50 psi), EtOH, THF, RT; (f) 3-oxo-3,4-dihydro-2H-pyrido[1,4]thiazine-6-carboxaldehyde, CH$_2$Cl$_2$, EtOH; then NaBH$_4$.

Alcohol VII-3 was oxidized to the corresponding ketone using an appropriate chromium-based oxidant such as PCC or PDC to give ketone II-1. The ketone functionality was converted to an oxime XVI-2 by reaction with hydroxylamine in dry solvent. Deprotection of the Boc-amine was achieved with HCl in dioxane to give the secondary amine XVI-3. The secondary amine was then reacted with an electrophilic vinyl compound either neat or in a small amount of polar solvent providing XVI-4. Removal of the Cbz-group was achieved under hydrogenolysis conditions using a palladium catalyst in an alcoholic solvent under an atmosphere of hydrogen. The primary amine derivative was converted to an imine by reaction with an aldehyde in protic or aprotic solvents such as DMF, CH$_2$Cl$_2$, EtOH or CH$_3$CN. The imine was subsequently or simultaneously reacted with a suitable reducing agent such as NaBH$_4$, NaBH(OAc)$_3$ or NaBH$_3$CN in solvent to give the amine XVI-5. Depending on whether acid neutralization is required, an added base, such as triethylamine (Et$_3$N), diisopropylethylamine ((i-Pr)$_2$NEt), or K$_2$CO$_3$, may be used. Many additional methods for reductive aminations are known, and can be found in standard reference books, such as "Compendium of Organic Synthetic Methods", Vol. I-VI (published by Wiley-Interscience).

Scheme XVII

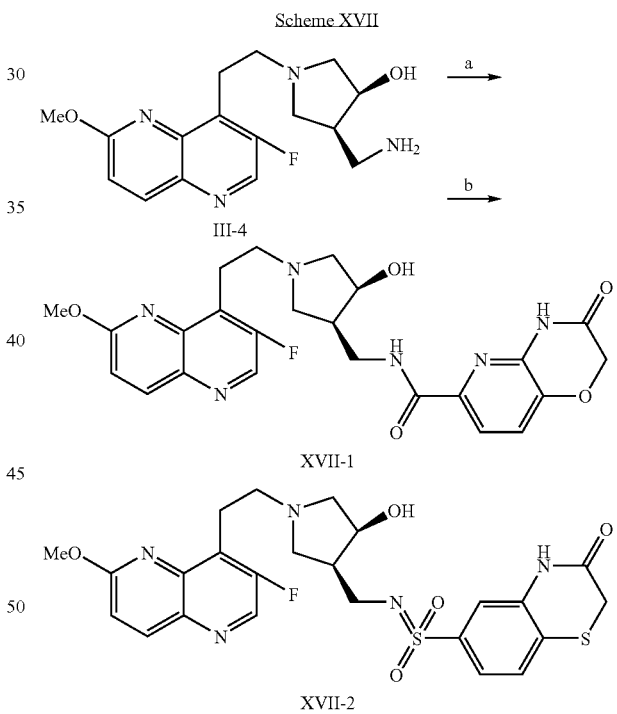

Reagents and conditions: (a) EDC, HOBt, (i-Pr)$_2$NEt, DMF, 3-oxo-3,4-dihydro-2H-pyrido[3,2-b][1,4]oxazine-6-carboxylic acid; (b) 3-oxo-3,4-dihydro-2H-1,4-benzothiazine-6-sulfonyl chloride, Et$_3$N, DCM.

A suitable carboxylic acid, for instance 3-oxo-3,4-dihydro-2H-pyrido[3,2-b][1,4]oxazine-6-carboxylic acid, is converted to an activated form using, for example, EDC and HOBt, or SOCl$_2$, and the activated form is subsequently reacted with an appropriate amine, for instance amine III-4, in a suitable solvent such as DMF, CH$_2$Cl$_2$, or CH$_3$CN, to afford XVII-1. Depending on whether acid neutralization is required, an added base, such as triethylamine (Et₃N), diisopropylethylamine ((i-Pr)₂NEt), or pyridine, may be used. Many additional methods for converting a carboxylic acid to an amide are known, and can be found in standard reference books, such as "Compendium of Organic Synthetic Methods", Vol. I-VI (published by Wiley-Interscience), or Bodansky, "The Practice of Peptide Synthesis" (published by Springer-Verlag). A sulfonyl halide, in conjunction with a suitable base such as triethylamine, will react with III-4 to give the corresponding sulfonamide XVII-2.

CH₂Cl₂, EtOH or CH₃CN. The imine was subsequently or simultaneously reacted with a suitable reducing agent such as NaBH₄, NaBH(OAc)₃ or NaBH₃CN in solvent to give the amine XVIII-5. Depending on whether acid neutralization is required, an added base, such as triethylamine (Et₃N), diisopropylethylamine ((i-Pr)₂NEt), or K₂CO₃, may be used. Many additional methods for reductive aminations are known, and can be found in standard reference books, such as "Compendium of Organic Synthetic Methods", Vol. I-VI (published by Wiley-Interscience).

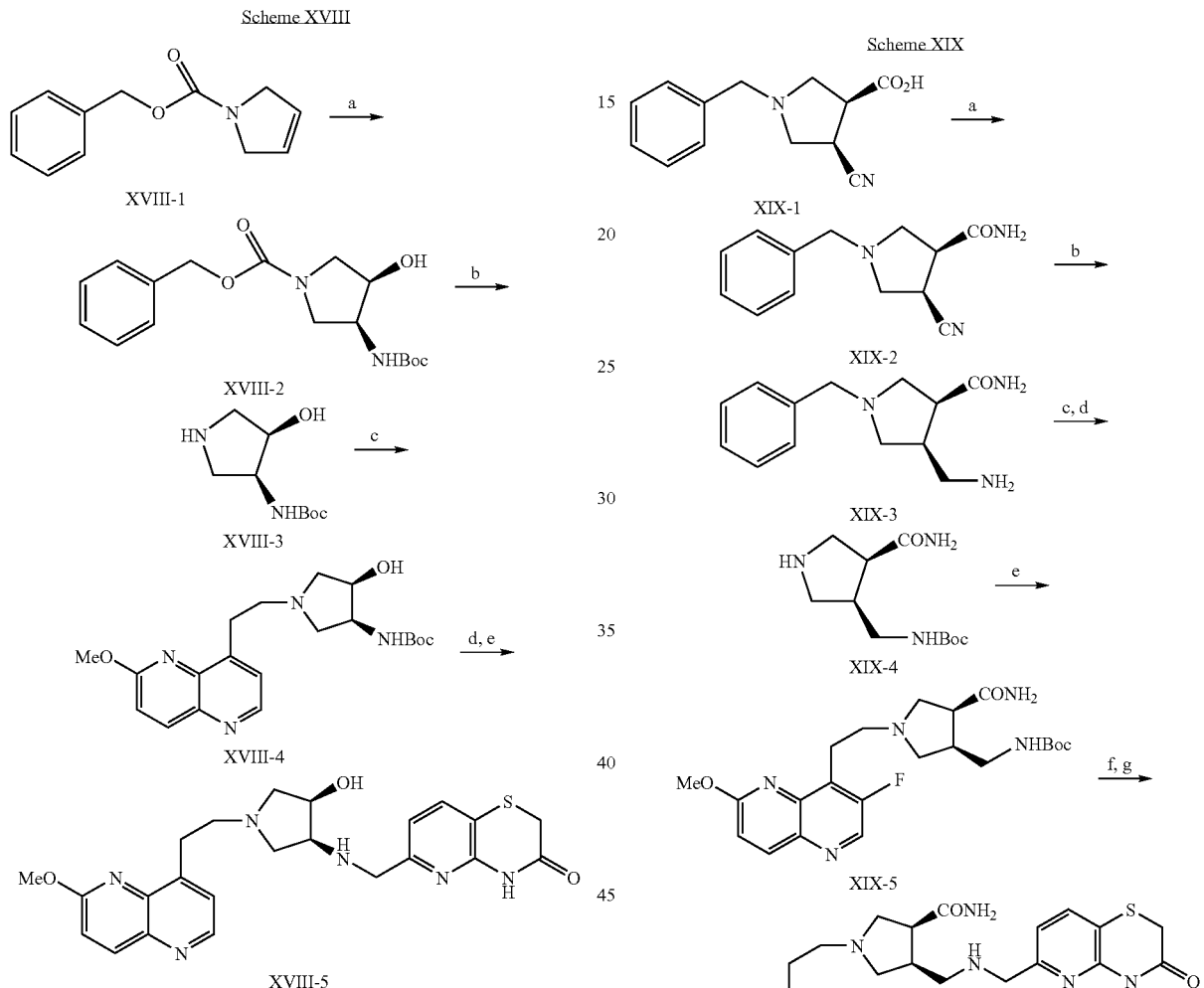

Reagents and conditions: (a) K₂OsO₂(OH)₂, t-BuOCl, n-PrOH, NaOH, (Boc)₂O; (b) Pd/C, H₂, EtOH; (c) 8-ethenyl-2-(methyloxy)-1,5-naphthyridine, EtOH, 85° C.; (d) TFA, DCM, RT, 2 h; (e) 3-oxo-3,4-dihydro-2H-pyrido[1,4]thiazine-6-carboxaldehyde, CH₂Cl₂, EtOH; then NaBH(OAc)₃.

Alkene XVIII-1 was converted to a Boc-protected syn-vicinal aminoalcohol using K₂OsO₂(OH)₂, t-BuOCl, NaOH, and (Boc)₂O. Removal of the Cbz-group was achieved under hydrogenolysis conditions using a palladium catalyst in an alcoholic solvent under an atmosphere of hydrogen. The secondary amine XVIII-3 was then reacted with a electrophilic vinyl compound, such as 8-ethenyl-2-(methyloxy)-1,5-naphthyridine, either neat or in a small amount of solvent providing XVIII-4. Deprotection of the Boc-amine was achieved with TFA in DCM to give a primary amine. The primary amine derivative was converted to an imine by reaction with an aldehyde in protic or aprotic solvents such as DMF, Reagents and conditions: (a) NMM, isobutylchloroformate, NH₃, THF; (b) NiCl₂, NaBH₄, MeOH; (c) (Boc)₂O, DCM, Et₃N; (d) Pd(OH)₂, H₂, MeOH; (e) 8-ethenyl-7-fluoro-2-(methyloxy)-1,5-naphthyridine, EtOH, 85° C.; (f) TFA, DCM, RT; (g) 3-oxo-3,4-dihydro-2H-pyrido[1,4]thiazine-6-carboxaldehyde, NaHCO₃, MeOH-DCM; then NaBH₄.

The racemic carboxylic acid XIX-1 (prepared by the base hydrolysis of the commercially available ethyl ester (Asta Tech)) was reacted with a hindered chloroformate to produce a mixed anhydride. Ammonia was reacted with the anhydride in situ to provide amide XIX-2. The Cyano functionality of XIX-2 was selectively reduced with NiCl₂ in combination with NaBH₄ giving amine XIX-3. The primary amine was protected with Boc anhydride and the secondary amine subsequently unmasked by removal of a benzyl group under hydrogenolysis conditions using Pd/C in a polar protic solvent under H₂. The resulting secondary amine XIX-4 was heated together with a vinyl electrophile such as 8-ethenyl-7-fluoro-2-(methyloxy)-1,5-naphthyridine either under neat conditions or in an appropriate solvent such as DMF, dioxane or DME to give the product XIX-5. The BOC protecting group was removed via treatment with acid, in this example TFA in DCM was used, to provide the primary amine. The primary amine derivative was then converted to an imine by reaction with an aldehyde in protic or aprotic solvents such as DMF, CH₂Cl₂, EtOH or CH₃CN. The imine was subsequently or simultaneously reacted with a suitable reducing agent such as NaBH₄, NaBH(OAc)₃ or NaBH₃CN in solvent to give the amine XIX-6. Depending on whether acid neutralization is required, an added base, such as triethylamine (Et₃N), diisopropylethylamine ((i-Pr)₂NEt), or K₂CO₃, may be used. Many additional methods for reductive aminations are known, and can be found in standard reference books, such as "Compendium of Organic Synthetic Methods", Vol. I-VI (published by Wiley-Interscience).

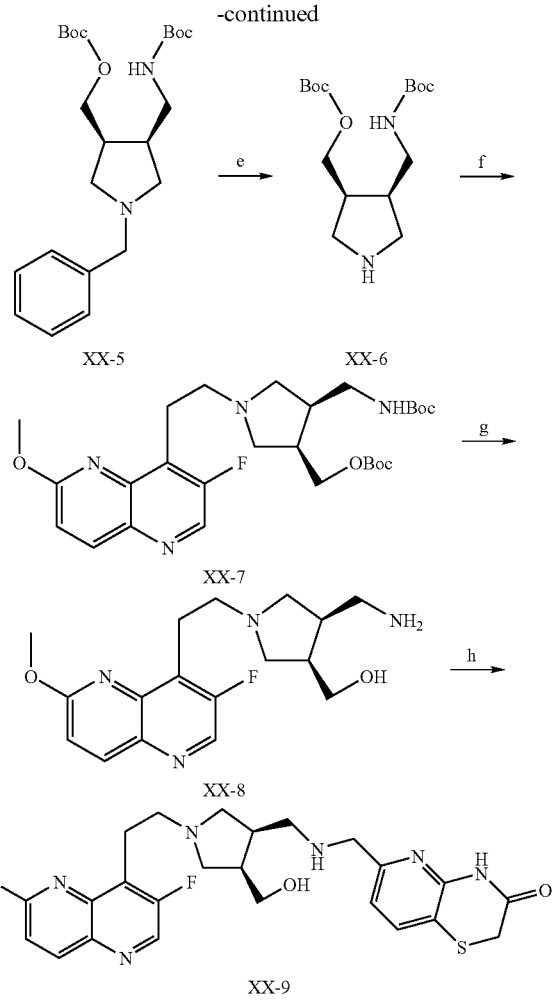

Reagents and conditions: (a) KCN, HCl, HCOH; THF, (b) Ethyl-cis-beta-cyanoacrylate, AgF; CH CN, (c) LiAlH, THF; 0° C.; d) Boc₂O, Et N, CH₂Cl₂; e) H₂, 10% Pd/C CH OH; f) DMF, 90° C.; (f) 8-ethenyl-7-fluoro-2-(methyloxy)-1,5-naphthyridine, EtOH, 85° C.; (g) 4N HCl/dioxane, DCM; (h) 3-oxo-3,4-dihydro-2H-pyrido[1,4]thiazine-6-carboxaldehyde, NaHCO, MeOH-DCM; then NaBH.

Amine XX-1 was reacted with KCN and formaldehyde under acidic conditions to give the acetonitrile derivative XX-2. Reaction of XX-2 with AgF and an appropriate cyano acrylate will provide the pyrrolidine XX-3. Simultaneous reduction of both the ester and cyano functionality of XX-3 with a strong reducing agent such as LiAlH, provided amino alcohol XX-4. Protection of the amine and alcohol groups was performed with Boc anhydride in DCM with the addition of a base such as Et N. Removal of the benzyl group was achieved under hydrogenolysis conditions using a palladium catalyst in an alcoholic solvent under an atmosphere of hydrogen. The secondary amine XX-6 was then reacted with a electrophilic vinyl compound, such as 8-ethenyl-2-(methyloxy)-1,5-naphthyridine, either neat or in a small amount of solvent providing XX-7. Deprotection of the Boc-amine and Boc-protected alcohol was achieved with HCl in dioxane/DCM to give the primary amine XX-8. The primary amine derivative was converted to an imine by reaction with an aldehyde in protic or aprotic solvents such as DMF, CH₂Cl₂, EtOH or CH$_3$CN. The imine was subsequently or simultaneously reacted with a suitable reducing agent such as NaBH$_4$, NaBH(OAc)$_3$ or NaBH$_3$CN in solvent to give the amine XX-9. Depending on whether acid neutralization is required, an added base, such as triethylamine (Et$_3$N), diisopropylethylamine ((i-Pr)$_2$NEt), or K$_2$CO$_3$, may be used. Many additional methods for reductive aminations are known, and can be found in standard reference books, such as "Compendium of Organic Synthetic Methods", Vol. I-VI (published by Wiley-Interscience).

EXPERIMENTALS

General

Proton nuclear magnetic resonance ($^1$H NMR) spectra were recorded at 400 MHz, and chemical shifts are reported in parts per million (δ) downfield from the internal standard tetramethylsilane (TMS). Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. CDCl$_3$ is deuteriochloroform, DMSO-d$_6$ is hexadeuteriodimethylsulfoxide, and CD$_3$OD is tetradeuteriomethanol. Mass spectra were obtained using electrospray (ES) ionization techniques. Elemental analyses were performed by Quantitative Technologies Inc., Whitehouse, N.J. Melting points were obtained on a Thomas-Hoover melting point apparatus and are uncorrected. All temperatures are reported in degrees Celsius. E. Merck Silica Gel 60 F-254 thin layer plates were used for thin layer chromatography. Flash chromatography was carried out on E. Merck Kieselgel 60 (230-400 mesh) silica gel. Analytical HPLC was performed on Beckman chromatography systems. Preparative HPLC was performed using Gilson chromatography systems. ODS refers to an octadecylsilyl derivatized silica gel chromatographic support. YMC ODS-AQ® is an ODS chromatographic support and is a registered trademark of YMC Co. Ltd., Kyoto, Japan. PRP-1® is a polymeric (styrene-divinylbenzene) chromatographic support, and is a registered trademark of Hamilton Co., Reno, Nev. Celite® is a filter aid composed of acid-washed diatomaceous silica, and is a registered trademark of Manville Corp., Denver, Colo. Nomenclature of base structures was generally provided by the ACD program used as a plug-in for the structure drawing program ISIS. Racemic compounds with more than one stereocenter which are present as a single, or essentially single diastereomer, are generally referred to by indicating that the compound is racemic via (±) and the relative stereochemistry of the diastereomers indicated by the R,S designations of each center, or by their relative orientations (cis or trans)

Preparation 1

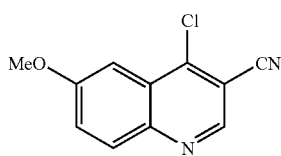

Preparation of
4-chloro-6-(methyloxy)-3-quinolinecarbonitrile a) Diethyl({[4-(methyloxy)phenyl]
amino}methylidene)propanedioate To a solution of 4-aminoanisole (50 g, 0.406 mol) in EtOH (500 mL) was added diethyl ethoxymethylenemalonate (81 mL, 0.406 mol). The reaction solution was refluxed for 4 h; LCMS showed complete reaction. The reaction solution was concentrated under reduced pressure to give the desired product (118 g, 100%) as a crystalline solid.

b) Ethyl
4-hydroxy-6-(methyloxy)-3-quinolinecarboxylate

Diethyl({[4-(methyloxy)phenyl]amino}methylidene)propanedioate (100 g, 0.34 mol) was taken up in Dowtherm (500 mL) and heated at 250° C. for 1.5 h; 75% conversion. The reaction solution was cooled, treated with hexanes (750 mL) and cooled to 0° C. in ice bath. The brown solid was filtered off and washed with hexanes (2×) and dried under vacuum to give 60 g (71%).

c) Ethyl
4-bromo-6-(methyloxy)-3-quinolinecarboxylate

To a vigorously stirred solution of ethyl 4-bromo-6-(methyloxy)-3-quinolinecarboxylate (10 g, 40.5 mmol) in DMF (40 mL) was added PBr$_3$ (4.4 mL, 42.5 mmol) via dropwise addition over 15 min at rt. The reaction was allowed to stir at ambient temperature for 45 min after which was added water (150 mL). The reaction was neutralized with aq. NaHCO$_3$. The solid was collected by filtration and washed with water and dried under vacuum to give the desired product (12 g, 95%).

d) 4-Bromo-6-(methyloxy)-3-quinolinecarboxylic
acid

To a solution of the ethyl 4-bromo-6-(methyloxy)-3-quinolinecarboxylate (12 g, 38.7 mmol) in THF (120 mL) was added 2N NaOH (45 mL, 90 mmol) dropwise over 15 min. The reaction solution was stirred for 24 h and then neutralized with 2N HCl (pH 6). The THF was removed in vacuo and the resulting aqueous solution was acidified to pH 2. The product was collected by filtration and washed with water and fully dried under vacuum (48 h). Isolated 10.8 g (100%).

e) 4-Chloro-6-(methyloxy)-3-quinolinecarboxamide

To a suspension of dried 4-bromo-6-(methyloxy)-3-quinolinecarboxylic acid (1.4 g, 5 mmol) in CH$_2$Cl$_2$ (20 mL) at 0° C. was added oxalyl chloride (2M in CH$_2$Cl$_2$, 5.0 mL, 10 mmol). After 1 h, an aliquot was quenched with NH$_4$OH and LCMS indicated desired product was formed. Excess NH$_4$OH (2 mL) was slowly added to the reaction solution, maintained at 0° C. (very exothermic), and the reaction was stirred an additional 2 h. The product was isolated via filtration to give 1.0 g (83%).

f) 4-Chloro-6-(methyloxy)-3-quinolinecarbonitrile

To a suspension of 4-chloro-6-(methyloxy)-3-quinolinecarboxamide (0.92 g, 3.9 mmol) in CH$_2$Cl$_2$ (8 mL) and Et$_3$N (4 mL) at 0° C. was added TFAA (2.0 mL, 14 mmol) over 5 min. The reaction was warmed to rt and then stirred at this temperature for 2 h (complete by LCMS). The reaction solution was partitioned between water and CH$_2$Cl$_2$ and the organic phase was collected. The aqueous phase was further extracted with CH$_2$Cl$_2$. The organic layers were combined and washed with brine and dried over MgSO$_4$. The solution was filtered and the solvent was removed in vacuo. The resulting material was redissolved in EtOAc and the product was precipitated via the addition of hexane. The solid material was collected by filtration and washed with cold hexanes and water to remove remaining Et₃N. Isolated 580 mg (65%) of pure product as an off-white solid: LC/MS (ES) m/e 219 (M+H)⁺.

Preparation 2

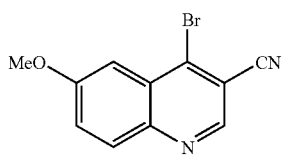

Preparation of
4-bromo-6-(methyloxy)-3-quinolinecarbonitrile a) Methyl 2-{[(1E)-(dimethylamino)methylidene]amino}-5-(methyloxy)benzoate A suspension of 5-hydroxy-anthrilinic acid (2.5 g, 16.4 mmol, 1 eq) and dimethylformamide-dimethylacetal (7 mL, 52.6 mmol, 3.2 eq) in DMF (15 mL) was heated at 150° C. for 1 h, while methanol was distilled off through a short distillation apparatus. An additional dimethylformamide-dimethylacetal (4 mL) was added and heating resumed for another hour. The reaction mixture was concentrated under vacuum to remove excess DMF and DMF-DMA. The residue was partitioned between saturated NaHCO solution and DCM. The combined extracts were dried and evaporated to give the titled compound (3.6 g, 93% yield) as dark-grey oil, which was used for the next reaction without purification.

b) 4-Hydroxy-6-(methyloxy)-3-quinolinecarbonitrile

To a cold solution of acetonitrile (2 mL, 38 mmol, 2.8 eq) in THF (30 mL) at −72° C. (Dry-ice/IPA) was added dropwise nBuLi (12 mL, 30 mmol, 2.2 eq) under argon atmosphere. The reaction mixture became an orange suspension after 1 h. A solution of methyl 2-{[(1E)-(dimethylamino)methylidene]amino}-5-(methyloxy)benzoate (3.2 g, 13.6 mmol, 1 eq) in THF (30 mL) was then added dropwise while the internal temperature was maintained at −72° C. The resulting mixture was slowly warmed to RT overnight. To the resulting light-brown suspension was added glacial acetic acid (6 mL) with slight cooling. After stirring for 1 h, the suspension was then quenched with water (60 mL) and filtered to give the titled compound (2.3 g, 85% yield).

c) 4-Bromo-6-(methyloxy)-3-quinolinecarbonitrile

To a suspension of 4-hydroxy-6-(methyloxy)-3-quinolinecarbonitrile (2.19 g, 10.9 mmol, 1 eq) in DMF (20 mL) at 0° C. was added dropwise PBr (1.1 mL, 11.6 mmol, 1.06 eq) with efficient stirring. After stirring for 1 h, the suspension was then quenched with NaOH (2.5 N, 200 mL) and filtered to give the titled compound (2.6 g, 90% yield) as an off-white solid: LC/MS (ES) m/e 264 (M+H)⁺.

Preparation 3

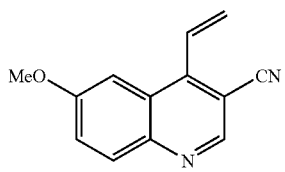

Preparation of
4-ethenyl-6-(methyloxy)-3-quinolinecarbonitrile

To a solution of 4-chloro-6-(methyloxy)-3-quinolinecarbonitrile (1.1 g, 5.03 mmol), potassium carbonate (0.76 g, 5.53 mmol), tetrakis-triphenylphosphine (120 mg, 0.10 mmol) in DME (30 mL) and H₂O (10 mL) was added 2,4,6-trivinylcycloborane-pyridine complex (1.33 g, 5.53 mmol). After stirring for 5 hours at 85° C. the reaction contents was concentrated and the product purified by chromatography on silica gel (hexanes/EtOAc, 4:1) to give a light brown solid (0.9 g, 86%): LC/MS (ES) m/e 211 (M+H)⁺.

Preparation 4

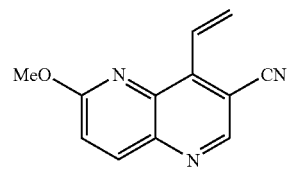

Preparation of 4-ethenyl-6-(methyloxy)-1,5-naphthyridine-3-carbonitrile a) (2-[(6-Methoxypyridin-3-ylamino)methylene]malonic acid diethyl ester A solution of 5-amino-2-methoxypyridine (Aldrich, 100 g, 0.806 mole) and diethyl ethoxymethylenemalonate (Aldrich, 163 mL, 0.806 mole) in EtOH (1 L) was heated at reflux for 4 hours, then was cooled to RT. Concentration to dryness gave the title compound (238 g, quantitative).

b) 6-Methoxy-4-oxo-1,4-dihydro-[1,5]naphthyridine-3-carboxylic acid ethyl ester

Dowtherm A (Fluka, 500 mL) was brought to boiling (250° C.) in a 2 L 3-neck flask fitted with a still-head and a reflux condenser. 2-[(6-Methoxypyridin-3-ylamino)methylene]malonic acid diethyl ester (100 g, 0.34 mole) was added portionwise over 5 min. The solution was heated at reflux for an additional 15 min, allowing some solvent to distil over. The resulting solution was cooled to RT and diluted with hexanes (750 mL). The mixture was cooled in ice for 1 hr, then the brown solid was filtered off, washed with hexanes, and dried under vacuum to afford the title compound (61.72 g, 73%).

c) 4-Bromo-6-methoxy-[1,5]naphthyridine-3-carboxylic acid ethyl ester

A suspension of 6-methoxy-4-oxo-1,4-dihydro-[1,5]naphthyridine-3-carboxylic acid ethyl ester (74.57 g, 300 mmole) in dry DMF (260 mL) under argon was stirred efficiently* in a water bath (to maintain approximately RT—may need slight ice-cooling on a large scale). Phosphorus tribromide (30.0 mL, 316 mmole) was added dropwise over 15 min and stirring was continued for an additional 30 min. Water (1 L) was added, followed by saturated sodium carbonate solution to pH 7. The solid was collected by suction filtration, washed with water and dried under vacuum over phosphorus pentoxide to give the title compound (83.56 g, 90%).

d) 4-Bromo-6-methoxy-[1,5]naphthyridine-3-carboxylic acid

2 N NaOH (300 mL, 600 mmole) was added dropwise over 30 min to a stirred solution of 4-bromo-6-methoxy-[1,5]naphthyridine-3-carboxylic acid ethyl ester (83.56 g, 268 mmole) in THF (835 mL). Stirring was continued overnight, at which time LC/MS showed that the saponification was complete. 2 N HCl was added to pH 6 and the THF was removed in vacuo. 2 N HCl was added to pH 2, then water (250 mL) was added, and the mixture was cooled thoroughly in ice. The solid was collected by suction filtration, washed with water and dried (first using a rotary evaporator at 50° C. and then under high vacuum at 50° C. overnight) to give the title compound (76.7 g, slightly over quantitative). This material was used without further purification.

(e) 4-Chloro-6-(methyloxy)-1,5-naphthyridine-3-carboxamide

To a solution of 4-Bromo-6-methoxy-[1,5]naphthyridine-3-carboxylic acid ethyl ester (840 mg, 3.0 mmol) in toluene (10 mL) was added thionyl chloride (3 mL) as one portion under N2 protection. After refluxing at 100° C. for 2 h, the mixture was concentrated and azotropically dried with toluene to afford a yellow solid, which was dissolved in anhydrous DCM (3 mL). The resulting solution was cooled down to 0° C. and treated with NH solution (5 mL, 50% in water). After stirring at 0° C. for 30 min, the reaction mixture was warmed up to 25° C. and stirred for 12 h. DCM was removed, and the solid was collected by suction filtration, washed with water and dried under vacuum over phosphorus pentoxide to give the title compound (648 mg, 91%).

(f) 4-Chloro-6-(methyloxy)-1,5-naphthyridine-3-carbonitrile

To a solution of 4-chloro-6-(methyloxy)-1,5-naphthyridine-3-carboxamide (647 mg, 2.7 mmol) in anhydrous DCM (2 mL) with triethyamine (2 mL) at 0° C. was added trifluororacetic anhydride (1 mL) slowly. The resulting solution was warmed up to 25° C. and stirred for 1 h. The mixture was partitioned between CHCl and H₂O. The aqueous layer was extracted several times with CHCl. The organic fractions were combined, concentrated and purified with column chromatography (silica, 0-25% ethyl acetate/hexane) affording the title compound as an off-white solid (540 mg, 91%): LC/MS (ES) m/e 220 (M+H)⁺.

(g) 4-Ethenyl-6-(methyloxy)-1,5-naphthyridine-3-carbonitrile

To a solution of 4-chloro-6-(methyloxy)-1,5-naphthyridine-3-carbonitrile (280 mg, 1.28 mmol), potassium carbonate (885 mg, 6.4 mmole), tetrakis-triphenylphosphine (30 mg, 0.026 mmole) in DME/H₂O (20 mL, 3:1) was added 2,4,6-trivinylcycloborane-pyridine complex (154 mg, 0.64 mmole). After stirring for 1 h at 90° C., another batch of tetrakis-triphenylphosphine (30 mg, 0.026 mmol) was added. After refluxing for another 1.5 h, the mixture contents were cooled down to room temperature and extrated with diethyl ether. The ether fractions were combined, concentrated and purified by column chromatography (silica, 0-10% ethyl acetate in hexane) to give the title compound as a light yellow solid (176 mg, 65%): LC/MS (ES) m/e 212 (M+H)⁺.

Preparation 5

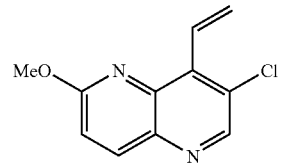

Preparation of
7-chloro-8-ethenyl-2-(methyloxy)-1,5-naphthyridine (a) 3-Chloro-6-methoxy-quinolin-4-ol 6-Methoxy-quinolin-4-ol (18.5 g) in acetic acid (750 mL) was treated with N-chlorosuccinimide (15.52 g) and the mixture was heated at 60° C. for 4.5 hr, cooled, and evaporated. Excess sodium bicarbonate solution was added and the solid collected and washed with water and dried in vacuo at 40° C. overnight, to give a yellow solid (21.3 g).
MS (ES) m/z 210/212 (M+H)⁺.

(b) 4-Bromo-3-chloro-6-methoxy-quinoline

3-Chloro-6-methoxy-quinolin-4-ol from above in dry DMF (80 mL) was cooled in ice and phosphorus tribromide (15.6 mL) added drop-wise, and the mixture was stirred, with ice-cooling for 30 minutes then allowed to warm to room temperature and stirred for a further 3.5 hours. It was cooled in ice and sodium carbonate solution was added and the solid was collected, washed well with water, and dried in vacuo, to afford a pale yellow solid (13.2 g). MS (ES) m/z 272/274/276 (M+H)⁺.

(c) 7-Chloro-2-methoxy-8-vinyl-quinoline

4-Bromo-3-chloro-6-methoxy-quinoline (0.5 g) in DME (14 mL) under argon, was treated with tetrakis(triphenylphosphine)palladium(0) (0.104 g) and the mixture stirred at room temperature for 20 minutes. Anhydrous potassium carbonate (0.25 g), water (4 mL), and vinylborane:pyridine complex was added and the mixture was heated at 100° C. for 1 hr. It was cooled, diluted with water and extracted with ether, dried (sodium sulfate) and evaporated to dryness. As starting material (4b) was still present the crude reaction product was reacted again, as above, and heated for a further 6 hours. After work-up the product was chromatographed on silica gel, eluting with DCM to afford a white solid (0.35 g): MS (ES) m/z 220/222 (M+H)⁺.

Preparation 6

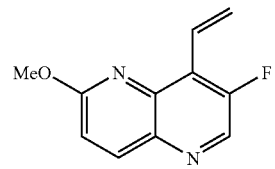

8-ethenyl-7-fluoro-2-(methyloxy)-1,5-naphthyridine a) (2-[(6-Methoxypyridin-3-ylamino)methylene]malonic acid diethyl ester A solution of 5-amino-2-methoxypyridine (Aldrich, 100 g, 0.806 mole) and diethyl ethoxymethylenemalonate (Aldrich, 163 mL, 0.806 mole) in EtOH (1 L) was heated at reflux for 4 h, then was cooled to RT. Concentration to dryness gave the title compound (238 g, quantitative).

(b) 6-Methoxy-4-oxo-1,4-dihydro-[1,5]naphthyridine-3-carboxylic acid ethyl ester Dowtherm A (Fluka, 500 mL) was brought to boiling (250° C.) in a 2 L 3-neck flask fitted with a still-head and a reflux condenser. 2-[(6-Methoxypyridin-3-ylamino)methylene] malonic acid diethyl ester (100 g, 0.34 mole) was added portionwise over 5 min. The solution was heated at reflux for an additional 15 min, allowing some solvent to distil over. The resulting solution was cooled to room temperature and diluted with hexane (750 mL). The mixture was cooled in ice for 1 h, then the brown solid was filtered off, washed with hexane, and dried under vacuum to afford the title compound (61.72 g, 73%).

(c) 4-Bromo-6-methoxy-[1,5]naphthyridine-3-carboxylic acid ethyl ester

A suspension of 6-methoxy-4-oxo-1,4-dihydro-[1,5]naphthyridine-3-carboxylic acid ethyl ester (74.57 g, 300 mmol) in dry DMF (260 mL) under argon was stirred efficiently* in a water bath (to maintain approximately room temperature— may need slight ice-cooling on a large scale). Phosphorus tribromide (30.0 mL, 316 mmol) was added dropwise over 15 min and stirring was continued for an additional 30 min. Water (1 L) was added, followed by saturated sodium carbonate solution to pH 7. The solid was collected by suction filtration, washed with water and dried under vacuum over phosphorus pentoxide to give the title compound (83.56 g, 90%).

(d) 4-Bromo-6-methoxy-[1,5]naphthyridine-3-carboxylic acid

2 N NaOH (300 mL, 600 mmol) was added dropwise over 30 min to a stirred solution of 4-bromo-6-methoxy-[1,5] naphthyridine-3-carboxylic acid ethyl ester (83.56 g, 268 mmol) in THF (835 mL). Stirring was continued overnight, at which time LC/MS showed that the saponification was complete. 2 N HCl was added to pH 6 and the THF was removed in vacuo. 2 N HCl was added to pH 2, then water (250 mL) was added, and the mixture was cooled thoroughly in ice. The solid was collected by suction filtration, washed with water and dried (first using a rotary evaporator at 50° C. and then under high vacuum at 50° C. overnight) to give the title compound (76.7 g, slightly over quantitative). This material was used without further purification.

(e) 4-Bromo-6-methoxy-[1,5]naphthyridin-3-ylamine

A suspension of 4-bromo-6-methoxy-[1,5]naphthyridine-3-carboxylic acid (50 g, 177 mmol) in dry DMF (600 mL) was treated with triethylamine (222.5 mL, 1.60 mole), tert-butanol (265 mL, 2.77 mole) and diphenylphosphoryl azide (41.75 mL, 194 mmol). The reaction was stirred under argon at 100° C. for 1 h, then was cooled to room temperature and concentrated to low volume. Ethyl acetate and excess aqueous sodium bicarbonate solution were added, the mixture was shaken, and some insoluble solid was filtered off. The layers were separated and the organic phase was washed with water (2×) and dried (MgSO$_4$). Concentration to dryness gave a crude mixture of 4-bromo-6-methoxy-[1,5]naphthyridin-3-ylamine (minor product) and (4-bromo-6-methoxy-[1,5] naphthyridin-3-ylamine)carbamic acid tert-butyl ester (major product) along with impurities.

Without further purification, this mixture was dissolved in CH$_2$Cl$_2$ (150 mL) and treated with trifluoroacetic acid (100 mL). The reaction was stirred for 3 h then was concentrated to dryness. The residue was partitioned between CHCl$_3$ and saturated sodium bicarbonate solution and the layers were separated. The aqueous phase was extracted with CHCl$_3$, and the combined organic fractions were dried (MgSO$_4$) and concentrated to low volume. The solid was collected by suction filtration, washed with a small volume of CHCl$_3$ and dried under vacuum to afford a first crop of the title compound (31.14 g). The filtrate was purified by flash chromatography on silica gel (30% EtOAc in CHCl$_3$) to afford further material (2.93 g, total=34.07 g, 76%). Alternatively, the filtrate was left at room temperature overnight and then filtered to give a second crop of the title compound (2.5 g).

(f) 4-Bromo-6-methoxy-[1,5]naphthyridine-3-diazonium tetrafluoroborate

A solution of 4-bromo-6-methoxy-[1,5]naphthyridin-3-ylamine (25.2 g, 99.2 mmol) in dry THF (400 mL) was maintained at −5° C. while nitrosonium tetrafluoroborate (12.9 g, 110 mmol) was added portionwise over 30 min (approximately 2 g portions). The reaction was continued for an additional 1 h at −5° C., at which time TLC* and LC/MS indicated that the reaction was complete. The orange solid was collected by suction filtration, washed with ice-cold THF and dried under vacuum to provide the title compound (31.42 g, 90%).

(g) 4-Bromo-3-fluoro-6-methoxy-[1,5]naphthyridine

A suspension of 4-bromo-6-methoxy-[1,5]naphthyridine-3-diazonium tetrafluoroborate (31.42 g, 89.0 mmol) in decalin (mixed isomers, 500 mL) in a 2 L flask* was heated to 180° C. and held at this temperature for 5 min. The mixture was cooled and diluted with CHCl$_3$ (500 mL, to keep the product in solution), and the resulting mixture was stirred vigorously for 30 min to break up a black solid byproduct. The mixture was then poured onto a column of silica gel and the column was eluted with CHCl$_3$ to remove decalin and then with 3% EtOAc/CHCl$_3$ to afford the title compound (9.16 g, 40%).

(h) 8-ethenyl-7-fluoro-2-(methyloxy)-1,5-naphthyridine

To a solution of 8-bromo-7-fluoro-2-(methyloxy)-1,5-naphthyridine (2.0 g, 7.81 mmol), potassium carbonate (1.08 g, 7.81 mmol), tetrakis-triphenylphosphine (90 mg, 0.08 mmol) in DME (60 mL) and H$_2$O (20 mL) was added 2,4,6-trivinylcycloborane-pyridine complex (0.94 g, 3.91 mmol). After stirring for 10 h at 85° C. the reaction contents were concentrated and the product purified by chromatography (silica, 25% EtOAc in hexane) to give the title compound as a low melting solid (1.43 g, 90%): MS (ES) m/z 206 (M+H)$^+$.

Preparation 7

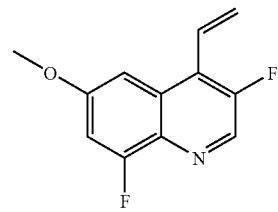

Preparation of 4-ethenyl-3,8-difluoro-6-(methoxy)quinoline a) 3-fluoro-4-nitrophenyl methyl ether

A solution of 3-fluoro-4-nitrophenol (25 g, 0.159 mmol) in acetonitrile (500 mL) and methanol (500 mL) was treated with diisopropyl ethylamine (28 mL). The reaction mixture was cooled in an ice-bath and after 30 minutes, trimethylsilyldiazomethane was added dropwise. The mixture was stirred at room temperature for 18 hours then evaporated under vacuum to afford the product as an oil (29.4 g, 100%). MS (+ve ion electrospray) m/z 172 (MH+).

b) 2-fluoro-4-(methoxy)aniline

A solution of 3-fluoro-4-nitrophenyl methyl ether (28.1 g, 164 mmol) in ethanol (200 mL) was hydrogenated with palladium on charcoal. The reaction mixture was filtered through Kieselguhr and evaporated under vacuum to afford the product as an oil (22.8 g, 98%); MS (+ve ion electrospray) m/z 141 (MH+).

c) ethyl 8-fluoro-6-(methoxy)-4-oxo-1,4-dihydro-3-quinolinecarboxylate

A mixture of aniline 2-fluoro-4-(methoxy)aniline (22.8 g, 162 mmol) and diethyl [(ethyloxy)methylidene]propanedioate (32.6 mL) were heated to reflux in Dowtherm A under a flow of argon. After 15 minutes (when all ethanol was removed), the mixture was allowed to cool down and was diluted with pentane. A precipitate was formed which was triturated with pentane, filtered and dried under vacuum to afford the product as an oil (33.06 g, 77%); MS (+ve ion electrospray) m/z 265 (M+H)+.

d) ethyl 4-bromo-8-fluoro-6-(methoxy)-3-quinolinecarboxylate

To a solution of ethyl 8-fluoro-6-(methoxy)-4-oxo-1,4-dihydro-3-quinolinecarboxylate (12 g, 45 mmol) in DMF (56 ml) was added dropwise phosphorus tribromide (4.5 ml, 47 mmol) over fifteen minutes (slightly exothermic). The reaction was held at 0° C., with an ice bath, for one hour and allowed to warm to room temperature then stirred for a further 2 hours. The mixture was then diluted with water (400 mL). A solution of sodium bicarbonate was added to reach pH 7. The reaction mixture was stirred for one hour at 0° C. then filtered. The precipitate was washed with water and dried in vacuo to afford the product as a yellow solid (12.2 g, 82%).
MS (+ve ion electrospray) m/z 329 (MH+).

e) 4-bromo-8-fluoro-6-(methoxy)-3-quinolinecarboxylic acid

A solution of ethyl 4-bromo-8-fluoro-6-(methoxy)-3-quinolinecarboxylate (12.2 g, 37.3 mmol) in tetrahydrofuran (450 mL) was diluted by addition of a solution of sodium hydroxide 2N (27 mL) in water (75 mL). The reaction mixture was stirred overnight at room temperature then acidified to pH 3 with a solution of hydrogen chloride 5N. The solvents were evaporated to half the volume in vacuo. The reaction mixture was acidified to pH 1 by further addition of hydrogen chloride 5N, cooled to 4° C. for 30 minutes then filtered. The precipitate was dried in vacuo to afford the product as a white solid (10.1 g, 90%); MS (+ve ion electrospray) m/z 301 (MH+).

f) 1,1-dimethylethyl[4-bromo-8-fluoro-6-(methoxy)-3-quinolinyl]carbamate

A solution of 4-bromo-8-fluoro-6-(methoxy)-3-quinolinecarboxylic acid (7.5 g, 25 mmol) in butanol (40 mL) and DMF (88 mL) was treated with triethylamine (30 mL) then diphenylphosphoryl azide (5.8 mL, 27.5 mmol). The reaction mixture was heated at 100° C. for two hours under argon atmosphere. The mixture was then cooled down to room temperature and evaporated to half the volume in vacuo. Water (100 mL) was added to the mixture under vigorous stirring. A precipitate was formed, filtered and dried in vacuo. This crude product was chromatographed on silica gel eluting with 10% methanol in dichloromethane to afford the product as a white solid (6.4 g, 69%). MS (+ve ion electrospray) m/z 372 (MH+).

g) 4-bromo-8-fluoro-6-(methoxy)-3-quinolinamine 1,1-Dimethylethyl[4-bromo-8-fluoro-6-(methoxy)-3-quinolinyl]carbamate (6.4 g, 17.3 mmol)) was treated with trifluoroacetic acid (50 ml) in dichloromethane (50 ml) at room temperature for two hours then evaporated to dryness. The residue was basified with sodium bicarbonate. A precipitate was formed which was filtered and dried in vacuo to afford the product as a white solid (4.7 g, 100%). MS (+ve ion electrospray) m/z 272 (MH+).

h) 4-bromo-6-methoxy-8-fluoroquinolin-3-yl-diazonium tetrafluoroborate

A solution of 4-bromo-8-fluoro-6-(methoxy)-3-quinolinamine (3 g, 11.1 mmol) in anhydrous THF (40 mL) cooled down to −9° C., with an ethanol/ice bath, was treated with nitrosonium tetrafluoroborate (1.4 g, 12.2 mmol) added portionwise over 20 minutes. The reaction mixture was stirred for 30 minutes at −2° C. under argon atmosphere. A precipitate was formed which was filtered, washed with cold THF and dried in vacuo overnight to afford the product as a yellow solid (3.2 g, 79%). MS (+ve ion electrospray) m/z 370 (MH+).

i) 4-bromo-3,8-difluoro-6-(methoxy)quinoline

4-Bromo-6-methoxy-8-fluoroquinolin-3-yl-diazonium tetrafluoroborate (2.4 g, 6.5 mmol) was added to hot Decalin® (45 mL). The reaction mixture was maintained at 170° C. for 5 minutes. Cold Decalin® (20 mL) was added and the reaction mixture was cooled down with an ice bath. The Decalin® layer was decanted off the dark residue and washed with a solution of sodium bicarbonate, brine and water. The organic layer was dried over magnesium sulfate. Solvents from the work-up were evaporated under vacuum and the Decalin® layer was cooled down to 4° C. A precipitate was formed (product) which was filtered off. The decalin filtrate and the dark residue obtained before work-up were combined and chromatographed eluting with dichloromethane to afford the further product as a white solid (combined yield, 0.75 g, 42%). MS (+ve ion electrospray) m/z 275 (MH+).

j) 4-ethenyl-3,8-difluoro-6-(methoxy)quinoline

4-Bromo-3,8-difluoro-6-(methoxy)quinoline (0.63 g, 2.3 mmol) in DME (26 mL) under argon, was treated with tetrakis (triphenylphosphine)palladium(0) (0.13 g, 0.115 mmol) and the mixture stirred at room temperature for 20 minutes. Anhydrous potassium carbonate (0.32 g, 2.3 mmol), water (7 mL), and vinylborane:pyridine complex (see F. Kerins and D O'Shea J. Org. Chem. 2002, 67, 4968-4971) (0.22 g, 0.92 mmol) were added and the mixture was heated at 100° C. for 2 hr. It was cooled, diluted with water and extracted with ether, dried over magnesium sulfate and evaporated to dryness. After work-up the product was chromatographed on silica gel, eluting with 10% methanol in DCM to afford a white solid (0.46 g, 90%). MS (+ve ion electrospray) m/z 221 (MH+).

Preparation 8

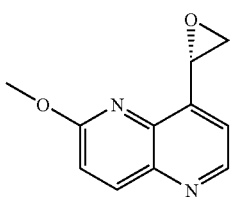

Preparation of (S)-2-(6-Methoxy-[1,5]-naphthyridin-4-yl)oxirane a) 4-Hydroxy-6-methoxy-[1,5]-naphthyridine 5-Amino-2-methoxypyridine (55 g, 0.44 mol) in methanol (1000 ml) with methyl propiolate (40 ml, 0.44 mol) was stirred for 48 hours, then evaporated and the product purified by chromatography on silica gel (dichloromethane) followed by recrystallisation from dichloromethane-hexane (44.6 g, 48%).

The unsaturated ester (10.5 g, 0.05 mol) in warm Dowtherm A (50 ml) was added over 3 minutes to refluxing Dowtherm A, and after a further 20 minutes at reflux the mixture was cooled and poured into ether. The precipate was filtered to give the title compound (6.26 g, 70%)

b) Bromomethyl-(6-methoxy-[1,5]-naphthyridin-4-yl)-ketone

4-Hydroxy-6-methoxy-[1,5]-naphthyridine (10 g, 0.057 mol) in dichloromethane (200 ml) containing 2,6-lutidine (9.94 ml, 0.086 mol) and 4-dimethylaminopyridine (0.07 g, 0.0057 mol) was cooled in ice and treated with trifluoromethanesulfonic anhydride (10.5 ml, 0.063 mol). After stirring for 2.5 hours the mixture was washed with saturated ammonium chloride solution, dried, evaporated and purified on silica (dichloromethane). The triflate (13.2 g, 0.044 mol) in DMF (200 ml) with triethylamine (12 ml, 0.086 mol) butyl vinyl ether (22 ml, 0.17 mol), palladium (II) acetate (0.97 g, 0.0044 mol) and 1,3-bis(diphenylphosphino)propane (1.77 g, 0.0044 mol) was heated at 60° C. for 3 hours then evaporated and chromatographed on silica gel (dichloromethane) to give a yellow solid (10.7 g, 95%). This was dissolved in THF (250 ml), water (40 ml) and treated with N-bromosuccinimide (7.4 g. 0.042 mol) for 1 hour, then evaporated and chromatographed on silica gel (dichloromethane) to give the ketone (10.42 g, 98%).

c) (R)-2-Bromo-1-(6-methoxy-[1,5]-naphthyridin-4-yl)ethanol

Bromomethyl-(6-methoxy-[1,5]-naphthyridin-4-yl)-ketone (6.6 g, 0.023 mol) in toluene was treated with (+)-B-chlorodiisopinocamphenylborane ((+)-DIP-chloride) (12 g, 0.037 mol) and stirred overnight, then diethanolamine (15 g, 0.14 mol) added and the mixture stirred for 3 hours, filtered and evaporated. Chromatography on silica gel (ethyl acetate-hexane) gave a white solid (4.73 g, 73%).

d) (R)-2-(6-Methoxy-[1,5]-naphthyridin-4-yl)oxirane (R)-2-Bromo-1-(6-methoxy-[1,5]-naphthyridin-4-yl) ethanol (4.8 g, 0.017 mol) in methanol (20 ml) was stirred with potassium carbonate (2.6 g, 0.019 mol) for 1 hour, then evaporated and chromatographed on silica gel (ethyl acetate-hexane-dichloromethane) to give a solid (3.14 g, 92%), (91% ee by chiral HPLC).

MS (+ve ion electrospray) m/z 203 (M+H+).

Preparation 9

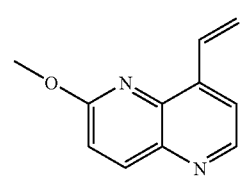

Preparation of 8-ethenyl-2-(methyloxy)-1,5-naphthyridine

To a solution of 6-(methyloxy)-1,5-naphthyridin-4-yl trifluoromethanesulfonate (from Prep. 5b) (5.0 g, 16.23 mmole) in DME (80 mL) and H$_2$O (40 mL) was added trivinyl boronate (1.96 g, 8.1 mmole), K$_2$CO$_3$ (2.23 g, 16.23 mmole) and Pd(PPh$_3$)$_4$ (0.19 g, 0.16 mmole). After 3 h at 90° C. under N$_2$, the reaction solution was concentrated under vacuum and purified on silica (hexanes, EtOAc, 4:1) to give a yellow oil (2.44 g, 81%): LC-MS (m/z) (ES) 187 (M+H)$^+$.

Preparation 10

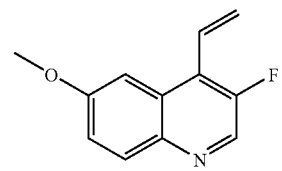

Preparation of 4-ethenyl-3-fluoro-6-(methyloxy)quinoline a) 4-Hydroxy-6-methoxy-quinoline-3-carboxylic acid ethyl ester A solution of 4-methoxyaniline (40 g, 0.32 mole) and diethyl ethoxymethylenemalonate (65 mL, 0.32 mole) in Dowtherm A (500 mL) was heated at reflux in a flask fitted with side-arm and condenser, and heating was continued until all the ethanol had distilled off (ca. 0.5 hr). The solution was cooled and pentane was added to give a sticky precipitate. The solvents were decanted off and the residue was treated with more pentane and allowed to stand overnight. The solid was filtered off and washed well with pentane to give the title compound (62.4 g; 78%, contains traces of Dowtherm A).

b) 4-Bromo-6-methoxy-quinoline-3-carboxylic acid ethyl ester

PBr$_3$ (64.5 g, 22.5 mL, 0.239 mole) was added dropwise to a stirred, ice cold suspension of 4-hydroxy-6-methoxyquinoline-3-carboxylic acid ethyl ester (59 g, 0.239 mole) in DMF (750 mL); the temperature rose to 15-20° C. for 30 min and then dropped to ca. 5° C. (the starting material dissolved fairly quickly and a new solid precipitated out). After 3 hr the solid was collected, washed sequentially with cold DMF, hexane, and water, then was dried at 40° C. in vacuo overnight to give the title compound (41 g, 78%): LC/MS (ES) m/e 310/312 (M+H)$^+$.

c) 4-Bromo-6-methoxyquinoline-3-carboxylic acid

4-Bromo-6-methoxy-quinoline-3-carboxylic acid ethyl ester (41 g, 0.132 mole), partially dissolved in THF (600 mL), was treated dropwise with aqueous 2 M sodium hydroxide (198.4 mL, 0.396 mole). After 24 hr, the reaction was complete by TLC (2% MeOH/CH$_2$Cl$_2$). The mixture was neutralized with 5 M HCl then the THF was removed in vacuo. The residue was dissolved in water and acidified with 5 M HCl. The solid product was collected under suction, washed well with water, and dried in vacuo to give the title compound (34 g, 91%) as a white solid: MS (ES) m/e 282/284 (M+H)$^+$.

d) (4-Bromo-6-methoxy-quinolin-3-yl)-carbamic acid tert-butyl ester

To a solution of 4-Bromo-6-methoxyquinoline-3-carboxylic acid (34 g, 0.121 mole), triethylamine (141 mL) and tert-butanol (181 mL) in dry DMF (400 mL) was added diphenylphosphoryl azide (36.6 g, 28.6 mL, 0.133 mole). The mixture was heated at 100° C. for 1 h (see Note), then cooled and concentrated. The residue was dissolved in CH$_2$Cl$_2$ and washed with water (some insoluble material was removed by filtration). The aqueous phase was extracted with dichloromethane and the combined organics were dried (Na$_2$SO$_4$) and concentrated. Chromatography on silica gel (1 kg, 1:1 ether/light petroleum ether) gave the carbamate (22.7 g, 53%): MS (ES) m/e 309/311 (M+H)$^+$, 354/6.

Further elution with ether gave several mixed fractions then pure 3-amino-4-bromo-6-methoxyquinoline (2.0 g, 6.5%): MS (ES) m/e 309/311 (M+H)$^+$, 254/6.

e) 3-Amino-4-bromo-6-methoxyquinoline (4-Bromo-6-methoxy-quinolin-3-yl)-carbamic acid tert-butyl ester (22.7 g, 0.0643 mole) was dissolved in CH$_2$Cl$_2$ (200 mL) and treated with trifluoroacetic acid (100 mL). After 3.5 hr at RT, the mixture was concentrated and the residue was dissolved in water. The solution was made basic with aqueous sodium carbonate. The precipitate was filtered off, washed with water, and dried at 40° C. in vacuo overnight, to give the title compound (16.46 g, 101%) as a white solid: MS (ES) m/e 254/256 (M+H)$^+$.

f) 4-Bromo-3-methoxyquinolin-3-yl-diazonium tetrafluoroborate

3-Amino-4-bromo-6-methoxyquinoline (18.4 g, 0.0727 mole) was dissolved in dry THF (250 mL) and the solution was cooled to −8° C. (EtOH-ice bath). Nitrosonium tetrafluoroborate (9.34 g, 0.08 mole) was added in portions over 10 min, keeping the temperature less than −2° C. The mixture was stirred at −5 to 0° C. for 30 min, then the yellow precipitate was filtered off and washed sequentially with cold THF and hexane. Drying in vacuo gave the title compound (19.4 g, 76%) an insoluble orange-yellow solid.

g) 4-Bromo-3-fluoro-6-methoxyquinoline

A well stirred solution of decahydronaphthalene (mixed isomers, 120 mL) was heated to ca. 167-170° C. (internal temperature) and the diazonium tetrafluoroborate salt (6.0 g) was added portionwise over 30 sec, when the solid turned black. The reaction mixture was immediately cooled and the decahydronaphthalene was filtered off. The filtrate was saved for further processing. The residue was extracted with dichloromethane (3×). Some insoluble material remained. The solution was concentrated and the residue was chromatographed on silica gel (CH$_2$Cl$_2$ then CHCl$_3$) to give the title compound (1.1 g) as a white solid: MS (ES) m/e 256/258 (M+H)$^+$, Rt=2.65 min. About 4% of a dibromo impurity was present: MS (ES) m/e 316/318/320 (M+H)$^+$ Rt=2.94 min.

The decahydronaphthalene solution was treated with excess ethereal HCl and the solid hydrochloride salt was collected and washed with hexane. This was converted to the free base by reaction with aqueous sodium carbonate followed by extraction with CH$_2$Cl$_2$. This gave additional title compound (0.87 g; total yield=1.97 g, 45%).

h) 4-ethenyl-3-fluoro-6-(methyloxy)quinoline

4-Bromo-3,fluoro-6-(methoxy)quinoline (2.3 mmol) in DME (26 mL) under argon, was treated with tetrakis(triphenylphosphine)palladium(0) (0.13 g, 0.115 mmol) and the mixture stirred at room temperature for 20 minutes. Anhydrous potassium carbonate (0.32 g, 2.3 mmol), water (7 mL), and vinylborane:pyridine complex (see F. Kerins and D O'Shea J. Org. Chem. 2002, 67, 4968-4971) (0.22 g, 0.92 mmol) were added and the mixture was heated at 100° C. for 2 hr. It was cooled, diluted with water and extracted with ether, dried over magnesium sulfate and evaporated to dryness. After work-up the product was chromatographed on silica gel, eluting with 10% methanol in DCM to afford a white solid (0.44 g, 90%). MS (+ve ion electrospray) m/z 203 (MH+).

Preparation 10a

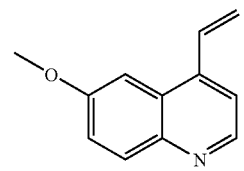

Preparation of 4-ethenyl-6-(methyloxy)quinoline a) 4-bromo-6-methoxy quinoline

To a stirred solution of 4-hydroxy-6-methoxyquinoline (1.20 g, 70.5 mmole) in DMF (60 mL) at RT was added PBr$_3$ (8.0 mL, 84.6 mmole) dropwise. After 2 h, the reaction contents were poured onto H$_2$O (300 mL) and the product filtered and washed with H$_2$O to give, after drying under high vacuum, the title compound (14.3 g, 87%) as a light yellow solid: LC-MS (ES) m/e 233 (M+H)$^+$.

b) 4-ethenyl-6-(methyloxy)quinoline

To a solution of 6-(methyloxy)-1,5-naphthyridin-4-yl trifluoromethanesulfonate (5.0 g, 16.23 mmol) in DME (80 mL)

and H₂O (40 mL) was added trivinyl boronate (1.96 g, 8.1 mmol), K₂CO₃ (2.23 g, 16.23 mmol) and Pd(PPh₃)₄ (0.19 g, 0.16 mmol). After 3 h at 90° C. under N₂, the reaction solution was concentrated under vacuum and purified on silica (hexane/EtOAc, 4:1) to give the title compound as a yellow oil (2.44 g, 81%): LC/MS (m/z) (ES) 186 (M+H)⁺.

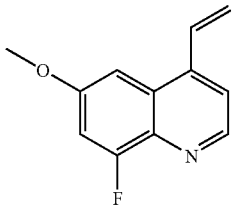

Preparation 10b

Preparation of
4-ethenyl-8-fluoro-6-(methyloxy)quinoline a) 8-Fluoro-6-methoxy-quinolin-4-ol 2-Fluoro-4-methoxyphenylamine (3.80 g, 26.7 mmole) and methyl propiolate (2.37 ml, 0.267 mole) in methanol (100 ml) was stirred for 72 hours at room temperature, then heated at 50° C. for 24 hours. It was evaporated and the product purified by chromatography on silica gel (dichloromethane) to give a solid (1.66 g), a portion of which was recrystallised from dichloromethane-hexane. The unsaturated ester (0.96 g) in warm Dowtherm A (5 ml) was added over 3 minutes to refluxing Dowtherm A (15 ml), and after a further 20 minutes at reflux the mixture was cooled and poured into diethyl ether. The precipitate was filtered to give the title compound (0.50 g, 61%). MS (ES) m/e 196 (M+H)⁺.

b) 1,1,1-Trifluoromethanesulfonic acid
8-fluoro-6-methoxy-quinolin-4-yl ester

8-Fluoro-6-methoxyquinolin-4-ol (0.48 g, 2.46 mmole) and dimethylaminopyridine (0.03 g) in dichloromethane (20 mL) and 2,6-lutidine (0.48 mL) was treated dropwise with triflic anhydride (0.48 ml) and the mixture was stirred at room temperature for 4 hours. It was washed with saturated ammonium chloride, dried, evaporated, and chromatographed on silica gel (dichloromethane) to afford a yellow solid (0.69 g, 86%). MS (ES) m/e 326 (M+H)⁺.

c) 4-ethenyl-8-fluoro-6-(methyloxy)quinoline

To a solution of 1,1,1-trifluoromethanesulfonic acid 8-fluoro-6-methoxy-quinolin-4-yl ester (1.0 g, 3.1 mmol), potassium carbonate (1.28 g, 9.3 mmole), tetrakis-triphenylphosphine (350 mg, 0.3 mmole) in DME/H₂O (20 mL, 3:1) was added 2,4,6-trivinylcycloborane-pyridine complex (460 mg, 1.5 mmole). After stirring for 3 h at 90° C., the mixture contents were cooled to room temperature and extracted with diethyl ether. The ether fractions were combined, concentrated and purified by column chromatography (silica, 0-10% ethyl acetate in hexane) to give the title compound as a light yellow solid (428 mg, 65%): LC/MS (ES) m/e 212 (M+H)⁺.

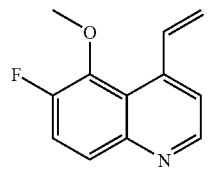

Preparation 10c

Preparation of
4-ethenyl-6-fluoro-5-(methyloxy)quinoline a) 4-bromo-2-fluorophenyl ethyl carbamate A solution of 4-bromo-2-fluorophenol (25 g, 130 mmol) and triethyl amine (21.6, 155 mmoles) in DCM (120 mL) at 0 C was treated with a solution of ethylchlororformate (14.8 mL, 155 mmol) in DCM (40 mL) dropwise. The reaction mixture was stirred at 0 C for 1 h and allowed to reach room temperature. The reaction mixture was washed with water and dried over magnesium sulfate. The reaction solution was concentrated under vacuum to afford the title compound (32 g, 93%) as a colorless oil. LC-MS (ES) (M+H)⁺ m/z=263.

b) 4-bromo-2-fluoro-5-nitrophenyl ethyl carbonate

To a solution of 4-bromo-2-fluorophenyl ethyl carbamate (32 g, 130 mmol) in concentrated sulfuric acid (55 mL) at 10 C, was added fuming nitric acid (8.5 mL, 195 mmol) dropwise. After 2 h, the reaction mixture was poured onto ice-water and extracted several times with ethyl acetate. The combined organics were dried over magnesium sulfate and evaporate under vacuum to afford the title compound (35 g, 92%) as a yellow oil. LC-MS (ES) (M+H)⁺ m/z=309.

c) 4-bromo-2-fluoro-5-nitrophenol

A solution of 4-bromo-2-fluoro-5-nitrophenyl ethyl carbonate (35 g, 113 mmole) in MeOH (200 mL) was treated with sodium bicarbonate (19 g, 227 mmole). The reaction mixture was stirred at 60 C for 4 hours. The methanol was evaporated under vacuum. Water (55 mL) was added to the residue and the aqueous layer was acidified to pH=5 by addition of a solution of 6N hydrogen chloride. The aqueous layer was extracted twice with ethyl acetate. The combined organic layers were dried over magnesium sulfate and evaporated under vacuum to afford the title compound (25 g, 93%) as a yellow solid. LC-MS (ES) (M+H)⁺ m/z=237.

d) 4-bromo-2-fluoro-5-nitrophenyl methyl ether

A solution of 4-bromo-2-fluoro-5-nitrophenol (25 g, 106 mmol) in DMF (200 mL) was treated with potassium carbonate (28.9 g, 212 mmol) and methyl iodide (12.8 mL, 212 mmol). The reaction mixture was stirred at 60 C for 5 hours and evaporated in vacuo. The mixture was partitioned between water and ethyl acetate. The organic layer was dried over magnesium sulfate and evaporated under vacuum to afford the product (25.6 g, 97%) as a yellow solid. LC-MS (ES) (M+H)⁺ m/z=251.

e) 2-bromo-4-fluoro-(methyloxy)aniline

A mixture of 4-bromo-2-fluoro-5-nitrophenyl methyl ether (25.5 g, 102 mmol), acetic acid (250 mL), ethanol (250 mL)

and iron powder (22.7 g, 408 mmol) was heated to 100 C for 4 hours. The reaction mixture was cooled to room temperature, diluted with water, neutralised by addition of potassium carbonate and filtered through Celite. The aqueous layer was extracted thrice with DCM. The combined organic layers were dried over magnesium sulfate and evaporated under vacuum to afford the title compound (15 g, 67%) as a white solid. LC-MS (ES) (M+H)$^+$ m/z=220.

f) 5-({[2-bromo-4-fluoro-5-(methyloxy)phenyl] amino}methylidene)-2,2-dimethyl-1,3-dioxane-4,6-dione A mixture of 2-bromo-4-fluoro-(methyloxy)aniline (15 g, 68 mmol), 2,2-dimethyl-[1,3]dioxane-4,6-dione (11.8 g, 82 mmol) and trimethylorthoformate (13.6 mL) in ethanol (70 mL) was refluxed for 3 hours. After cooling, the solid was filtered off, washed with ethanol and air dried. To give the product (23.3 g, 92%) as a white solid. LC-MS (ES) (M+H)$^+$ m/z=374.

g) 8-bromo-6-fluoro-5-(methyloxy)-4-(1H)-quinilone

Intermediate 5-({[2-bromo-4-fluoro-5-(methyloxy)phenyl]amino}methylidene)-2,2-dimethyl-1,3-dioxane-4,6-dione (13 g, 34.8 mmol) was slowly added over five minutes to refluxing Dowtherm A (40 mL). After an additional five minutes at reflux, the mixture was allowed to cool to room temperature and ether was added. The product was filtered off, thoroughly washed with ether and then dried to afford the title compound (5.4 g, 57%) as a gold colored solid. LC-MS (ES) (M+H)$^+$ m/z=273.

h) 6-fluoro-5-(methyoxy)-4(1H)-quinilinone

A suspension of 8-bromo-6-fluoro-5-(methyloxy)-4-(1H)-quinilone (3.5 g, 12.8 mmol) in dioxane/water (300/100 mL) was treated with a solution of sodium hydroxide 1N (12.8 mL, 12.8 mmol). The solution was hydrogenated with palladium on charcoal. The reaction mixture was filtered through Kieselguhr, acidified by addition of a solution of hydrogen bromide and evaporated to dryness. The residue was treated with water (30 mL), filtered and dried in vacuo to afford the product (3.0 g, 60%) as a white solid. LC-MS (ES) (M+H)$^+$ m/z=194.

i) 4-bromo-5-fluoro-6-methyloxy)quinoline

To a solution of 6-fluoro-5-(methyoxy)-4(1H)-quinilinone (2 g, 10 mmole) in DMF (13 mL) was added dropwise phosphorus tribromide (1.2 mL, 12.4 mmol) over 5 minutes. The reaction was allowed to cool to room temperature and was then diluted with ice-water and stirred 1 hour, then diluted with additional water. The product was filtered, washed with water and dried in vacuo to afford the product (1.8 g, 71%) as a white solid.
LC-MS (ES) (M+H)$^+$ m/z=257.

j) 4-ethenyl-6-fluoro-5-(methyloxy)quinoline

To a solution of 4-bromo-5-fluoro-6-(methyloxy)quinoline (0.80 g, 3.1 mmol), potassium carbonate (1.28 g, 9.3 mmole), tetrakis-triphenylphosphine (350 mg, 0.3 mmole) in DME/H$_2$O (20 mL, 3:1) was added 2,4,6-trivinylcycloborane-pyridine complex (460 mg, 1.5 mmole). After stirring for 3 h at 90° C., the mixture contents were cooled to room temperature and extracted with diethyl ether. The ether fractions were combined, concentrated and purified by column chromatography (silica, 0-10% ethyl acetate in hexane) to give the title compound as a light yellow solid (0.41 g, 65%): LC/MS (ES) m/e 205 (M+H)$^+$.

Preparation 10d

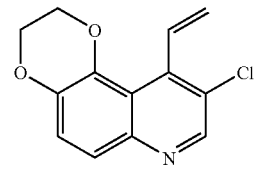

Preparation of 9-Chloro-10-vinyl-2,3-dihydro-[1,4] dioxino[2,3-f]quinoline a) 7-Bromo-2,3-dihydro-benzo[1,4]dioxin-6-ylamine

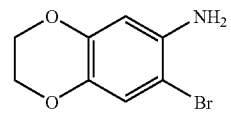

A solution of 2,3-dihydro-benzo[1,4]dioxin-6-ylamine (80 g, 530 mmol, 1 eq) in tetrahydrofuran (1000 mL) at −78° C. was treated with concentrated sulfuric acid (50 drops) then N-bromosuccinimide (94.2 g, 530 mmol, 1 eq) was added over 0.5 hour. After the addition the mixture was stirred at −78° C. for 1 hour then treated with solid sodium carbonate (12 g, 113 mmol, 0.21 eq). The mixture was evaporated and the residue partitioned between ether and water. The organic extract was dried, filtered and evaporated to give to oil that was chromatographed on silica gel eluting with dichloromethane to afford oil (141 g, 92%). LC/MS (ES) m/z 230 (MH$^+$ 91%); 1H-NMR (400 MHz, d6-DMSO), 6.85 (1H, s, CHCNH$_2$), 6.34 (1H, s, CHCBr), 4.79 (2H, s, NH2), 4.16 (4H, dd, J=16, 2×(CH2O))

b) 5-[(7-Bromo-2,3-dihydro-benzo[1,4]dioxin-6-ylamino)-methylene]-2,2-dimethyl-[1,3]dioxane-4,6-dione

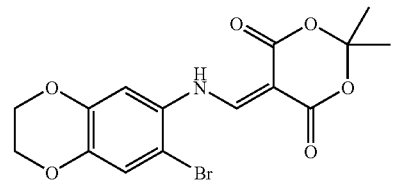

A mixture of 7-Bromo-2,3-dihydro-benzo[1,4]dioxin-6-ylamine (14.8 g, 64.3 mmol, 1 eq), triethyl orthoformate (12.7 cm3, 77.2 mmol, 1.2 eq) and 2,2-dimethyl-[1,3]dioxane-4,6-dione (Meldrum's acid) (11.1 g, 77.2 mmol, 1.2 eq) in ethanol (70 mL) was heated to reflux. After 1 hour the mixture was allowed to cool to room temperature then filtered, washing with ethanol then ether, to afford a white solid (22.9 g, 93%). LC/MS (ES) m/z 384 (MH$^+$ 100%); 1H-NMR (400 MHz, d4-DMSO), 11.43 (1H, br d, J=20, NH), 8.6 (1H, d, J=12, NCH═C), 7.49 (1H, s, CHCBr), 7.28 (1H, s, CHCN), 4.30-4.27 (4H, m, 2×(CH2O)), 1.68 (6H, s, (CH3)2C)

c) 6-Bromo-2,3-dihydro-7H-[1,4]dioxino[2,3-f]quinolin-10-one

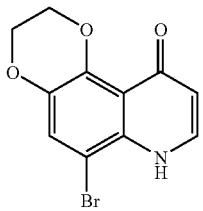

5-[(7-Bromo-2,3-dihydro-benzo[1,4]dioxin-6-ylamino)-methylene]-2,2-dimethyl-[1,3]dioxane-4,6-dione (22.9 g, 59.6 mmol) was added portionwise to refluxing Dowtherm A® (45 mL) over 3 minutes. After a further 3 minutes at reflux the mixture was cooled to room temperature. Ethyl acetate/hexane (10 mL/20 mL) was added and a black solid isolated by filtration. This residue was dissolved in hot methanol (400 mL) and filtered through Keiselguhr. Water (800 mL) was added and the mixture stored at 5° C. overnight. Filtration and drying afforded a pale yellow solid (10.3 g, 61%).

MS (APCl⁻) m/z 281 [M−H]⁻; 1H-NMR (400 MHz, d6-DMSO), 10.61 (1H, br s, NH), 7.64 (1H, d, J=8, CHNHC), 7.48 (1H, s, CHCBr), 5.88 (1H, br d, J=7.04, CH═CO), 4.28-4.27 (4H, br m, 2×(CH2O)).

d) 2,3-Dihydro-7H-[1,4]dioxino[2,3-f]quinolin-10-one

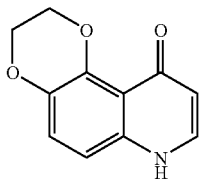

A suspension of 6-bromo-2,3-dihydro-7H-[1,4]dioxino[2,3-f]quinolin-10-one (3.4 g, 12 mmol) in water/dioxane (150 mL/80 mL) was treated with 1M aqueous sodium hydroxide solution then hydrogenated over 10% palladium on charcoal (1.5 g) for 20 hours. The mixture was filtered then acidified with 5M aqueous hydrochloric acid. On concentrating to ca 100 mL, a solid began to crystallise out. The mixture was stored at 5° C. overnight. Filtration and drying afforded a pale yellow solid (2.8 g, 100%). LC/MS (ES) m/z 203 (MH⁺ 92%); 1H-NMR (400 MHz, d6-DMSO), 11.4 (1H, s, NH), 7.64 (1H, d, J=7.2, CHNHC), 7.15 (1H, d, J=9.2, CHCO), 6.95 (1H, d, J=8.8, CHCN), 5.80 (1H, d, J=7.2, CH═CO), 4.26-4.27 (4H, m, 2×(CH2O)).

e) 9-Chloro-2,3-dihydro-[1,4]dioxino[2,3-f]quinolin-10-ol

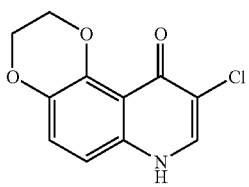

2,3-Dihydro-7H-[1,4]dioxino[2,3-f]quinolin-10-one (6.93 g, 34.1 mmol, 1 eq) in acetic acid (95.9 mL) was sonicated and warmed until all had dissolved, and then it was treated with N-chlorosuccinimide (5.01 g, 37.5 mmol, 1.1 eq) and the mixture was heated at 35° C. for 18 hr, cooled and the solid collected and washed with acetic acid and dried in vacuo at 40 oC overnight, to give a white solid (5.93 g, 73%). LC/MS (ES) m/z 237 (MH⁺ 84%); 1H-NMR (400 MHz, d6-DMSO), 8.17 (1H, d, J=6.28, CHNHC), 7.21 (1H, d, J=8.96 Hz, CHCO), 7.01 (1H, d, J=9, CHCN), 4.29-4.25 (4H, m, 2×(CH2O)).

f) 10-Bromo-9-chloro-2,3-dihydro-[1,4]dioxino[2,3-f]quinoline

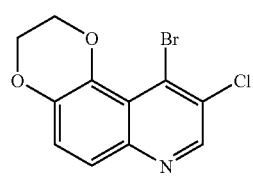

9-Chloro-2,3-dihydro-[1,4]dioxino[2,3-f]quinolin-10-ol (3.12 g, 13.1 mmol) in dry DMF (16.7 mL) was cooled in ice and phosphorus tribromide (4.78 mL) added drop-wise, and the mixture was stirred, with ice-cooling for 30 minutes then allowed to warm to room temperature and stirred for a further 2 hours. It was cooled in ice and sodium carbonate solution was added and the solid was collected, washed well with water, and dried in vacuo, to afford a pale yellow solid (3.55 g, 90%). LC/MS (ES) m/z 300 (MH⁺ 100%); 1H-NMR (400 MHz, DMSO), 8.73 (1H, s, CHNHC), 7.62 (1H, d, J=9.12, CHCOCH2), 7.47 (1H, d, J=9.08, CHCN), 4.43 (4H, m, 2×(CH2O)).

g) 9-Chloro-10-vinyl-2,3-dihydro-[1,4]dioxino[2,3-f]quinoline

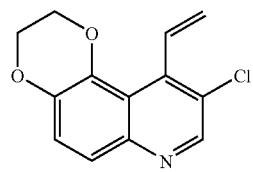

To a solution of 10-Bromo-9-chloro-2,3-dihydro-[1,4]dioxino[2,3-f]quinoline (11.5 g, 38.4 mmol, 1 eq) in DME (425 mL, degassed with Argon), was added Pd(PPh3)4, the reaction was stirred under Argon for 20 mins. Water (122 mL), K2CO3 (5.32 g, 38.4 mmol, 1 eq) and the 2,4,6-trivinylcyclotriboroxane-pyridine complex (2.49 g, 15.4 mmol, 0.4 eq) were added, the mixture was then heated to reflux at 100° C. overnight. The reaction was then cooled, the product was extracted with water and DCM, dried over Na2SO4, filtered and evaporated to dryness. The solid obtained was the passed through silica with as a pale yellow solid (5.5 g, 58%). LC/MS (ES) m/z 247 (MH⁺ 100%); 1H-NMR (400 MHz, CDCl), 8.69 (1H, s, CHNHC), 7.59 (1H, d, J=9.2, CHCO), 7.18 (1H, dd, J=18, 12, CCH═C), 5.68 (1H, dd, J=12, 1, Hcis of CH2═C), 5.49 (1H, dd, J=18, 1, H trans of CH2═C), 4.37-4.339 (4H, m, 2×(CH2O)).

Preparation 10e

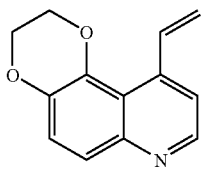

Preparation of
10-vinyl-2,3-dihydro-[1,4]dioxino[2,3-f]quinoline a) 10-Bromo-2,3-dihydro-
[1,4]dioxino[2,3-f]quinoline 2,3-dihydro-[1,4]dioxino[2,3-f]quinolin-10-ol (2.8 g) in dry DMF (8 mL) was cooled in ice and phosphorus tribromide (0.7 mL) added drop-wise, and the mixture was stirred, with ice-cooling for 30 minutes then allowed to warm to room temperature and stirred for a further 2 hours. It was cooled in ice and sodium carbonate solution was added and the solid was collected, washed well with water, and dried in vacuo, to afford a pale yellow solid (1.65 g, 90%). LC/MS (ES) m/z 267.

b) 10-vinyl-2,3-dihydro-[1,4]dioxino[2,3-f]quinoline

To a solution of 10-Bromo-2,3-dihydro-[1,4]dioxino[2,3-f]quinoline (0.8 g, 38.4 mmol, 1 eq) in toluene (15 mL) was added vinyltributyl tin (1.05 mL) and Pd(PPh$_3$)$_4$, (173 mg). The reaction was stirred under Argon for 18 hours at 130 C. The reaction was then cooled and evaporated to dryness. The solid obtained was passed through silica gel to obtain the title compound with as a pale yellow solid (0.50 g, 64%). LC/MS (ES) m/z 214.

Preparation 11

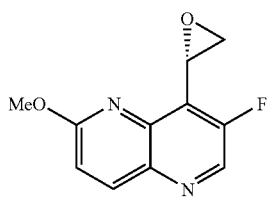

Preparation of 7-fluoro-2-(methyloxy)-8-[(2S)-2-oxiranyl]-1,5-naphthyridine (a) 1-[3-fluoro-6-(methoxy)-1,5-naphthyridin-4-yl]-1,2-ethanediol To a solution of AD-mixβ (50 g) in tert-butanol/water (200 mL/200 mL), cooled in an ice-bath for 30 minutes, 8-ethenyl-7-fluoro-2-(methyloxy)-1,5-naphthyridine (Preparation 6) (8 g, 39.2 mmol) was added and the reaction mixture was stirred at room temperature for 48 hours. Sodium sulfite (75 g) was added and the mixture was stirred for a further 30 minutes. It was extracted with diethyl ether then several times with 10% methanol in chloroform. The organic extract was evaporated under vacuum to afford the desired product as an oil (8.93 g, 96%). MS (+ve ion electrospray) m/z 239 (MH+); enantiomeric excess=44%, as determined by chiral analytical HPLC.

(b) 2-[3-fluoro-6-(methoxy)-1,5-naphthyridin-4-yl]-2-hydroxyethyl 4-methylbenzenesulfonate To a solution of 1-[3-fluoro-6-(methoxy)-1,5-naphthyridin-4-yl]-1,2-ethanediol (16.5 g, 71 mmol)) in dichloromethane (200 mL), triethylamine (10 mL) and dibutyltin oxide (350 mg) was added tosyl chloride (13.2 g). After 3 hours, the mixture was diluted with water/sodium bicarbonate and extracted several times with chloroform. The combined organic extracts were dried over magnesium sulfate and evaporated under vacuum. The residue was chromatographed on silica gel eluting with 20-30% ethyl acetate in chloroform to afford the desired product (20.3 g, 75%). MS (+ve ion electrospray) m/z 393 (M+H)$^+$.

(c) 7-fluoro-2-(methoxy)-8-(2-oxiranyl)-1,5-naphthyridine

To a suspension of 2-[3-fluoro-6-(methoxy)-1,5-naphthyridin-4-yl]-2-hydroxyethyl 4-methylbenzenesulfonate (10.5 g, 26.7 mmol) in anhydrous methanol (160 mL), cooled in an ice-bath, potassium carbonate (7.03 g, 50.9 mmol) was added. After 15 minutes with cooling, the mixture was stirred at room temperature for a further 1.75 hours. It was then diluted with water, extracted several times with dichloromethane, dried over magnesium sulfate and evaporated under vacuum. The residue was chromatographed on silica gel eluting with dichloromethane, chloroform then 20% ethyl acetate in chloroform to afford the title product as an oil (5.55 g, 94%). MS (+ve ion electrospray) m/z 221 (M+H)$^+$.

Preparation 12

Preparation of 7-methyl-3-oxo-3,4-dihydro-2H-pyrido[3,2-b][1,4]thiazine-6-carbaldehyde a) Methyl 7-bromo-3-oxo-3,4-dihydro-2H-pyrido[3,2-b][1,4]thiazine-6-carboxylate A solution of ethyl 2-mercaptoacetate (18.4 ml) in DMF (650 ml) was ice-cooled and treated with sodium hydride (6.78 g of a 60% dispersion in oil). After 1 hour methyl 6-amino-3,5-dibromopyridine-2-carboxylate (50 g) (T. R. Kelly and F. Lang, *J. Org. Chem.* 61, 1996, 4623-4633) was added and the mixture stirred for 16 hours at room temperature. The solution was partitioned between EtOAc and water (2 liters each), shaken, separated and the EtOAc along with solid that crystallised out washed with water (2×1 liter). The EtOAc was evaporated to low volume, solid filtered, washed with water and EtOAc and dried. The filtrate was separated, EtOAc dried and evaporated. The residue was taken up in AcOH and heated to 100° C. overnight, then evaporated. The white solid was triturated uder EtOAc, filtered off, washed with a little EtOAc and dried (Na$_2$SO$_4$). Combining the 2 batches of ester gave 33.35 g (70%). MS (APCl$^-$) m/z 223 ([M−H]$^-$, 100%).

b) Methyl 7-methyl-3-oxo-3,4-dihydro-2H-pyrido[3,2-b][1,4]thiazine-6-carboxylate Methyl 7-bromo-3-oxo-3,4-dihydro-2H-pyrido[3,2-b][1,4]thiazine-6-carboxylate (1.44 g, 4.75 mmol) was dissolved in DMF (20 mL) and treated with PdCl$_2$(PPh$_3$)$_2$ (167 mg, 0.238 mmol), LiCl (604 mg, 14.2 mmol) and Me₄Sn (0.66 mL, 4.75 mmol). The reaction was heated at 100° C. for 30 min, at which point the reaction was no longer proceeding. An additional 0.25 mL of Me₄Sn was added and the reaction was heated for an additional 4 h. After cooling, the reaction was diluted with DCM and water. The product was extracted into DCM and the combined extract was dried (Na₂SO₄) and filtered and the concentrated in vacuo. Purification provided product (500 mg).

c) 6-(Hydroxymethyl)-7-methyl-2H-pyrido[3,2-b][1,4]thiazin-3(4H)-one

Methyl 7-methyl-3-oxo-3,4-dihydro-2H-pyrido[3,2-b][1,4]thiazine-6-carboxylate (54 mg, 0.195 mmol) was dissolved in THF (5 mL), cooled to −10° C. and treated with 1.0M LiH₃BNMe₂ (0.42 mL, 0.42 mmol). The reaction was maintained at −10° C. for 1 h and then quenched with 6N HCl. The reaction solution was diluted with EtOAc and water and the aqueous phase was extracted with EtOAc. The combined organic phases were dried (Na₂SO₄), filtered and concentrated. The crude product (30.3 mg) was used directly in the next step without further purification.

d) 7-Methyl-3-oxo-3,4-dihydro-2H-pyrido[3,2-b][1,4]thiazine-6-carbaldehyde

To a solution of 6-(hydroxymethyl)-7-methyl-2H-pyrido[3,2-b][1,4]thiazin-3(4H)-one (290 mg, 1.38 mmol) in MeCl₂ (20 mL) and was added MnO2 (1.2 g, 13.8 mmol). The reaction was vigorously stirred at RT for 12 h and then filtered and the solvent was removed at reduced pressure. Purification provided 176 mg of the desired aldehyde: MS (ES) m/z 209 (M+H)⁺.

Preparation 13

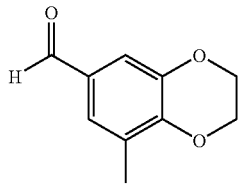

Preparation of 8-methyl-2,3-dihydro-1,4-benzodioxin-6-carbaldehyde (a) (a) 3-Bromo-4-hydroxy-5-methoxybenzaldehyde To a solution of vanillin (30.40 g, 0.20 mol) in glacial acetic acid (200 mL) was added bromine (46.79 g, 0.29 mol) in glacial acetic acid (20 mL) at 10° over a period of 1 h. Additional acetic acid (100 mL) was added to the thickening mixture and the reaction was stirred for 24 h at ambient temperature. The reaction was diluted with ice/water (300 mL); the precipitate was filtered and washed well with water. A light beige solid (40.69 g, 89%) was obtained after vacuum drying: MS (ES) m/z 230.0. (M+H)⁺.

(b) 3-Bromo-4,5-dihydroxybenzaldehyde

To a solution of the compound of Example (a) (12.1 g, 0.52 mol) in CH₂Cl₂ (200 mL) was added 1.0 M boron tribromide in CH₂Cl₂ (2.2 eq, 115 mL) at 0°. The reaction was stirred at 0° for 20 min, then at ambient temperature for 2.5 h. The reaction was then cooled to 0°, and quenched by the slow addition of methanol. The solvents were removed under reduced pressure and the trimethyl borate was removed by azeotropation with added methanol. Vacuum drying yielded a dark green-brown solid (11.51 g, 100%) which was used without further purification: MS (ES) m/z 217.2. (M+H)⁺.

(c) 8-Bromo-2,3-dihydro-1,4-benzodioxin-6-carbaldehyde

To a solution of the compound of Example (c) (11.5 g, 0.52 mol) in DMF (220 mL) was added cesium carbonate (50.7 g, 1.56 mol). The mixture was stirred at ambient temperature for 30 min, then 1,2-dibromoethane (12.76 g, 0.68 mol) were added. After heating at 80° for 4 h, the DMF was removed under reduced pressure. The residue was partitioned between water and ethyl acetate, and the organic layer was washed with brine and dried (MgSO₄). The crude product was purified by flash column chromatography (silica gel, 4:1 hexane:ethyl acetate) to give an off-white solid (9.57 g, 75%): MS (ES) m/z 243.2 (M+H)⁺.

(d) 8-methyl-2,3-dihydro-1,4-benzodioxin-6-carbaldehyde

To a solution of 8-bromo-2,3-dihydro-1,4-benzodioxin-6-carbaldehyde (240 mg, 0.987 mmol) in DMF (5 mL) were added LiCL (126 mg, 2.96 mmol), Me Sn (0.137 mL, 0.987 mmol) and PdCL₂(PPh)₂ (35 mg, 0.049 mmol). After heated at 70° C. for 12 hr, the mixture was cooled down to room temperature and diluted with aqueous KF solution. The resulting solution was extracted several times with DCM. The organic parts were combined, concentrated and purified with column chromatography (silica, 10-40% Ethyl acetate in hexane) affording the title compound as an off-white solid (145 mg, 83%): MS (ES) m/z 179 (M+H)⁺.

Preparation 14

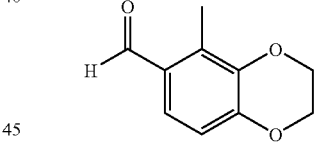

Preparation of 5-methyl-2,3-dihydro-1,4-benzodioxin-6-carbaldehyde

To a solution of N,N,N'-trimethylethylenediamine (3.3 g, 32.3 mmol) in THF (100 mL) at −15° C. was dropwise added n-BuLi (19.2 mL, 30.5 mmol, 1.6 M in THF). After stirring at −15° C. for 15 minutes, a solution of solution of 1,4-benzodioxane-6-aldehyde (5.0 g, 30.5 mmol) in THF (10 mL). After 20 minutes, another batch of n-BuLi (5 mL, 3.1 mmol, 1.6 M in THF) was added and stirred for 3 h. The resulting solution was cooled down to −72° C. and the mixture was treated with MeI (25.9 g, 182.5 mmol) slowly. After stirring at −72° C. for 3 h, the mixture was diluted with HCl solution (1M in water). The aqueous layer was extracted several times with diethyl ether. The organic fractions were combined, concentrated and purified with column chromatography (silica, 5-40% ethyl acetate in hexane) to provide the title compound as an off-white compound (1.0 g, 18%): %): MS (ES) m/z 179 (M+H)⁺.

Preparation 15

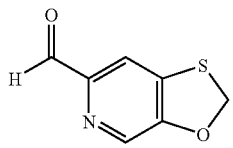

Preparation of
[1,3]Oxathiolo[5,4-c]pyridine-6-carbaldehyde a) 2-(hydroxymethyl)-5-({[4-(methoxy)phenyl]methyl}oxy)-4(1/H)-pyrone To a solution of Kojic acid (50 g, 0.352 mol) in DMF (650 mL) under an argon atmosphere, cooled to 0° C., was added a solution of potassium t-butoxide (39.5 g, 0.352 mol) in DMF (100 mL) and the resultant suspension was vigorously stirred (overhead stirring) for 1 hour at 5-10° C. 4-methoxybenzyl chloride was added dropwise and the mixture was heated to 50° C. for 30 hours, followed by 90° C. for 5 hours, after which the mixture was evaporated to a minimum volume of DMF. 750 mL of distilled water was added and the mixture refrigerated overnight. The resultant solid was collected by filtration and dried in vacuo at 50° C. to afford the product as a light brown solid (85 g, 64%); MS (+ve ion electrospray) m/z 263 (M+H+).

b) 2-(hydroxymethyl)-5-({[4-(methoxy)phenyl]methyl}oxy)-4(1H)-pyridinone

To a suspension of 2-(hydroxymethyl)-5-({[4-(methoxy)phenyl]methyl}oxy)-4(1H)-pyrone (40 g, 153 mmol) in ethanol (105 mL) was added concentrated aqueous ammonia (295 mL) and refluxed for 18 hours. The mixture was cooled, then refrigerated for 3 hours, and cooled in an ice-bath for 45 minutes. The solid was filtered off, washed with cold ethanol, followed by cold petroleum ether and dried in vacuo to afford the product as brown solid (26.21 g, 66%).

c) [5-({[4-(methoxy)phenyl]methyl}oxy)-4-oxo-1,4-dihydro-2-pyridinyl]methyl acetate A solution of 2-(hydroxymethyl)-5-({[4-(methoxy)phenyl]methyl}oxy)-4(1H)-pyridinone (26 g, 0.1 mol) in pyridine (150 mL) was cooled to 5° C. and treated with acetyl chloride (10.48 ml, 0.149 mol). The reaction mixture was stirred and allowed to warm to room temperature then heated at 60° C. for 18 hours. Pyridine was evaporated under vacuum and the residue was triturated with water (250 mL), cooled in an ice-bath for 30 minutes. The solid formed was filtered off, washed with cold water and dried in vacuo to afford the product as a solid (15.7 g, 50%); MS (+ve ion electrospray) m/z 304 (MH+).

d) (5-({[4-(methoxy)phenyl]methyl}oxy)-4-{[(trifluoromethyl)sulfonyl]oxy}-2-pyridinyl)methyl acetate

[5-({[4-(methoxy)phenyl]methyl}oxy)-4-oxo-1,4-dihydro-2-pyridinyl]methyl acetate (25 g, 82 mmol) was dissolved in dry dichloromethane (600 mL). Triethylamine (23 mL, 164 mmol) was added and the reaction cooled to 0° C. Trifluoromethane sulfonic anhydride (21 mL, 123 mmol) was added dropwise and the reaction left to stir at room temperature overnight. The reaction was poured into water, the organic layer collected and dried (Mg SO4). The crude product was chromatographed on silica eluting with 10-20% Ethyl acetate in hexane. Product containing fractions were combined and dried to afford the product as a solid (24.95 g, 70%); MS (+ve ion electrospray) m/z 436 (MH+).

e) [4-[(1,1-dimethylethyl)thio]-5-({[4-(methoxy)phenyl]methyl}oxy)-2-pyridinyl]methyl acetate To a solution of (5-({[4-(methoxy)phenyl]methyl}oxy)-4-{[(trifluoromethyl)sulfonyl]oxy}-2-pyridinyl)methyl acetate (10 g, 23 mmol) in anhydrous toluene, (R)-(+)-2,2 bis(diphenylphosphino)-1,1-binaphthyl (312 mg, 0.4 mmol) was added. The reaction mixture was degassed before adding palladium acetate (103 mg, 0.4 mmol). Sodium 2-methyl-2-propanethiolate was added, the system degassed again and the reaction mixture was stirred at 60° C. for 3 hours, under argon atmosphere then at 70 oC for a further 18 hours. The reaction mixture was filtered and the filtrate was evaporated under vacuum. The residue was partitioned between ethyl acetate and water. The aqueous layer was extracted several times with ethyl acetate. The combined organic extracts were dried over magnesium sulfate and evaporated under vacuum. The residue was chromatographed on silica gel eluting with 20-35% ethyl acetate in hexane to afford the product as an oil (9.1 g, 100%); MS (+ve ion electrospray) m/z 376 (MH+).

f) {4-[(1,1-dimethylethyl)thio]-5-hydroxy-2-pyridinyl}methyl acetate

A solution of [4-[(1,1-dimethylethyl)thio]-5-({[4-(methoxy)phenyl]methyl}oxy)-2-pyridinyl]methyl acetate (9 g, 24 mmol) in dichloromethane (100 mL) was treated with triethylsilane (3.86 mL, 24 mmol). The reaction mixture was stirred for 10 minutes before adding trifluoroacetic acid (10 mL). The reaction mixture was stirred at room temperature for 3 hours under argon atmosphere. The solvents were evaporated under vacuum. The residue was taken up in dichloromethane and chromatographed on silica gel eluting with 10%-30% ethyl acetate in hexane to afford the product as an oil (5.1 g, 83%); MS (+ve ion electrospray) m/z 256 (MH+).

g) 6-(hydroxymethyl)-4-mercapto-3-pyridinol

{4-[(1,1-dimethylethyl)thio]-5-hydroxy-2-pyridinyl}methyl acetate (2.5 g, 9.8 mmol) was dissolved in concentrated HCl and the mixture was heated at 80° C. for 18 hours. The solvent was evaporated under vacuum and the residue was triturated with diethyl ether to afford the product as a solid (1.35 g, 88%); MS (+ve ion electrospray) m/z 158 (MH+).

h) [1,3]oxathiolo[5,4-c]pyridine-6-methanol

To a solution of 6-(hydroxymethyl)-4-mercapto-3-pyridinol (500 mg, 3.2 mmol) in anhydrous DMF, potassium carbonate was added. The reaction mixture was stirred for 10 minutes and dibromomethane (0.44 mL, 6.4 mmol) was added. The reaction mixture was stirred at 70° C. for 18 hours under an argon atmosphere. DMF was removed in vacuo and the residue was partitioned between 5% MeOH in dichloromethane and water. The aqueous layer was extracted several times with 5% methanol in dichloromethane. The combined organic extracts were dried over magnesium sulfate and evaporated under vacuum. The residue was chromatographed on silica gel eluting with 3-5% methanol in dichloromethane to afford the product as a solid (381 mg, 70%); MS (+ve ion electrospray) m/z 170 (MH+).

i) [1,3]oxathiolo[5,4-c]pyridine-6-carbaldehyde

[1,3]oxathiolo[5,4-c]pyridine-6-methanol (0.92 g, 5.44 mmole) was treated with manganese (IV) oxide (3.83 g, 44 mmole) at RT in DCM (50 mL) to afford the aldehyde (567 mg, 62%) as a solid; MS (+ve ion electrospray) m/z 168 (MH+).

Preparation 16

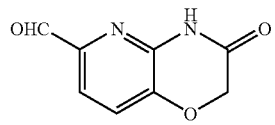

Preparation of 3-Oxo-3,4-dihydro-2H-pyrido[3,2-b][1,4]oxazine-6-carboxaldehyde a) 2-Bromo-5-hydroxy-6-nitropyridine 3-Hydroxy-2-nitropyridine (20 g, 0.143 mole) was dissolved in methanol (400 mL) and a solution of 25% sodium methoxide in methanol (33 mL, 0.13 mole) was added at room temperature. The mixture was stirred for 30 min, then was cooled to 0° C., and bromine (7.2 mL, 0.14 mole) was added slowly. The reaction was stirred at 0° C. for 30 min, then was quenched with glacial AcOH (2.5 mL). The solvent was removed in vacuo to afford material (30 g, 96%), which was used without further purification.
MS (ES) m/z 219.0 (M+H)+.

b) Ethyl(6-bromo-2-nitro-pyridin-3-yloxy)acetate

2-Bromo-5-hydroxy-6-nitropyridine (30 g, 0.14 mole) was suspended in acetone (200 ml), and potassium carbonate (39 g, 0.28 mole) was added, followed by ethyl bromoacetate (15.7 ml, 0.14 mmole). The reaction was heated at reflux for 10 hr, then was cooled to room temperature and diluted with Et₂O. The precipitate was removed by suction filtration, and the filtrate was concentrated in vacuo to afford material (38 g, 89%), which was used without further purification; MS (ES) m/z 305.0 (M+H)+.

c) 6-Bromo-4H-pyrido[3,2-b][1,4]oxazin-3-one

Ethyl(6-bromo-2-nitro-pyridin-3-yloxy)acetate (38 g, 0.125 mole) was dissolved in glacial AcOH (150 mL), and iron powder (20 g, 0.36 mole) was added. The mixture was mechanically stirred and heated at 90° C. for 5 hr, then was cooled to room temperature and diluted with EtOAc (300 mL). The mixture was filtered through a pad of silica gel and the filtrate was concentrated in vacuo and the residue recrystallized from MeOH (15 g, 52%); MS (ES) m/z 229.0 (M+H)+.

d) 6-((E)-Styryl)-4H-pyrido[3,2-b][1,4]oxazin-3-one

6-Bromo-4H-pyrido[3,2-b][1,4]oxazin-3-one (6.0 g, 26.3 mmole) and trans-2-phenylvinylboronic acid (3.9 g, 26.3 mmole) were dissolved in 1,4-dioxane (150 mL) and the solution was degassed with argon. (Ph₃P)₄Pd (230 mg, 0.2 mmole) was added, followed by a solution of potassium carbonate (6.9 g, 50 mmole) in H₂O (20 mL). The reaction was heated at reflux under argon overnight, then was cooled to room temperature and diluted with EtOAc (200 mL). The solution was washed sequentially with H₂O and brine, dried (Na₂SO₄), and concentrated in vacuo. The solid residue was purified by flash chromatography on silica gel (5-10% EtOAc/CHCl₃) to afford a solid (2.5 g, 38%).
MS (ES) m/z 253.0 (M+H)+.

e) 3-Oxo-3,4-dihydro-2H-pyrido[3,2-b][1,4]oxazine-6-carboxaldehyde 6-((E)-Styryl)-4H-pyrido[3,2-b][1,4]oxazin-3-one (1.2 g, 4.8 mmole) was dissolved in CH₂Cl₂ (200 mL) and the solution was cooled to –78° C. Ozone was bubbled through the solution with stirring until a pale blue color appeared, then the excess ozone was removed by bubbling oxygen through the solution for 15 min. Dimethylsulfide (1.76 mL, 24 mmole) was added to the solution, and the reaction was stirred at –78° C. for 3 hr, then at room temperature overnight. The solvent was removed in vacuo, and the residue was triturated with Et₂O (50 mL). The collected solid was washed with additional Et₂O and dried to afford a solid (700 mg, 82%).
MS (ES) m/z 179.0 (M+H)+.

Preparation 17

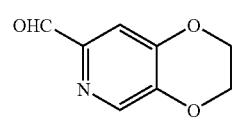

Preparation of 2,3-Dihydro-[1,4]dioxino[2,3-c]pyridine-7-carboxaldehyde a) 5-Benzyloxy-2-hydroxymethyl-1H-pyridin-4-one A mixture of 5-benzyloxy-2-hydroxymethyl-4-pyrone (prepared from Kojic acid by the method of D. Erol, J. Med. Chem., 1994, 29, 893) (9.7 g, 40 mmol), concentrated aqueous (880) ammonia (100 mL), and ethanol (20 mL) was heated to reflux overnight. The mixture was allowed to cool to room temperature then filtered. The resultant solid was washed with ether and dried in vacuo (5.9 g); MS (APCl+) m/z 232 (MH+).

b) (2,3-Dihydro-[1,4]dioxino[2,3-c]pyridin-7-yl)-methanol

A solution of 5-Benzyloxy-2-hydroxymethyl-1H-pyridin-4-one (2 g, 8.7 mmol) in water (220 mL) containing sodium hydroxide (17 mmol) was hydrogenated over 10% palladium on charcoal (1 g) for 4 hours. The mixture was filtered and evaporated to give a white solid. This solid was dissolved in N,N-dimethylformamide (8 mL) then treated with potassium carbonate (2.9 g) and 1,2-dibromoethane (0.6 mL, 7 mmol). The mixture was heated at 85° C. overnight. The cooled mixture was evaporated onto silica and chromatographed eluting with 10-30% methanol in ethyl acetate affording a white solid (250 mg, 21%); MS (APCl+) m/z 168 (MH+).

c) 2,3-Dihydro-[1,4]dioxino[2,3-c]pyridine-7-carboxaldehyde

A solution of (2,3-Dihydro-[1,4]dioxino[2,3-c]pyridin-7-yl)-methanol (250 mg, 1.5 mmol) in dichloromethane (5 mL)

was treated with manganese dioxide (650 mg, 7.5 mmol). After 3 days the mixture was filtered and evaporated affording a white solid (150 mg, 61%); MS (APCl+) m/z 166 (MH+).

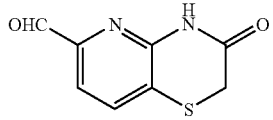

Preparation 18

Preparation of 3-Oxo-3,4-dihydro-2H-pyrido[3,2-b][1,4]thiazine-6-carboxaldehyde a) Methyl 3-oxo-3,4-dihydro-2H-pyrido[3,2-b][1,4]thiazine-6-carboxylate A solution of ethyl 2-mercaptoacetate (1.473 mL) in DMF (48 mL) was ice-cooled and treated with sodium hydride (540 mg of a 60% dispersion in oil). After 1 hour methyl 6-amino-5-bromopyridine-2-carboxylate (3 g) (T. R. Kelly and F. Lang, *J. Org. Chem.* 61, 1996, 4623-4633) was added and the mixture stirred for 16 hours at room temperature. The solution was diluted with EtOAc (1 liter), washed with water (3×300 mL), dried and evaporated to about 10 mL. The white solid was filtered off and washed with a little EtOAc to give the ester (0.95 g); MS (APCl−) m/z 223 ([M−H]−, 100%).

b) 3-Oxo-3,4-dihydro-2H-pyrido[3,2-b][1,4]thiazine-6-carboxylic acid

A solution of Methyl 3-oxo-3,4-dihydro-2H-pyrido[3,2-b][1,4]thiazine-6-carboxylate (788 mg) in dioxan (120 ml)/water (30 mL) was treated dropwise over 2 hours with 0.5M NaOH solution (8 mL) and stirred overnight. After evaporation to approx. 3 ml, water (5 mL) was added and 2M HCl to pH4. The precipitated solid was filtered off, washed with a small volume of water and dried under vacuum to give a solid (636 mg); MS (APCl−) m/z 209 ([M−H]−, 5%), 165([M-COOH]−, 100%).

c) 6-Hydroxymethyl-3-oxo-3,4-dihydro-2H-pyrido[3,2-b][1,4]thiazine

A solution of 3-Oxo-3,4-dihydro-2H-pyrido[3,2-b][1,4]thiazine-6-carboxylic acid (500 mg) in THF (24 mL) with triethylamine (0.396 mL) was cooled to −10° C. and isobutyl chloroformate (0.339 ml) added. After 20 minutes the suspension was filtered through kieselguhr into an ice-cooled solution of sodium borohydride (272 mg) in water (8 mL), the mixture stirred 30 minutes and the pH reduced to 7 with dilute HCl. The solvent was evaporated and the residue triturated under water. The product was filtered and dried under vacuum to give a white solid (346 mg); MS (APCl−) m/z 195 ([M−H]−, 50%), 165(100%).

d) 3-Oxo-3,4-dihydro-2H-pyrido[3,2-b][1,4]thiazine-6-carboxaldehyde

A solution of 6-Hydroxymethyl-3-oxo-3,4-dihydro-2H-pyrido[3,2-b][1,4]thiazine (330 mg) in dichloromethane (30 mL)/THF (30 mL) was treated with manganese dioxide (730 mg) and stirred at room temperature. Further manganese dioxide was added after 1 hour (730 mg) and 16 hours (300 mg). After a total of 20 hours the mixture was filtered through kieselguhr and the filtrate evaporated. The product was triturated with EtOAc/hexane (1:1) and collected to give a solid (180 mg); MS (APCl−) m/z 195 ([M−H]−, 95%), 165 (100%).

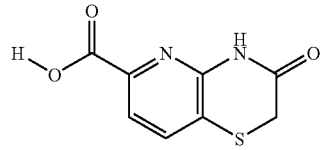

Preparation 19

Preparation of 3-oxo-3,4-dihydro-2H-pyrido[3,2-b][1,4]thiazine-6-carboxylic acid This acid was prepared from 3-Oxo-3,4-dihydro-2H-pyrido[3,2-b][1,4]thiazine-6-carboxaldehyde (890 mg) by oxidation with Oxone (potassium peroxymonosulphate) (3.1 g) in a DMF solution (50 mL). After 1.5 hours at room temperature, dilution with water (50 mL) filtration and drying in vacuo afforded the acid as a white solid (750 mg, 77%).

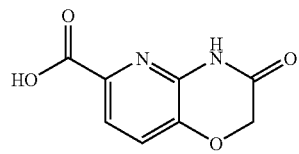

Preparation 19a

Preparation of 3-oxo-3,4-dihydro-2H-pyrido[3,2-b][1,4]oxazine-6-carboxylic acid a) 2-Bromo-5-hydroxy-6-nitropyridine 3-Hydroxy-2-nitropyridine (20 g, 0.143 mole) was dissolved in methanol (400 mL) and a solution of 25% sodium methoxide in methanol (33 mL, 0.13 mole) was added at room temperature. The mixture was stirred for 30 min, then was cooled to 0° C., and bromine (7.2 mL, 0.14 mole) was added slowly. The reaction was stirred at 0° C. for 30 min, then was quenched with glacial AcOH (2.5 mL). The solvent was removed in vacuo to afford material (30 g, 96%), which was used without further purification.

MS (ES) m/z 219.0 (M+H)+.

b) Ethyl(6-bromo-2-nitro-pyridin-3-yloxy)acetate

2-Bromo-5-hydroxy-6-nitropyridine (30 g, 0.14 mole) was suspended in acetone (200 ml), and potassium carbonate (39 g, 0.28 mole) was added, followed by ethyl bromoacetate (15.7 ml, 0.14 mmole). The reaction was heated at reflux for 10 hr, then was cooled to room temperature and diluted with Et2O. The precipitate was removed by suction filtration, and the filtrate was concentrated in vacuo to afford material (38 g, 89%), which was used without further purification; MS (ES) m/z 305.0 (M+H)+.

c) 6-Bromo-4H-pyrido[3,2-b][1,4]oxazin-3-one

Ethyl(6-bromo-2-nitro-pyridin-3-yloxy)acetate (38 g, 0.125 mole) was dissolved in glacial AcOH (150 mL), and iron powder (20 g, 0.36 mole) was added. The mixture was mechanically stirred and heated at 90° C. for 5 hr, then was cooled to room temperature and diluted with EtOAc (300 mL). The mixture was filtered through a pad of silica gel and the filtrate was concentrated in vacuo and the residue recrystallized from MeOH (15 g, 52%); MS (ES) m/z 229.0 (M+H)+.

d) 6-((E)-Styryl)-4H-pyrido[3,2-b][1,4]oxazin-3-one

6-Bromo-4H-pyrido[3,2-b][1,4]oxazin-3-one (6.0 g, 26.3 mmole) and trans-2-phenylvinylboronic acid (3.9 g, 26.3 mmole) were dissolved in 1,4-dioxane (150 mL) and the solution was degassed with argon. (Ph$_3$P)$_4$Pd (230 mg, 0.2 mmole) was added, followed by a solution of potassium carbonate (6.9 g, 50 mmole) in H$_2$O (20 mL). The reaction was heated at reflux under argon overnight, then was cooled to room temperature and diluted with EtOAc (200 mL). The solution was washed sequentially with H$_2$O and brine, dried (Na$_2$SO$_4$), and concentrated in vacuo. The solid residue was purified by flash chromatography on silica gel (5-10% EtOAc/CHCl$_3$) to afford a solid (2.5 g, 38%): LCMS (ES) m/z 253.0 (M+H)+.

e) 3-Oxo-3,4-dihydro-2H-pyrido[3,2-b][1,4]oxazine-6-carboxaldehyde 6-((E)-Styryl)-4H-pyrido[3,2-b][1,4]oxazin-3-one (1.2 g, 4.8 mmole) was dissolved in CH$_2$Cl$_2$ (200 mL) and the solution was cooled to –78° C. Ozone was bubbled through the solution with stirring until a pale blue color appeared, then the excess ozone was removed by bubbling oxygen through the solution for 15 min. Dimethylsulfide (1.76 mL, 24 mmole) was added to the solution, and the reaction was stirred at –78° C. for 3 hr, then at room temperature overnight. The solvent was removed in vacuo, and the residue was triturated with Et$_2$O (50 mL). The collected solid was washed with additional Et$_2$O and dried to afford a solid (700 mg, 82%).
MS (ES) m/z 179.0 (M+H)+.

f) 3-oxo-3,4-dihydro-2H-pyrido[3,2-b][1,4]oxazine-6-carboxylic acid

This acid was prepared from 3-Oxo-3,4-dihydro-2H-pyrido[3,2-b][1,4]oxazine-6-carboxaldehyde (900 mg) by oxidation with Oxone (potassium peroxymonosulphate) (3.7 g) in a DMF solution (50 mL). After 1.5 hours at room temperature, dilution with water (50 mL) filtration and drying in vacuo afforded the acid as an off-white solid (687 mg, 70%): LCMS (ES) m/e 195 (M+H)+; $^1$H NMR δ 7.81 (d, J=8.1 Hz, 1H), 7.41 (d, J=8.1 Hz, 1H), 4.77 (s, 2H).

Preparation 19b

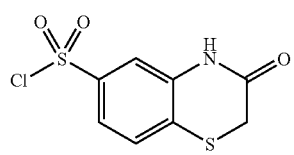

Preparation of 3-oxo-3,4-dihydro-2H-1,4-benzothiazine-6-sulfonyl chloride

To an ice-cold solution of chlorosulfonic acid (22 mL, 33.1 mmol) was added the benzothiazinone (6 g, 36.3 mmol) portion-wise. The dark blue solution was warmed to 25° C. over 1 h, then heated at 45° C. for 2 h. After cooling, addition of the solution to ice-water resulted in the formation of a white precipitate. The solid was filtered, washed with H$_2$O/hexane and dried affording the title compound as a white solid (8.46 g, 88%); MS (APCl+) m/z 246 (M+H)+.

Preparation 20

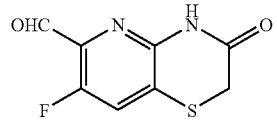

Preparation of 7-Fluoro-3-oxo-3,4-dihydro-2H-pyrido[3,2-b][1,4]thiazine-6-carboxaldehyde a) Methyl 6-amino-5-bromo-3-fluoropyridine-2-carboxylate A mixture of methyl 6-amino-5-bromopyridine-2-carboxylate (19.8 g) (T. R. Kelly and F. Lang, J. Org. Chem. 61, 1996, 4623-4633) and 1-chloromethyl-4-fluoro-1,4-diazoniabicyclo[2.2.2]octane bis(tetrafluoroborate) (34.3 g) in acetonitrile (340 mL) under argon was heated to 40° C. for 1 hour, 60° C. for 1 hour and then 80° C. overnight. After partitioning between EtOAc and water (500 mL each) the aqueous fraction was re-extracted with EtOAc (300 mL) and the combined organic solution dried with MgSO$_4$ and evaporated. Chromatography (20% then 30% EtOAc in hexane) separated various byproducts from the required ester (2.09 g); MS (+ve ion electrospray) m/z 249 and 251 (MH+, 100%)

b) Methyl 6-amino-5-ethoxycarbonylmethylthio-3-fluoropyridine-2-carboxylate

A solution of ethyl mercaptoacetate (1.15 mL) in DMF (40 mL) was ice-cooled under argon, treated with sodium hydride (420 mg of a 60% dispersion in oil) and stirred until all was in solution (about 1 hour). The ester (308a) (2.48 g) was added, the mixture allowed to warm to room temp. and stirred overnight. EtOAc (150 mL) was added, the solution washed with water (3×150 mL), dried and evaporated. Chromatography of the residue (30 then 40% EtOAc in hexane) gave the product as an oil (1.7 g).
MS (+ve ion electrospray) m/z 289 (MH+, 100%)

c) Methyl 7-fluoro-3-oxo-3,4-dihydro-2H-pyrido[3,2-b][1,4]thiazine-6-carboxylate A solution of the fluoropyridine (13b) (1.7 g) in acetic acid (100 mL) was heated at 110° C. overnight, evaporated and dried under vacuum to give the product as a white solid (1.55 g, containing 0.33 equivalent of acetic acid); MS (+ve ion electrospray) m/z 243 (MH+, 85%), 211 (100%)

d) 7-Fluoro-3-oxo-3,4-dihydro-2H-pyrido[3,2-b][1,4]thiazine-6-carboxylic acid

This compound was prepared from methyl 7-fluoro-3-oxo-3,4-dihydro-2H-pyrido[3,2-b][1,4]thiazine-6-carboxylate by the method of Preparation 9b (86%).

e) 7-Fluoro-6-hydroxymethyl-3-oxo-3,4-dihydro-2H-pyrido[3,2-b][1,4]thiazine

This compound was prepared from 7-Fluoro-3-oxo-3,4-dihydro-2H-pyrido[3,2-b][1,4]thiazine-6-carboxylic acid by the method of Preparation 9c (73%); MS (−ve ion electrospray) m/z 213 ([M−H]⁻, 100%)

f) 7-Fluoro-3-oxo-3,4-dihydro-2H-pyrido[3,2-b][1,4]thiazine-6-carboxaldehyde

A mixture of the 7-fluoro-pyridothiazinone (13e) (971 mg), manganese dioxide (3.72 g), THF (70 mL) and 1,2-dichloroethane (70 mL) was heated at 60° C. under argon for 20 hours. Filtration through kieselguhr and evaporation of solvent gave a solid which was triturated under EtOAc/hexane 1:3 and collected (608 mg); MS (+ve ion electrospray) m/z 213 (MH⁺, 100%).

Preparation 21

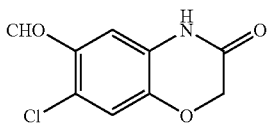

Preparation of 7-chloro-3-oxo-3,4-dihydro-2H-1,4-benzoxazine-6-carbaldehyde a) 2-Bromo-5-hydroxy-6-nitropyridine 3-Hydroxy-2-nitropyridine (20 g, 0.143 mole) was dissolved in methanol (400 mL) and a solution of 25% sodium methoxide in methanol (33 mL, 0.13 mole) was added at room temperature. The mixture was stirred for 30 min, then was cooled to 0° C., and bromine (7.2 mL, 0.14 mole) was added slowly. The reaction was stirred at 0° C. for 30 min, then was quenched with glacial AcOH (2.5 mL). The solvent was removed in vacuo to afford material (30 g, 96%), which was used without further purification.
MS (ES) m/z 219.0 (M+H)⁺.

b) Ethyl(6-bromo-2-nitro-pyridin-3-yloxy)acetate

The hydroxypyridine (30 g, 0.14 mole) was suspended in acetone (200 ml), and potassium carbonate (39 g, 0.28 mole) was added, followed by ethyl bromoacetate (15.7 ml, 0.14 mmole). The reaction was heated at reflux for 10 hr, then was cooled to room temperature and diluted with Et₂O. The precipitate was removed by suction filtration, and the filtrate was concentrated in vacuo to afford material (38 g, 89%), which was used without further purification.
MS (ES) m/z 305.0 (M+H)⁺.

c) 6-Bromo-4H-pyrido[3,2-b][1,4]oxazin-3-one

The nitropyridine (38 g, 0.125 mole) was dissolved in glacial AcOH (150 mL), and iron powder (20 g, 0.36 mole) was added. The mixture was mechanically stirred and heated at 90° C. for 5 hr, then was cooled to room temperature and diluted with EtOAc (300 mL). The mixture was filtered through a pad of silica gel and the filtrate was concentrated in vacuo and the residue recrystallized from MeOH (15 g, 52%).
MS (ES) m/z 229.0 (M+H)⁺.

d) 6-((E)-Styryl)-4H-pyrido[3,2-b][1,4]oxazin-3-one

The bromopyridine (10c) (6.0 g, 26.3 mmole) and trans-2-phenylvinylboronic acid (3.9 g, 26.3 mmole) were dissolved in 1,4-dioxane (150 mL) and the solution was degassed with argon. (Ph₃P)₄Pd (230 mg, 0.2 mmole) was added, followed by a solution of potassium carbonate (6.9 g, 50 mmole) in H₂O (20 mL). The reaction was heated at reflux under argon overnight, then was cooled to room temperature and diluted with EtOAc (200 mL). The solution was washed sequentially with H₂O and brine, dried (Na₂SO₄), and concentrated in vacuo. The solid residue was purified by flash chromatography on silica gel (5-10% EtOAc/CHCl₃) to afford a solid (2.5 g, 38%).
MS (ES) m/z 253.0 (M+H)⁺.

e) 3-Oxo-3,4-dihydro-2H-pyrido[3,2-b][1,4]oxazine-6-carboxaldehyde

The pyridine (10d) (1.2 g, 4.8 mmole) was dissolved in CH₂Cl₂ (200 mL) and the solution was cooled to −78° C. Ozone was bubbled through the solution with stirring until a pale blue color appeared, then the excess ozone was removed by bubbling oxygen through the solution for 15 min. Dimethylsulfide (1.76 mL, 24 mmole) was added to the solution, and the reaction was stirred at −78° C. for 3 hr, then at room temperature overnight. The solvent was removed in vacuo, and the residue was triturated with Et₂O (50 mL). The collected solid was washed with additional Et₂O and dried to afford a solid (700 mg, 82%); MS (ES) m/z 179.0 (M+H)⁺.

f) 6-Bromo-7-chloro-4H-pyrido[3,2-b][1,4]oxazin-3-one

6-Bromo-4H-pyrido[3,2-b][1,4]oxazin-3-one (20 g, 87.7 mmole) was dissolved in DMF (175 mL) and cooled in an ice bath. Chlorine gas was then slowly bubbled in for 45 minutes, and then the saturated solution was stirred in the ice bath for 2 hours. The mixture was purged with nitrogen and slowly added with stirring to 1 L of ice water which contained 100 g of Na₂SO, making sure to keep the temperature<15° C. After stirring 30 minutes the product was filtered, washed thoroughly with water and dried to afford (22.5 g, 98%) of a white solid.
¹H NMR (400 MHz, DMSO-d6): 4.76 (2H, s), 7.78 (1H, s), 11.71 (1H, s).

g) 7-Chloro-6-((E)-styryl)-4H-pyrido[3,2-b][1,4]oxazin-3-one

6-Bromo-7-chloro-4H-pyrido[3,2-b][1,4]oxazin-3-one (22 g, 83.7 mmole) and trans-2-phenylvinylboronic acid (17.33 g, 117 mmole) were dissolved in 1,4-dioxane (300 mL) and the solution was degassed with argon. (Ph₃P)₄Pd (1.9 g, 2 mole %) was added, followed by a solution of potassium hydrogen carbonate (21 g, 210 mmole) in H₂O (100 mL). The reaction was heated at reflux under argon overnight, then was cooled to room temperature and diluted with ethyl acetate (1 L). The solution was washed sequentially with H₂O and brine, dried (Na₂SO₄), and concentrated in vacuo. The residue was slurried with chloroform (120 mL), then diluted with diethyl ether (100 mL). The precipitated product was collected by filtration and washed with ether to provide the product (16.4 g, 68%) as an off-white solid.
¹H NMR (400 MHz, DMSO-d6): 4.71 (2H, s), 7.32-7.46 (3H, m), 7.54-7.74 (4H, m), 11.6 (1H, s).

h) 7-Chloro-3-oxo-3,4-dihydro-2H-pyrido[3,2-b][1,4]oxazine-6-carboxaldehyde

7-Chloro-6-((E)-styryl)-4H-pyrido[3,2-b][1,4]oxazin-3-one (8.0 g, 27.9 mmole) was dissolved in a mixture of DMF (400 mL) and methanol (40 mL), and the solution was cooled to −78° C. Ozone was bubbled through the solution with stirring for 45 minutes, then the excess ozone was removed by bubbling oxygen through the solution for 30 min. Dimethylsulfide (21 mL, 279 mmole) was added to the solution, and the reaction was stirred at −78° C. for 3 hr, then at room temperature overnight. The solvent was removed in vacuo, and the residue was triturated with Et$_2$O (150 mL). The collected solid was washed with additional Et$_2$O and dried to afford a white solid (4 g, 68%).

$^1$H NMR (400 MHz, DMSO-d6): 4.86 (2H, m), 7.73 (1H, s); 10.05 (1H, s), 11.84 (1H, s).

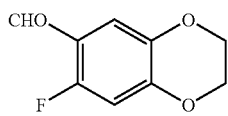

Preparation 22

Preparation of 7-fluoro-2,3-dihydrobenzo[1,4]dioxine-6-carboxaldehyde

7-Fluoro-2,3-dihydrobenzo[1,4]dioxine-6-carboxaldehyde was prepared from 6-fluoro-2,3-dihydrobenzo[1,4]dioxine [V. Daukas et al Chemija, 1999, 10 (1), 59] by reaction of dichloromethyl methyl ether and titanium tetrachloride: LC-MS (ES) m/e 155 (M+H)$^+$.

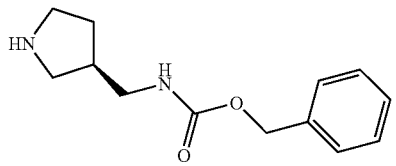

Preparation 23

Preparation of phenylmethyl[(3R)-3-pyrrolidinylmethyl]carbamate a) 1,1-dimethylethyl(3S)-3-[({[(phenylmethyl)oxy]carbonyl}amino)methyl]-1-pyrrolidinecarboxylate To a solution of (S)-3-(aminomethyl)-1-N-Boc-pyrrolidine (3.0 g, 14.98 mmole) in DMF (40 mL) was added triethylamine (2.5 mL, 17.94 mmole) and N-(benzyloxycarbonyloxy)succinimide (4.46 g, 17.90 mmole). After 18 hours, the reaction solution was concentrated under vacuum and redissolved in diethyl ether (250 mL). The organic solution was washed with H$_2$O (2×150 mL), brine (100 mL) and dried over Na$_2$SO$_4$ and concentrated. The remaining residue was purified on silica (CHCl$_3$/MeOH, 9:1 containing 5% NH$_4$OH) to give the title compound (4.46 g, 91%) as a light yellow oil: LC-MS (ES) m/e 335 (M+H)$^+$.

b) phenylmethyl[(3R)-3-pyrrolidinylmethyl]carbamate

To a solution of 1,1-dimethylethyl(3S)-3-[({[(phenylmethyl)oxy]carbonyl}amino)methyl]-1-pyrrolidinecarboxylate in DCM (100 mL) at RT was added TFA (50 mL). After 2 h, the reaction solution was concentrated under vacuum and purified on silica (CHCl$_3$/MeOH, 9:1 containing 5% NH$_4$OH) to give the title compound (2.93 g, 94%) as a light yellow oil: LC-MS (ES) m/e 235 (M+H)$^+$.

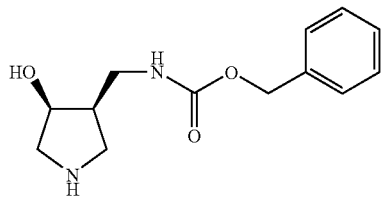

Preparation 24

Preparation of (±)-phenylmethyl {[cis-4-hydroxy-3-pyrrolidinyl]methyl}carbamate a) (±)-1,1-dimethylethyl-2-(phenylmethyl)hexahydro-5H-pyrrolo[3,4-d]isoxazole-5-carboxylate

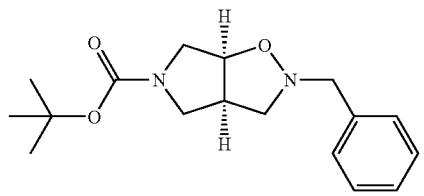

To a solution of 1,1-dimethylethyl 2,5-dihydro-1H-pyrrole-1-carboxylate (10.0 g, 59.1 mmole) in toluene (300 mL) and EtOH (100 mL) was added paraformaldehyde (8.87 g, 295.5 mmole), N-hydroxybenzylamine hydrochloride (13.92 g, 88.65 mmole) and triethylamine (12.4 mL, 88.65 mmole). After 24 hours at 80° C., the reaction solution was concentrated under vacuum and redissolved in hexanes/EtOAc, 1:1 (200 mL) and filtered. The organic solution was concentrated and then purified on silica (hexanes/EtOAc, 1:1) to give the title compound (15.27 g, 85%) as a colorless oil: LC-MS (ES) m/e 305 (M+H)$^+$.

b) (±)-1,1-dimethylethyl-cis-3-(aminomethyl)-4-hydroxy-1-pyrrolidinecarboxylate

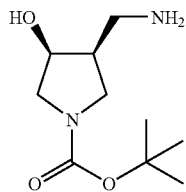

To a solution of (±)-1,1-dimethylethyl-2-(phenylmethyl)hexahydro-5H-pyrrolo[3,4-d]isoxazole-5-carboxylate (14.0 g, 46.0 mmole) in EtOH (100 mL) in a Parr flask was added Pd(OH)$_2$ (~400 mg). The reaction contents were shaken under 50 psi of H$_2$ overnight at RT. The reaction contents were filtered through Celite® (MeOH) and concentrated to give the title compound (10.0 g, 99%) as a low melting white solid: LC-MS (ES) m/e 217 (M+H)$^+$.

c) (±)-1,1-dimethylethyl cis-3-hydroxy-4-[({[(phenylmethyl)oxy]carbonyl}amino)methyl]-1-pyrrolidinecarboxylate

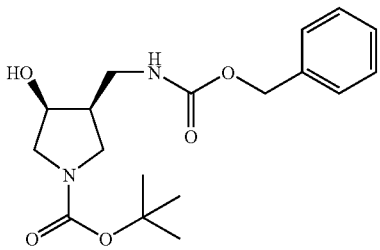

To a solution of (±)-1,1-dimethylethyl cis-3-(aminomethyl)-4-hydroxy-1-pyrrolidinecarboxylate (10.0 g, 46.0 mmole) in DMF (50 mL) at RT was added Et$_3$N (8.4 mL, 60.0 mmole) and N-(benzyloxycarbonyloxy)succinimide (14.95 g, 60.0 mmole). After 18 h, the DMF was removed under vacuum and the residue purified on silica (25-50% DCM/EtOAc) to give the title compound (15.3 g, 95%) as a white foam: LC-MS (ES) m/e 351 (M+H)$^+$; and a small amount of an N-methylated byproduct [1,1-dimethylethyl (3S,4S)-3-hydroxy-4-[(methyl{[(phenylmethyl)oxy]carbonyl}amino)methyl]-1-pyrrolidinecarboxylate] (0.33 g, 2%): LC-MS (ES) m/e 365 (M+H)$^+$.

The racemic title compound was separated into its chiral constituents via preparative chiral column chromatography. The first eluting enantiomer (E1, [α]$_D$=+17.7°, c=0.5, MeOH) and second eluting enantiomer (E2, [α]$_D$=−16.7°, c=0.5, MeOH) were then used directly. (see below)

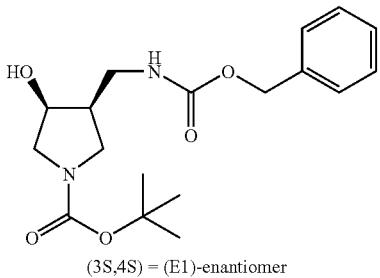
(3S,4S) = (E1)-enantiomer

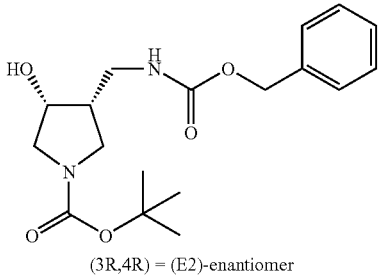
(3R,4R) = (E2)-enantiomer

The absolute stereochemistries of the intermediates above were determined by vibrational circular dichroism.

d) (±)-phenylmethyl {[cis-4-hydroxy-3-pyrrolidinyl]methyl}carbamate

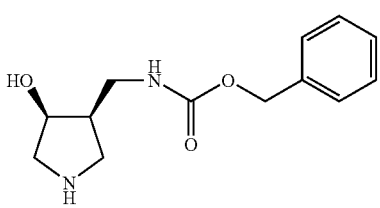

To a solution of (±)-1,1-dimethylethyl cis-3-hydroxy-4-[({[(phenylmethyl)oxy]carbonyl}amino)methyl]-1-pyrrolidinecarboxylate (15.3 g, 43.7 mmole) in DCM (150 mL) at RT was added TFA (50 mL). After 2 h, the reaction solution was concentrated under vacuum and the residue placed under high vacuum for 3 hr. The residue was dissolved in DCM (200 mL) and MP-carbonate resin (175 mmole, 65 g) was added with vigorous stirring at RT. After 4 h, the reaction contents were filtered through a scintered-glass funnel washing with MeOH (100 mL). The filtrate was concentrated under vacuum to give the title compound (10.38 g, 95%) as a white foam: LC-MS (ES) m/e 251 (M+H)$^+$.

Example 1

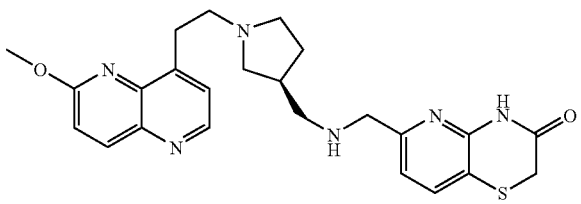

Preparation of 6-({[((3S)-1-{2-[6-(methyloxy)-1,5-naphthyridin-4-yl]ethyl}-3-pyrrolidinyl)methyl]amino}methyl)-2H-pyrido[3,2-b][1,4]thiazin-3(4H)-one a) 1,1-dimethylethyl(3S)-3-{[(trifluoroacetyl)amino]methyl}-1-pyrrolidinecarboxylate To a stirred solution of (S)-3-(aminomethyl)-1-N-Boc-pyrrolidine (2.0 g, 10.0 mmole), in dry CH$_2$Cl$_2$ (50 mL) at RT was added diisopropylethyl amine (2.6 mL, 15.0 mmole) and trifluoroacetic anhydride (1.39 mL, 10.0 mmole). After 3 h at RT, the reaction contents were concentrated under vacuum. Purification on silica (EtOAc) afforded the title compound (2.96 g, 99%) as an off-white solid: LC-MS (ES) m/e 297 (M+H)$^+$.

b) 2,2,2-trifluoro-N-[(3R)-3-pyrrolidinylmethyl]acetamide

To a stirred solution of 1,1-dimethylethyl(3S)-3{[(trifluoroacetyl)amino]methyl}-1-pyrrolidinecarboxylate (2.96 g, 10.0 mmole), in CH$_2$Cl$_2$ (50 mL) at RT was added TFA (25 mL). After 2 h, the reaction contents were concentrated under vacuum. The remaining residue was dissolved in (CHCl$_3$/i-PrOH, 10:1) and washed with saturated aqueous NaHCO$_3$. The organic phase was separated and dried over Na$_2$SO$_4$. Concentration under vacuum afforded the title compound (1.86 g, 95%) as a yellow oil: LC-MS (ES) m/e 197 (M+H)$^+$.

c) ethyl[((3S)-1-{2-[6-(methyloxy)-1,5-naphthyridin-4-yl]ethyl}-3-pyrrolidinyl)methyl]carbamate To a stirred solution of 2,2,2-trifluoro-N-[(3R)-3-pyrrolidinylmethyl]acetamide (1.0 g, 5.1 mmole), in DMF (20 mL) was added 8-ethenyl-2-(methyloxy)-1,5-naphthyridine (1.41 g, 7.65 mmole). After 24 h at 100° C., the reaction contents were concentrated under vacuum and purified on silica (CHCl$_3$/MeOH, 9:1 containing 5% NH$_4$OH) to give the title compound (1.42 g, 73%) as yellow oil: LC-MS (ES) m/e 383 (M+H)$^+$.

d) [((3S)-1-{2-[6-(methyloxy)-1,5-naphthyridin-4-yl]ethyl}-3-pyrrolidinyl)methyl]amine To a stirred solution of ethyl[((3S)-1-{2-[6-(methyloxy)-1,5-naphthyridin-4-yl]ethyl}-3-pyrrolidinyl)methyl]carbamate (0.80 g, 2.09 mmole) in MeOH (30 mL) and H$_2$O (15 mL) at RT was added potassium carbonate (1.44 g, 10.5 mmole). After 18 h, the reaction contents were concentrated under reduced pressure and filtered through celite (EtOH) to give the title compound (0.59 g, 99%) as a light brown oil: LC-MS (ES) m/e 289 (M+H)$^+$.

e) 6-({[((3S)-1-{2-[6-(methyloxy)-1,5-naphthyridin-4-yl]ethyl}-3-pyrrolidinyl)methyl]amino}methyl)-2H-pyrido[3,2-b][1,4]thiazin-3(4H)-one To a stirred solution of [((3S)-1-{2-[6-(methyloxy)-1,5-naphthyridin-4-yl]ethyl}-3-pyrrolidinyl)methyl]amine (0.22 g, 0.77 mmole) in dry CH$_2$Cl$_2$ (25 mL) and dry EtOH (10 mL) at RT was added 3-oxo-3,4-dihydro-2H-pyrido[1,4]thiazine-6-carboxaldehyde (0.15 g, 0.77 mmole). After 24 h, at RT was added NaBH$_4$ (0.03 g, 0.85 mmole). After 24 h, silica gel (5 g) was added to the reaction solution and the suspension was concentrated under vacuum to a dry solid. Purification on silica (CHCl$_3$/MeOH, 9:1 containing 5% NH$_4$OH) afforded the title compound (0.25 g, 70%) as light yellow solid: $^1$H NMR (400 MHz, CD$_3$OD) δ 8.78 (d, J=4.5 Hz, 1H), 18.29 (d, J=9.1 Hz, 1H), 7.85 (m, 2H), 7.36 (d, J=9.1 Hz, 1H), 7.15 (d, J=5.8 Hz, 1H), 4.38 (s, 2H), 4.19 (s, 3H), 3.91 (m, 2H), 3.82 (m, 4H), 3.67 (s, 2H), 3.31 (m, 2H), 3.18 (m, 1H), 2.55 (m, 2H), 2.10 (m, 2H). LC-MS (ES) m/e 465 (M+H)$^+$.

This material, as a solution in MeOH, was treated with an excess of 4M HCl in diethyl ether and evaporated to dryness to provide the dihydrochloride salt of the title compound.

Example 2

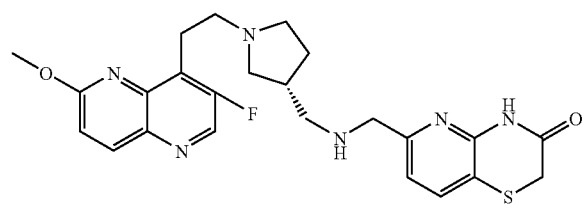

Preparation of 6-({[((3R)-1-{2-[3-fluoro-6-(methyloxy)-1,5-naphthyridin-4-yl]ethyl}-3-pyrrolidinyl)methyl]amino}methyl)-2H-pyrido[3,2-b][1,4]thiazin-3(4H)-one Prepared essentially according to the procedure of Example 1, except substituting [((3R)-1-{2-[3-fluoro-6-(methyloxy)-1,5-naphthyridin-4-yl]ethyl}-3-pyrrolidinyl)methyl]amine (0.30 g, 1.0 mmole) for [((3S)-1-{2-[6-(methyloxy)-1,5-naphthyridin-4-yl]ethyl}-3-pyrrolidinyl)methyl]amine, the title compound (0.33 g, 70%) was prepared as an off-white solid following flash chromatography on silica gel (CHCl$_3$/MeOH, 9:1, containing 5% NH$_4$OH): $^1$H NMR (400 MHz, CD$_3$OD) δ 8.81 (s, 1H), 8.30 (d, J=9.1 Hz, 1H), 7.84 (d, J=7.8 Hz, 1H), 7.29 (d, J=9.1 Hz, 1H), 7.15 (d, J=7.8 Hz, 1H), 4.37 (m, 2H), 4.20 (s, 3H), 3.98 (m, 2H), 3.75 (m, 5H), 3.61 (m, 2H), 3.13 (m, 2H), 2.50 (m, 2H), 2.04 (m, 2H). LC-MS (ES) m/e 483 (M+H)$^+$.

This material, as a solution in MeOH, was treated with an excess of 4M HCl in diethyl ether and evaporated to dryness to provide the dihydrochloride salt of the title compound.

Example 3

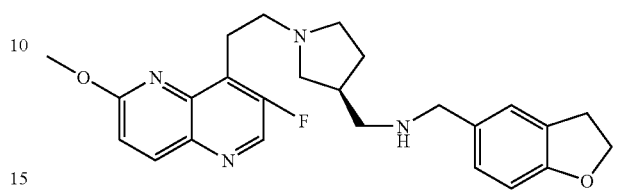

Preparation of (2,3-dihydro-1-benzofuran-5-ylmethyl)[((3S)-1-{2-[3-fluoro-6-(methyloxy)-1,5-naphthyridin-4-yl]ethyl}-3-pyrrolidinyl)methyl]amine a) phenylmethyl[((3S)-1-{2-[3-fluoro-6-(methyloxy)-1,5-naphthyridin-4-yl]ethyl}-3-pyrrolidinyl)methyl]carbamate To a solution of phenylmethyl[(3S)-3-pyrrolidinylmethyl]carbamate (127 mg, 0.54 mmole) in DMF (1 mL) was added 8-ethenyl-7-fluoro-2-(methyloxy)-1,5-naphthyridine (0.10 g, 0.49 mmole). After 24 h at 100° C., the reaction contents were purified on silica gel (CHCl$_3$/MeOH, 9:1, containing 5% NH$_4$OH) to afford the title compound (0.16 g, 77%) as a light yellow oil: LC-MS (ES) m/e 439 (M+H)$^+$.

b) [((3S)-1-{2-[3-fluoro-6-(methyloxy)-1,5-naphthyridin-4-yl]ethyl}-3-pyrrolidinyl)methyl]amine To a solution of phenylmethyl[((3S)-1-{2-[3-fluoro-6-(methyloxy)-1,5-naphthyridin-4-yl]ethyl}-3-pyrrolidinyl)methyl]carbamate (0.13 g, 0.29 mmole) in MeOH (50 mL) was added Pd(OH)$_2$ (100 mg). The reaction contents were placed under a balloon of H$_2$ and stirred for 18 hours. The reaction contents were filtered through Celite (MeOH) and concentrated under vacuum to give the title compound (66 mg, 76%) as a light yellow oil: LC-MS (ES) m/e 305 (M+H)$^+$.

c) (2,3-dihydrofuro[2,3-c]pyridin-5-ylmethyl)[((3S)-1-{2-[3-fluoro-6-(methyloxy)-1,5-naphthyridin-4-yl]ethyl}-3-pyrrolidinyl)methyl]amine To a stirred solution of [((3S)-1-{2-[3-fluoro-6-(methyloxy)-1,5-naphthyridin-4-yl]ethyl}-3-pyrrolidinyl)methyl]amine (66 mg, 0.22 mmole) in dry CH$_2$Cl$_2$ (25 mL) and dry EtOH (20 mL) at RT was added 2,3-dihydro-1-benzofuran-5-carbaldehyde (37 mg, 0.25 mmole). After 24 h, at RT was added NaBH$_4$ (11 mg, 0.29 mmole). After 2 h, silica gel (5 g) was added to the reaction solution and the suspension was concentrated under vacuum to a dry solid. Purification on silica (CHCl$_3$/MeOH, 9:1 containing 5% NH$_4$OH) afforded the title compound (58 mg, 60%) as light yellow solid: $^1$H NMR (400 MHz, CDCl$_3$) δ 8.61 (s, 1H), 8.16 (m, 1H), 8.02 (s, 1H), 7.16 (s, 1H), 7.06 (m, 1H), 7.03 (d, 1H), 6.73 (m, 2H), 4.56 (m, 2H), 4.08 (s, 3H), 3.72 (s, 2H), 3.41 (m, 2H), 3.19 (m, 2H), 2.92 (m, 21H), 2.70-2.90 (m, 3H), 2.55-2.68 (m, 3H), 2.31-2.48 (m, 2H), 2.04 (m, 1H), 1.51 (m, 1H). LC-MS (ES) m/e 437 (M+H)$^+$.

This material, as a solution in MeOH, was treated with an excess of 4M HCl in diethyl ether and evaporated to dryness to provide the dihydrochloride salt of the title compound.

Example 4

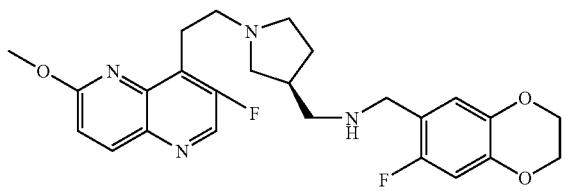

Preparation of [(7-fluoro-2,3-dihydro-1,4-benzo-dioxin-6-yl)methyl][((3S)-1-{2-[3-fluoro-6-(methyloxy)-1,5-naphthyridin-4-yl]ethyl}-3-pyrrolidinyl)methyl]amine Prepared essentially according to the procedure for Example 3, except substituting 7-fluoro-2,3-dihydro-1,4-benzodioxin-6-carbaldehyde (57 mg, 0.31 mmole) for 2,3-dihydro-1-benzofuran-5-carbaldehyde, the title compound (74 mg, 50%) was prepared as a light yellow solid: $^1$H NMR (400 MHz, CD$_3$OD) δ 8.59 (s, 1H), 8.15 (d, J=6.2 Hz, 1H), 7.13 (d, J=5.8 Hz, 1H), 6.83 (d, J=6.7 Hz, 1H), 6.56 (d, J=10.5 Hz, 1H), 4.19 (s, 4H), 4.07 (s, 3H), 3.66 (s, 2H), 3.39 (m, 2H), 2.94 (m, 1H), 2.70-2.89 (m, 3H), 2.65 (m, 1H), 2.56 (d, 2H), 2.30-2.46 (m, 2H), 2.03 (m, 1H), 1.49 (m, 1H). LC-MS (ES) m/e 471 (M+H)$^+$.

This material, as a solution in MeOH, was treated with an excess of 4M HCl in diethyl ether and evaporated to dryness to provide the dihydrochloride salt of the title compound.

Example 5

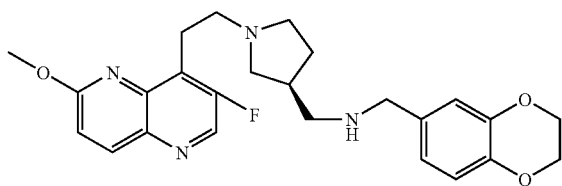

Preparation of (2,3-dihydro-1,4-benzodioxin-6-ylmethyl)[((3S)-1-{2-[3-fluoro-6-(methyloxy)-1,5-naphthyridin-4-yl]ethyl}-3-pyrrolidinyl)methyl]amine Prepared essentially according to the procedure for Example 3, except substituting 2,3-dihydro-1,4-benzodioxin-6-carbaldehyde (45 mg, 0.27 mmole) for 2,3-dihydro-1-benzofuran-5-carbaldehyde, the title compound (50 mg, 40%) was prepared as a light yellow solid: $^1$H NMR (400 MHz, CD$_3$OD) δ 8.60 (s, 1H), 8.16 (d, J=9.1 Hz, 1H), 7.14 (d, J=9.1 Hz, 1H), 6.80 (s, 1H), 6.75 (s, 2H), 4.20 (s, 4H), 4.08 (s, 3H), 3.62 (s, 2H), 3.41 (m, 2H), 2.94 (m, 1H), 2.69-2.89 (m, 3H), 2.64 (m, 1H), 2.54 (m, 2H), 2.31-2.44 (m, 2H), 2.03 (m, 1H), 1.48 (m, 1H). LC-MS (ES) m/e 453 (M+H)$^+$.

This material, as a solution in MeOH, was treated with an excess of 4M HCl in diethyl ether and evaporated to dryness to provide the dihydrochloride salt of the title compound.

Example 6

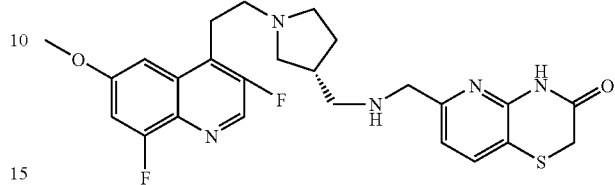

Preparation of 6-({[((3R)-1-{2-[3,8-difluoro-6-(methyloxy)-4-quinolinyl]ethyl}-3-pyrrolidinyl)methyl]amino}methyl)-2H-pyrido[3,2-b][1,4]thiazin-3(4H)-one Prepared essentially according to the procedure for Example 3, except substituting 3-oxo-3,4-dihydro-2H-pyrido[1,4]thiazine-6-carboxaldehyde (0.15 g, 0.78 mmole) for 2,3-dihydro-1-benzofuran-5-carbaldehyde, and substituting [((3R)-1-{2-[3,8-difluoro-6-(methyloxy)-4-quinolinyl]ethyl}-3-pyrrolidinyl)methyl]amine (0.25 g, 0.78 mmole) for [((3S)-1-{2-[3-fluoro-6-(methyloxy)-1,5-naphthyridin-4-yl]ethyl}-3-pyrrolidinyl)methyl]amine, the title compound (375 mg, 75%) was prepared as a light yellow solid: $^1$H NMR (400 MHz, CDCl$_3$) δ 8.61 (s, 1H), 7.56 (d, J=7.80 Hz, 1H), 7.02-7.07 (m, 2H), 6.95 (d, J=7.8 Hz, 1H), 3.93 (s, 3H), 3.81 (s, 2H), 3.46 (s, 2H), 3.23 (m, 2H), 2.91 (m, 1H), 2.58-2.81 (m, 6H), 2.35-2.49 (m, 2H), 2.06 (m, 1H), 1.52 (m, 1H). LC-MS (ES) m/e 500 (M+H)$^+$.

This material, as a solution in MeOH, was treated with an excess of 4M HCl in diethyl ether and evaporated to dryness to provide the dihydrochloride salt of the title compound.

Example 7

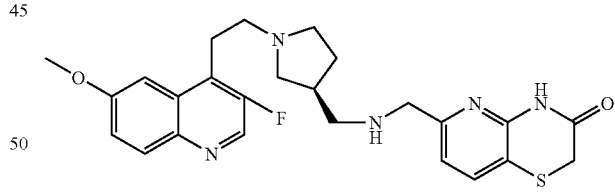

Preparation of 6-({[((3S)-1-{2-[3-fluoro-6-(methyloxy)-4-quinolinyl]ethyl}-3-pyrrolidinyl)methyl]amino}methyl)-2H-pyrido[3,2-b][1,4]thiazin-3(4H)-one Prepared essentially according to the procedure for Example 3, except substituting 3-oxo-3,4-dihydro-2H-pyrido[1,4]thiazine-6-carboxaldehyde (34 mg, 0.17 mmole) for 2,3-dihydro-1-benzofuran-5-carbaldehyde, and substituting [((3S)-1-{2-[3-fluoro-6-(methyloxy)-4-quinolinyl]ethyl}-3-pyrrolidinyl)methyl]amine (53 mg, 0.17 mmole) for [((3S)-1-{2-[3-fluoro-6-(methyloxy)-1,5-naphthyridin-4-yl]ethyl}-3-pyrrolidinyl)methyl]amine, the title compound (38 mg, 45%) was prepared as a light yellow solid: $^1$H NMR (400 MHz, CD$_3$OD) δ 8.54 (d, J=1.2 Hz, 1H), 7.92 (d, J=9.1 Hz, 1H), 7.66 (d, J=7.8 Hz, 1H), 7.31-7.38 (m, 2H), 7.00 (d, J=7.8 Hz, 1H), 3.97 (s, 3H), 3.78 (s, 2H), 3.50 (s, 2H), 3.28 (m, 2H), 2.92 (m, 1H), 2.65-2.79 (m, 4H), 2.62 (m, 2H), 2.40-2.47 (m, 2H), 2.17 (m, 1H), 1.54 (m, 1H). LC-MS (ES) m/e 482 (M+H)$^+$.

This material, as a solution in MeOH, was treated with an excess of 4M HCl in diethyl ether and evaporated to dryness to provide the dihydrochloride salt of the title compound.

Example 8

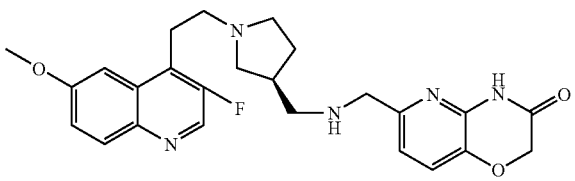

Preparation of 6-({[((3S)-1-{2-[3-fluoro-6-(methyloxy)-4-quinolinyl]ethyl}-3-pyrrolidinyl)methyl]amino}methyl)-2H-pyrido[3,2-b][1,4]oxazin-3(4H)-one Prepared essentially according to the procedure for Example 3, except substituting 3-oxo-3,4-dihydro-2H-pyrido[1,4]oxazine-6-carboxaldehyde (28 mg, 0.16 mmole) for 2,3-dihydro-1-benzofuran-5-carbaldehyde, and substituting [((3S)-1-{2-[3-fluoro-6-(methyloxy)-4-quinolinyl]ethyl}-3-pyrrolidinyl)methyl]amine (48 mg, 0.16 mmole) for [((3S)-1-{2-[3-fluoro-6-(methyloxy)-1,5-naphthyridin-4-yl]ethyl}-3-pyrrolidinyl)methyl]amine, the title compound (42 mg, 57%) was prepared as a light yellow solid: $^1$H NMR (400 MHz, CD$_3$OD) δ 8.53 (s, 1H), 7.90 (d, J=9.1 Hz, 1H), 7.22-7.34 (m, 2H), 6.94 (d, J=8.0 Hz, 1H), 4.61 (s, 2H), 3.95 (s, 3H), 3.73 (s, 2H), 3.24 (m, 2H), 2.91 (m, 1H), 2.56-2.80 (m, 6H), 2.57 (m, 1H), 2.35-2.49 (m, 2H), 2.07 (m, 1H), 1.52 (m, 1H). LC-MS (ES) m/e 466 (M+H)$^+$.

This material, as a solution in MeOH, was treated with an excess of 4M HCl in diethyl ether and evaporated to dryness to provide the dihydrochloride salt of the title compound.

Example 9

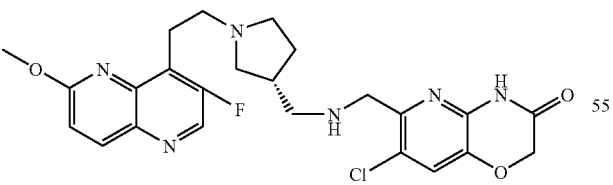

Preparation of 7-chloro-6-({[((3R)-1-{2-[3-fluoro-6-(methyloxy)-1,5-naphthyridin-4-yl]ethyl}-3-pyrrolidinyl)methyl]amino}methyl)-2H-pyrido[3,2-b][1,4]oxazin-3(4H)-one Prepared essentially according to the procedure for Example 3, except substituting 7-chloro-3-oxo-3,4-dihydro-2H-pyrido[3,2-b][1,4]oxazine-6-carbaldehyde (170 mg, 0.79 mmole) for 2,3-dihydro-1-benzofuran-5-carbaldehyde, and substituting [((3R)-1-{2-[3-fluoro-6-(methyloxy)-4-naphthyridyl]ethyl}-3-pyrrolidinyl)methyl]amine (240 mg, 0.79 mmole) for [((3S)-1-{2-[3-fluoro-6-(methyloxy)-1,5-naphthyridin-4-yl]ethyl}-3-pyrrolidinyl)methyl]amine, the title compound (250 mg, 64%) was prepared as a light yellow solid: $^1$H NMR (400 MHz, CDCl$_3$) δ 8.52 (s, 1H), 8.11 (d, J=9.1 Hz, 1H), 7.14 (s, 1H), 6.98 (d, J=9.1 Hz, 1H), 4.52 (m, 2H), 4.00 (s, 3H), 3.85 (m, 2H), 3.39 (m, 2H), 2.99 (m, 1H), 2.84 (m, 3H), 2.76 (m, 3H), 2.46 (m, 2H), 2.02 (m, 1H), 1.46 (m, 1H). LC-MS (ES) m/e 501 (M+H)$^+$.

This material, as a solution in MeOH, was treated with an excess of 4M HCl in diethyl ether and evaporated to dryness to provide the dihydrochloride salt of the title compound.

Example 10

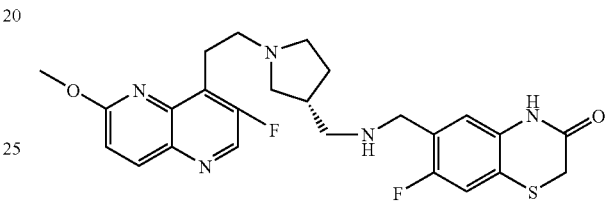

Preparation of 7-fluoro-6-({[((3R)-1-{2-[3-fluoro-6-(methyloxy)-1,5-naphthyridin-4-yl]ethyl}-3-pyrrolidinyl)methyl]amino}methyl)-2H-1,4-benzothiazin-3(4H)-one Prepared essentially according to the procedure for Example 3, except substituting 7-fluoro-3-oxo-3,4-dihydro-2H-1,4-benzothiazine-6-carbaldehyde (165 mg, 0.78 mmole) for 2,3-dihydro-1-benzofuran-5-carbaldehyde, and substituting [((3R)-1-{2-[3-fluoro-6-(methyloxy)-4-naphthyridyl]ethyl}-3-pyrrolidinyl)methyl]amine (240 mg, 0.79 mmole) for [((3S)-1-{2-[3-fluoro-6-(methyloxy)-1,5-naphthyridin-4-yl]ethyl}-3-pyrrolidinyl)methyl]amine, the title compound (240 mg, 62%) was prepared as a light yellow solid: $^1$H NMR (400 MHz, CDCl$_3$) δ 8.57 (s, 1H), 8.15 (d, J=9.1 Hz, 1H), 7.04 (d, J=9.1 Hz, 1H), 6.96 (d, J=9.2 Hz, 1H), 6.87 (d, J=6.4 Hz, 1H), 4.05 (s, 3H), 3.75 (m, 2H), 3.39 (m, 4H), 2.71-2.92 (m, 7H), 2.43 (m, 2H), 2.02 (m, 1H), 1.48 (m, 1H). LC-MS (ES) m/e 500 (M+H)$^+$.

This material, as a solution in MeOH, was treated with an excess of 4M HCl in diethyl ether and evaporated to dryness to provide the dihydrochloride salt of the title compound.

Example 11

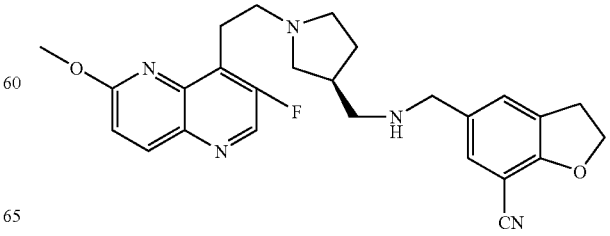

Preparation of 5-({[((3S)-1-{2-[3-fluoro-6-(methyloxy)-1,5-naphthyridin-4-yl]ethyl}-3-pyrrolidinyl)methyl]amino}methyl)-2,3-dihydro-1-benzofuran-7-carbonitrile Prepared essentially according to the procedure of example 3 except substituting 5-formyl-2,3-dihydro-1-benzofuran-7-carbonitrile (85 mg, 0.53 mmole) for 2,3-dihydro-1-benzofuran-5-carboxaldehyde, the title compound (0.17 g, 70%) was prepared as a light yellow solid: $^1$H NMR (400 MHz, CD$_3$OD) δ 8.79 (s, 1H), 8.16 (d, J=9.0 Hz, 1H), 7.60 (s, 1H), 7.50 (s, 1H), 7.21 (d, J=9.0 Hz, 1H), 4.67 (t, J=8.2 Hz, 2H), 4.11 (s, 2H), 4.07 (s, 3H), 3.85 (m, 2H), 3.61 (m, 4H), 3.33 (m, 2H), 3.25 (m, 4H), 2.35 (m, 2H), 1.97 (m, 1H). LC-MS (ES) m/e 462 (M+H)$^+$.

This material, as a solution in MeOH, was treated with an excess of 4M HCl in diethyl ether and evaporated to dryness to provide the dihydrochloride salt of the title compound.

Example 12

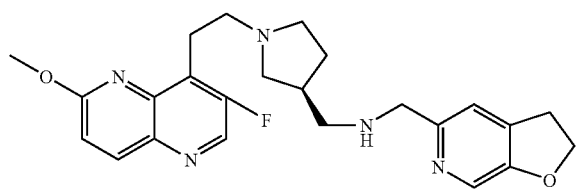

Preparation of (2,3-dihydrofuro[2,3-c]pyridin-5-ylmethyl)[((3S)-1-{2-[3-fluoro-6-(methyloxy)-1,5-naphthyridin-4-yl]ethyl}-3-pyrrolidinyl)methyl]amine Prepared essentially according to the procedure for Example 3, except substituting 2,3-dihydrofuro[2,3-c]pyridine-5-carbaldehyde (188 mg, 0.62 mmole) for 2,3-dihydro-1-benzofuran-5-carboxaldehyde, the title compound (223 mg, 82%) was prepared as a light yellow solid: $^1$H NMR (400 MHz, CDCl$_3$) δ 8.61 (1H, s), 8.16 (1H, d), 8.02 (1H, s), 7.16 (1H, s), 7.06 (1H, d), 7.03 (1H, d), 6.73 (2H, d), 4.56 (2H, t), 4.08 (3H, s), 3.72 (2H, s), 3.41 (2H, t), 3.19 (2H, t), 2.92 (2 1H, m), 2.70-2.90 (3H, m), 2.55-2.68 (3H, m), 2.31-2.48 (2H, m), 2.04 (1H, m), 1.51 (1H, m). LC-MS (ES) m/e 438 (M+H)$^+$.

This material, as a solution in MeOH, was treated with an excess of 4M HCl in diethyl ether and evaporated to dryness to provide the dihydrochloride salt of the title compound.

Example 13

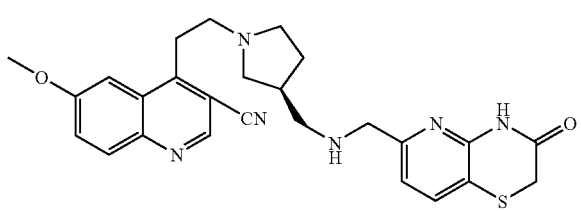

Preparation of 6-(methyloxy)-4-{2-[(3S)-3-({[(3-oxo-3,4-dihydro-2H-pyrido[3,2-b][1,4]thiazin-6-yl)methyl]amino}methyl)-1-pyrrolidinyl]ethyl}-3-quinolinecarbonitrile Prepared essentially according to the procedure of Example 3 except substituting 4-{2-[(3S)-3-(aminomethyl)-1-pyrrolidinyl]ethyl}-6-(methyloxy)-3-quinolinecarbonitrile (100 mg, 0.32 mmol) for [((3S)-1-{2-[3-fluoro-6-(methyloxy)-1,5-naphthyridin-4-yl]ethyl}-3-pyrrolidinyl)methyl]amine, and substituting 3-oxo-3,4-dihydro-2H-pyrido[3,2-b][1,4]thiazine-6-carboxaldehyde (60 mg, 0.32 mmol) for 2,3-dihydro-1-benzofuran-5-carboxaldehyde, the title compound (10 mg, 60%) was prepared as light yellow solid: LC/MS (ES) m/e 489 (M+H)$^+$; $^1$H NMR (CD$_3$OD, 400 MHz) δ 9.07 (s, 1H), 8.08 (d, J=9.1 Hz, 1H)), 7.71 (d, J=8.1 Hz, 1H), 7.4 (s, 1H), 7.36 (d, J=5.1 Hz, 1H), 7.22 (d, J=8.1 Hz, 1H), 4.45 (s, 2H), 4.35 (s, 2H), 4.15 (s, 4H), 3.95 (m, 4H), 3.6 (m, 4H), 3.4 (m, 1H), 3.35 (m, 2H), 2.9-3.1 (m, 1H), 2.4-2.6 (m, 1H), 1.9-2.1 (m, 1H).

This material, as a solution in MeOH, was treated with an excess of 4M HCl in diethyl ether and evaporated to dryness to provide the dihydrochloride salt of the title compound.

Example 14

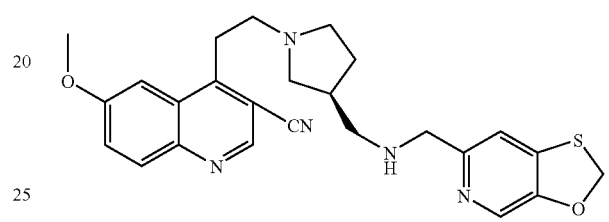

Preparation of 6-(methyloxy)-4-[2-((3S)-3-{[([1,3]oxathiolo[5,4-c]pyridin-6-ylmethyl)amino]methyl}-1-pyrrolidinyl)ethyl]-3-quinolinecarbonitrile Prepared essentially according to the procedure for Example 3, except substituting [1,3]oxathiolo[5,4-c]pyridine-6-carbaldehyde (50 mg, 0.29 mmol) for 2,3-dihydro-1-benzofuran-5-carbaldehyde and substituting 4-{2-[(3S)-3-(aminomethyl)-1-pyrrolidinyl]ethyl}-6-(methyloxy)-3-quinolinecarbonitrile (100 mg, 0.32 mmol) for [((3S)-1-{2-[3-fluoro-6-(methyloxy)-1,5-naphthyridin-4-yl]ethyl}-3-pyrrolidinyl)methyl]amine. The title compound (100 mg, 75%) was obtained as a yellow solid: LC/MS (ES) m/e 462 (M+H)$^+$; $^1$H NMR (CD$_3$OD, 400 MHz) δ 9.07 (s, 1H), 8.10 (d, J=9.6 Hz, 1H)), 8.0 (s, 1H), 7.8 (s, 1H), 7.7 (d, J=5.1 Hz, 1H), 7.55 (d, J=6.6 Hz, 1H), 6.1 (s, 2H), 5.95 (s, 2H), 5.45 (s, 1H), 4.8 (s, 2H), 4.35 (s, 2H), 4.15 (s, 3H), 3.95 (m, 4H), 3.6 (m, 4H), 3.4 (m, 1H), 3.35 (m, 2H), 2.9-3.1 (m, 1H), 2.4-2.6 (m, 1H), 1.9-2.1 (m, 1H).

This material, as a solution in MeOH, was treated with an excess of 4M HCl in dioxane and evaporated to dryness to provide the hydrochloride salt of the title compound.

Example 15

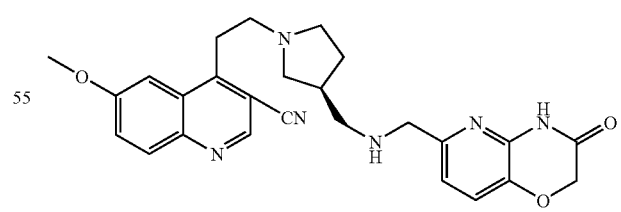

Preparation of 6-(methyloxy)-4-{2-[(3S)-3-({[(3-oxo-3,4-dihydro-2H-pyrido[3,2-b][1,4]oxazin-6-yl)methyl]amino}methyl)-1-pyrrolidinyl]ethyl}-3-quinolinecarbonitrile Prepared essentially according to the procedure for Example 3, except substituting 3-oxo-3,4-dihydro-2H-pyrido[3,2-b][1,4]oxazine-6-carbaldehyde (55 mg, 0.32 mmol) for 2,3-dihydro-1-benzofuran-5-carbaldehyde, and substituting 4-{2-[(3S)-3-(aminomethyl)-1-pyrrolidinyl]ethyl}-6-(methyloxy)-3-quinolinecarbonitrile (100 mg, 0.32 mmol) for [((3S)-1-{2-[3-fluoro-6-(methyloxy)-1,5-naphthyridin-4-yl]ethyl}-3-pyrrolidinyl)methyl]amine. The title compound (100 mg, 33%) was obtained as a light yellow solid: LC/MS (ES) m/e 473 (M+H)+; 1H NMR (CD3OD, 400 MHz) δ 8.91 (s, 1H), 8.07 (d, J=9.3 Hz, 1H)), 7.64 (d, J=7.6 Hz, 1H), 7.38 (d, J=8.1 Hz, 1H), 7.1 (d, J=8.1 Hz, 1H), 4.65 (s, 2H), 4.3 (s, 2H), 4.1 (s, 3H), 3.95 (m, 4H), 3.65 (s, 2H), 3.55 (m, 4H), 3.35 (m, 4H), 2.9-3.1 (m, 1H), 2.4-2.6 (m, 1H), 1.9-2.1 (m, 1H).

This material, as a solution in MeOH, was treated with an excess of 4M HCl in dioxane and evaporated to dryness to provide the hydrochloride salt of the title compound.

Example 16

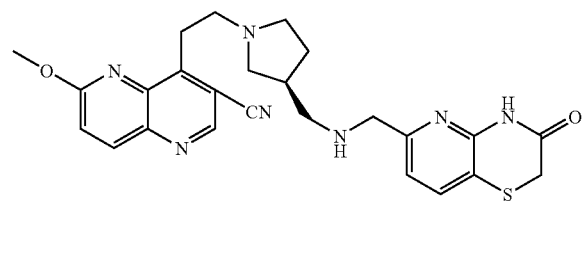

Preparation of 6-(methyloxy)-4-{2-[(3S)-3-({[(3-oxo-3,4-dihydro-2H-pyrido[3,2-b][1,4]thiazin-6-yl)methyl]amino}methyl)-1-pyrrolidinyl]ethyl}-1,5-naphthyridine-3-carbonitrile Prepared essentially according to the procedure for Example 3, except substituting 4-ethenyl-6-(methyloxy)-1,5-naphthyridine-3-carbonitrile (100 mg, 0.32 mmol) for [((3S)-1-{2-[3-fluoro-6-(methyloxy)-1,5-naphthyridin-4-yl]ethyl}-3-pyrrolidinyl)methyl]amine, and substituting 3-oxo-3,4-dihydro-2H-pyrido[3,2-b][1,4]thiazine-6-carbaldehyde (62 mg, 0.32 mmol) for 2,3-dihydro-1-benzofuran-5-carbaldehyde, the title compound (20 mg) was obtained as an off-white solid: LC/MS (ES) m/e 490 (M+H)+; 1H NMR (400 MHz, CD3OD) δ 8.84 (s, 1H), 8.15 (d, J=9.10 Hz, 1H), 7.65 (d, J=7.85 Hz, 1H), 7.22 (d, J=9.08 Hz, 1H), 7.02 (d, J=7.89 Hz, 1H), 3.96 (m, 2H), 3.90 (s, 3H), 3.63 (m, 1H), 3.52 (m, 2H), 3.30 (s, 2H), 3.29, (M, 1H), 3.01 (m, 2H), 2.74 (m, 1H), 2.10 (m, 1H), 1.98 (M, 1H), 2.61 (M, 1H), 2.58 (M, 2H), 1.77 (m, 1H), 1.60 (m, 1H).

This material, as a solution in MeOH, was treated with an excess of 4M HCl in diethyl ether and evaporated to dryness to provide the dihydrochloride salt of the title compound.

Example 17

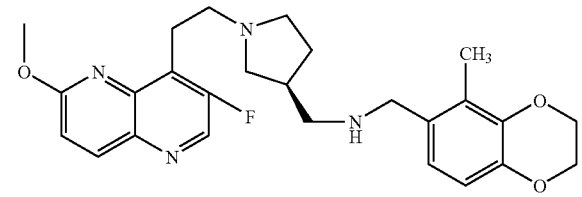

Preparation of 1-((3S)-1-{2-[3-fluoro-6-(methyloxy)-1,5-naphthyridin-4-yl]ethyl}-3-pyrrolidinyl)-N-[(5-methyl-2,3-dihydro-1,4-benzodioxin-6-yl)methyl]methanamine Prepared essentially according to the procedure for Example 3, except substituting 5-methyl-2,3-dihydro-1,4-benzodioxin-6-carbaldehyde (44 mg) for 2,3-dihydro-1-benzofuran-5-carbaldehyde, the title compound (63 mg) was obtained as an off-white solid: LC/MS (ES) m/e 467 (M+H)+; 1H NMR (400 MHz, CDCl3) δ 8.53 (s, 1H), 8.08 (d, J=9.04 Hz, 1H), 6.98 (d, J=9.04 Hz, 1H), 6.67 (d, J=8.30, 1H) 6.60 (d, J=8.28 Hz, 2H), 4.19 (m, 2H), 4.14 (m, 2H), 4.01 (s, 3H), 3.62 (s, 2H), 3.33 (t, J=7.58 Hz, 2H), 2.84 (m, 1H), 2.74 (m, 1H), 2.67 (M, 2H), 2.58 (M, 1H), 2.56 (M, 2H), 2.30 (M, 2H), 2.12 (S, 3H), 1.95 (m, 1H), 1.44 (m, 1H).

This material, as a solution in MeOH, was treated with an excess of 4M HCl in diethyl ether and evaporated to dryness to provide the dihydrochloride salt of the title compound.

Example 18

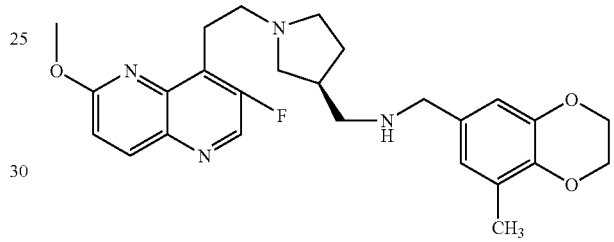

Preparation of 1-((3S)-1-{2-[3-fluoro-6-(methyloxy)-1,5-naphthyridin-4-yl]ethyl}-3-pyrrolidinyl)-N-[(8-methyl-2,3-dihydro-1,4-benzodioxin-6-yl)methyl]methanamine Prepared essentially according to the procedure for Example 3, except substituting 8-methyl-2,3-dihydro-1,4-benzodioxin-6-carbaldehyde (37 mg) for 2,3-dihydro-1-benzofuran-5-carbaldehyde, the title compound (51 mg) was obtained as an off-white solid: LC/MS (ES) m/e 467 (M+H)+; 1H NMR (400 MHz, CDCl3) δ 8.53 (s, 1H), 8.08 (d, J=9.0 Hz, 1H), 6.98 (d, J=9.03 Hz, 1H), 6.58 (d, J=2.3 Hz, 2H), 4.19 (m, 2H), 4.15 (m, 2H), 4.01 (s, 3H), 3.57 (s, 2H), 3.33 (t, J=7.81 Hz, 2H), 2.74 (m, 1H), 2.67 (M, 2H), 2.54 (M, 1H), 2.54 (M, 2H), 2.29 (M, 2H), 2.11 (S, 3H), 1.94 (m, 1H), 1.44 (m, 1H).

This material, as a solution in MeOH, was treated with an excess of 4M HCl in diethyl ether and evaporated to dryness to provide the dihydrochloride salt of the title compound.

Example 19

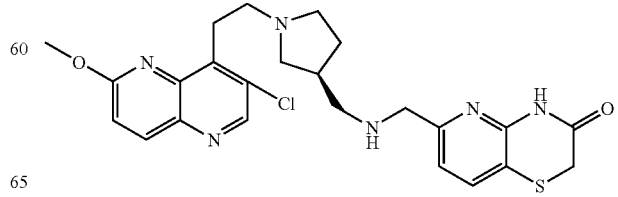

Preparation of 6-({[((3S)-1-{2-[3-chloro-6-(methyloxy)-1,5-naphthyridin-4-yl]ethyl}-3-pyrrolidinyl)methyl]amino}methyl)-2H-pyrido[3,2-b][1,4]thiazin-3(4H)-one a) Phenylmethyl[((3S)-1-{2-[3-chloro-6-(methyloxy)-1,5-naphthyridin-4-yl]ethyl}-3-pyrrolidinyl)methyl]carbamate

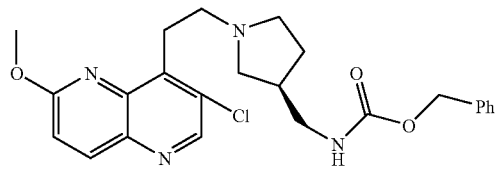

To a solution of 7-chloro-8-ethenyl-2-(methyloxy)-1,5-naphthyridine (1.68 g, 7.6 mmol) in DMF (5 mL) was added phenylmethyl[(3R)-3-pyrrolidinylmethyl]carbamate hydrochloride (2.1 g, 7.6 mmol) and diisopropylethylamine (3.9 mL, 22.8 mmol)). The reaction was heated at 100° C. for 18 h. Upon cooling to room temperature, the crude reaction mixture was directly added to a silica gel column and purified to give a light brown oil (1.3 g): LC/MS (ES) m/e 455 (M+H)+.

b) [((3S)-1-{2-[3-Chloro-6-(methyloxy)-1,5-naphthyridin-4-yl]ethyl}-3-pyrrolidinyl)methyl]amine

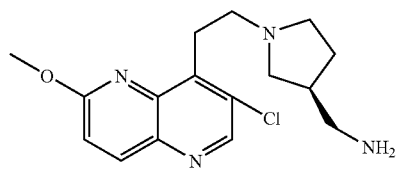

A solution of phenylmethyl[((3S)-1-{2-[3-chloro-6-(methyloxy)-1,5-naphthyridin-4-yl]ethyl}-3-pyrrolidinyl)methyl]carbamate (1.0 g, 2.2 mmol) in MeOH (30 mL) was treated with 40% KOH (15 mL, 107 mmol) and heated at 100° C. for 3 h. The MeOH was stripped off at reduced pressure and the residue was treated with water. The product was extracted into CHCl3 and the combined organic phases were dried (K2CO3) and filtered. Purification of silica gel provided the product as a light brown oil (0.36 g, 51%): LC/MS (ES) m/e 321 (M+H)+.

c) 6-({[((3S)-1-{2-[3-chloro-6-(methyloxy)-1,5-naphthyridin-4-yl]ethyl}-3-pyrrolidinyl)methyl]amino}methyl)-2H-pyrido[3,2-b][1,4]thiazin-3(4H)-one

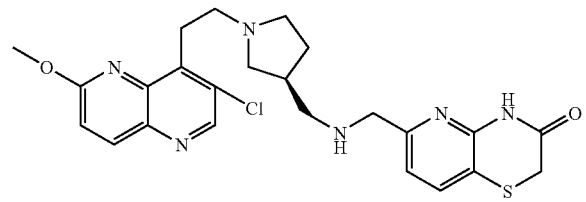

To a stirred solution of [((3S)-1-{2-[3-Chloro-6-(methyloxy)-1,5-naphthyridin-4-yl]ethyl}-3-pyrrolidinyl)methyl]amine (100 mg, 0.31 mmol) in dry CH2Cl2 (5 mL) and dry EtOH (5 mL) at RT was added 3-oxo-3,4-dihydro-2H-pyrido[3,2-b][1,4]thiazine-6-carboxaldehyde (67 mg, 0.34 mmol) along with a small amount of Na2SO4 and NaHCO3. After 24 h at RT, NaBH4 (12 mg, 0.32 mmol) was added. After 2 h, silica gel (5 g) was added to the reaction solution and the suspension was concentrated under vacuum to a dry solid. Purification on silica gel afforded the title compound as a light yellow solid (15 mg, 9.4%): LC/MS (ES) m/e 499/501 (M+H)+; 1H NMR (CD3OD, 400 MHz) δ 8.78 (s, 1H), 8.25 (d, J=9.1 Hz, 1H), 7.83 (d, J=7.8 Hz, 1H), 7.28 (d, J=9.1 Hz, 1H), 7.12 (d, J=7.8 Hz, 1H), 4.35 (s, 2H), 4.1 (s, 3H), 3.9 (m, 4H), 3.66 (s, 4H), 3.5 (m, 4H), 3.3 (m, 2H), 2.9-3.0 (m, 1H), 2.2-2.3 (m, 1H), 1.95-2.05 (m, 1H).

This material, as a solution in MeOH, was treated with 3 equivalents of 4M HCl in dioxane and evaporated to dryness to provide the hydrochloride salt of the title compound.

Example 20

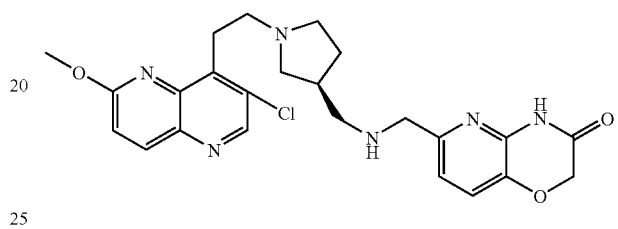

Preparation of 6-({[((3S)-1-{2-[3-chloro-6-(methyloxy)-1,5-naphthyridin-4-yl]ethyl}-3-pyrrolidinyl)methyl]amino}methyl)-2H-pyrido[3,2-b][1,4]oxazin-3(4H)-one Prepared essentially according to the procedure for Example 19, except substituting 3-oxo-3,4-dihydro-2H-pyrido[3,2-b][1,4]oxazine-6-carbaldehyde (61 mg, 0.34 mmol) for 3-oxo-3,4-dihydro-2H-pyrido[3,2-b][1,4]thiazine-6-carboxaldehyde. The title compound (150 mg, 92%) was obtained as a light yellow solid: LC/MS (ES) m/e 483/485 (M+H)+; 1H NMR (CD3OD, 400 MHz) δ 8.78 (s, 1H), 8.25 (d, J=9.1 Hz, 1H), 7.83 (d, J=8.1 Hz, 1H), 7.28 (d, J=9.1 Hz, 1H), 7.11 (d, J=8.1 Hz, 1H), 4.7 (s, 2H), 4.3 (s, 2H), 4.2 (s, 3H), 3.9 (m, 4H), 3.66 (s, 4H), 3.5 (m, 4H), 3.3 (m, 2H), 3.0 (m, 1H), 2.2-2.3 (m, 1H), 1.95-2.05 (m, 1H).

This material, as a solution in MeOH, was treated with an excess of 4M HCl in dioxane and evaporated to dryness to provide the hydrochloride salt of the title compound.

Example 21

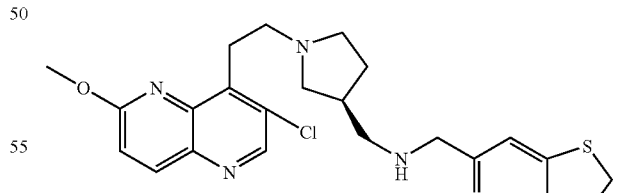

Preparation of [((3S)-1-{2-[3-chloro-6-(methyloxy)-1,5-naphthyridin-4-yl]ethyl}-3-pyrrolidinyl)methyl]([1,3]oxathiolo[5,4-c]pyridin-6-ylmethyl)amine Prepared essentially according to the procedure for Example 19, except substituting [1,3]oxathiolo[5,4-c]pyridine-6-carbaldehyde (57 mg, 0.34 mmol) for 3-oxo-3,4-dihydro-2H-pyrido[3,2-b][1,4]thiazine-6-carboxaldehyde. The title compound (140 mg) was obtained as a light yellow solid: LC/MS (ES) m/e 472/474 (M+H)+; 1H NMR (CD3OD, 400 MHz) δ 8.85 (s, 1H), 8.22 (d, J=9.1 Hz, 1H), 8.08 (d, J=3.0 Hz, 1H), 7.71 (d, J=6.8 Hz, 1H), 7.28 (d, J=9.1 Hz, 1H), 5.94 (bs, 2H), 5.4 (s, 1H), 4.35 (s, 2H), 4.11 (s, 3H), 3.85 (m, 4H), 3.52 (m, 4H), 3.25 (m, 3H), 3.0 (m, 1H), 2.3-2.5 (m, 1H), 1.8-2.0 (m, 1H).

This material, as a solution in MeOH, was treated with an excess of 4M HCl in dioxane and evaporated to dryness to provide the hydrochloride salt of the title compound.

Example 22

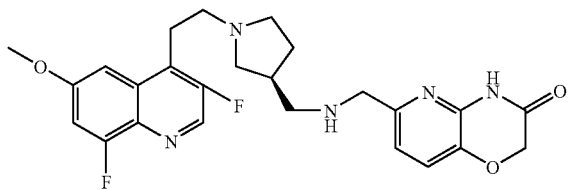

Preparation of 6-({[((3S)-1-{2-[3,8-difluoro-6-(methyloxy)-4-quinolinyl]ethyl}-3-pyrrolidinyl)methyl]amino}methyl)-2H-pyrido[3,2-b][1,4]oxazin-3(4H)-one a) 1,1-dimethylethyl(3S)-3-({[(3-oxo-3,4-dihydro-2H-pyrido[3,2-b][1,4]thiazin-6-yl)methyl]amino}methyl)-1-pyrrolidinecarboxylate To a solution of 1,1-dimethylethyl(3S)-3-(aminomethyl)-1-pyrrolidinecarboxylate (0.41 g, 2.07 mmole) in dry CH2Cl2 (25 mL) and dry EtOH (20 mL) at RT was added 3-oxo-3,4-dihydro-2H-pyrido[3,2-b][1,4]oxazine-6-carbaldehyde (0.36 g, 2.07 mmole). After 24 h, at RT was added NaBH4 (79 mg, 2.08 mmole). After 2 h, silica gel (5 g) was added to the reaction solution and the suspension was concentrated under vacuum to a dry solid. Purification on silica (CHCl3/MeOH, 9:1 containing 5% NH4OH) afforded the title compound (0.40 g, 53%) as light yellow solid: LC-MS (ES) m/e 363 (M+H)+.

b) 6-({[(3S)-3-pyrrolidinylmethyl]amino}methyl)-2H-pyrido[3,2-b][1,4]thiazin-3(4H)-one To a stirred solution of 1,1-dimethylethyl(3S)-3-({[(3-oxo-3,4-dihydro-2H-pyrido[3,2-b][1,4]oxazin-6-yl)methyl]amino}methyl)-1-pyrrolidinecarboxylate (0.40 g, 1.10 mmole) in DCM (10 mL) was added 4M HCl (2 mL, 4M in dioxane). After 3 h at RT, the suspension was concentrated under vacuum and purified on silica (CHCl3/MeOH, 9:1 containing 5% NH4OH) afforded the title compound (282 mg, 98%) as light yellow solid: LC-MS (ES) m/e 263 (M+H)+.

c) 6-({[((3S)-1-{2-[3,8-difluoro-6-(methyloxy)-4-quinolinyl]ethyl}-3-pyrrolidinyl)methyl]amino}methyl)-2H-pyrido[3,2-b][1,4]oxazin-3(4H)-one To a stirred solution of 8-ethenyl-4,7-difluoro-2-(methyloxy)-1,5-naphthyridine (0.27 g, 1.10 mmole) in DMF (2 mL) was added 6-({[(3S)-3-pyrrolidinylmethyl]amino}methyl)-2H-pyrido[3,2-b][1,4]oxazin-3(4/H)-one (0.29 g, 1.1 mmole). After 24 h at 90° C., the reaction contents were purified on silica (CHCl3/MeOH, 9:1 containing 5% NH4OH) affording the title compound (96 mg, 18%) as a light yellow solid: 1H NMR (400 MHz, CDCl3) δ 8.60 (s, 1H), 7.18 (d, J=8.0 Hz, 1H), 7.01-7.06 (m, 2H), 6.91 (d, J=8.0 Hz, 1H), 4.62 (s, 2H), 3.92 (s, 3H), 3.80 (s, 2H), 3.23 (t, 2H), 2.75 (m, 1H), 2.54-2.82 (m, 6H), 2.32-2.49 (m, 2H), 2.06 (m, 1H), 1.52 (m, 1H). LC-MS (ES) m/e 484 (M+H)+.

This material, as a solution in MeOH, was treated with an excess of 4M HCl in diethyl ether and evaporated to dryness to provide the dihydrochloride salt of the title compound.

Example 23

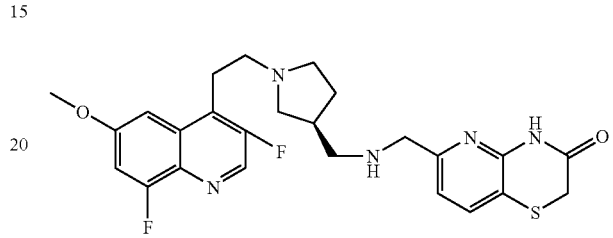

Preparation of 6-({[((3S)-1-{2-[3,8-difluoro-6-(methyloxy)-4-quinolinyl]ethyl}-3-pyrrolidinyl)methyl]amino}methyl)-2H-pyrido[3,2-b][1,4]thiazin-3(4H)-one Prepared essentially according to the procedure for Example 22, except substituting 6-({[(3S)-3-pyrrolidinylmethyl]amino}methyl)-2H-pyrido[3,2-b][1,4]thiazin-3(4H)-one (266 mg, 0.95 mmole) for 6-({[(3S)-3-pyrrolidinylmethyl]amino}methyl)-2H-pyrido[3,2-b][1,4]oxazin-3(4H)-one, the title compound (220 mg, 46%) was prepared as a light yellow solid: 1H NMR (400 MHz, CDCl3) δ 8.61 (s, 1H), 7.56 (d, J=7.8 Hz, 1H), 7.02-7.07 (m, 2H), 6.95 (d, J=7.8 Hz, 1H), 3.93 (s, 3H), 3.81 (s, 2H), 3.46 (s, 2H), 3.23 (m 2H), 2.91 (m, 1H), 2.58-2.81 (m, 6H), 2.35-2.49 (m, 2H), 2.06 (m, 1H), 1.52 (m, 1H). LC-MS (ES) m/e 500 (M+H)+.

This material, as a solution in MeOH, was treated with an excess of 4M HCl in diethyl ether and evaporated to dryness to provide the dihydrochloride salt of the title compound.

Example 24

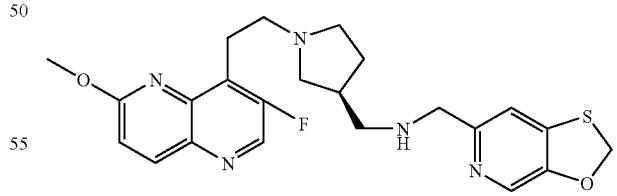

Preparation of [((3S)-1-{2-[3-fluoro-6-(methyloxy)-1,5-naphthyridin-4-yl]ethyl}-3-pyrrolidinyl)methyl]([1,3]oxathiolo[5,4-c]pyridin-6-ylmethyl)amine Prepared essentially according to the procedure for Example 22, except substituting 8-ethenyl-7-fluoro-2-(methyloxy)-1,5-naphthyridine (110 mg, 0.54 mmole) for 8-ethenyl-4,7-difluoro-2-(methyloxy)-1,5-naphthyridine, and substituting ([1,3]oxathiolo[5,4-c]pyridin-6-ylmethyl)[(3S)-3-pyrrolidinylmethyl]amine (68 mg, 0.27 mmole) for 6-({[(3S)-3-pyrrolidinylmethyl]amino}methyl)-2H-pyrido[3,2-b][1,4]oxazin-3(4H)-one, the title compound (56 mg, 44%) was prepared as a light yellow solid: $^1$H NMR (400 MHz, CDCl$_3$) δ 8.61 (s, 1H), 8.16 (d, J=9.0 Hz, 1H), 8.02 (s, 1H), 7.19 (s, 1H), 7.06 (d, J=9.0 Hz, 1H), 5.73 (s, 2H), 4.08 (s, 3H), 3.80 (s, 2H), 3.41 (t, 2H), 2.92 (m, 1H), 2.68-2.88 (m, 3H), 2.57-2.67 (m, 3H), 2.33-2.44 (m, 2H), 2.03 (m, 1H), 1.52 (m, 1H). LC-MS (ES) m/e 456 (M+H)$^+$.

This material, as a solution in MeOH, was treated with an excess of 4M HCl in diethyl ether and evaporated to dryness to provide the dihydrochloride salt of the title compound.

Example 25

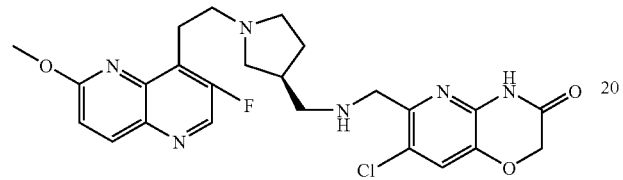

Preparation of 7-chloro-6-({[((3S)-1-{2-[3-fluoro-6-(methyloxy)-1,5-naphthyridin-4-yl]ethyl}-3-pyrrolidinyl)methyl]amino}methyl)-2H-pyrido[3,2-b][1,4]oxazin-3(4H)-one Prepared essentially according to the procedure for Example 22, except substituting 8-ethenyl-7-fluoro-2-(methyloxy)-1,5-naphthyridine (100 mg, 0.49 mmole) for 8-ethenyl-4,7-difluoro-2-(methyloxy)-1,5-naphthyridine, and substituting 7-chloro-6-({[(3S)-3-pyrrolidinylmethyl]amino}methyl)-2H-pyrido[3,2-b][1,4]oxazin-3(4H)-one (129 mg, 0.43 mmole) for 6-({[(3S)-3-pyrrolidinylmethyl]amino}methyl)-2H-pyrido[3,2-b][1,4]oxazin-3(4H)-one, the title compound (31 mg, 4%) was prepared as a light yellow solid: $^1$H NMR (400 MHz, CDCl$_3$) δ 8.58 (s, 1H), 8.14 (d, J=9.0 Hz, 1H), 7.22 (s, 1H), 7.04 (d, J=9.0 Hz, 1H), 4.61 (s, 2H), 4.06 (s, 3H), 3.89 (s, 2H), 3.49 (s, 1H), 3.40 (m, 2H), 2.95 (m, 1H), 2.76-2.91 (m, 4H), 2.79 (m, 2H), 2.42 (m, 2H), 2.04 (m, 2H), 1.51 (m, 2H). LC-MS (ES) m/e 501 (M+H)$^+$.

This material, as a solution in MeOH, was treated with an excess of 4M HCl in diethyl ether and evaporated to dryness to provide the dihydrochloride salt of the title compound.

Example 26

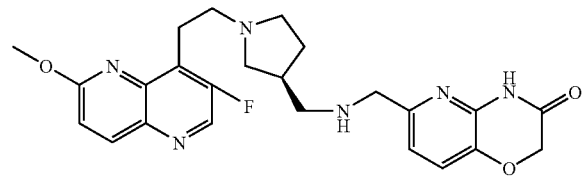

Preparation of 6-({[((3S)-1-{2-[3-fluoro-6-(methyloxy)-1,5-naphthyridin-4-yl]ethyl}-3-pyrrolidinyl)methyl]amino}methyl)-2H-pyrido[3,2-b][1,4]oxazin-3(4H)-one Prepared essentially according to the procedure for Example 22, except substituting 8-ethenyl-7-fluoro-2-(methyloxy)-1,5-naphthyridine (143 mg, 0.70 mmole) for 8-ethenyl-4,7-difluoro-2-(methyloxy)-1,5-naphthyridine, the title compound (32 mg, 10%) was prepared as a light yellow solid: $^1$H NMR (400 MHz, CD$_3$OD) δ 8.51 (s, 1H), 8.06 (d, J=9.1 Hz, 1H), 7.18 (d, J=7.9 Hz, 1H), 7.04 (d, J=9.1 Hz, 1H), 6.90 (d, J=8.0 Hz, 1H), 4.54 (s, 3H), 4.00 (s, 3H), 3.87 (s, 2H), 3.37 (m, 2H), 2.70-3.05 (m, 8H), 2.57 (m, 1H), 2.48 (m, 1H), 2.07 (m, 1H), 1.56 (m, 1H). MS (ES) m/e 467 (M+H)$^+$.

This material, as a solution in MeOH, was treated with an excess of 4M HCl in diethyl ether and evaporated to dryness to provide the dihydrochloride salt of the title compound.

Example 27

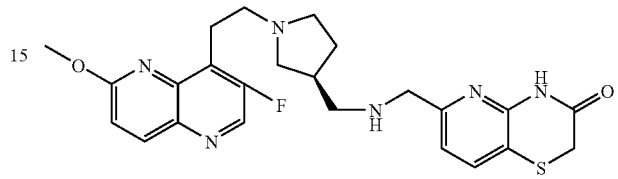

Preparation of 6-({[((3S)-1-{2-[3-fluoro-6-(methyloxy)-1,5-naphthyridin-4-yl]ethyl}-3-pyrrolidinyl)methyl]amino}methyl)-2H-pyrido[3,2-b][1,4]thiazin-3(4H)-one Prepared essentially according to the procedure for Example 22, except substituting 8-ethenyl-7-fluoro-2-(methyloxy)-1,5-naphthyridine (143 mg, 0.70 mmole) for 8-ethenyl-4,7-difluoro-2-(methyloxy)-1,5-naphthyridine, and substituting 6-({[(3S)-3-pyrrolidinylmethyl]amino}methyl)-2H-pyrido[3,2-b][1,4]thiazin-3(4H)-one, (195 mg, 0.70 mmole) for 6-({[(3S)-3-pyrrolidinylmethyl]amino}methyl)-2H-pyrido[3,2-b][1,4]oxazin-3(4H)-one, the title compound (124 mg, 37%) was prepared as a light yellow solid: $^1$H NMR (400 MHz, CD$_3$OD) δ 8.67 (s, 1H), 8.23 (d, J=9.1 Hz, 1H), 7.75 (d, J=7.8 Hz, 1H), 7.21 (d, J=9.1 Hz, 1H), 7.06 (d, J=7.9 Hz, 1H), 4.13 (s, 3H), 4.00 (s, 2H), 3.55 (s, 2H), 3.53 (m, 2H), 3.08 (m, 3H), 2.96 (m, 2H), 2.86 (m, 2H), 2.69 (m, 1H), 2.56 (m, 1H), 2.16 (m, 1H), 1.65 (m, 1H). LC-MS (ES) m/e 483 (M+H)$^+$.

This material, as a solution in MeOH, was treated with an excess of 4M HCl in diethyl ether and evaporated to dryness to provide the dihydrochloride salt of the title compound.

Example 28

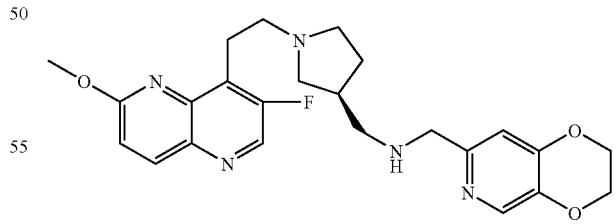

Preparation of (2,3-dihydro[1,4]dioxino[2,3-c]pyridin-7-ylmethyl)[((3S)-1-{2-[3-fluoro-6-(methyloxy)-1,5-naphthyridin-4-yl]ethyl}-3-pyrrolidinyl)methyl]amine Prepared essentially according to the procedure for Example 22, except substituting 8-ethenyl-7-fluoro-2-(methyloxy)-1,5-naphthyridine (143 mg, 0.70 mmole) for 8-ethenyl-4,7-difluoro-2-(methyloxy)-1,5-naphthyridine, and substituting 2,3-dihydro[1,4]dioxino[2,3-c]pyridine-7-carbaldehyde (115 mg, 0.70 mmole) for 6-({[(3S)-3-pyrrolidinylmethyl]amino}methyl)-2H-pyrido[3,2-b][1,4]oxazin-3(4H)-one, the title compound was prepared as an orange hygroscopic solid: LC/MS (ES) m/e 454 (M+H)+; 1H NMR (DMSO, 400 MHz) δ 9.8 (bs, 1H), 8.85 (s, 1H), 8.4 (d, J=5.6 Hz, 1H), 8.33 (d, J=9.1 Hz, 1H), 7.51 (d, J=11.6 Hz, 1H), 7.29 (d, J=9.1 Hz, 1H), 4.5 (m, 3H), 4.25 (s, 2H), 4.1 (s, 3H), 3.8 (m, 1H), 3.7 (m, 2H), 3.6 (m, 2H), 3.5 (m, 2H), 3.25 (m, 2H), 3.1 (s, 2H), 2.85 (m, 2H), 2.25 (m, 1H), 1.8 (m, 1H), 1.3 (s, 1H), 0.8 (m, 1H).

This material, as a solution in MeOH, was treated with an excess of 4M HCl in dioxane and evaporated to dryness to provide the hydrochloride salt of the title compound.

Example 29

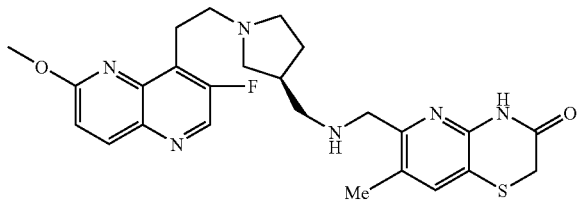

Preparation of 6-({[((3S)-1-{2-[3-fluoro-6-(methyloxy)-1,5-naphthyridin-4-yl]ethyl}-3-pyrrolidinyl)methyl]amino}methyl)-7-methyl-2H-pyrido[3,2-b][1,4]thiazin-3(4H)-one Prepared essentially according to the procedure for Example 22, except substituting 7-methyl-3-oxo-3,4-dihydro-2H-pyrido[3,2-b][1,4]thiazine-6-carbaldehyde (75 mg, 0.25 mmol) for 2,3-dihydro-1-benzofuran-5-carbaldehyde, and substituting substituting 8-ethenyl-7-fluoro-2-(methyloxy)-1,5-naphthyridine (43 mg, 0.25 mmole) for 8-ethenyl-4,7-difluoro-2-(methyloxy)-1,5-naphthyridine, the title compound was obtained as an off-white solid (66 mg, 53%): LC/MS (ES) m/e 497 (M+H)+; 1H NMR (400 MHz, CDCl3) δ 8.52 (s, 1H), 8.09 (d, J=9.04 Hz, 1H), 7.27 (s, 1H), 6.97 (d, J=9.04 Hz, 1H), 4.00 (s, 3H), 3.71 (s, 2H), 3.34 (s, 2H), 3.32, (M, 1H), 2.86 (m, 1H), 2.77 (m, 1H), 2.70 (M, 2H), 2.61 (M, 1H), 2.58 (M, 2H), 2.36 (M, 2H), 2.15 (S, 3H), 1.98 (m, 1H), 1.47 (m, 1H).

This material, as a solution in MeOH, was treated with an excess of 4M HCl in dioxane and evaporated to dryness to provide the dihydrochloride salt of the title compound.

Example 30

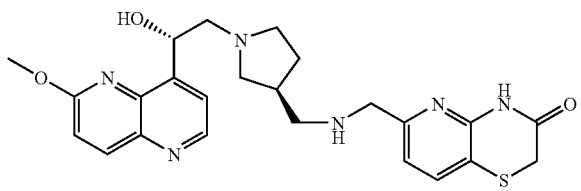

Preparation of 6-({[((3S)-1-{(2S)-2-hydroxy-2-[6-(methyloxy)-1,5-naphthyridin-4-yl]ethyl}-3-pyrrolidinyl)methyl]amino}methyl)-2H-pyrido[3,2-b][1,4]thiazin-3(4H)-one a) phenylmethyl[((3S)-1-{(2S)-2-hydroxy-2-[6-(methyloxy)-1,5-naphthyridin-4-yl]ethyl}-3-pyrrolidinyl)methyl]carbamate To a solution of phenylmethyl[(3S)-3-pyrrolidinylmethyl]carbamate (0.53 g, 2.27 mmole) and LiClO4 (0.24 g, 2.27 mmole) in DMF (1 mL) was added 2-(methyloxy)-8-[(2S)-2-oxiranyl]-1,5-naphthyridine (0.45 g, 2.25 mmole). After 24 h at 80° C., the reaction contents were purified on silica gel (CHCl3/MeOH, 9:1, containing 5% NH4OH) to afford the title compound (0.24 g, 25%) as a light yellow oil: LC-MS (ES) m/e 437 (M+H)+.

b) (1S)-2-[(3S)-3-(aminomethyl)-1-pyrrolidinyl]-1-[6-(methyloxy)-1,5-naphthyridin-4-yl]ethanol To a solution of phenylmethyl[((3S)-1-{(2S)-2-hydroxy-2-[6-(methyloxy)-1,5-naphthyridin-4-yl]ethyl}-3-pyrrolidinyl)methyl]carbamate (0.24 g, 0.56 mmole) in MeOH (50 mL) was added Pd(OH)2 (100 mg). The reaction contents were placed under a balloon of H2 and stirred for 18 hours. The reaction contents were filtered through Celite (MeOH) and concentrated under vacuum to give the title compound (0.16 g, 98%) as a light yellow oil: LC-MS (ES) m/e 303 (M+H)+.

c) 6-({[((3S)-1-{(2S)-2-hydroxy-2-[6-(methyloxy)-1,5-naphthyridin-4-yl]ethyl}-3-pyrrolidinyl)methyl]amino}methyl)-2H-pyrido[3,2-b][1,4]thiazin-3(4H)-one To a stirred solution of (1S)-2-[(3S)-3-(aminomethyl)-1-pyrrolidinyl]-1-[6-(methyloxy)-1,5-naphthyridin-4-yl]ethanol (72 mg, 0.24 mmole) in dry CH2Cl2 (25 mL) and dry EtOH (20 mL) at RT was added 3-oxo-3,4-dihydro-2H-pyrido[3,2-b][1,4]thiazine-6-carbaldehyde (47 mg, 0.24 mmole). After 24 h at RT, was added NaBH4 (10 mg, 0.26 mmole). After 2 h, silica gel (5 g) was added to the reaction solution and the suspension was concentrated under vacuum to a dry solid. Purification on silica (CHCl3/MeOH, 9:1 containing 5% NH4OH) afforded the title compound (61 mg, 54%) as light yellow solid: 1H NMR (400 MHz, CDCl3) δ 8.81 (d, J=4.5 Hz, 1H), 8.23 (d, J=9.1 Hz, 1H), 7.84 (d, J=4.5 Hz, 1H), 7.56 (d, J=8.0 Hz, 1H), 7.12 (d, J=9.1 Hz, 1H), 6.92 (d, J=8.0 Hz, 1H), 5.74 (m, 1H), 4.04 (s, 3H), 3.82 (s, 2H), 3.46 (s, 2H), 3.00-3.11 (m, 1H), 2.58-2.83 (m, 6H), 2.33-2.58 (m, 1H), 2.01 (m, 2H), 1.65 (m, 1H). LC-MS (ES) m/e 481 (M+H)+.

This material, as a solution in MeOH, was treated with an excess of 4M HCl in diethyl ether and evaporated to dryness to provide the dihydrochloride salt of the title compound.

Example 31

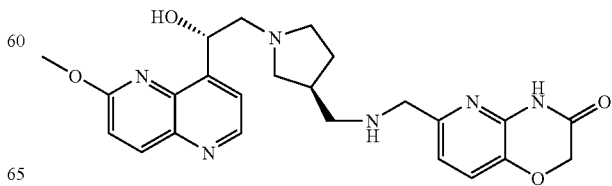

Preparation of 6-({[((3S)-1-{(2S)-2-hydroxy-2-[6-(methyloxy)-1,5-naphthyridin-4-yl]ethyl}-3-pyrrolidinyl)methyl]amino}methyl)-2H-pyrido[3,2-b][1,4]oxazin-3(4H)-one Prepared essentially according to the procedure for Example 30, except substituting 3-oxo-3,4-dihydro-2H-pyrido[3,2-b][1,4]oxazine-6-carbaldehyde (51 mg, 0.29 mmole) for 3-oxo-3,4-dihydro-2H-pyrido[3,2-b][1,4]thiazine-6-carbaldehyde, The title compound (79 mg, 67%) was prepared as a light yellow solid: $^1$H NMR (400 MHz, CDCl$_3$) δ 8.80 (d, J=4.5 Hz, 1'H); 823 (d, J=9.1 Hz, 1H), 7.80 (d, J=4.5 Hz, 1H), 7.17 (d, J=8.0 Hz, 1H), 7.10 (d, J=9.1 Hz, 1H), 6.87 (d, J=8.0 Hz, 1H), 5.73 (m, 1H), 4.62 (s, 2H), 4.02 (s, 3H), 3.81 (s, 2H), 3.11-2.94 (m, 2H), 2.51-2.86 (m, 6H), 2.33-2.51 (m, 1H), 2.02 (m, 1H), 1.62 (m, 1H). LC-MS (ES) m/e 465 (M+H)$^+$.

This material, as a solution in MeOH, was treated with an excess of 4M HCl in diethyl ether and evaporated to dryness to provide the dihydrochloride salt of the title compound.

Example 32

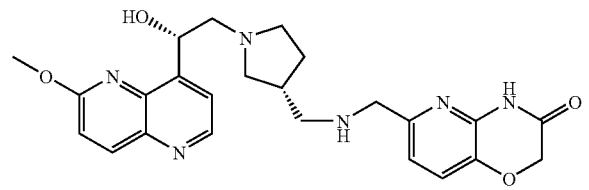

Preparation of 6-({[((3R)-1-{(2S)-2-hydroxy-2-[6-(methyloxy)-1,5-naphthyridin-4-yl]ethyl}-3-pyrrolidinyl)methyl]amino}methyl)-2H-pyrido[3,2-b][1,4]oxazin-3(4H)-one Prepared essentially according to the procedure for Example 30, except substituting 3-oxo-3,4-dihydro-2H-pyrido[3,2-b][1,4]oxazine-6-carbaldehyde (71 mg, 0.40 mmole) for 3-oxo-3,4-dihydro-2H-pyrido[3,2-b][1,4]thiazine-6-carbaldehyde, and substituting (1S)-2-[(3R)-3-(aminomethyl)-1-pyrrolidinyl]-1-[6-(methyloxy)-1,5-naphthyridin-4-yl]ethanol (0.12 g, 0.41 mmole) for (1S)-2-[(3S)-3-(aminomethyl)-1-pyrrolidinyl]-1-[6-(methyloxy)-1,5-naphthyridin-4-yl]ethanol, the title compound (100 mg, 53%) was prepared as a light yellow solid: $^1$H NMR (400 MHz, CDCl$_3$) δ 8.80 (d, J=4.5 Hz, 1H), 8.24 (d, J=9.1 Hz, 1H), 7.80 (d, J=4.5 Hz, 1H), 7.18 (d, J=8.0 Hz, 1H), 7.10 (d, J=9.1 Hz, 1H), 6.87 (d, J=8.0 Hz, 1H), 5.73 (m, 1H), 4.63 (s, 2H), 4.01 (s, 3H), 3.80 (s, 2H), 3.11-2.95 (m, 2H), 2.84 (m, 1H), 2.49-2.79 (m, 5H), 2.40 (m, 1H), 2.04 (m, 1H), 1.62 (m, 1H). LC-MS (ES) m/e 465 (M+H)$^+$.

This material, as a solution in MeOH, was treated with an excess of 4M HCl in diethyl ether and evaporated to dryness to provide the dihydrochloride salt of the title compound.

Example 33

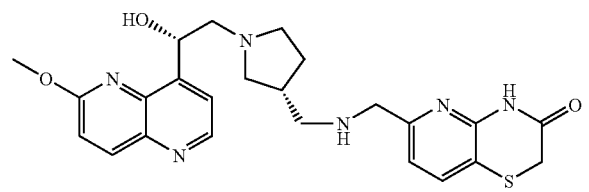

Preparation of 6-({[((3R)-1-{(2S)-2-hydroxy-2-[6-(methyloxy)-1,5-naphthyridin-4-yl]ethyl}-3-pyrrolidinyl)methyl]amino}methyl)-2H-pyrido[3,2-b][1,4]thiazin-3(4H)-one Prepared essentially according to the procedure for Example 30, except substituting (1S)-2-[(3R)-3-(aminomethyl)-1-pyrrolidinyl]-1-[6-(methyloxy)-1,5-naphthyridin-4-yl]ethanol (102 mg, 0.34 mmole) for (1S)-2-[(3S)-3-(aminomethyl)-1-pyrrolidinyl]-1-[6-(methyloxy)-1,5-naphthyridin-4-yl]ethanol, the title compound (80 mg, 49%) was prepared as a light yellow solid: $^1$H NMR (400 MHz, CDCl$_3$) δ 8.80 (d, J=4.5 Hz, 1H), 8.24 (d, J=9.1 Hz, 1H), 7.83 (d, J=4.4 Hz, 1H), 7.56 (d, J=7.8 Hz, 1H), 7.11 (d, J=9.1 Hz, 1H), 6.92 (d, J=7.8 Hz, 1H), 5.72 (dd, 1H), 4.03 (s, 3H), 3.83 (s, 2H), 3.47 (s, 2H), 2.98-3.12 (m, 1H), 2.58-2.87 (m, 4H), 2.48-2.58 (m, 2H), 2.38 (m, 1H), 2.05 (m, 1H), 1.63 (m, 1H). LC-MS (ES) m/e 481 (M+H)$^+$.

This material, as a solution in MeOH, was treated with an excess of 4M HCl in diethyl ether and evaporated to dryness to provide the dihydrochloride salt of the title compound.

Example 34

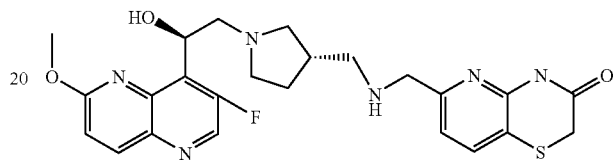

Preparation of 6-({[((3S)-1-{(2R)-2-[3-fluoro-6-(methyloxy)-1,5-naphthyridin-4-yl]-2-hydroxyethyl}-3-pyrrolidinyl)methyl]amino}methyl)-2H-pyrido[3,2-b][1,4]thiazin-3(4H)-one (a) phenylmethyl[((3S)-1-{(2R)-2-[3-fluoro-6-(methyloxy)-1,5-naphthyridin-4-yl]-2-hydroxyethyl}-3-pyrrolidinyl)methyl]carbamate

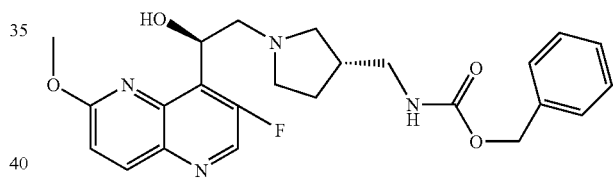

To a solution of 7-fluoro-2-(methyloxy)-8-[(2S)-2-oxiranyl]-1,5-naphthyridine (220 mg, 1.0 mmol) in acetonitrile (5 mL) were added phenylmethyl[(3R)-3-pyrrolidinylmethyl]carbamate (235 mg, 1.0 mmol) followed by Lithium perchlorate (106 mg, 1.0 mmol). After heated at 43° C. for 48 h, the resulting mixture was cooled down to room temperature, concentrated and purified with column chromatography (silica, 1-5% methanol in DCM (1% NH$_4$OH)) to provide the title compound as an off-white solid (250 mg, 55%): LC/MS (ES) m/e 455 (M+H)$^+$.

(b) (1R)-2-[(3S)-3-(aminomethyl)-1-pyrrolidinyl]-1-[3-fluoro-6-(methyloxy)-1,5-naphthyridin-4-yl]ethanol

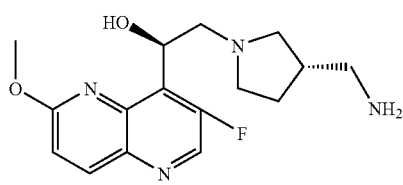

To a solution of phenylmethyl[((3S)-1-{(2R)-2-[3-fluoro-6-(methyloxy)-1,5-naphthyridin-4-yl]-2-hydroxyethyl}-3-pyrrolidinyl)methyl]carbamate (250 mg, 0.55 mmol) in EtOH (5 mL) was added Pd(OH)$_2$ (20 mg). The suspension was hydrogenated at 1 atm of H$_2$ using a balloon. After 12 h, the mixture was filtered and washed several times with MeOH. The filtrate was concentrated to afford the title compound (175 mg, 100%) as an off-white foam, which was used without further purification: LC/MS (ES) m/e 321 (M+H)$^+$.

(c) 6-({[((3S)-1-{(2R)-2-[3-fluoro-6-(methyloxy)-1,5-naphthyridin-4-yl]-2-hydroxyethyl}-3-pyrrolidinyl)methyl]amino}methyl)-2H-pyrido[3,2-b][1,4]thiazin-3(4H)-one

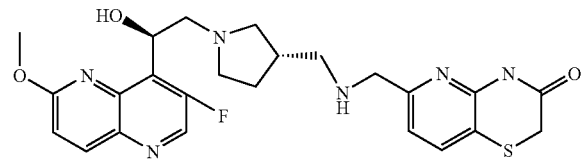

To a stirred solution of (1R)-2-[(3S)-3-(aminomethyl)-1-pyrrolidinyl]-1-[3-fluoro-6-(methyloxy)-1,5-naphthyridin-4-yl]ethanol (90 mg, 0.28 mmol) in dry CH$_2$Cl$_2$ (2 mL) and dry EtOH (2 mL) was added 3-oxo-3,4-dihydro-2H-pyrido[3,2-b][1,4]thiazine-6-carboxaldehyde (55 mg, 0.28 mmol) along with Na$_2$SO$_4$ (350 mg, 2.46 mmol). After 18 h at room temperature, NaBH$_4$ (24 mg, 0.56 mmol) was added. After 2 h, the solution wa partitioned between ethyl acetate and the aqueous solution of sodium bicarbonate. The aqueous solution was extreacted several times with ethyl acetate. The organic fraction were pooled, concentrated and purified with column chromatography (silica, 0-8% MeOH in DCM (1% NH$_4$OH)) affording a light yellow solid, which was completed with chiral purification. The title compound (5 mg, 3.6%) was provided as a white solid: LC/MS (ES) m/e 499 (M+H)$^+$; $^1$H NMR (400 MHz, CD$_3$OD): δ 8.56 (s, 1H), 8.14 (d, J=9.0 Hz, 1H), 7.57 (d, J=7.6 Hz, 1H), 7.10 (d, J=9.2 Hz, 1H), 6.89 (d, J=7.6 Hz, 1H), 5.82-5.84 (m, 1H), 4.03 (s, 3H), 3.64 (s, 2H), 3.39-3.41 (m, 1H), 3.09-3.12 (m, 1H), 2.87-3.07 (m, 2H), 2.59-2.67 (m, 2H), 2.48-2.52 (m, 2H), 2.28-2.36 (m, 2H), 1.86-1.97 (m, 1H), 1.37-1.46 (m, 1H), 1.16-1.18 (m, 1H).

This material, as a solution in MeOH, was treated with 3 equivalents of 4M HCl in dioxane and evaporated to dryness to provide the hydrochloride salt of the title compound.

Example 35

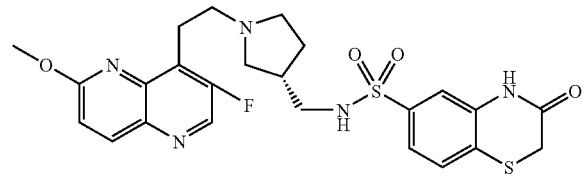

Preparation of N-[((3S)-1-{2-[3-fluoro-6-(methyloxy)-1,5-naphthyridin-4-yl]ethyl}-3-pyrrolidinyl)methyl]-3-oxo-3,4-dihydro-2H-1,4-benzothiazine-6-sulfonamide To a stirred solution of [((3R)-1-{2-[3-fluoro-6-(methyloxy)-1,5-naphthyridin-4-yl]ethyl}-3-pyrrolidinyl)methyl]amine (0.50 g, 1.65 mmole) in dry CH$_2$Cl$_2$ (25 mL) at RT was added triethylamine (0.34 mL, 2.48 mmole) and 3-oxo-3,4-dihydro-2H-1,4-benzothiazine-6-sulfonyl chloride (0.47 g, 1.80 mmole). After 24 h, the reaction solution was concentrated under vacuum. Purification on silica (CHCl$_3$/MeOH, 9:1 containing 5% NH$_4$OH) afforded the title compound (0.80 g, 91%) as light yellow solid: $^1$H NMR (400 MHz, CDCl$_3$) δ 8.59 (s, 1H), 8.16 (d, J=9.0 Hz, 1H), 7.34 (m, 3H), 7.03 (d, J=9.0 Hz, 1H), 4.04 (s, 3H), 3.47 (s, 2H), 3.34 (m, 2H), 2.95 (m, 3H), 2.79 (m, 2H), 2.61 (m, 1H), 2.52 (m, 2H), 2.34 (m, 1H), 1.97 (m, 1H), 1.55 (m, 1H). LC-MS (ES) m/e 532 (M+H)$^+$.

This material, as a solution in MeOH, was treated with an excess of 4M HCl in diethyl ether and evaporated to dryness to provide the dihydrochloride salt of the title compound.

Example 36

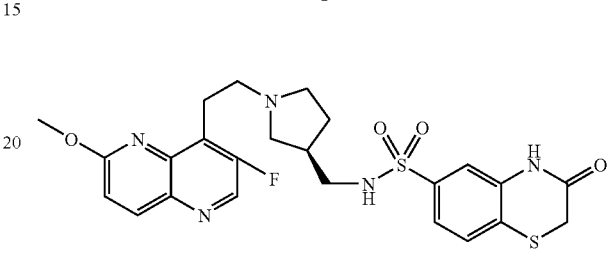

Preparation of N-[((3R)-1-{2-[3-fluoro-6-(methyloxy)-1,5-naphthyridin-4-yl]ethyl}-3-pyrrolidinyl)methyl]-3-oxo-3,4-dihydro-2H-1,4-benzothiazine-6-sulfonamide Prepared essentially according to the procedure for Example 35, except substituting [((3S)-1-{2-[3-fluoro-6-(methyloxy)-1,5-naphthyridin-4-yl]ethyl}-3-pyrrolidinyl)methyl]amine (164 mg, 0.54 mmole) for [((3R)-1-{2-[3-fluoro-6-(methyloxy)-1,5-naphthyridin-4-yl]ethyl}-3-pyrrolidinyl)methyl]amine, the title compound (376 mg, 70%) was prepared as a light yellow solid: $^1$H NMR (400 MHz, CDCl$_3$) δ 9.39 (br, 1H), 8.63 (s, 1H), 8.19 (d, J=9.04 Hz, 1H), 7.31-7.38 (m, 2H), 7.25 (d, J=6.23 Hz, 1H), 7.07 (d, J=9.05 Hz, 1H), 4.07 (s, 3H), 3.46 (s, 2H), 3.38 (t, 2H), 2.71-3.06 (br m, 5H), 2.56 (d, 2H), 2.40 (m, 2H), 2.00 (m, 1H), 1.56 (m, 1H). LC-MS (ES) m/e 532(M+H)$^+$.

This material, as a solution in MeOH, was treated with an excess of 4M HCl in diethyl ether and evaporated to dryness to provide the dihydrochloride salt of the title compound.

Example 37

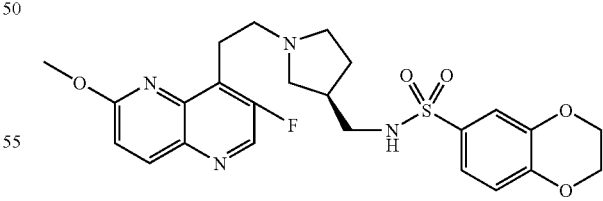

Preparation of N-[((3R)-1-{2-[3-fluoro-6-(methyloxy)-1,5-naphthyridin-4-yl]ethyl}-3-pyrrolidinyl)methyl]-2,3-dihydro-1,4-benzodioxin-6-sulfonamide Prepared essentially according to the procedure for Example 35, except substituting 2,3-dihydro-1,4-benzodioxin-6-sulfonyl chloride (94 mg, 0.40 mmole) for 3-oxo-3,4-dihydro-2H-1,4-benzothiazine-6-sulfonyl chloride, and substituting [((3S)-1-{2-[3-fluoro-6-(methyloxy)-1,5-naphthyridin-4-yl]ethyl}-3-pyrrolidinyl)methyl]amine (150 mg, 0.50 mmole) for [((3R)-1-{2-[3-fluoro-6-(methyloxy)-1,5-naphthyridin-4-yl]ethyl}-3-pyrrolidinyl)methyl]amine, the title compound (200 mg, 99%) was prepared as a light yellow solid: $^1$H NMR (400 MHz, CDCl$_3$) δ 8.64 (s, 1H), 8.18 (d, J=9.01 Hz, 1H), 7.24-7.30 (m, 2H), 7.08 (d, J=9.04 Hz, 1H), 6.91 (d, J=8.49 Hz, 1H), 4.28 (m, 4H), 4.09 (s, 3H), 3.37 (t, 2H), 2.96 (m, 3H), 2.80 (m, 2H), 2.54 (m, 2H), 2.30-2.46 (m, 2H), 1.99 (m, 1H), 1.54 (m, 1H). LC-MS (ES) m/e 503 (M+H)$^+$.

This material, as a solution in MeOH, was treated with an excess of 4M HCl in diethyl ether and evaporated to dryness to provide the dihydrochloride salt of the title compound.

Example 38

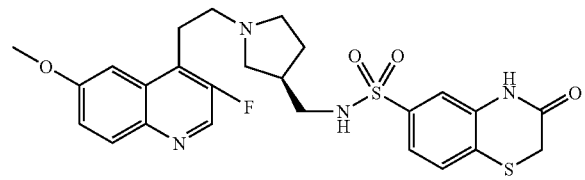

Preparation of N-[((3R)-1-{2-[3-fluoro-6-(methyloxy)-4-quinolinyl]ethyl}-3-pyrrolidinyl)methyl]-3-oxo-3,4-dihydro-2H-1,4-benzothiazine-6-sulfonamide Prepared essentially according to the procedure for Example 35, except substituting [((3S)-1-{2-[3-fluoro-6-(methyloxy)-4-quinolinyl]ethyl}-3-pyrrolidinyl)methyl]amine (108 mg, 0.35 mmole) for [((3R)-1-{2-[3-fluoro-6-(methyloxy)-1,5-naphthyridin-4-yl]ethyl}-3-pyrrolidinyl)methyl]amine, the title compound (100 mg, 55%) was prepared as a light yellow solid: $^1$H NMR (400 MHz, CDCl$_3$) δ 9.53 (br s, 1H), 8.60 (s, 1H), 7.96 (d, J=9.20 Hz, 1H), 7.24-7.41 (m, 4H), 7.15 (d, J=2.59 Hz, 1H), 3.94 (s, 3H), 3.46 (s, 2H), 3.18 (m, 2H), 2.94 (m, 3H), 3.72 (m, 2H), 2.31-2.68 (m, 4H), 2.01 (m, 1H), 1.56 (m, 1H).

LC-MS (ES) m/e 531 (M+H)$^+$.

This material, as a solution in MeOH, was treated with an excess of 4M HCl in diethyl ether and evaporated to dryness to provide the dihydrochloride salt of the title compound.

Example 39

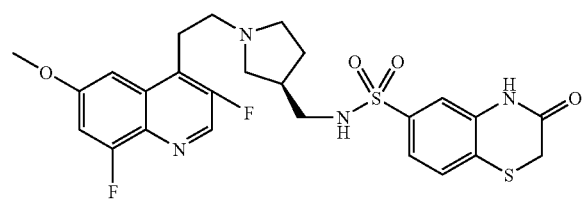

Preparation of N-[((3R)-1-{2-[3,8-difluoro-6-(methyloxy)-4-quinolinyl]ethyl}-3-pyrrolidinyl)methyl]-3-oxo-3,4-dihydro-2H-1,4-benzothiazine-6-sulfonamide Prepared essentially according to the procedure for Example 35, except substituting [((3S)-1-{2-[3,8-difluoro-6-(methyloxy)-4-quinolinyl]ethyl}-3-pyrrolidinyl)methyl]amine (96 mg, 0.30 mmole) for [((3R)-1-{2-[3-fluoro-6-(methyloxy)-1,5-naphthyridin-4-yl]ethyl}-3-pyrrolidinyl) methyl]amine, the title compound (57 mg, 35%) was prepared as a light yellow solid: $^1$H NMR (400 MHz, CDCl$_3$) δ 8.60 (s, 1H), 7.37 (s, 1H), 7.34 (s, 1H), 6.98-7.05 (m, 2H), 3.94 (s, 3H), 3.46 (s, 2H), 3.18 (m, 2H), 2.94 (d, 2H), 3.87 (m, 1H), 2.45-2.82 (br m, 5H), 2.41 (m, 1H), 2.00 (m, 1H), 1.53 (m, 1H). LC-MS (ES) m/e 549 (M+H)$^+$.

This material, as a solution in MeOH, was treated with an excess of 4M HCl in diethyl ether and evaporated to dryness to provide the dihydrochloride salt of the title compound.

Example 40

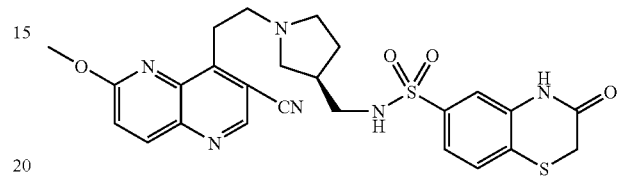

Preparation of N-[((3R)-1-{2-[3-cyano-6-(methyloxy)-1,5-naphthyridin-4-yl]ethyl}-3-pyrrolidinyl) methyl]-3-oxo-3,4-dihydro-2H-1,4-benzothiazine-6-sulfonamide Prepared essentially according to the procedure for Example 35, except substituting 4-{2-[(3S)-3-(aminomethyl)-1-pyrrolidinyl]ethyl}-6-(methyloxy)-1,5-naphthyridine-3-carbonitrile (10 mg, 0.03 mmole) for [((3R)-1-{2-[3-fluoro-6-(methyloxy)-1,5-naphthyridin-4-yl]ethyl}-3-pyrrolidinyl)methyl]amine, the title compound (10 mg, 62%) was prepared as a light yellow solid: $^1$H NMR (400 MHz, CDCl$_3$) δ 8.87 (s, 1H), 8.82 (m, 1H), 8.24 (d, J=9.08 Hz, 1H), 7.41 (s, 1H), 7.36 (s, 1H), 7.24 (s, 1H), 4.10 (s, 3H), 3.68 (m, 1H), 3.44-3.54 (m, 3H), 3.16 (m, 1H), 2.94 (m, 2H), 2.86 (m, 1H), 2.65 (m, 1H), 2.51 (m, 1H), 2.28-2.43 (m, 2H), 2.04 (m, 1H), 1.58 (m, 1H), 0.85 (m, 1H). LC-MS (ES) m/e 539 (M+H)$^+$.

This material, as a solution in MeOH, was treated with an excess of 4M HCl in diethyl ether and evaporated to dryness to provide the dihydrochloride salt of the title compound.

Example 41

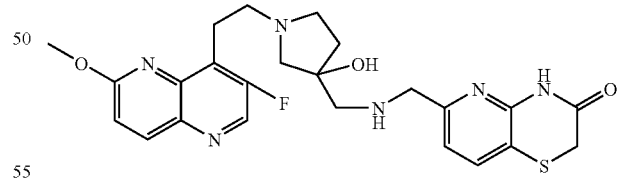

Preparation of (±)-6-({[(1-{2-[3-fluoro-6-(methyloxy)-1,5-naphthyridin-4-yl]ethyl}-3-hydroxy-3-pyrrolidinyl)methyl]amino}methyl)-2H-pyrido[3,2-b][1,4]thiazin-3(4H)-one a) (±)-phenylmethyl 3-cyano-3-hydroxy-1-pyrrolidinecarboxylate To a stirred solution of phenylmethyl 3-oxo-1-pyrrolidinecarboxylate (1.0 g, 4.56 mmole) and KCN (0.81 g, 12.54 mmole) in THF (5 mL) and H₂O (15 mL) at 0° C. was added NaHSO₃ (1.14 g, 10.9 mmole) in H₂O (5.0 mL). After 3 h, the reaction contents were concentrated in vacuo, extracted with CHCl₃ (2×100 mL), and the organics dried over Na₂SO₄. Purification on silica (hexanes/EtOAc, 1:1) afforded the title compound (0.92 g, 82%) as a light yellow oil: LC-MS (ES) m/e 247 (M+H)⁺.

b) (±)-phenylmethyl 3-(aminomethyl)-3-hydroxy-1-pyrrolidinecarboxylate

To a stirred solution of phenylmethyl 3-cyano-3-hydroxy-1-pyrrolidinecarboxylate (0.92 g, 3.74 mmole), in THF (50 mL) at RT was added LiAlH₄ (3.75 mL, 1M in THF). After 24 h, the reaction was quenched with H₂O (0.15 mL), 20% NaOH (0.30 mL) and then H₂O (0.35 mL). The reaction contents were filtered through a scinter-glass funnel and concentrated under vacuum to afford the title compound (0.50 g, 79%) as a yellow oil: LC-MS (ES) m/e 250 (M+H)⁺.

c) (±)-phenylmethyl 3-[({[(1,1-dimethylethyl)oxy]carbonyl}amino)methyl]-3-hydroxy-1-pyrrolidinecarboxylate To a stirred solution of phenylmethyl 3-(aminomethyl)-3-hydroxy-1-pyrrolidinecarboxylate (0.5 g, 2.33 mmole) at RT in EtOH (50 mL) was added Boc anhydride (1.09 g, 5.0 mmole). After 24 h, the reaction contents were concentrated under vacuum and purified on silica (hexanes/EtOAc, 1:1) to give the title compound (0.81 g, 99%) as yellow oil: LC-MS (ES) m/e 351 (M+H)⁺.

d) (±)-1,1-dimethylethyl[(3-hydroxy-3-pyrrolidinyl)methyl]carbamate

To a stirred solution of phenylmethyl 3-[({[(1,1-dimethylethyl)oxy]carbonyl}amino)methyl]-3-hydroxy-1-pyrrolidinecarboxylate (0.81 g, 2.31 mmole) in MeOH (30 mL) at RT was added Pd(OH)₂ (100 mg). After 18 h under H₂ (1 atm) with stirring, the reaction contents were filtered through Celite (MeOH) and concentrated under reduced pressure to give the title compound (0.47 g, 95%) as a light yellow oil: LC-MS (ES) m/e 217 (M+H)⁺.

e) (±)-3-(aminomethyl)-1-{2-[3-fluoro-6-(methyloxy)-1,5-naphthyridin-4-yl]ethyl}-3-pyrrolidinol hydrochloride salt To a stirred solution of 8-ethenyl-7-fluoro-2-(methyloxy)-1,5-naphthyridine (0.12 g, 0.60 mmole) in EtOH (10 mL) was added 1,1-dimethylethyl[(3-hydroxy-3-pyrrolidinyl)methyl]carbamate (0.13 g, 0.60 mmole). After 24 h at 80° C. the reaction contents were purified on silica (CHCl₃/MeOH, 9:1 containing 5% NH₄OH) affording 1,1-dimethylethyl[(1-{2-[3-fluoro-6-(methyloxy)-1,5-naphthyridin-4-yl]ethyl}-3-hydroxy-3-pyrrolidinyl)methyl]carbamate (90 mg, 36%) as light yellow solid: LC-MS (ES) m/e 421 (M+H)⁺.
The material was dissolved in dioxane (5 mL) and treated with 4M HCl in dioxane (10 mL) for 2 hours at RT. The solvent was removed under vacuum to give the title compound as a light yellow solid: LC-MS (ES) m/e 321 (M+H−HCl)⁺.

f) (±)-6-({[(1-{2-[3-fluoro-6-(methyloxy)-1,5-naphthyridin-4-yl]ethyl}-3-hydroxy-3-pyrrolidinyl)methyl]amino}methyl)-2H-pyrido[3,2-b][1,4]thiazin-3(4H)-one To a stirred solution of 3-(aminomethyl)-1-{2-[3-fluoro-6-(methyloxy)-1,5-naphthyridin-4-yl]ethyl}-3-pyrrolidinol hydrochloride salt (0.21 mmole) in dry CH₂Cl₂ (25 mL) and dry EtOH (20 mL) at RT was added 3-oxo-3,4-dihydro-2H-pyrido[1,4]thiazine-6-carboxaldehyde (0.04 g, 0.21 mmole) and Et₃N (0.06 mL, 0.42 mmole). After 24 h at RT was added NaBH₄ (0.01 g, 0.23 mmole). After 2 h, silica gel (5 g) was added to the reaction solution and the suspension was concentrated under vacuum to a dry solid. Purification on silica (CHCl₃/MeOH, 9:1 containing 5% NH₄OH) afforded the title compound (0.075 g, 72%) as light yellow solid: ¹H NMR (400 MHz, CDCl₃) δ 8.51 (s, 1H), 8.08 (d, J=9.0 Hz, 1H), 7.54 (d, J=7.8 Hz, 1H), 7.00 (d, J=9.0 Hz, 1H), 6.88 (d, J=7.8 Hz, 1H), 4.38 (s, 2H), 4.03 (s, 3H), 3.81 (m, 2H), 3.37 (m, 4H), 3.12 (m, 4H), 2.72 (m, 2H), 2.54 (m, 2H), 1.92 (m, 2H). LC-MS (ES) m/e 499 (M+H)⁺.

This material, as a solution in MeOH, was treated with an excess of 4M HCl in diethyl ether and evaporated to dryness to provide the dihydrochloride salt of the title compound.

Example 42

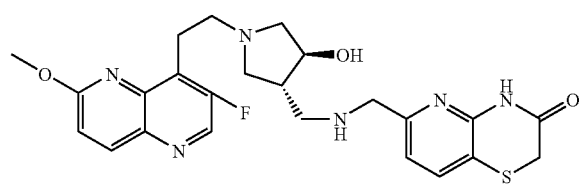

Preparation of (±)-6-({[(trans-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]thiazin-3(4H)-one a) 1,1-dimethylethyl 6-oxa-3-azabicyclo[3.1.0]hexane-3-carboxylate To a stirred solution of 1,1-dimethylethyl 2,5-dihydro-1H-pyrrole-1-carboxylate (5.0 g, 29.55 mmole) in DCM (200 mL) at RT was added MCPBA (7.65 g, 44.3 mmole). After 24 h, the reaction contents were washed with 10% aqueous NaHCO₃ and dried over Na₂SO₄. Purification on silica (hexanes/EtOAc, 1:1) afforded the title compound (4.5 g, 82%) as a yellow oil: LC-MS (ES) m/e 186 (M+H)⁺.

b) (±)-1,1-dimethylethyl-trans-3-cyano-4-[(trimethylsilyl)oxy]-1-pyrrolidinecarboxylate To a stirred solution of diethyl aluminum chloride (0.65 mL, 1M in heptane) and TMS nitrile (3.13 g, 31.6 mmole) at RT was added 1,1-dimethylethyl 6-oxa-3-azabicyclo[3.1.0]hexane-3-carboxylate (4.5 g, 24.3 mmole) in CH₂Cl₂ (15 mL) over 20 minutes. After 24 h, H₂O (0.1 mL) and EtOAc (100 mL) were added and the reaction contents were filtered through a scinter-glass funnel and concentrated under vacuum. Purification on silica (hexanes/EtOAc, 1:1) afforded the title compound (6.14 g, 89%) as an light yellow low-melting solid: LC-MS (ES) m/e 285 (M+H)⁺.

c) (±)-1,1-dimethylethyl-trans-3-(aminomethyl)-4-hydroxy-1-pyrrolidinecarboxylate To a stirred solution of (±)-1,1-dimethylethyl-trans-3-cyano-4-[(trimethylsilyl)oxy]-1-pyrrolidine carboxylate (4.67 g, 16.5 mmole), in THF (100 mL) at RT was added LiAlH₄ (33 mL, 1M in THF). After 24 h, the reaction was quenched with H₂O (1.32 mL), 20% NaOH (1.0 mL) and then H₂O (4.6 mL). The reaction contents were filtered through a scinter-glass funnel and concentrated under vacuum to afford the title compound (3.0 g, 84%) as a yellow oil: LC-MS (ES) m/e 217 (M+H)⁺.

d) (±)-1,1-dimethylethyl trans-3-hydroxy-4-[({[(phenylmethyl)oxy]carbonyl}amino)methyl]-1-pyrrolidinecarboxylate

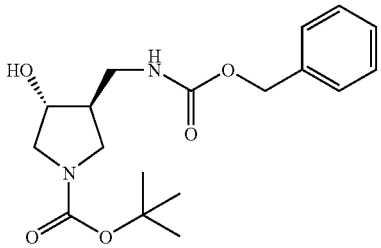

To a solution of (±)-1,1-dimethylethyl-trans-3-(aminomethyl)-4-hydroxy-1-pyrrolidinecarboxylate (6.0 g, 23.0 mmole) in DMF (50 mL) at RT was added Et$_3$N (5.0 mL, 36.1 mmole) and N-(benzyloxycarbonyloxy)succinimide (9.0 g, 36.1 mmole). After 18 h, the DMF was removed under vacuum and the residue purified on silica (25-50% DCM/EtOAc) to give the title compound (8.76 g, 90%) as a white foam: LC-MS (ES) m/e 351 (M+H)$^+$.

e) (±)-phenylmethyl {[trans-4-hydroxy-3-pyrrolidinyl]methyl}carbamate

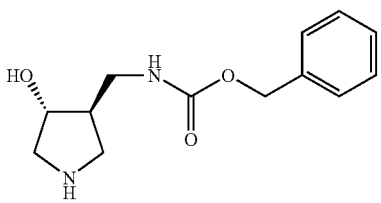

To a stirred solution of (±)-1,1-dimethylethyl trans-3-hydroxy-4-[({[(phenylmethyl)oxy]carbonyl}amino)methyl]-1-pyrrolidinecarboxylate (4.44 g, 12.7 mmole) in DCM (75 mL) was added TFA (25 mL). After stirring for 2 h, the reaction contents were concentrated under vacuum and the residue dissolved in DCM (150 mL). MP-carbonate resin (18.8 g, 50.8 mmole) was added and the reaction contents were stirred vigorously overnight. The reaction contents were filtered through a scinter-glass funnel and the resin washed with MeOH. The filtrate was concentrated and dried under vacuum to give an off-white foam: LC-MS (ES) m/e 251 (M+H)$^+$.

f) (±)-phenylmethyl[(trans-1-{2-[3-fluoro-6-(methyloxy)-1,5-naphthyridin-4-yl]ethyl}-4-hydroxy-3-pyrrolidinyl)methyl]carbamate

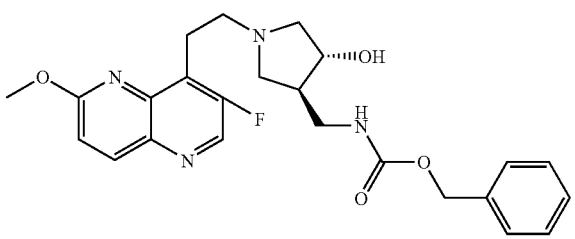

To a stirred solution of 8-ethenyl-7-fluoro-2-(methyloxy)-1,5-naphthyridine (2.55 g, 12.5 mmole) in EtOH (10 mL) was added phenylmethyl(±)-{[trans-4-hydroxy-3-pyrrolidinyl]methyl}carbamate (3.12 g, 12.5 mmole). After 24 h at 80° C. the reaction contents were purified on silica (CHCl$_3$/MeOH, 9:1 containing 5% NH$_4$OH) affording the title compound (5.56 g, 98%) as a light yellow foam: LC-MS (ES) m/e 455 (M+H)$^+$.

g) (±)-Trans-4-(aminomethyl)-1-{2-[3-fluoro-6-(methyloxy)-1,5-naphthyridin-4-yl]ethyl}-3-pyrrolidinol

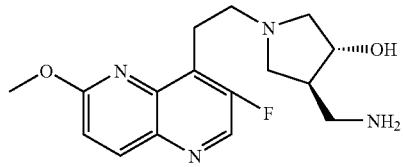

To a solution of (±)-phenylmethyl[(trans-1-{2-[3-fluoro-6-(methyloxy)-1,5-naphthyridin-4-yl]ethyl}-4-hydroxy-3-pyrrolidinyl)methyl]carbamate (1.8 g, 3.96 mmole) in MeOH (100 mL) in a round bottom flask was added Pd(OH)$_2$ (~100 mg). The reaction contents were stirred under a balloon of H$_2$ overnight at RT. The reaction contents were filtered through Celite® (MeOH) and concentrated to give the title compound (1.3 g, quant.) as a light yellow foam: LC-MS (ES) m/e 321 (M+H)$^+$.

h) (±)-6-({[(trans-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]thiazin-3(4H)-one To a stirred solution of (±)-trans-4-(aminomethyl)-1-{2-[3-fluoro-6-(methyloxy)-1,5-naphthyridin-4-yl]ethyl}-3-pyrrolidinol (0.62 g, 1.94 mmole) in dry CH$_2$Cl$_2$ (25 mL) and dry EtOH (10 mL) at RT was added 3-oxo-3,4-dihydro-2H-pyrido[1,4]thiazine-6-carboxaldehyde (0.38 g, 1.94 mmole). After 24 h, at RT was added NaBH(OAc)$_3$ (0.61 g, 2.91 mmole). After 2 h, the reaction solution was concentrated under vacuum and purified on silica (CHCl$_3$/MeOH, 9:1 containing 5% NH$_4$OH) to afford the title compound (0.60 g, 62%) as light yellow solid: $^1$H NMR (400 MHz, CDCl$_3$) δ 8.60 (s, 1H), 8.15 (d, J=9.0 Hz, 1H), 7.58 (d, J=7.8 Hz, 1H), 7.05 (d, J=9.0 Hz, 1H), 6.94 (d, J=7.8 Hz, 1H), 4.11 (s, 3H), 4.05 (m, 4H), 3.52 (m, 4H), 3.42 (s, 2H), 3.19 (m, 2H), 2.98 (m, 2H), 2.70 (m, 2H). LC-MS (ES) m/e 499 (M+H)$^+$.

This material, as a solution in MeOH, was treated with an excess of 4M HCl in diethyl ether and evaporated to dryness to provide the dihydrochloride salt of the title compound.

The racemic title compound above was separated into its enentiomerically pure constituents using chiral chromatography to give:

42 E1: 6-({[(trans-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]thiazin-3(4H)-one: $^1$H NMR (400 MHz, CDCl$_3$) δ 8.60 (s, 1H), 8.15 (d, J=9.0 Hz, 1H), 7.58 (d, J=7.8 Hz, 1H), 7.05 (d, J=9.0 Hz, 1H), 6.94 (d, J=7.8 Hz, 1H), 4.11 (s, 3H), 4.05 (m, 4H), 3.52 (m, 4H), 3.42 (s, 2H), 3.19 (m, 2H), 2.98 (m, 2H), 2.70 (m, 2H). LC-MS (ES) m/e 499 (M+H)$^+$.

This material, as a solution in MeOH, was treated with an excess of 4M HCl in diethyl ether and evaporated to dryness to provide the dihydrochloride salt of the title compound.

42 E2: 6-({[(trans-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]thiazin-3(4H)-one: $^1$H NMR (400 MHz), 8.15 (d, J=9.0 CDCl₃) δ 8.60 (s, 1H Hz, 1H), 7.58 (d, J=7.8 Hz, 1H), 7.05 (d, J=9.0 Hz, 1H), 6.94 (d, J=7.8 Hz, 1H), 4.11 (s, 3H), 4.05 (m, 4H), 3.52 (m, 4H), 3.42 (s, 2H), 3.19 (m, 2H), 2.98 (m, 2H), 2.70 (m, 2H). LC-MS (ES) m/e 499 (M+H)⁺.

This material, as a solution in MeOH, was treated with an excess of 4M HCl in diethyl ether and evaporated to dryness to provide the dihydrochloride salt of the title compound.

Example 43

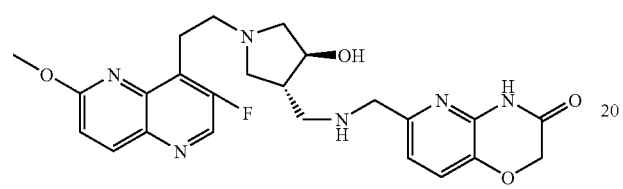

Preparation of (±)-6-({[(trans-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]oxazin-3(4H)-one Prepared essentially according to the procedure of Example 42, except substituting 3-oxo-3,4-dihydro-2H-pyrido[1,4]oxazine-6-carboxaldehyde (0.34 g, 1.94 mmole) for 3-oxo-3,4-dihydro-2H-pyrido[1,4]thiazine-6-carboxaldehyde, the title compound (0.60 g, 64%) was prepared as an off-white solid following flash chromatography on silica gel (CHCl₃/MeOH, 9:1, containing 5% NH₄OH): $^1$H NMR (400 MHz, CDCl₃) δ 8.51 (s, 1H), 8.07 (d, J=9.0 Hz, 1H), 7.15 (d, J=8.0 Hz, 1H), 6.98 (d, J=9.0 Hz, 1H), 6.88 (d, J=8.0 Hz, 1H), 4.50 (s, 2H), 4.09 (s, 3H), 3.67 (m, 2H), 3.49 (m, 4H), 3.21 (m, 2H), 2.85 (m, 4H), 2.43 (m, 2H). LC-MS (ES) m/e 483 (M+H)⁺.

This material, as a solution in MeOH, was treated with an excess of 4M HCl in diethyl ether and evaporated to dryness to provide the dihydrochloride salt of the title compound.

The racemic title compound above was separated into its enentiomerically pure constituents using chiral chromatography to give:

Example 43 E1: 6-({[(trans-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]oxazin-3 (4H)-one: $^1$H NMR (400 MHz, CDCl₃) δ 8.51 (s, 1H), 8.07 (d, J=9.0 Hz, 1H), 7.15 (d, J=8.0 Hz, 1H), 6.98 (d, J=9.0 Hz, 1H), 6.88 (d, J=8.0 Hz, 1H), 4.50 (s, 2H), 4.09 (s, 3H), 3.67 (m, 2H), 3.49 (m, 4H), 3.21 (m, 2H), 2.85 (m, 4H), 2.43 (m, 2H). LC-MS (ES) m/e 483 (M+H)⁺.

This material, as a solution in MeOH, was treated with an excess of 4M HCl in diethyl ether and evaporated to dryness to provide the dihydrochloride salt of the title compound.

Example 43 E2: 6-({[(trans-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]oxazin-3 (4H)-one: $^1$H NMR (400 MHz, CDCl₃) δ 8.51 (s, 1H), 8.07 (d, J=9.0 Hz, 1H), 7.15 (d, J=8.0 Hz, 1H), 6.98 (d, J=9.0 Hz, 1H), 6.88 (d, J=8.0 Hz, 1H), 4.50 (s, 2H), 4.09 (s, 3H), 3.67 (m, 2H), 3.49 (m, 4H), 3.21 (m, 2H), 2.85 (m, 4H), 2.43 (m, 2H). LC-MS (ES) m/e 483 (M+H)⁺.

This material, as a solution in MeOH, was treated with an excess of 4M HCl in diethyl ether and evaporated to dryness to provide the dihydrochloride salt of the title compound.

Example 44

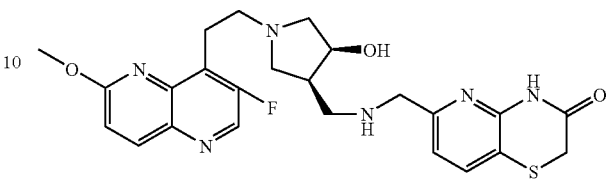

Preparation of (±)-6-({[(cis-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]thiazin-3(4H)-one a) (±)-phenylmethyl[(cis-1-{2-[3-fluoro-6-(methyloxy)-1,5-naphthyridin-4-yl]ethyl}-4-hydroxy-3-pyrrolidinyl)methyl]carbamate

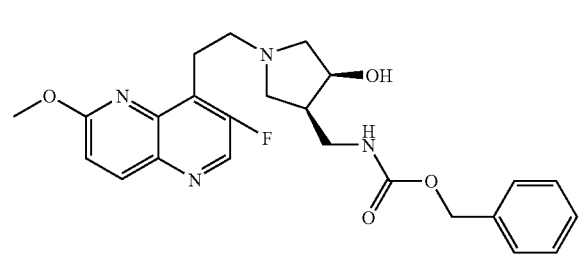

To a stirred solution of 8-ethenyl-7-fluoro-2-(methyloxy)-1,5-naphthyridine (0.73 g, 3.60 mmole) in EtOH (5 mL) was added (±)-phenylmethyl{[cis-4-hydroxy-3-pyrrolidinyl]methyl}carbamate (0.90 g, 3.60 mmole). After 24 h at 80° C. the reaction contents were purified on silica (CHCl₃/MeOH, 9:1 containing 5% NH₄OH) affording the title compound (1.57 g, 96%) as a light yellow foam: LC-MS (ES) m/e 455 (M+H)⁺.

b) (±)-cis-4-(aminomethyl)-1-{2-[3-fluoro-6-(methyloxy)-1,5-naphthyridin-4-yl]ethyl}-3-pyrrolidinol

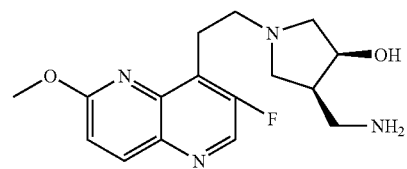

To a solution of phenylmethyl(±)-[(cis-1-{2-[3-fluoro-6-(methyloxy)-1,5-naphthyridin-4-yl]ethyl}-4-hydroxy-3-pyrrolidinyl)methyl]carbamate (1.57 g, 3.46 mmole) in MeOH (100 mL) in a round bottom flask was added Pd(OH)₂ (~100 mg). The reaction contents were stirred under a balloon of H₂ overnight at RT. The reaction contents were filtered through Celite® (MeOH) and concentrated to give the title compound (1.11 g, quant.) as a light yellow foam: LC-MS (ES) m/e 321 (M+H)⁺.

c) (±)-6-({[(Cis-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]thiazin-3(4H)-one To a stirred solution of (±)-cis-4-(aminomethyl)-1-{2-[3-fluoro-6-(methyloxy)-1,5-naphthyridin-4-yl]ethyl}-3-pyrrolidinol (0.23 g, 0.72 mmole) in dry CH$_2$Cl$_2$ (25 mL) and dry EtOH (10 mL) at RT was added 3-oxo-3,4-dihydro-2H-pyrido[1,4]thiazine-6-carboxaldehyde (0.14 g, 0.72 mmole). After 24 h, at RT was added NaBH(OAc)$_3$ (0.23 g, 1.08 mmole). After 2 h, the reaction solution was concentrated under vacuum and purified on silica (CHCl$_3$/MeOH, 9:1 containing 5% NH$_4$OH) to afford the title compound (0.24 g, 66%) as light yellow solid: $^1$H NMR (400 MHz, CD$_3$OD) δ 8.65 (s, 1H), 8.19 (d, J=9.0 Hz, 1H), 7.77 (d, J=7.8 Hz, 1H), 7.17 (d, J=9.0 Hz, 1H), 7.11 (d, J=8.0 Hz, 1H), 4.21 (s, 2H), 4.12 (s, 3H), 3.52 (m, 4H), 3.33 (s, 4H), 3.21 (m, 2H), 3.09 (m, 2H), 2.98 (m, 2H). LC-MS (ES) m/e 499 (M+H)$^+$.

This material, as a solution in MeOH, was treated with an excess of 4M HCl in diethyl ether and evaporated to dryness to provide the dihydrochloride salt of the title compound.

Example 45

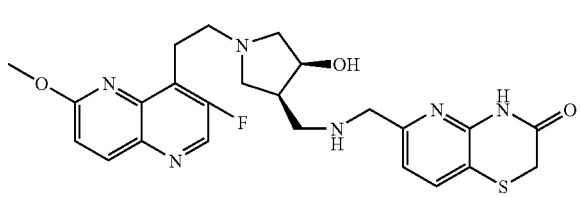

Preparation of 6-({[((3S,4S)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]thiazin-3(4H)-one Prepared essentially according to the procedure of Example 44, except substituting (3S,4S)-4-(aminomethyl)-1-{2-[3-fluoro-6-(methyloxy)-1,5-naphthyridin-4-yl]ethyl}-3-pyrrolidinol (0.60 g, 1.87 mmole) for (±)-4-(aminomethyl)-1-{2-[3-fluoro-6-(methyloxy)-1,5-naphthyridin-4-yl]ethyl}-3-pyrrolidinol, the title compound (0.42 g, 45%) was prepared as an off-white solid following flash chromatography on silica gel (CHCl$_3$/MeOH, 9:1, containing 5% NH$_4$OH): $^1$H NMR (400 MHz, CD$_3$OD) δ 8.65 (s, 1H), 8.19 (d, J=9.0 Hz, 1H), 7.77 (d, J=7.8 Hz, 1H), 7.17 (d, J=9.0 Hz, 1H), 7.11 (d, J=8.0 Hz, 1H), 4.21 (s, 2H), 4.12 (s, 3H), 3.52 (m, 4H), 3.33 (s, 4H), 3.21 (m, 2H), 3.09 (m, 2H), 2.98 (m, 2H). LC-MS (ES) m/e 499 (M+H)$^+$.

This material, as a solution in MeOH, was treated with an excess of 4M HCl in diethyl ether and evaporated to dryness to provide the dihydrochloride salt of the title compound.

Example 46

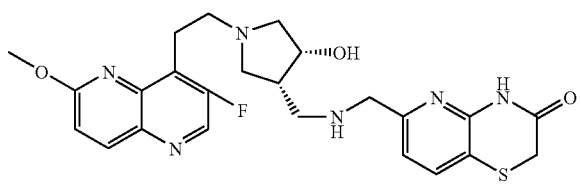

Preparation of 6-({[((3S,4S)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]thiazin-3(4H)-one Prepared essentially according to the procedure of Example 44, except substituting (3R,4R)-4-(aminomethyl)-1-{2-[3-fluoro-6-(methyloxy)-1,5-naphthyridin-4-yl]ethyl}-3-pyrrolidinol (0.60 g, 1.87 mmole) for (±)-4-(aminomethyl)-1-{2-[3-fluoro-6-(methyloxy)-1,5-naphthyridin-4-yl]ethyl}-3-pyrrolidinol, the title compound (0.57 g, 61%) was prepared as an off-white solid following flash chromatography on silica gel (CHCl$_3$/MeOH, 9:1, containing 5% NH$_4$OH): $^1$H NMR (400 MHz, CD$_3$OD) δ 8.65 (s, 1H), 8.19 (d, J=9.0 Hz, 1H), 7.77 (d, J=7.8 Hz, 1H), 7.17 (d, J=9.0 Hz, 1H), 7.11 (d, J=8.0 Hz, 1H), 4.21 (s, 2H), 4.12 (s, 3H), 3.52 (m, 4H), 3.33 (s, 4H), 3.21 (m, 2H), 3.09 (m, 2H), 2.98 (m, 2H). LC-MS (ES) m/e 499 (M+H)$^+$.

This material, as a solution in MeOH, was treated with an excess of 4M HCl in diethyl ether and evaporated to dryness to provide the dihydrochloride salt of the title compound.

Example 47

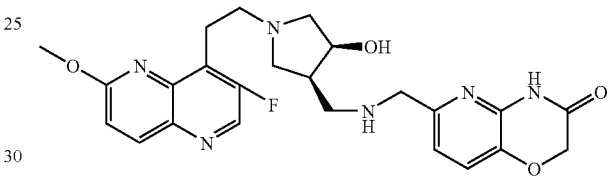

Preparation of 6-({[((3S,4S)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]oxazin-3(4H)-one Prepared essentially according to the procedure of Example 44, except substituting 3-oxo-3,4-dihydro-2H-pyrido[1,4]oxazine-6-carboxaldehyde (0.28 g, 1.56 mmole) for 3-oxo-3,4-dihydro-2H-pyrido[1,4]thiazine-6-carboxaldehyde, and substituting (3S,4S)-4-(aminomethyl)-1-{2-[3-fluoro-6-(methyloxy)-1,5-naphthyridin-4-yl]ethyl}-3-pyrrolidinol (0.50 g, 1.56 mmole) for (±)-4-(aminomethyl)-1-{2-[3-fluoro-6-(methyloxy)-1,5-naphthyridin-4-yl]ethyl}-3-pyrrolidinol, the title compound (0.45 g, 60%) was prepared as an off-white solid following flash chromatography on silica gel (CHCl$_3$/MeOH, 9:1, containing 5% NH$_4$OH): $^1$H NMR (400 MHz, CD$_3$OD) δ 8.67 (s, 1H), 8.20 (d, J=9.0 Hz, 1H), 7.35 (d, J=7.9 Hz, 1H), 7.19 (d, J=9.0 Hz, 1H), 7.11 (d, J=8.0 Hz, 1H), 4.68 (app s, 2H), 4.27 (s, 2H), 4.15 (s, 3H), 3.60 (m, 2H), 3.47 (m, 4H), 3.31 (m, 2H), 3.25 (m, 2H). LC-MS (ES) m/e 483 (M+H)$^+$.

This material, as a solution in MeOH, was treated with an excess of 4M HCl in diethyl ether and evaporated to dryness to provide the dihydrochloride salt of the title compound.

Example 48

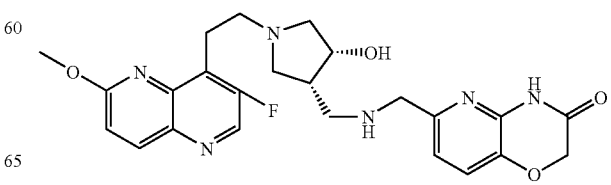

Preparation of 6-({[((3S,4S)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]oxazin-3(4H)-one Prepared essentially according to the procedure of Example 44, except substituting 3-oxo-3,4-dihydro-2H-pyrido[1,4]oxazine-6-carboxaldehyde (0.22 g, 1.25 mmole) for 3-oxo-3,4-dihydro-2H-pyrido[1,4]thiazine-6-carboxaldehyde, and substituting (3R,4R)-4-(aminomethyl)-1-{2-[3-fluoro-6-(methyloxy)-1,5-naphthyridin-4-yl]ethyl}-3-pyrrolidinol (0.40 g, 1.25 mmole) for (±)-4-(aminomethyl)-1-{2-[3-fluoro-6-(methyloxy)-1,5-naphthyridin-4-yl]ethyl}-3-pyrrolidinol, the title compound (0.21 g, 35%) was prepared as an off-white solid following flash chromatography on silica gel (CHCl$_3$/MeOH, 9:1, containing 5% NH$_4$OH): $^1$H NMR (400 MHz, CD$_3$OD) δ 8.67 (s, 1H), 8.20 (d, J=9.0 Hz, 1H), 7.35 (d, J=7.9 Hz, 1H), 7.19 (d, J=9.0 Hz, 1H), 7.11 (d, J=8.0 Hz, 1H), 4.68 (app s, 2H), 4.27 (s, 2H), 4.15 (s, 3H), 3.60 (m, 2H), 3.47 (m, 4H), 3.31 (m, 2H), 3.25 (m, 2H). LC-MS (ES) m/e 483 (M+H)$^+$.

This material, as a solution in MeOH, was treated with an excess of 4M HCl in diethyl ether and evaporated to dryness to provide the dihydrochloride salt of the title compound.

Example 49

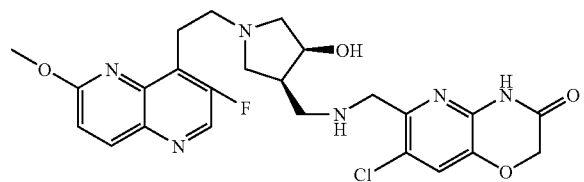

Preparation of (±)-7-chloro-6-({[(cis-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]oxazin-3(4H)-one Prepared essentially according to the procedure of Example 44, except substituting 7-chloro-3-oxo-3,4-dihydro-2H-pyrido[3,2-b][1,4]oxazine-6-carbaldehyde (0.20 g, 0.93 mmole) for 3-oxo-3,4-dihydro-2H-pyrido[1,4]thiazine-6-carboxaldehyde, the title compound (0.43 g, 89%) was prepared as an off-white solid following flash chromatography on silica gel (CHCl$_3$/MeOH, 9:1, containing 5% NH$_4$OH): $^1$H NMR (400 MHz, CD$_3$OD) δ 8.67 (s, 1H), 8.20 (d, J=9.0 Hz, 1H), 7.48 (s, 1H), 7.19 (d, J=9.0 Hz, 1H), 4.72 (app s, 2H), 4.27 (s, 2H), 4.14 (s, 3H), 3.57 (m, 2H), 3.38 (m, 5H), 3.20 (m, 4H), 3.81 (m, 1H). LC-MS (ES) m/e 517 (M+H)$^+$.

This material, as a solution in MeOH, was treated with an excess of 4M HCl in diethyl ether and evaporated to dryness to provide the dihydrochloride salt of the title compound.

Example 50

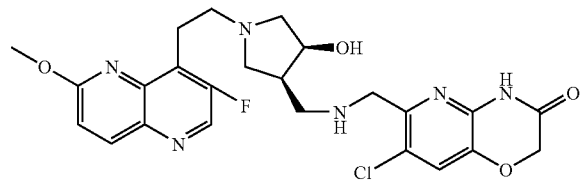

Preparation of 7-chloro-6-({[((3S,4S)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]oxazin-3(4H)-one Prepared essentially according to the procedure of Example 44, except substituting 7-chloro-3-oxo-3,4-dihydro-2H-pyrido[3,2-b][1,4]oxazine-6-carbaldehyde (0.33 g, 1.56 mmole) for 3-oxo-3,4-dihydro-2H-pyrido[1,4]thiazine-6-carboxaldehyde, and substituting (3S,4S)-4-(aminomethyl)-1-{2-[3-fluoro-6-(methyloxy)-1,5-naphthyridin-4-yl]ethyl}-3-pyrrolidinol (0.50 g, 1.56 mmole) for (±)-4-(aminomethyl)-1-{2-[3-fluoro-6-(methyloxy)-1,5-naphthyridin-4-yl]ethyl}-3-pyrrolidinol, the title compound (0.48 g, 59%) was prepared as an off-white solid following flash chromatography on silica gel (CHCl$_3$/MeOH, 9:1, containing 5% NH$_4$OH): $^1$H NMR (400 MHz, CD$_3$OD) δ 8.67 (s, 1H), 8.20 (d, J=9.0 Hz, 1H), 7.48 (s, 1H), 7.19 (d, J=9.0 Hz, 1H), 4.72 (app s, 2H), 4.27 (s, 2H), 4.14 (s, 3H), 3:57 (m; 2H), 3.38 (m, 5H), 3.20 (m, 4H), 3.81 (m, 1H). LC-MS (ES) m/e 517 (M+H)$^+$.

This material, as a solution in MeOH, was treated with an excess of 4M HCl in diethyl ether and evaporated to dryness to provide the dihydrochloride salt of the title compound.

Example 51

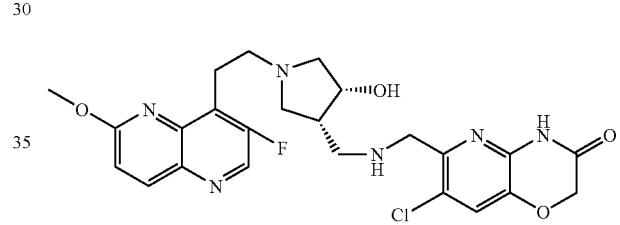

Preparation of 7-chloro-6-({[((3S,4S)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]oxazin-3(4H)-one Prepared essentially according to the procedure of Example 44, except substituting 7-chloro-3-oxo-3,4-dihydro-2H-pyrido[3,2-b][1,4]oxazine-6-carbaldehyde (0.26 g, 1.25 mmole) for 3-oxo-3,4-dihydro-2H-pyrido[1,4]thiazine-6-carboxaldehyde, and substituting (3R,4R)-4-(aminomethyl)-1-{2-[3-fluoro-6-(methyloxy)-1,5-naphthyridin-4-yl]ethyl}-3-pyrrolidinol (0.40 g, 1.25 mmole) for (±)-4-(aminomethyl)-1-{2-[3-fluoro-6-(methyloxy)-1,5-naphthyridin-4-yl]ethyl}-3-pyrrolidinol, the title compound (0.21 g, 32%) was prepared as an off-white solid following flash chromatography on silica gel (CHCl$_3$/MeOH, 9:1, containing 5% NH$_4$OH): $^1$H NMR (400 MHz, CD$_3$OD) δ 8.67 (s, 1H), 8.20 (d, J=9.0 Hz, 1H), 7.48 (s, 1H), 7.19 (d, J=9.0 Hz, 1H), 4.72 (app s, 2H), 4.27 (s, 2H), 4.14 (s, 3H), 3.57 (m, 2H), 3.38 (m, 5H), 3.20 (m, 4H), 3.81 (m, 1H). LC-MS (ES) m/e 517 (M+H)$^+$.

This material, as a solution in MeOH, was treated with an excess of 4M HCl in diethyl ether and evaporated to dryness to provide the dihydrochloride salt of the title compound.

Example 52

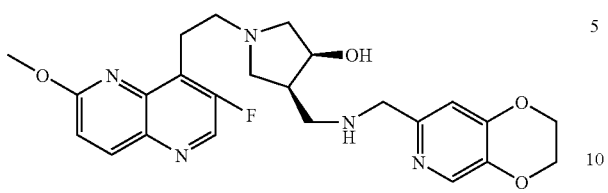

Preparation of (±)-cis-4-{[(2,3-dihydro[1,4]dioxino[2,3-c]pyridin-7-ylmethyl)amino]methyl}-1-{2-[3-fluoro-6-(methyloxy)-1,5-naphthyridin-4-yl]ethyl}-3-pyrrolidinol Prepared essentially according to the procedure of Example 44, except substituting 2,3-dihydro[1,4]dioxino[2,3-c]pyridine-7-carbaldehyde (0.12 g, 0.72 mmole) for 3-oxo-3,4-dihydro-2H-pyrido[1,4]thiazine-6-carboxaldehyde, the title compound (0.19 g, 55%) was prepared as an off-white solid following flash chromatography on silica gel (CHCl$_3$/MeOH, 9:1, containing 5% NH$_4$OH): $^1$H NMR (400 MHz, CDCl$_3$) δ 8.52 (s, 1H), 8.09 (d, J=9.05 Hz, 1H), 8.03 (s, 1H), 7.00 (d, J=9.04 Hz, 1H), 6.68 (s, 1H), 4.42 (m, 1H), 4.24 (m, 4H), 4.02 (s, 3H), 3.70 (m, 2H), 3.33 (m, 2H), 3.04 (m, 1H), 2.78 (m, 5H), 2.64 (m, 1H), 2.46 (m, 1H), 2.44 (m, 1H). LC-MS (ES) m/e 470 (M+H)$^+$.

This material, as a solution in MeOH, was treated with an excess of 4M HCl in diethyl ether and evaporated to dryness to provide the dihydrochloride salt of the title compound.

Example 53

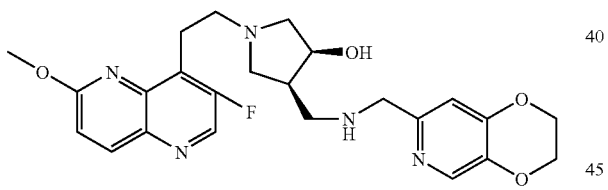

Preparation of (3S,4S)-4-{[(2,3-dihydro[1,4]dioxino[2,3-c]pyridin-7-ylmethyl)amino]methyl}-1-{2-[3-fluoro-6-(methyloxy)-1,5-naphthyridin-4-yl]ethyl}-3-pyrrolidinol Prepared essentially according to the procedure of Example 44, except substituting 2,3-dihydro[1,4]dioxino[2,3-c]pyridine-7-carbaldehyde (259 mg, 1.57 mmole) for 3-oxo-3,4-dihydro-2H-pyrido[1,4]thiazine-6-carboxaldehyde, and substituting (3S,4S)-4-(aminomethyl)-1-{2-[3-fluoro-6-(methyloxy)-1,5-naphthyridin-4-yl]ethyl}-3-pyrrolidinol (0.48 g, 1.50 mmole) for (±)-4-(aminomethyl)-1-{2-[3-fluoro-6-(methyloxy)-1,5-naphthyridin-4-yl]ethyl}-3-pyrrolidinol, the title compound (411 mg, 56%) was prepared as an off-white solid following flash chromatography on silica gel (CHCl$_3$/MeOH, 9:1, containing 5% NH$_4$OH): $^1$H NMR (400 MHz, CDCl$_3$) δ 8.52 (s, 1H), 8.09 (d, J=9.05 Hz, 1H), 8.03 (s, 1H), 7.00 (d, J=9.04 Hz, 1H), 6.68 (s, 1H), 4.42 (m, 1H), 4.24 (m, 4H), 4.02 (s, 3H), 3.70 (m, 2H), 3.33 (m, 2H), 3.04 (m, 1H), 2.78 (m, 5H), 2.64 (m, 1H), 2.46 (m, 1H), 2.44 (m, 1H). LC-MS (ES) m/e 470 (M+H)$^+$.

This material, as a solution in MeOH, was treated with an excess of 4M HCl in diethyl ether and evaporated to dryness to provide the dihydrochloride salt of the title compound.

Example 54

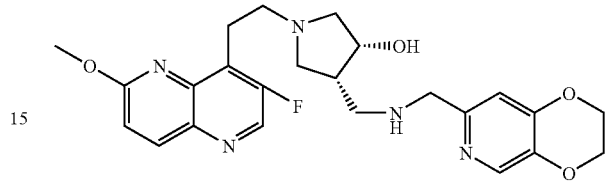

Preparation of (3S,4S)-4-{[(2,3-dihydro[1,4]dioxino[2,3-c]pyridin-7-ylmethyl)amino]methyl}-1-{2-[3-fluoro-6-(methyloxy)-1,5-naphthyridin-4-yl]ethyl}-3-pyrrolidinol Prepared essentially according to the procedure of Example 44, except substituting 2,3-dihydro[1,4]dioxino[2,3-c]pyridine-7-carbaldehyde (248 g, 1.50 mmole) for 3-oxo-3,4-dihydro-2H-pyrido[1,4]thiazine-6-carboxaldehyde, and substituting (3R,4R)-4-(aminomethyl)-1-{2-[3-fluoro-6-(methyloxy)-1,5-naphthyridin-4-yl]ethyl}-3-pyrrolidinol (0.50 g, 1.58 mmole) for (±)-4-(aminomethyl)-1-{2-[3-fluoro-6-(methyloxy)-1,5-naphthyridin-4-yl]ethyl}-3-pyrrolidinol, the title compound (306 mg, 44%) was prepared as an off-white solid following flash chromatography on silica gel (CHCl$_3$/MeOH, 9:1, containing 5% NH$_4$OH): $^1$H NMR (400 MHz, CDCl$_3$) δ 8.52 (s, 1H), 8.09 (d, J=9.05 Hz, 1H), 8.03 (s, 1H), 7.00 (d, J=9.04 Hz, 1H), 6.68 (s, 1H), 4.42 (m, 1H), 4.24 (m, 4H), 4.02 (s, 3H), 3.70 (m, 2H), 3.33 (m, 2H), 3.04 (m, 1H), 2.78 (m, 5H), 2.64 (m, 1H), 2.46 (m, 1H), 2.44 (m, 1H). LC-MS (ES) m/e 470 (M+H)$^+$.

This material, as a solution in MeOH, was treated with an excess of 4M HCl in diethyl ether and evaporated to dryness to provide the dihydrochloride salt of the title compound.

Example 55

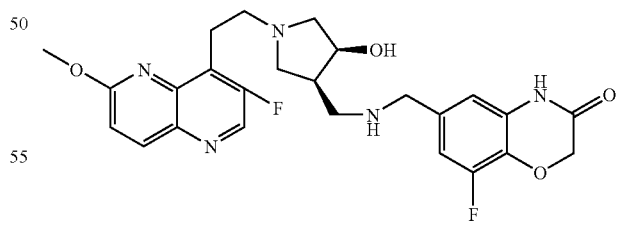

Preparation of 8-fluoro-6-({[((3S,4S)-1-{2-[3-fluoro-6-(methyloxy)-1,5-naphthyridin-4-yl]ethyl}-4-hydroxy-3-pyrrolidinyl)methyl]amino}methyl)-2H-1,4-benzoxazin-3(4H)-one Prepared essentially according to the procedure of Example 44, except substituting 8-fluoro-3-oxo-3,4-dihydro- 2H-1,4-benzoxazine-6-carbaldehyde (104 g, 0.53 mmole) for 3-oxo-3,4-dihydro-2H-pyrido[1,4]thiazine-6-carboxaldehyde, and substituting (3S,4S)-4-(aminomethyl)-1-{2-[3-fluoro-6-(methyloxy)-1,5-naphthyridin-4-yl]ethyl}-3-pyrrolidinol (168 mg, 0.53 mmole) for (±)-4-(aminomethyl)-1-{2-[3-fluoro-6-(methyloxy)-1,5-naphthyridin-4-yl]ethyl}-3-pyrrolidinol, the title compound (70 mg, 27%) was prepared as an off-white solid following flash chromatography on silica gel (CHCl$_3$/MeOH, 9:1, containing 5% NH$_4$OH): $^1$H NMR (400 MHz, CDCl$_3$) δ 8.56 (s, 1H), 8.15 (d, J=9.05 Hz, 1H), 7.06 (d, J=9.04 Hz, 1H), 6.66 (d, J=10.65 Hz, 1H), 6.55 (s, 1H), 4.59 (q, 2H), 4.48 (m, 1H), 4.06 (s, 2H), 3.61 (m, 2H), 3.50 (s, 3H), 3.37 (m, 2H), 3.05 (m, 1H), 2.69-2.95 (m, 6H), 2.74 (m, 1H), 2.68 (m, 1H), 2.45 (m, 1H). LC-MS (ES) m/e 500 (M+H)$^+$.

This material, as a solution in MeOH, was treated with an excess of 4M HCl in diethyl ether and evaporated to dryness to provide the dihydrochloride salt of the title compound.

Example 56

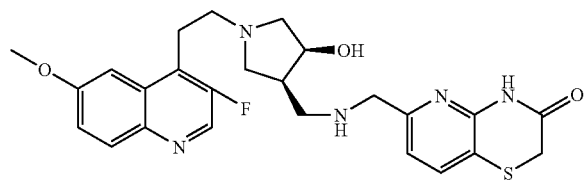

Preparation of 6-({[((3S,4S)-1-{2-[3-fluoro-6-(methyloxy)-4-quinolinyl]ethyl}-4-hydroxy-3-pyrrolidinyl)methyl]amino}methyl)-2H-pyrido[3,2-b][1,4]thiazin-3(4H)-one Prepared essentially according to the procedure of Example 44, except substituting (3S,4S)-4-(aminomethyl)-1-{2-[3-fluoro-6-(methyloxy)-4-quinolinyl]ethyl}-3-pyrrolidinol (0.55 g, 1.72 mmole) for (±)-4-(aminomethyl)-1-{2-[3-fluoro-6-(methyloxy)-1,5-naphthyridin-4-yl]ethyl}-3-pyrrolidinol, the title compound (0.57 g, 66%) was prepared as an off-white solid following flash chromatography on silica gel (CHCl$_3$/MeOH, 9:1, containing 5% NH$_4$OH): $^1$H NMR (400 MHz, CDCl$_3$) δ 8.58 (s, 1H), 8.00 (d, J=9.20 Hz, 1H), 7.57 (d, J=7.79 Hz, 1H), 7.32 (d, J=9.18 Hz, 1H), 7.24 (s, 1H), 6.89 (d, J=7.82 Hz, 1H), 4.53 (m, 1H), 3.97 (s, 3H), 3.86 (q, 2H), 3.50 (s, 2H), 3.45 (s, 2H), 3.28 (m, 2H), 3.05 (m, 1H), 2.83-2.96 (m, 6H), 2.69 (m, 1H), 2.53 (m, 1H). LC-MS (ES) m/e 498 (M+H)$^+$.

This material, as a solution in MeOH, was treated with an excess of 4M HCl in diethyl ether and evaporated to dryness to provide the dihydrochloride salt of the title compound.

Example 57

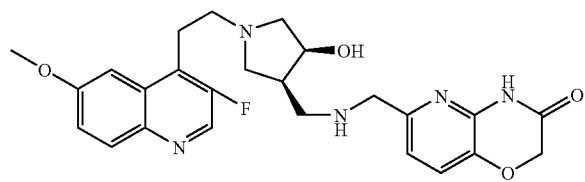

Preparation of 6-({[((3S,4S)-1-{2-[3-fluoro-6-(methyloxy)-4-quinolinyl]ethyl}-4-hydroxy-3-pyrrolidinyl)methyl]amino}methyl)-2H-pyrido[3,2-b][1,4]oxazin-3(4H)-one Prepared essentially according to the procedure of Example 44, except substituting (3S,4S)-4-(aminomethyl)-1-{2-[3-fluoro-6-(methyloxy)-4-quinolinyl]ethyl}-3-pyrrolidinol (0.52 g, 1.61 mmole) for (±)-4-(aminomethyl)-1-{2-[3-fluoro-6-(methyloxy)-1,5-naphthyridin-4-yl]ethyl}-3-pyrrolidinol, and substituting 3-oxo-3,4-dihydro-2H-pyrido[1,4]oxazine-6-carboxaldehyde (0.29 g, 1.62 mmole) for 3-oxo-3,4-dihydro-2H-pyrido[1,4]thiazine-6-carboxaldehyde, the title compound (0.41 g, 53%) was prepared as an off-white solid following flash chromatography on silica gel (CHCl$_3$/MeOH, 9:1, containing 5% NH$_4$OH): $^1$H NMR (400 MHz, CDCl$_3$) δ 8.59 (s, 1H), 8.01 (d, J=9.19 Hz, 1H), 7.33 (d, J=9.19 Hz, 1H), 7.22 (d, J=9.22 Hz, 1H), 6.86 (d, J=8.05 Hz, 1H), 4.62 (s, 2H), 4.54 (m, 1H), 3.97 (s, 3H), 3.85 (m, 2H), 3.28 (m, 2H), 3.04 (m, 1H), 2.78-3.00 (m, 6H), 2.66 (m, 1H), 2.55 (m, 1H). LC-MS (ES) m/e 482 (M+H)$^+$.

This material, as a solution in MeOH, was treated with an excess of 4M HCl in diethyl ether and evaporated to dryness to provide the dihydrochloride salt of the title compound.

Example 58

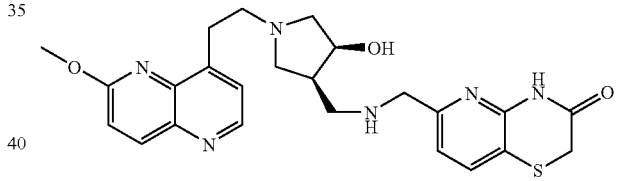

Preparation of (±)-6-({[(cis-4-hydroxy-1-{2-[6-(methyloxy)-1,5-naphthyridin-4-yl]ethyl}-3-pyrrolidinyl)methyl]amino}methyl)-2H-pyrido[3,2-b][]1,4] thiazin-3(4H)-one Prepared essentially according to the procedure of Example 44, except substituting (±)-4-(aminomethyl)-1-{2-[6-(methyloxy)-1,5-naphthyridin-4-yl]ethyl}-3-pyrrolidinol (0.35 g, 1.16 mmole) for (±)-4-(aminomethyl)-1-{2-[3-fluoro-6-(methyloxy)-1,5-naphthyridin-4-yl]ethyl}-3-pyrrolidinol, the title compound (0.39 g, 70%) was prepared as an off-white solid following flash chromatography on silica gel (CHCl$_3$/MeOH, 9:1, containing 5% NH$_4$OH): $^1$H NMR (400 MHz, CD$_3$OD) δ 9.06 (m, 1H), 8.52 (d, J=9.0 Hz, 1H), 8.38 (m, 1H), 7.83 (d, J=7.8 Hz, 1H), 7.65 (d, J=9.0 Hz, 1H), 7.17 (d, J=7.8 Hz, 1H), 4.41 (s, 2H), 4.39 (s, 3H), 3.95 (m, 4H), 3.88 (m, 2H), 3.75 (m, 2H), 3.53 (m, 4H), 3.37 (m, 2H). LC-MS (ES) m/e 481 (M+H)$^+$.

This material, as a solution in MeOH, was treated with an excess of 4M HCl in diethyl ether and evaporated to dryness to provide the dihydrochloride salt of the title compound.

Example 59

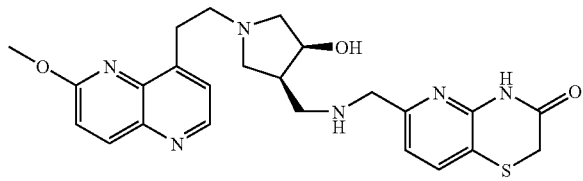

Preparation of 6-({[((3S,4S)-4-hydroxy-1-{2-[6-(methyloxy)-1,5-naphthyridin-4-yl]ethyl}-3-pyrrolidinyl)methyl]amino}methyl)-2H-pyrido[3,2-b][1,4]thiazin-3(4H)-one Prepared essentially according to the procedure of Example 44, except substituting (3S,4S)-4-(aminomethyl)-1-{2-[6-(methyloxy)-1,5-naphthyridin-4-yl]ethyl}-3-pyrrolidinol (0.63 g, 2.07 mmole) for (±)-4-(aminomethyl)-1-{2-[3-fluoro-6-(methyloxy)-1,5-naphthyridin-4-yl]ethyl}-3-pyrrolidinol, the title compound (0.62 g, 62%) was prepared as an off-white solid following flash chromatography on silica gel (CHCl$_3$/MeOH, 9:1, containing 5% NH$_4$OH): $^1$H NMR (400 MHz, CD$_3$OD) δ 9.06 (m, 1H), 8.52 (d, J=9.0 Hz, 1H), 8.38 (m, 1H), 7.83 (d, J=7.8 Hz, 1H), 7.65 (d, J=9.0 Hz, 1H), 7.17 (d, J=7.8 Hz, 1H), 4.41 (s, 2H), 4.39 (s, 3H), 3.95 (m, 4H), 3.88 (m, 2H), 3.75 (m, 2H), 3.53 (m, 4H), 3.37 (m, 2H). LC-MS (ES) m/e 481 (M+H)$^+$.

This material, as a solution in MeOH, was treated with an excess of 4M HCl in diethyl ether and evaporated to dryness to provide the dihydrochloride salt of the title compound.

Example 60

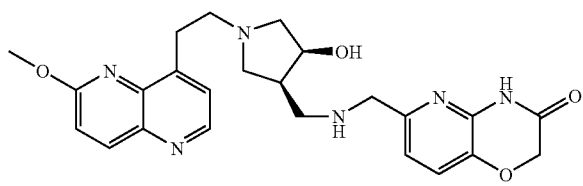

Preparation of (±)-6-({[(cis-4-hydroxy-1-{2-[6-(methyloxy)-1,5-naphthyridin-4-yl]ethyl}-3-pyrrolidinyl)methyl]amino}methyl)-2H-pyrido[3,2-b][1,4]oxazin-3(4H)-one Prepared essentially according to the procedure of Example 44, except substituting (±)-4-(aminomethyl)-1-{2-[6-(methyloxy)-1,5-naphthyridin-4-yl]ethyl}-3-pyrrolidinol (0.35 g, 1.16 mmole) for (±)-4-(aminomethyl)-1-{2-[3-fluoro-6-(methyloxy)-1,5-naphthyridin-4-yl]ethyl}-3-pyrrolidinol, and substituting 3-oxo-3,4-dihydro-2H-pyrido[1,4]oxazine-6-carboxaldehyde (0.21 g, 1.16 mmole) for 3-oxo-3,4-dihydro-2H-pyrido[1,4]thiazine-6-carboxaldehyde, the title compound (0.32 g, 59%) was prepared as an off-white solid following flash chromatography on silica gel (CHCl$_3$/MeOH, 9:1, containing 5% NH$_4$OH): $^1$H NMR (400 MHz, CD$_3$OD) δ 9.06 (m, 1H), 8.52 (d, J=9.0 Hz, 1H), 8.36 (m, 1H), 7.65 (d, J=9.0 Hz, 1H), 7.38 (d, J=8.0 Hz, 1H), 7.15 (d, J=8.0 Hz, 1H), 4.71 (s, 2H), 4.34 (s, 3H), 4.11 (m, 2H), 3.95 (m, 4H), 3.79 (m, 2H), 3.50 (m, 4H), 3.21 (m, 2H). LC-MS (ES) m/e 465 (M+H)$^+$.

This material, as a solution in MeOH, was treated with an excess of 4M HCl in diethyl ether and evaporated to dryness to provide the dihydrochloride salt of the title compound.

Example 61

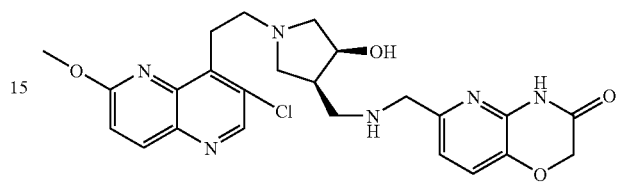

Preparation of 6-({[((3S,4S)-1-{2-[3-chloro-6-(methyloxy)-1,5-naphthyridin-4-yl]ethyl}-4-hydroxy-3-pyrrolidinyl)methyl]amino}methyl)-2H-pyrido[3,2-b][1,4]oxazin-3(4H)-one Prepared essentially according to the procedure of Example 44, except substituting (3S,4S)-4-(aminomethyl)-1-{2-[3-chloro-6-(methyloxy)-1,5-naphthyridin-4-yl]ethyl}-3-pyrrolidinol (74 mg, 0.22 mmole) for (±)-4-(aminomethyl)-1-{2-[3-fluoro-6-(methyloxy)-1,5-naphthyridin-4-yl]ethyl}-3-pyrrolidinol, and substituting 3-oxo-3,4-dihydro-2H-pyrido[1,4]oxazine-6-carboxaldehyde (39 mg, 0.22 mmole) for 3-oxo-3,4-dihydro-2H-pyrido[1,4]thiazine-6-carboxaldehyde, the title compound (94 mg, 85%) was prepared as an off-white solid following flash chromatography on silica gel (CHCl$_3$/MeOH, 9:1, containing 5% NH$_4$OH): $^1$H NMR (400 MHz, CDCl$_3$) δ 8.61 (s, 1H), 8.12 (d, J=9.03 Hz, 1H), 7.13 (d, J=8.02 Hz, 1H), 7.04 (d, J=9.02 Hz, 1H), 6.82 (d, J=8.04 Hz, 1H), 4.54 (s, 2H), 4.49 (m, 1H), 4.04 (s, 3H), 3.78 (m, 2H), 3.51 (m, 2H), 3.07 (m, 1H), 2.75-2.91 (m, 6H), 2.63 (m, 1H), 2.51 (m, 1H). LC-MS (ES) m/e 499 (M+H)$^+$.

This material, as a solution in MeOH, was treated with an excess of 4M HCl in diethyl ether and evaporated to dryness to provide the dihydrochloride salt of the title compound.

Example 62

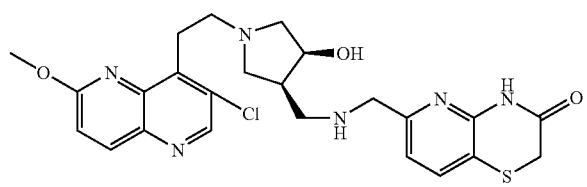

Preparation of 6-({[((3S,4S)-1-{2-[3-chloro-6-(methyloxy)-1,5-naphthyridin-4-yl]ethyl}-4-hydroxy-3-pyrrolidinyl)methyl]amino}methyl)-2H-pyrido[3,2-b][1,4]thiazin-3(4H)-one Prepared essentially according to the procedure of Example 44, except substituting (3S,4S)-4-(aminomethyl)-1-

{2-[3-chloro-6-(methyloxy)-1,5-naphthyridin-4-yl]ethyl}-3-pyrrolidinol (74 mg, 0.22 mmole) for (±)-4-(aminomethyl)-1-{2-[3-fluoro-6-(methyloxy)-1,5-naphthyridin-4-yl]ethyl}-3-pyrrolidinol, the title compound (107 mg, 94%) was prepared as an off-white solid following flash chromatography on silica gel (CHCl$_3$/MeOH, 9:1, containing 5% NH$_4$OH): $^1$H NMR (400 MHz, CDCl$_3$) δ 8.64 (s, 1H), 8.15 (d, J=9.02 Hz, 1H), 7.54 (d, J=7.78 Hz, 1H), 7.08 (d, J=9.01 Hz, 1H), 6.88 (d, J=7.81 Hz, 1H), 4.49 (m, 1H), 4.07 (s, 3H), 3.80 (m, 2H), 3.53 (m, 2H), 3.43 (s, 2H), 3.05 (m, 1H), 2.80-2.90 (m, 6H), 2.62 (m, 1H), 2.46 (m, 1H). LC-MS (ES) m/e 515 (M+H)$^+$.

This material, as a solution in MeOH, was treated with an excess of 4M HCl in diethyl ether and evaporated to dryness to provide the dihydrochloride salt of the title compound.

Example 63

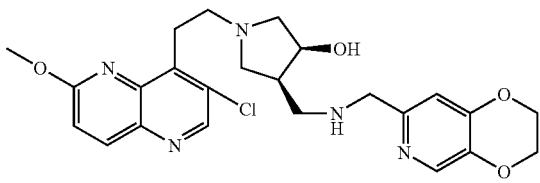

Preparation of (3S,4S)-1-{2-[3-chloro-6-(methyloxy)-1,5-naphthyridin-4-yl]ethyl}-4-{[(2,3-dihydro[1,4]dioxino[2,3-c]pyridin-7-ylmethyl)amino]methyl}-3-pyrrolidinol Prepared essentially according to the procedure of Example 44, except substituting (3S,4S)-4-(aminomethyl)-1-{2-[3-chloro-6-(methyloxy)-1,5-naphthyridin-4-yl]ethyl}-3-pyrrolidinol (74 mg, 0.22 mmole) for (±)-4-(aminomethyl)-1-{2-[3-fluoro-6-(methyloxy)-1,5-naphthyridin-4-yl]ethyl}-3-pyrrolidinol, and substituting 2,3-dihydro[1,4]dioxino[2,3-c]pyridine-7-carbaldehyde (36 mg, 0.22 mmole) for 3-oxo-3,4-dihydro-2H-pyrido[1,4]thiazine-6-carboxaldehyde, the title compound (57 mg, 53%) was prepared as an off-white solid following flash chromatography on silica gel (CHCl$_3$/MeOH, 9:1, containing 5% NH$_4$OH): $^1$H NMR (400 MHz, CDCl$_3$) δ 8.64 (s, 1H), 8.14 (d, J=9.02 Hz, 1H), 8.10 (s, 1H), 7.09 (d, J=9.01 Hz, 1H), 6.73 (s, 1H), 4.51 (m, 1H), 4.30 (m, 4H), 4.08 (s, 3H), 3.77 (m, 2H), 3.54 (m, 2H), 3.12 (m, 1H), 2.70-2.89 (m, 6H), 2.53 (m, 1H), 2.42 (m, 1H). LC-MS (ES) m/e 486 (M+H)$^+$.

This material, as a solution in MeOH, was treated with an excess of 4M HCl in diethyl ether and evaporated to dryness to provide the dihydrochloride salt of the title compound.

Example 64

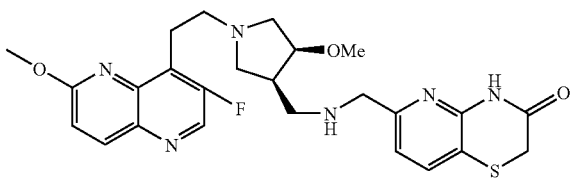

Preparation of (±)-6-[({[(cis-3,4)-1-{2-[3-fluoro-6-(methyloxy)-1,5-naphthyridin-4-yl]ethyl}-4-(methyloxy)-3-pyrrolidinyl]methyl}amino)methyl]-2H-pyrido[3,2-b][1,4]thiazin-3(4H)-one

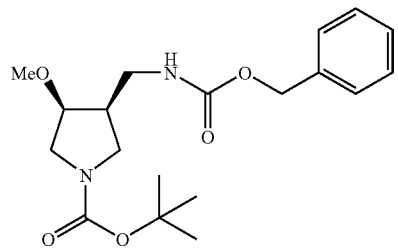

a) (±)-1,1-dimethylethyl(cis-3,4)-3-(methyloxy)-4-[({[(phenylmethyl)oxy]carbonyl}amino)methyl]-1-pyrrolidinecarboxylate To a solution of 1,1-dimethylethyl(cis-3,4)-3-hydroxy-4-[({[(phenylmethyl)oxy]carbonyl}amino)methyl]-1-pyrrolidinecarboxylate (3.9 g, 11.1 mmole) in toluene at RT was added caustic (14.5 mL), benzyltriethylamine chloride (25 mg, 0.11 mmole) and dimethyl sulfate (1.26 mL, 13.32 mmole). After stirring for 3 h, the reaction solution was diluted with H$_2$O (100 mL) and EtOAc (200 mL). the layers were separated and the organic layer dried over Na$_2$SO$_4$. Concentration under vacuum and purification on silica (hexanes/EtOAc, 1:1) afforded the title compound (2.9 g, 72%) as a colorless oil: LC-MS (ES) m/e 365 (M+H)$^+$.

b) (±)-phenylmethyl {[(cis-3,4)-4-(methyloxy)-3-pyrrolidinyl]methyl}carbamate

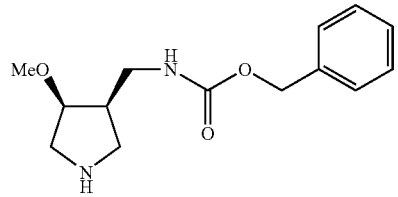

To a solution of (±)-1,1-dimethylethyl cis-3-hydroxy-4-[({[(phenylmethyl)oxy]carbonyl}amino)methyl]-1-pyrrolidinecarboxylate (1.6 g, 4.39 mmole) in DCM (150 mL) at RT was added TFA (50 mL). After 2 h, the reaction solution was concentrated under vacuum and the residue placed under high vacuum for 3 hr. The residue was dissolved in DCM (200 mL) and MP-carbonate resin (17.6 mmole, 6.5 g) was added with vigorous stirring at RT. After 4 h, the reaction contents were filtered through a scintered-glass funnel washing with MeOH (100 mL). The filtrate was concentrated under vacuum to give the title compound (0.89 g, 100%) as a white foam: LC-MS (ES) m/e 265 (M+H)$^+$.

c) (±)-phenylmethyl {[(cis-3,4)-1-{2-[3-fluoro-6-(methyloxy)-1,5-naphthyridin-4-yl]ethyl}-4-(methyloxy)-3-pyrrolidinyl]methyl}carbamate

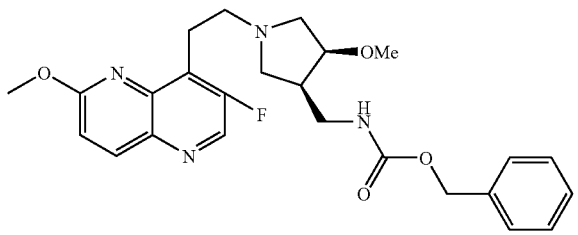

To a stirred solution of 8-ethenyl-7-fluoro-2-(methyloxy)-1,5-naphthyridine (0.89 g, 4.39 mmole) in EtOH (5 mL) was added (±)-phenylmethyl {[(cis-3,4)-4-(methyloxy)-3-pyrrolidinyl]methyl}carbamate (1.16 g, 4.39 mmole). After 24 h at 80° C. the reaction contents were purified on silica (CHCl$_3$/MeOH, 9:1 containing 5% NH$_4$OH) affording the title compound (1.62 g, 72%) as a light yellow foam: LC-MS (ES) m/e 469 (M+H)$^+$.

d) (±)-{[(cis-3,4)-1-{2-[3-fluoro-6-(methyloxy)-1,5-naphthyridin-4-yl]ethyl}-4-(methyloxy)-3-pyrrolidinyl]methyl}amine

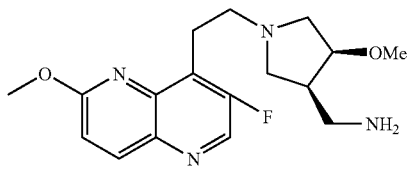

To a solution of (±)-phenylmethyl {[(cis-3,4)-1-{2-[3-fluoro-6-(methyloxy)-1,5-naphthyridin-4-yl]ethyl}-4-(methyloxy)-3-pyrrolidinyl]methyl}carbamate (1.78 g, 3.5 mmole) in MeOH (100 mL) in a round bottom flask was added Pd(OH)$_2$ (~100 mg). The reaction contents were stirred under a balloon of H$_2$ overnight at RT. The reaction contents were filtered through Celite® (MeOH) and concentrated to give the title compound (1.17 g, quant.) as a light yellow foam: LC-MS (ES) m/e 335 (M+H)$^+$.

e) (±)-6-[({[(cis-3,4)-1-{2-[3-fluoro-6-(methyloxy)-1,5-naphthyridin-4-yl]ethyl}-4-(methyloxy)-3-pyrrolidinyl]methyl}amino)methyl]-2H-pyrido[3,2-b][1,4]thiazin-3(4H)-one To a stirred solution of (±)-{[(cis-3,4)-1-{2-[3-fluoro-6-(methyloxy)-1,5-naphthyridin-4-yl]ethyl}-4-(methyloxy)-3-pyrrolidinyl]methyl}amine (0.70 g, 2.1 mmole) in dry CH$_2$Cl$_2$ (25 mL) and dry EtOH (10 mL) at RT was added 3-oxo-3,4-dihydro-2H-pyrido[1,4]thiazine-6-carboxaldehyde (0.41 g, 2.1 mmole). After 24 h, at RT was added NaBH(OAc)$_3$ (0.67 g, 3.15 mmole). After 2 h, the reaction solution was concentrated under vacuum and purified on silica (CHCl$_3$/MeOH, 9:1 containing 5% NH$_4$OH) to afford the title compound (0.70 g, 65%) as light yellow solid: $^1$H NMR (400 MHz, CD$_3$OD) □ 9.01 (s, 1H), 8.37 (d, J=9.0 Hz, 1H), 7.84 (d, J=7.8 Hz, 1H), 7.42 (d, J=9.0 Hz, 1H), 7.15 (d, J=7.8 Hz, 1H), 4.39 (s, 2H), 4.23 (s, 3H), 4.20 (m, 2H), 3.82 (m, 4H), 3.75 (m, 2H), 3.59 (s, 2H), 3.48 (m, 3H), 3.43 (s, 3H), 2.95 (m, 1H). LC-MS (ES) m/e 513 (M+H)$^+$.

This material, as a solution in MeOH, was treated with an excess of 4M HCl in diethyl ether and evaporated to dryness to provide the dihydrochloride salt of the title compound.

Example 65

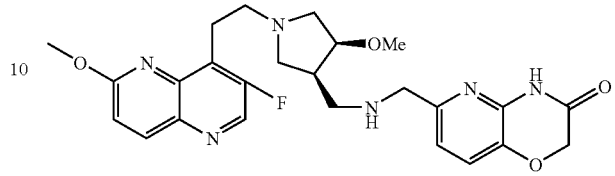

Preparation of (±)-6-[({[(cis-3,4)-1-{2-[3-fluoro-6-(methyloxy)-1,5-naphthyridin-4-yl]ethyl}-4-(methyloxy)-3-pyrrolidinyl]methyl}amino)methyl]-2H-pyrido[3,2-b][1,4]oxazin-3(4H)-one Prepared essentially according to the procedure of Example 64, except substituting 3-oxo-3,4-dihydro-2H-pyrido[1,4]oxazine-6-carboxaldehyde (0.37 g, 2.10 mmole) for 3-oxo-3,4-dihydro-2H-pyrido[1,4]thiazine-6-carboxaldehyde, the title compound (0.72 g, 69%) was prepared as an off-white solid following flash chromatography on silica gel (CHCl$_3$/MeOH, 9:1, containing 5% NH$_4$OH): $^1$H NMR (400 MHz, CD$_3$OD) δ 8.88 (s, 1H), 8.30 (d, J=9.0 Hz, 1H), 7.39 (d, J=7.8 Hz, 1H), 7.33 (d, J=9.0 Hz, 1H), 7.15 (d, J=7.8 Hz, 1H), 4.73 (s, 2H), 4.43 (s, 3H), 4.35 (m, 4H), 4.15 (m, 1H), 3.74 (m, 4H), 3.48 (m, 2H), 3.45 (s, 3H), 3.32 (s, 2H), 2.95 (m, 1H). LC-MS (ES) m/e 497 (M+H)$^+$.

This material, as a solution in MeOH, was treated with an excess of 4M HCl in diethyl ether and evaporated to dryness to provide the dihydrochloride salt of the title compound.

Example 66

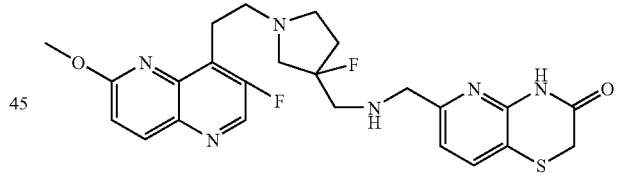

Preparation of (±)-6-({[(3-fluoro-1-{2-[3-fluoro-6-(methyloxy)-1,5-naphthyridin-4-yl]ethyl}-3-pyrrolidinyl)methyl]amino}methyl)-2H-pyrido[3,2-b][1,4]thiazin-3(4H)-one a) (±)-phenylmethyl 3-cyano-3-hydroxy-1-pyrrolidinecarboxylate To a stirred solution of phenylmethyl 3-oxo-1-pyrrolidinecarboxylate (1.0 g, 4.56 mmole) and KCN (0.81 g, 12.54 mmole) in THF (5 mL) and H$_2$O (15 mL) at 0° C. was added NaHSO$_3$ (1.14 g, 10.9 mmole) in H$_2$O (5.0 mL). After 3 h, the reaction contents were concentrated in vacuo, extracted with CHCl$_3$ (2×100 mL), and the organics dried over Na$_2$SO$_4$. Purification on silica (hexanes/EtOAc, 1:1) afforded the title compound (0.92 g, 82%) as a light yellow oil: LC-MS (ES) m/e 247 (M+H)$^+$.

b) (±)-phenylmethyl 3-cyano-3-fluoro-1-pyrrolidinecarboxylate

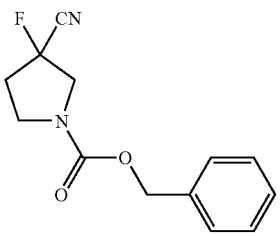

To a stirred solution of phenylmethyl 3-cyano-3-hydroxy-1-pyrrolidinecarboxylate (1.8 g, 7.31 mmole), in DCM (50 mL) at −78° C. was added DAST dropwise (0.98 mL, 8.04 mmole). After 2 h, Aqueous Na₂CO₃ was added to the reaction solution and the layers separated. The organic layer was dried over Na₂SO₄ and concentrated under vacuum. Purification on silica (hexanes/EtOAc, 1:1) provided the title compound (1.0 g, 55%) as a light orange oil: LC-MS (ES) m/e 249 (M+H)⁺.

c) (±)-phenylmethyl 3-[({[(1,1-dimethylethyl)oxy]carbonyl}amino)methyl]-3-fluoro-1-pyrrolidinecarboxylate

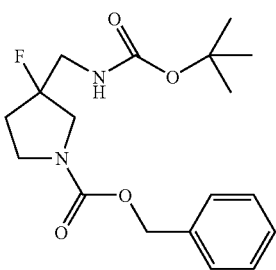

To a stirred solution of (±)-phenylmethyl 3-cyano-3-fluoro-1-pyrrolidinecarboxylate (1.0 g, 4.03 mmole), in THF (50 mL) at 0° C. was added B₂H₆ (12.1 mL, 1M in THF). After 24 h, the reaction was quenched with 6N HCl (5 mL) and stirred for 1 h at RT. The reaction solution was made basic (pH=8) with 6N NaOH and the solution was concentrated to a solid under vacuum. The reaction contents were extracted with EtOAc (100 mL) and THF (100 mL) and then concentrated under vacuum. The residue was dissolved in THF (75 mL) and (Boc)₂O (0.94 g, 4.28 mmole) in THF (15 mL) was added to the solution. After 12 hr at RT, the reaction solution was concentrated and purified on silica (hexanes/EtOAc, 1:1) to afford the title compound (1.0 g, 70%) as a colorless oil: LC-MS (ES) m/e 353 (M+H)⁺.

d) (±)-1,1-dimethylethyl[(3-fluoro-3-pyrrolidinyl)methyl]carbamate

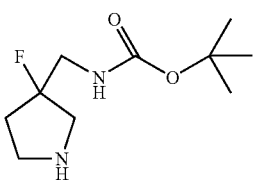

To a stirred solution of phenylmethyl 3-[({[(1,1-dimethylethyl)oxy]carbonyl}amino)methyl]-3-fluoro-1-pyrrolidinecarboxylate (0.90 g, 2.56 mmole) in MeOH (30 mL) at RT was added Pd(OH)₂ (100 mg). After 18 h under H₂ (1 atm) with stirring, the reaction contents were filtered through Celite (MeOH) and concentrated under reduced pressure to give the title compound (0.54 g, 98%) as an off-white solid: LC-MS (ES) m/e 219 (M+H)⁺.

e) (±)-1,1-dimethylethyl[(3-fluoro-1-{2-[3-fluoro-6-(methyloxy)-1,5-naphthyridin-4-yl]ethyl}-3-pyrrolidinyl)methyl]carbamate

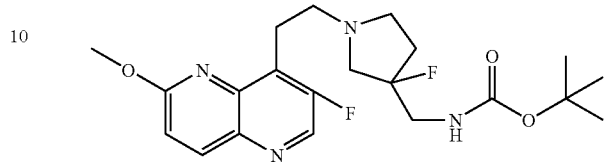

To a stirred solution of 8-ethenyl-7-fluoro-2-(methyloxy)-1,5-naphthyridine (0.51 g, 2.50 mmole) in EtOH (5 mL) was added 1,1-dimethylethyl[(3-fluoro-3-pyrrolidinyl)methyl]carbamate (0.53 g, 2.50 mmole). After 24 h at 80° C. the reaction contents were purified on silica (CHCl₃/MeOH, 9:1 containing 5% NH₄OH) to afford the title compound (0.90 g, 85%) as light yellow solid: LC-MS (ES) m/e 423 (M+H)⁺.

f) (±)-6-({[(3-fluoro-1-{2-[3-fluoro-6-(methyloxy)-1,5-naphthyridin-4-yl]ethyl}-3-pyrrolidinyl)methyl]amino}methyl)-2H-pyrido[3,2-b][1,4]thiazin-3(4H)-one To a stirred solution of 1,1-dimethylethyl[(3-fluoro-1-{2-[3-fluoro-6-(methyloxy)-1,5-naphthyridin-4-yl]ethyl}-3-pyrrolidinyl)methyl]carbamate (0.85 g, 2.0 mmole) in dioxane (50 mL) was added 4M HCl in dioxane (20 mL). After 4 h at RT, the reaction solution was concentrated to dryness under vacuum. To the amine hydrochloride salt in dry CH₂Cl₂ (25 mL) and dry EtOH (20 mL) at RT was added 3-oxo-3,4-dihydro-2H-pyrido[1,4]thiazine-6-carboxaldehyde (0.39 g, 2.0 mmole) and Et₃N (0.84 mL, 6.0 mmole). After 24 h at RT, NaBH₄ (0.01 g, 0.23 mmole) was added. After 2 h, silica gel (5 g) was added to the reaction solution and the suspension was concentrated under vacuum to a dry solid. Purification on silica (CHCl₃/MeOH, 9:1 containing 5% NH₄OH) afforded the title compound (0.67 g, 67%) as light yellow solid: ¹H NMR (400 MHz, CD₃OD) δ 8.67 (s, 1H), 8.19 (d, J=9.0 Hz, 1H), 7.77 (d, J=7.8 Hz, 1H), 7.15 (m, 2H), 4.31 (s, 2H), 4.13 (s, 3H), 3.75 (m, 2H), 3.64 (m, 2H), 3.60 (m, 4H), 3.57 (m, 4H), 2.54 (m, 2H). LC-MS (ES) m/e 501 (M+H)⁺.

The material was dissolved in dioxane (5 mL) and treated with 4M HCl in dioxane (10 mL) for 2 hours at RT. The solvent was removed under vacuum to give the title compound as a light yellow solid.

Example 67

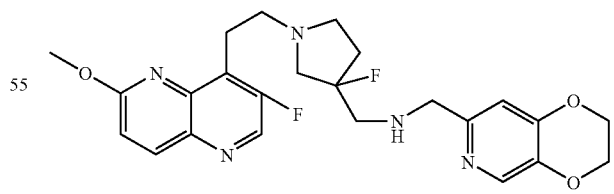

Preparation of (±)-(2,3-dihydro[1,4]dioxino[2,3-c]pyridin-7-ylmethyl)[(3-fluoro-1-{2-[3-fluoro-6-(methyloxy)-1,5-naphthyridin-4-yl]ethyl}-3-pyrrolidinyl)methyl]amine Prepared essentially according to the procedure of Example 66, except substituting 2,3-dihydro[1,4]dioxino[2, 3-c]pyridine-7-carbaldehyde (0.15 g, 0.93 mmole) for 3-oxo-3,4-dihydro-2H-pyrido[1,4]thiazine-6-carboxaldehyde, the title compound (0.26 g, 59%) was prepared as an off-white solid following flash chromatography on silica gel (CHCl$_3$/MeOH, 9:1, containing 5% NH$_4$OH): $^1$H NMR (400 MHz, CD$_3$OD) δ 8.74 (s, 1H), 8.35 (s, 1H), 8.25 (d, J=9.0 Hz, 1H), 7.39 (s, 1H), 7.23 (d, J=9.0 Hz, 1H), 4.65 (m, 2H), 4.49 (m, 2H), 4.43 (s, 2H), 4.19 (s, 3H), 3.75 (m, 8H), 2.65 (m, 2H). LC-MS (ES) m/e 472 (M+H)$^+$.

This material, as a solution in MeOH, was treated with an excess of 4M HCl in diethyl ether and evaporated to dryness to provide the dihydrochloride salt of the title compound.

Example 68

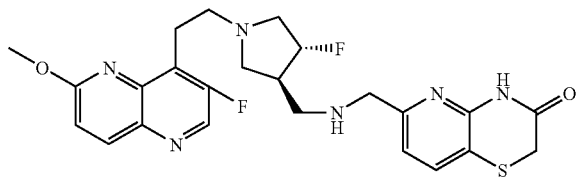

Preparation of (±)-6-({[(trans-4-fluoro-1-{2-[3-fluoro-6-(methyloxy)-1,5-naphthyridin-4-yl]ethyl}-3-pyrrolidinyl)methyl]amino}methyl)-2H-pyrido[3,2-b][1,4]thiazin-3(4H)-one a) (±)-1,1-dimethylethyl(3R,4S)-3-fluoro-4-[({[(phenylmethyl)oxy]carbonyl}amino)methyl]-1-pyrrolidinecarboxylate

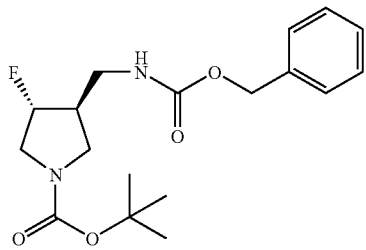

To a stirred solution of (±)-1,1-dimethylethyl cis-3-hydroxy-4-[({[(phenylmethyl)oxy]carbonyl}amino)methyl]-1-pyrrolidinecarboxylate (0.8 g, 2.29 mmole), in DCM (50 mL) at −78° C. was added DAST dropwise (0.59 mL, 4.80 mmole). After 2 h, Aqueous Na$_2$CO$_3$ was added to the reaction solution and the layers separated. The organic layer was dried over Na$_2$SO$_4$ and concentrated under vacuum. Purification on silica (hexanes/EtOAc, 1:1) provided the title compound (0.68 g, 85%) as a colorless oil: LC-MS (ES) m/e 353 (M+H)$^+$.

b) (±)-phenylmethyl {[cis-4-fluoro-3-pyrrolidinyl]methyl}carbamate

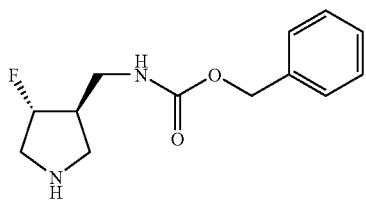

To a solution of (±)-1,1-dimethylethyl trans-3-fluoro-4-[({[(phenylmethyl)oxy]carbonyl}amino)methyl]-1-pyrrolidinecarboxylate (1.0 g, 2.84 mmole) in DCM (50 mL) at RT was added TFA (25 mL). After 2 h, the reaction solution was concentrated under vacuum and the residue placed under high vacuum for 3 hr. The residue was dissolved in DCM (200 mL) and MP-carbonate resin (11.4 mmole, 4.2 g) was added with vigorous stirring at RT. After 4 h, the reaction contents were filtered through a scintered-glass funnel washing with MeOH (100 mL). The filtrate was concentrated under vacuum to give the title compound (0.54 g, 75%) as a light orange oil: LC-MS (ES) m/e 253 (M+H)$^+$.

c) (±)-phenylmethyl[(trans-4-fluoro-1-{2-[3-fluoro-6-(methyloxy)-1,5-naphthyridin-4-yl]ethyl}-3-pyrrolidinyl)methyl]carbamate

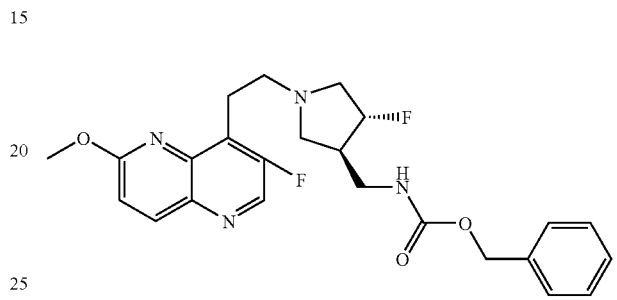

To a stirred solution of 8-ethenyl-7-fluoro-2-(methyloxy)-1,5-naphthyridine (0.44 g, 2.14 mmole) in EtOH (5 mL) was added (±)-phenylmethyl {[trans-4-fluoro-3-pyrrolidinyl]methyl}carbamate (0.54 g, 2.14 mmole). After 24 h at 80° C. the reaction contents were purified on silica (CHCl$_3$/MeOH, 9:1 containing 5% NH$_4$OH) affording the title compound (0.90 g, 92%) as a light yellow foam: LC-MS (ES) m/e 457 (M+H)$^+$.

d) (±)-[(trans-4-fluoro-1-{2-[3-fluoro-6-(methyloxy)-1,5-naphthyridin-4-yl]ethyl}-3-pyrrolidinyl)methyl]amine

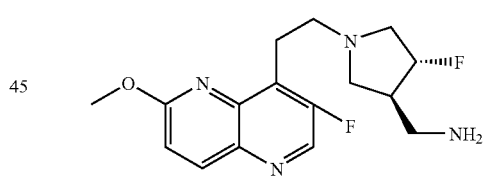

To a solution of (±)-phenylmethyl[(trans-1-{2-[3-fluoro-6-(methyloxy)-1,5-naphthyridin-4-yl]ethyl}-4-hydroxy-3-pyrrolidinyl)methyl]carbamate (0.40 g, 0.88 mmole) in MeOH (100 mL) in a round bottom flask was added Pd(OH)$_2$ (~100 mg). The reaction contents were stirred under a balloon of H$_2$ overnight at RT. The reaction contents were filtered through Celite® (MeOH) and concentrated to give the title compound (0.25 g, 88%) as a colorless oil: LC-MS (ES) m/e 323 (M+H)$^+$.

e) (±)-6-({[(trans-4-fluoro-1-{2-[3-fluoro-6-(methyloxy)-1,5-naphthyridin-4-yl]ethyl}-3-pyrrolidinyl)methyl]amino}methyl)-2H-pyrido[3,2-b][1,4]thiazin-3(4H)-one To a stirred solution of (±)-[(trans-4-fluoro-1-{2-[3-fluoro-6-(methyloxy)-1,5-naphthyridin-4-yl]ethyl}-3-pyrrolidinyl)methyl]amine (0.25 g, 0.77 mmole) in dry CH$_2$Cl$_2$ (25 mL) and dry EtOH (10 mL) at RT was added 3-oxo-3,4-dihydro-2H-pyrido[1,4]thiazine-6-carboxaldehyde (0.15 g, 0.77 mmole). After 24 h, at RT was added NaBH(OAc)$_3$ (0.24 g, 1.15 mmole). After 2 h, the reaction solution was concentrated under vacuum and purified on silica (CHCl$_3$/MeOH, 9:1 containing 5% NH$_4$OH) to afford the title compound (0.23 g, 60%) as light yellow solid: $^1$H NMR (400 MHz, CD$_3$OD) δ 8.75 (s, 1H), 8.25 (d, J=9.1 Hz, 1H), 7.83 (d, J=7.8 Hz, 1H), 7.25 (d, J=9.1 Hz, 1H), 7.15 (d, J=7.8 Hz, 1H), 4.43 (s, 2H), 4.19 (s, 3H), 3.90 (m, 2H), 3.77 (m, 4H), 3.65 (m, 4H), 3.57 (m, 2H), 3.32 (app s, 2H). LC-MS (ES) m/e 501 (M+H)$^+$.

This material, as a solution in MeOH, was treated with an excess of 4M HCl in diethyl ether and evaporated to dryness to provide the dihydrochloride salt of the title compound.

Example 69

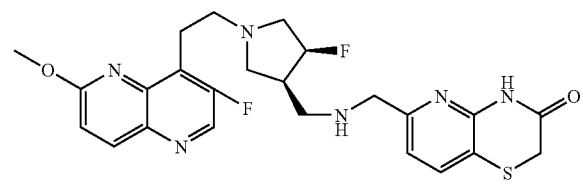

Preparation of (±)-6-({[(cis-4-fluoro-1-{2-[3-fluoro-6-(methyloxy)-1,5-naphthyridin-4-yl]ethyl}-3-pyrrolidinyl)methyl]amino}methyl)-2H-pyrido[3,2-b][1,4]thiazin-3(4H)-one a) (±)-1,1-dimethylethyl cis-3-cyano-4-fluoro-1-pyrrolidinecarboxylate

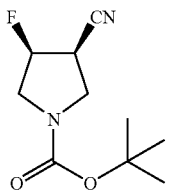

To a stirred solution of (±)-1,1-dimethylethyl trans-3-cyano-4-[(trimethylsilyl)oxy]-1-pyrrolidinecarboxylate (1.0 g, 3.52 mmole), in DCM (50 mL) at −78° C. was added DAST dropwise (0.90 mL, 7.40 mmole). After 3 h, Aqueous Na$_2$CO$_3$ was added to the reaction solution and the layers separated. The organic layer was dried over Na$_2$SO$_4$ and concentrated under vacuum. Purification on silica (hexanes/EtOAc, 1:1) provided the title compound (0.51 g, 67%) as a colorless oil: LC-MS (ES) m/e 215 (M+H)$^+$.

b) (±)-1,1-dimethylethyl cis-3-fluoro-4-[({[(phenylmethyl)oxy]carbonyl}amino)methyl]-1-pyrrolidinecarboxylate

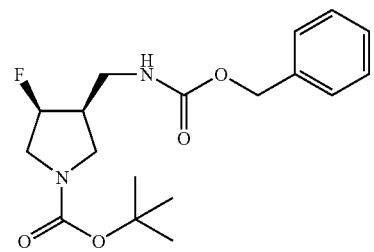

To a stirred solution of (±)-1,1-dimethylethyl cis-3-cyano-4-fluoro-1-pyrrolidinecarboxylate (0.51 g, 2.38 mmole), in THF (50 mL) at RT was added LiAlH$_4$ (2.4 mL, 1M in THF). After 24 h, the reaction was quenched with H$_2$O (0.096 mL), 20% NaOH (0.072 mL) and then H$_2$O (0.34 mL). The reaction contents were filtered through a scinter-glass funnel and concentrated under vacuum to afford the title compound as a yellow oil which was used directly: LC-MS (ES) m/e 219 (M+H)$^+$.

To the crude amine in DMF (50 mL) at RT was added Et$_3$N (0.42 mL, 3.0 mmole) and N-(benzyloxycarbonyloxy)succinimide (0.75 g, 3.0 mmole). After 18 h, the DMF was removed under vacuum and the residue purified on silica (25-50% DCM/EtOAc) to give the title compound (0.47 g, 56%) as a colorless oil: LC-MS (ES) m/e 353 (M+H)$^+$.

b) (±)-phenylmethyl {[cis-4-fluoro-3-pyrrolidinyl]methyl}carbamate

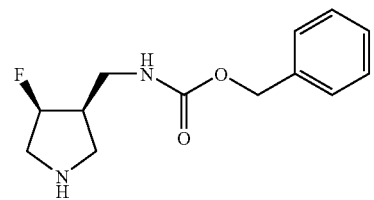

To a solution of (±)-1,1-dimethylethyl cis-3-fluoro-4-[({[(phenylmethyl)oxy]carbonyl}amino)methyl]-1-pyrrolidinecarboxylate (0.45 g, 1.28 mmole) in DCM (50 mL) at RT was added TFA (25 mL). After 2 h, the reaction solution was concentrated under vacuum and the residue placed under high vacuum for 3 hr. The residue was dissolved in DCM (200 mL) and MP-carbonate resin (5.12 mmole, 1.9 g) was added with vigorous stirring at RT. After 4 h, the reaction contents were filtered through a scintered-glass funnel washing with MeOH (100 mL). The filtrate was concentrated under vacuum to give the title compound (0.32 g, 99%) as a light orange oil: LC-MS (ES) m/e 253 (M+H)$^+$.

c) (±)-phenylmethyl[(cis-4-fluoro-1-{2-[3-fluoro-6-(methyloxy)-1,5-naphthyridin-4-yl]ethyl}-3-pyrrolidinyl)methyl]carbamate

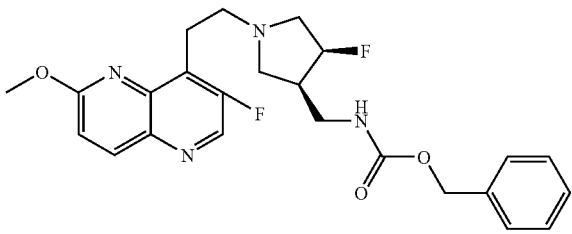

To a stirred solution of 8-ethenyl-7-fluoro-2-(methyloxy)-1,5-naphthyridine (0.26 g, 1.28 mmole) in EtOH (5 mL) was added (±)-phenylmethyl {[cis-4-fluoro-3-pyrrolidinyl]methyl}carbamate (0.32 g, 1.28 mmole). After 24 h at 80° C. the reaction contents were purified on silica (CHCl₃/MeOH, 9:1 containing 5% NH₄OH) affording the title compound (0.20 g, 34%) as a light yellow foam: LC-MS (ES) m/e 457 (M+H)⁺.

d) (±)-[(cis-4-fluoro-1-{2-[3-fluoro-6-(methyloxy)-1,5-naphthyridin-4-yl]ethyl}-3-pyrrolidinyl)methyl]amine

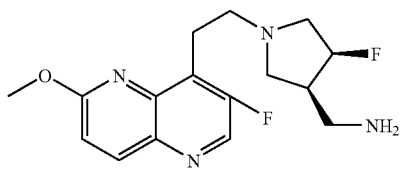

To a solution of (±)-phenylmethyl[(cis-1-{2-[3-fluoro-6-(methyloxy)-1,5-naphthyridin-4-yl]ethyl}-4-hydroxy-3-pyrrolidinyl)methyl]carbamate (0.20 g, 0.44 mmole) in MeOH (100 mL) in a round bottom flask was added Pd(OH)₂ (~100 mg). The reaction contents were stirred under a balloon of H₂ overnight at RT. The reaction contents were filtered through Celite® (MeOH) and concentrated to give the title compound (0.15 g, 99%) as a colorless oil: LC-MS (ES) m/e 323 (M+H)⁺.

e) (±)-6-({[(cis-4-fluoro-1-{2-[3-fluoro-6-(methyloxy)-1,5-naphthyridin-4-yl]ethyl}-3-pyrrolidinyl)methyl]amino}methyl)-2H-pyrido[3,2-b][1,4]thiazin-3(4H)-one To a stirred solution of (±)-[(cis-4-fluoro-1-{2-[3-fluoro-6-(methyloxy)-1,5-naphthyridin-4-yl]ethyl}-3-pyrrolidinyl)methyl]amine (0.15 g, 0.46 mmole) in dry CH₂Cl₂ (25 mL) and dry EtOH (10 mL) at RT was added 3-oxo-3,4-dihydro-2H-pyrido[1,4]thiazine-6-carboxaldehyde (0.077 g, 0.46 mmole). After 24 h, at RT was added NaBH(OAc)₃ (0.15 g, 0.69 mmole). After 2 h, the reaction solution was concentrated under vacuum and purified on silica (CHCl₃/MeOH, 9:1 containing 5% NH₄OH) to afford the title compound (0.10 g, 46%) as light yellow solid: ¹H NMR (400 MHz, CDCl₃) δ 8.67 (s, 1H), 8.21 (d, J=9.1 Hz, 1H), 7.60 (d, J=7.8 Hz, 1H), 7.10 (m, 2H), 4.13 (s, 2H), 4.10 (s, 3H), 3.62 (m, 2H), 3.49-3.43 (m, 6H), 3.21 (m, 2H), 2.99 (m, 2H), 2.32 (app s, 2H). LC-MS (ES) m/e 501 (M+H)⁺.

This material, as a solution in MeOH, was treated with an excess of 4M HCl in diethyl ether and evaporated to dryness to provide the dihydrochloride salt of the title compound.

Example 70 D1

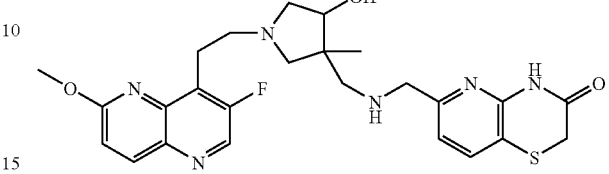

Preparation of (±)-6-({[(1-{2-[3-fluoro-6-(methyloxy)-1,5-naphthyridin-4-yl]ethyl}-4-hydroxy-3-methyl-3-pyrrolidinyl)methyl]amino}methyl)-2H-pyrido[3,2-b][1,4]thiazin-3(4H)-one-D1 a) 1,1-dimethylethyl 3-cyano-3-methyl-4-oxo-1-pyrrolidinecarboxylate

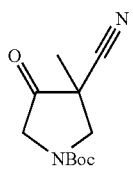

To a solution of 1,1-dimethylethyl 3-cyano-4-oxo-1-pyrrolidinecarboxylate (3.9 g, 18.6 mmol) in acetone (185 mL) were added K₂CO₃ (3.07 g, 22.3 mmol) and MeI (1.39 mL, 22.3 mmol). After 12 h at reflux, the solution was cooled and the solid precipitate filtered. The filtrate was then concentrated and the residue purified by column chromatography (silica, 0.5% MeOH in DCM (1% NH₄OH)) affording the title compound (2.3 g, 55%) as a yellow oil: LCMS (ES) m/e 225 (M+H)⁺.

b) 1,1-dimethylethyl 3-cyano-4-hydroxy-1-pyrrolidinecarboxylate

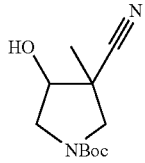

To a solution of 1,1-dimethylethyl 3-cyano-3-methyl-4-oxo-1-pyrrolidinecarboxylate (2.3 g, 10.2 mmol) in EtOH (100 mL) at 0° C. was added NaBH₄ (775 mg, 20.5 mmol) portion-wise. After 30 min., the solution was concentrated and the residue partitioned between H₂O-DCM. The aqueous phase was washed several times with DCM and the combined organic fractions were dried (Na₂SO₄), concentrated and purified by column chromatography (silica, 1% MeOH in DCM (1% NH₄OH)) affording the title compound as a yellow oil: LCMS (ES) m/e 227 (M+H)⁺.

c) 1,1-dimethylethyl 4-hydroxy-3-methyl-3-[({[(phenylmethyl)oxy]carbonyl}amino)methyl]-1-pyrrolidinecarboxylate

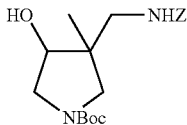

To a solution of the nitrile (1.6 g, 7.08 mmol) in THF (70 mL) at 0° C. was added dropwise a solution of LAH in THF (14 mL, 14.16 mmol, 1M in THF). After 1 h, the solution was quenched by dropwise addition of a saturated solution of potassium sodium tartrate. The aqueous phase was back-extracted several times with DCM and the combined organic fractions were dried ($Na_2SO_4$), concentrated and the resulting crude residue was used directly: LCMS (ES) m/e 231 (M+H)$^+$.

To the crude amine in DCM (70 mL) at 0° C. was added portion-wise N-(benzyloxycarbonyloxy)succinimide (1.94 g, 7.23 mmol). After 1 h, the solution was partitioned between DCM-$H_2O$. The aqueous phase was washed several times with DCM and the combined organic fractions were dried ($Na_2SO_4$), concentrated and the resulting diastereomers were separated by column chromatography (silica, 1% MeOH in DCM (1% $NH_4OH$)) yielding the higher eluting D1 diastereomer (660 mg, 26%) and the D2 diastereomer (610 mg, 24%) as yellow oils: LCMS (ES) m/e 365 (M+H)$^+$.

d) (±)-phenylmethyl[(4-hydroxy-3-methyl-3-pyrrolidinyl)methyl]carbamate (D1 diastereomer)

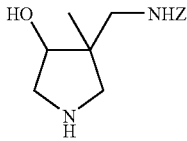

To a solution of the Boc-amine (660 mg, 1.81 mmol, D1 diastereomer) in MeOH (18 mL) at 25° C. was added dropwise a solution of HCl in dioxane (3.2 mL, 12.7 mmol, 4M in dioxane). After 12 h, the solution was concentrated and then neutralized by addition of excess DIPEA to the salt in DCM. The residue was then purified through a pad of silica (90:10:1 MeOH, DCM and $NH_4OH$) yielding the title compound (360 mg, 75%) as a yellow oil: LCMS (ES) m/e 265 (M+H)$^+$.

e) (±)-phenylmethyl[(1-{2-[3-fluoro-6-(methyloxy)-1,5-naphthyridin-4-yl]ethyl}-4-hydroxy-3-methyl-3-pyrrolidinyl)methyl]carbamate (D1 diastereomer)

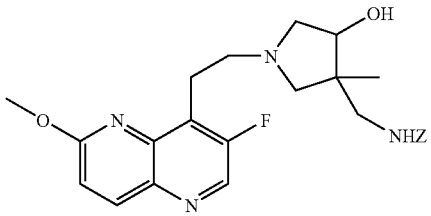

A solution of the pyrrolidine (360 mg, 1.36 mmol, D1 diastereomer) and 8-ethenyl-7-fluoro-2-(methyloxy)-1,5-naphthyridine (278 mg, 1.36 mmol) in EtOH (1 mL) was heated to 85° C. After 12 h, the solution was concentrated and the residue purified by column chromatography (silica, 2% MeOH in DCM (1% $NH_4OH$)) yielding the title compound as an orange oil: LCMS (ES) m/e 469 (M+H)$^+$.

f) (±)-4-(aminomethyl)-1-{2-[3-fluoro-6-(methyloxy)-1,5-naphthyridin-4-yl]ethyl}-4-methyl-3-pyrrolidinol (D1 diastereomer)

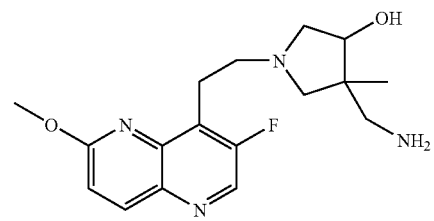

A solution of the Z-carbamate (340 mg, 468 mmol) and Pd(OH)$_2$ (170 mg, 50 wt %) in EtOH (7 mL) was hydrogenated at 50 psi using a Parr-Shaker. After 2 h, the solution was filtered through Celite®, concentrated and used directly in the reductive amination: LCMS (ES) m/e 335 (M+H)$^+$.

h) (±)-6-({[(1-{2-[3-fluoro-6-(methyloxy)-1,5-naphthyridin-4-yl]ethyl}-4-hydroxy-3-methyl-3-pyrrolidinyl)methyl]amino}methyl)-2H-pyrido[3,2-b][1,4]thiazin-3(4H)-one-(D1 diastereomer)

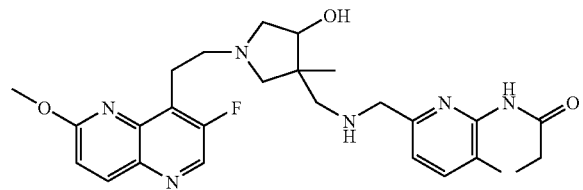

A solution of the amine (80 mg, 0.240 mmol), 3-oxo-3,4-dihydro-2H-pyrido[3,2-b][1,4]thiazine-6-carbaldehyde (47 mg, 0.240 mmol) and $Na_2SO_4$ (51 mg, 0.359 mmol) in DCM-EtOH (2 mL, 1:1) was stirred at 25° C. After 2 h, NaBH(OAc)$_3$ (76 mg, 0.359 mmol) was added and the reaction stirred an additional 1 h, was concentrated and purified via column chromatography (silica, 2% MeOH in DCM (1% $NH_4OH$)) yielding the title compound (38 mg, 31%) as a yellow foam: LCMS (ES) m/e 513 (M+H)+; $^1$H NMR (400 MHz, $CD_3OD$) δ 8.74 (s, 1H), 8.30 (d, J=9.1 Hz, 1H), 7.78 (d, J=7.8 Hz, 1H), 7.28 (d, J=9.1 Hz, 1H), 7.08 (d, J=7.8 Hz, 1H), 4.24 (s, 3H), 4.07-4.09 (m, 1H), 3.85 (s, 2H), 3.66 (s, 2H), 3.55-3.61 (m, 2H), 3.31-3.35 (m, 1H), 2.87-2.91 (m, 3H), 2.82-2.86 (m, 2H), 2.71-2.79 (d, J=11.6 Hz, 1H), 2.59-2.65 (d, J=9.5 Hz, 1H), 1.49 (s, 3H).

This material, as a solution in MeOH, was treated with an excess of 4M HCl in dioxane and evaporated to dryness to provide the dihydrochloride salt of the title compound.

Example 70 D2

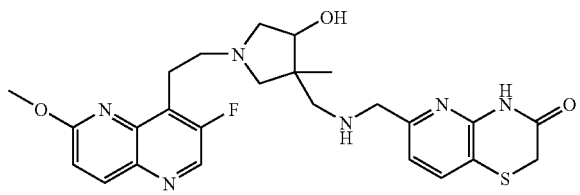

Preparation of (±)-6-({[(1-{2-[3-fluoro-6-(methyloxy)-1,5-naphthyridin-4-yl]ethyl}-4-hydroxy-3-methyl-3-pyrrolidinyl)methyl]amino}methyl)-2H-pyrido[3,2-b][1,4]thiazin-3(4H)-one (D2-diastereomer)

The title compound (142 mg, 74%) was prepared as a yellow foam prepared essentially according to Example 70 D1, except substituting the D2 diastereomer of 1,1-dimethylethyl 4-hydroxy-3-methyl-3-[({[(phenylmethyl)oxy]carbonyl}amino)methyl]-1-pyrrolidinecarboxylate (610 mg, 1.68 mmol) for the D1 diastereomer: LCMS (ES) m/e 513 (M+H); H NMR (400 MHz, CD OD) δ 8.77 (s, 1H), 8.36 (d, J=9.1 Hz, 1H), 7.83 (d, J=7.8 Hz, 1H), 7.32 (d, J=9.3 Hz, 1H), 7.14 (d, J=7.8 Hz, 1H), 4.22 (s, 3H), 2.93-2.95 (m, 1H), 3.62 (s, 2H), 3.52 (s, 2H), 3.49-3.50 (m, 2H), 3.34-3.40 (m, 1H), 2.85-3.01 (m, 3H), 2.49-2.55 (m, 4H), 1.02 (s, 3H).

This material, as a solution in MeOH, was treated with an excess of 4M HCl in dioxane and evaporated to dryness to provide the dihydrochloride salt of the title compound.

Example 71 D1/D2

Preparation of (±)-6-({[(1-{2-[3-fluoro-6-(methyloxy)-1,5-naphthyridin-4-yl]ethyl}-4-hydroxy-4-methyl-3-pyrrolidinyl)methyl]amino}methyl)-2H-pyrido[3,2-b][1,4]thiazin-3(4H)-one (D1 Diastereomer)

a) 1,1-dimethylethyl 3-hydroxy-4-[({[(phenylmethyl)oxy]carbonyl}amino)methyl]-1-pyrrolidinecarboxylate

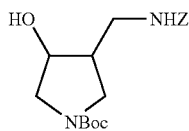

To a solution of 1,1-dimethylethyl 3-(aminomethyl)-4-hydroxy-1-pyrrolidinecarboxylate (3 g, 13.9 mmol) [Prepared according to Hong, C.-Y. *J. Med. Chem.* 1997, 40, 3584.] in DCM (100 mL) at 0° C. was added N-(benzyloxycarbonyloxy)succinimide (3.8 g, 15.3 mmol) portion-wise. After 1 h, the reaction was partitioned between H O-DCM. The aqueous phase was extracted several times with DCM and the combined organic fractions were dried (Na SO), concentrated and purified by column chromatography (silica, 3% MeOH in DCM (1% NH OH)) yielding the title compound (4.8 g, quant.) as a clear oil: LCMS (ES) m/e 351 (M+H).

b) 1,1-dimethylethyl 3-oxo-4-[({[(phenylmethyl)oxy]carbonyl}amino)methyl]-1-pyrrolidinecarboxylate

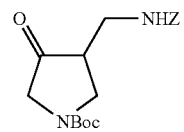

A solution of the alcohol (1 g, 2.88 mmol) in DMSO (4 mL) and Et N (1.2 mL) was cooled briefly in an ice-bath. SO-pyr. (819 mg, 5.14 mmol) was added portion-wise and the solution warmed to 25° C. After 2 h, the reaction was partitioned between H O-EtOAc and the aqueous phase was back-extracted several times with EtOAc. The combined organic fractions were dried (Na SO), concentrated and purified via column chromatography (silica, 0.5-1% MeOH in DCM (1% NH OH)) yielding the title compound (2.38 g, 63%) as a yellow oil: LCMS (ES) m/e 349 (M+H).

c) 1,1-dimethylethyl 3-hydroxy-3-methyl-4-[({[(phenylmethyl)oxy]carbonyl}amino)methyl]-1-pyrrolidinecarboxylate

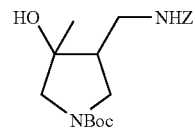

To a solution of the pyrrolidinone (1 g, 2.87 mmol) in toluene-THF (3:1, 14 mL) at 0° C. was added dropwise a solution of MeMgBr (8.2 mL, 1.4 M in toluene-THF) in toluene-THF (14 mL). The solution warmed to 25° C. over 12 h and was partitioned between brine-DCM. The aqueous phase was back-extracted several times with DCM and the combined organic fractions were dried (Na SO), concentrated and purified by column chromatography (silica, 2% MeOH in DCM (1% NH OH)) yielding the title compound (450 mg, 43%) as an inseparable mixture of diastereomers (3.5:1): LCMS (ES) m/e 365 (M+H).

d) (±)-6-({[(1-{2-[3-fluoro-6-(methyloxy)-1,5-naphthyridin-4-yl]ethyl}-4-hydroxy-4-methyl-3-pyrrolidinyl)methyl]amino}methyl)-2H-pyrido[3,2-b][1,4]thiazin-3(4H)-one: (D1 and D2 Diastereomers)

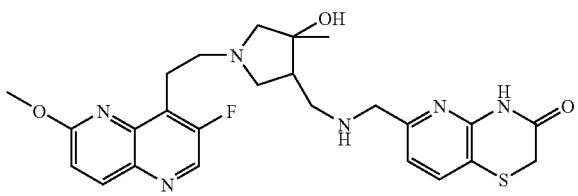

The title compounds D1 (higher eluting diastereomer, 69 mg, 17%) and D2 (247 mg, 60%) were prepared as yellow foams according to Example 1, except substituting 1,1-dimethylethyl 3-hydroxy-3-methyl-4-[({[(phenylmethyl)oxy]carbonyl}amino)methyl]-1-pyrrolidinecarboxylate (450 mg, 1.24 mmol, diastereomeric mixture) for 1,1-dimethylethyl 4-hydroxy-3-methyl-3-[({[(phenylmethyl)oxy]carbonyl}amino)methyl]-1-pyrrolidinecarboxylate (D1 diastereomer).

(D1): D1 LCMS (ES) m/e 513 (M+H); H NMR (400 MHz, CD OD) δ 8.61 (s, 1H), 8.17 (d, J=9.0 Hz, 1H), 7.66 (d, J=7.8 Hz, 1H), 7.15 (d, J=9.0 Hz, 1H), 6.99 (d, J=7.8 Hz, 1H), 4.11 (s, 3H), 3.76 (s, 2H), 3.50 (s, 2H), 3.39-3.43 (m, 2H), 3.04-3.08 (m, 1H), 2.82-2.92 (m, 4H), 2.71-2.73 (m, 1H), 2.58-2.67 (m, 2H), 2.13-2.15 (m, 1H), 1.36 (s, 3H).

(D2): D2 LCMS (ES) m/e 513 (M+H); H NMR (400 MHz, CD OD) δ 8.66 (s, 1H), 8.22 (d, J=9.0 Hz, 1H), 7.69 (d, J=7.7 Hz, 1H), 7.20 (d, J=9.0 Hz, 1H), 7.02 (d, J=7.7 Hz, 1H), 4.13 (s, 3H), 3.80 (s, 2H), 3.52 (s, 2H), 3.44-3.47 (m, 2H), 3.27-3.29 (m, 1H), 3.01 (d, J=9.8 Hz, 1H), 2.79-2.93 (m, 3H), 2.63 (d, J=10.1 Hz, 1H), 2.47-2.52 (m, 2H), 2.29-2.39 (m, 1H), 1.22 (s, 3H).

This material, as a solution in MeOH, was treated with an excess of 4M HCl in dioxane and evaporated to dryness to provide the dihydrochloride salt of the title compounds.

Example 72

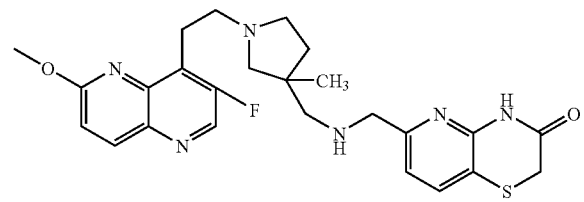

Preparation of (±)-6-({[(1-{2-[3-fluoro-6-(methyloxy)-1,5-naphthyridin-4-yl]ethyl}-3-methyl-3-pyrrolidinyl)methyl]amino}methyl)-2H-pyrido[3,2-b][1,4]thiazin-3(4H)-one (a) (±)-1,1-Dimethylethyl {[3-methyl-1-(phenylmethyl)-3-pyrrolidinyl]methyl}carbamate

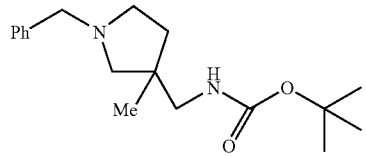

To a solution of (±)-{[3-methyl-1-(phenylmethyl)-3-pyrrolidinyl]methyl}amine (1.35 g, 6.6 mmol) in DCM (10 mL) was added Bis(1,1-dimethylethyl)dicarbonate (1.73 g, 7.9 mmol) and triethylamine (2.3 mL). After stirring at 25° C. for 18 h, the solution was partitioned between DCM and H O. The aqueous layer was extracted several times with DCM. The organic fractions were combined, dried over MgSO, concentrated and purified by column chromatography (silica, 30-50% ethyl acetate in hexane) to afford the title compound as a brown oil (2.0 g, quantitive): LC/MS m/z 305 (M+H)+.

(b) (±)-1,1-Dimethylethyl[(3-methyl-3-pyrrolidinyl)methyl]carbamate

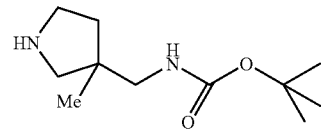

To a solution of (±)-1,1-dimethylethyl {[3-methyl-1-(phenylmethyl)-3-pyrrolidinyl]methyl}carbamate (2.0 g, 6.6 mmol) in MeOH (50 mL) was added Pd/C (1.3 g, 10 wet %). The suspension was hydrogenated at 50 psi of H using a Parr shaker. After 18 h, the mixture was filtered and washed several times with MeOH. The filtrate was concentrated to afford the title compound (1.3 g, 92%) as an off-white foam which was used without further purification; LC/MS (ES) m/e 293 (M+H).

(c) (±)-1,1-dimethylethyl[(1-{2-[3-fluoro-6-(methyloxy)-1,5-naphthyridin-4-yl]ethyl}-3-methyl-3-pyrrolidinyl)methyl]carbamate

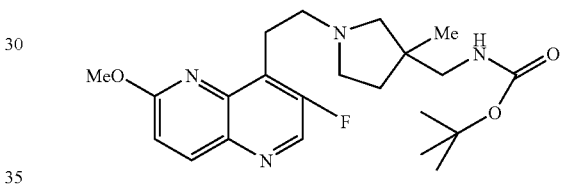

(±)-1,1-Dimethylethyl[(3-methyl-3-pyrrolidinyl)methyl]carbamate (500 mg, 2.34 mmol) and 8-ethenyl-7-fluoro-2-(methyloxy)-1,5-naphthyridine (500 mg, 2.34 mmol) were mixed in EtOH (1 mL) and heated at 90° C. over 24 h. The solution was then concentrated and the residue was purified via column chromatography (silica, 0-10% MeOH in DCM) yielding the title compound (520 mg, 53%) as an off-white foam; LC/MS (ES) m/e 419 (M+H).

(d) (±)-[(1-{2-[3-fluoro-6-(methyloxy)-1,5-naphthyridin-4-yl]ethyl}-3-methyl-3-pyrrolidinyl)methyl]amine

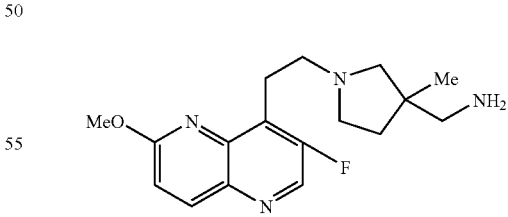

To a solution of (±)-1,1-dimethylethyl[(1-{2-[3-fluoro-6-(methyloxy)-1,5-naphthyridin-4-yl]ethyl}-3-methyl-3-pyrrolidinyl)methyl]carbamate (520 mg, 1.25 mmol) in DCM (15 mL) at 25° C. was added dropwise an HCl solution (1.2 mL, 4.8 mmol, 4M HCl in dioxane). After 24 h, the solution was concentrated to afford the HCl salt of the title compound (485 mg, quantit.) as a yellow foam which was used without further purification: LC/MS (ES) m/e 319 (M+H).

(e) (±)-6-({[(1-{2-[3-Fluoro-6-(methyloxy)-1,5-naphthyridin-4-yl]ethyl}-3-methyl-3-pyrrolidinyl)methyl]amino}methyl)-2H-pyrido[3,2-b][1,4]thiazin-3(4H)-one

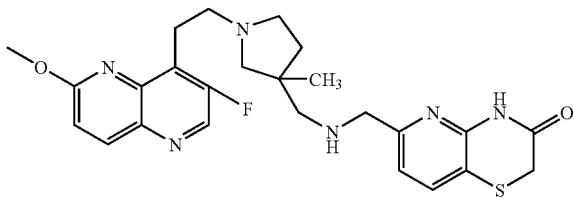

To a solution of the HCl salt of (±)-[(1-{2-[3-fluoro-6-(methyloxy)-1,5-naphthyridin-4-yl]ethyl}-3-methyl-3-pyrrolidinyl)methyl]amine (100 mg, 0.257 mmol) in MeOH (3 mL) were added NaHCO (215 mg, 2.57 mmol) followed by 3-oxo-3,4-dihydro-2H-pyrido[3,2-b][1,4]thiazine-6-carbaldehyde (51 mg, 0.317 mmol). After 24 h at 25° C., NaBH (15 mg, 0.398 mmol) was added. After 1 h, the reaction was concentrated and the residue was partitioned between DCM-H O. The aqueous phase was extracted several times with DCM and the combined organic fractions were dried over MgSO, concentrated and purified via column chromatography (silica, 4% MeOH in DCM (1% NH OH)) yielding the title compound (30 mg, 24%) as a brown oil: LC/MS (ES) m/e 497 (M+H)+; 1H NMR (CDCl3, 400 MHz) δ 8.8 (bs, 1H), 8.65 (s, 1H), 8.22 (d, J=9.0 Hz, 1H), 7.58 (d, J=7.8 Hz, 1H), 7.19 (d, J=9.0 Hz, 1H), 6.95 (d, J=7.8 Hz, 1H), 4.12 (s, 3H), 3.83 (s, 2H), 3.51 (s, 2H), 3.46-3.50 (m, 2H), 2.9 (m, 4H), 2.5 (m, 3H), 2.3 (m, 1H), 1.85 (m, 1H), 1.55 (m, 1H), 1.1 (s, 3H).

This material, as a solution in MeOH, was treated with an excess of 4M HCl in dioxane and evaporated to dryness to provide the dihydrochloride salt of the title compound.

Example 73

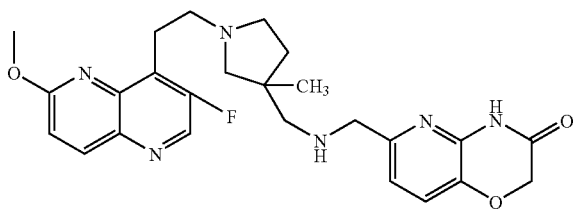

Preparation of (±)-6-({[(1-{2-[3-fluoro-6-(methyloxy)-1,5-naphthyridin-4-yl]ethyl}-3-methyl-3-pyrrolidinyl)methyl]amino}methyl)-2H-pyrido[3,2-b][1,4]oxazin-3(4H)-one Prepared essentially according to the procedure for Example 73, except substituting 3-oxo-3,4-dihydro-2H-pyrido[3,2-b][1,4]oxazine-6-carbaldehyde (47 mg, 0.26 mmol) for 3-oxo-3,4-dihydro-2H-pyrido[3,2-b][1,4]thiazine-6-carboxaldehyde. The title compound (20 mg, 16%) was obtained as an off-white solid: LC/MS (ES) m/e 481 (M+H)+; 1H NMR (CDCl3, 400 MHz) 8.65 (s, 1H), 8.22 (d, J=9.0 Hz, 1H), 7.2 (d, J=7.8 Hz, 1H), 7.10 (d, J=9.0 Hz, 1H), 6.90 (d, J=7.8 Hz, 1H), 4.6 (s, 2H), 4.05 (s, 3H), 3.8 (s, 2H), 3.50 (s, 2H), 3.3 (m, 2H), 2.8 (m, 4H), 2.5 (m, 3H), 2.3 (m, 1H), 1.85 (m, 1H), 1.55 (m, 1H), 1.1 (s, 3H).

This material, as a solution in MeOH, was treated with an excess of 4M HCl in dioxane and evaporated to dryness to provide the dihydrochloride salt of the title compound.

Example 74

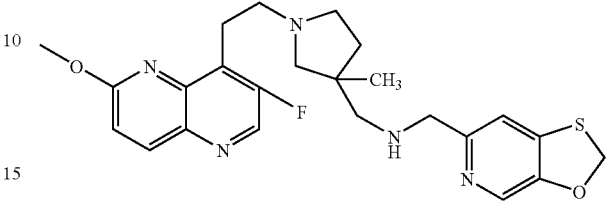

Preparation of (±)-[(1-{2-[3-fluoro-6-(methyloxy)-1,5-naphthyridin-4-yl]ethyl}-3-methyl-3-pyrrolidinyl)methyl]([1,3]oxathiolo[5,4-c]pyridin-6-ylmethyl)amine Prepared essentially according to the procedure for Example 73, except substituting [1,3]oxathiolo[5,4-c]pyridine-6-carbaldehyde (44 mg, 0.26 mmol) for 3-oxo-3,4-dihydro-2H-pyrido[3,2-b][1,4]thiazine-6-carboxaldehyde.
The title compound (39 mg, 32%) was obtained: LC/MS (ES) m/e 470 (M+H)+; 1H NMR (CDCl3, 400 MHz) 8.65 (s, 1H), 8.22 (d, J=9.0 Hz, 1H), 7.9 (s, 1H), 7.15 (s, 1H), 7.10 (d, J=9.0 Hz, 1H), 5.7 (s, 2H), 4.05 (s, 3H), 3.8 (s, 2H), 3.50 (m, 2H), 2.8 (m, 4H), 2.5 (m, 3H), 2.3 (m, 1H), 1.85 (m, 1H), 1.55 (m, 1H), 1.1 (s, 3H).

This material, as a solution in MeOH, was treated with an excess of 4M HCl in dioxane and evaporated to dryness to provide the dihydrochloride salt of the title compound.

Example 75

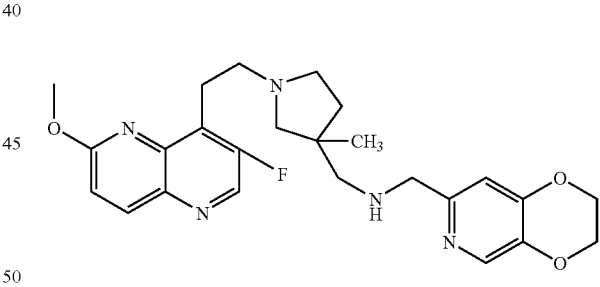

Preparation of (±)-(2,3-dihydro[1,4]dioxino[2,3-c]pyridin-7-ylmethyl)[1{-2-[3-fluoro-6-(methyloxy)-1,5-naphthyridin-4-yl]ethyl}-3-methyl-3-pyrrolidinyl)methyl]amine Prepared essentially according to the procedure for Example 72, except 2,3-dihydro[1,4]dioxino[2,3-c]pyridine-7-carbaldehyde (42 mg, 0.26 mmol) for 3-oxo-3,4-dihydro-2H-pyrido[3,2-b][1,4]thiazine-6-carboxaldehyde. The title compound (27 mg, 22%) was obtained: LC/MS (ES) m/e 468 (M+H)+; 1H NMR (CDCl3, 400 MHz) δ 8.65 (s, 1H), 8.22 (d, J=9.0 Hz, 1H), 8.05 (s, 1H), 7.10 (d, J=9.0 Hz, 1H), 6.8 (s, 1H), 5.7 (s, 2H), 4.32 (m, 2H), 4.30 (m, 2H), 4.05 (s, 3H), 3.8 (d, 2H), 3.50 (m, 2H), 2.8 (m, 4H), 2.5 (m, 3H), 2.3 (m, 1H), 1.85 (m, 1H), 1.55 (m, 1H), 1.1 (s, 3H).

This material, as a solution in MeOH, was treated with an excess of 4M HCl in dioxane and evaporated to dryness to provide the dihydrochloride salt of the title compound.

Example 76

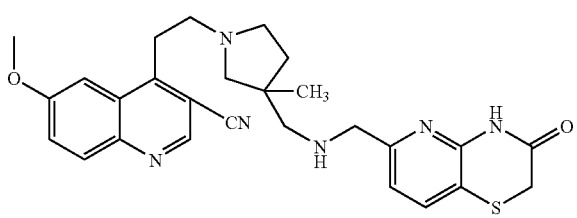

Preparation of (±)-4-{2-[3-methyl-3-({[(3-oxo-3,4-dihydro-2H-pyrido[3,2-b][1,4]-thiazin-6-yl)methyl]amino}methyl)-1-pyrrolidinyl]ethyl}-6-(methyloxy)-3-quinolinecarbonitrile (a) (±)-1,1-dimethylethyl[(1-{2-[3-cyano-6-(methyloxy)-4-quinolinyl]ethyl}-3-methyl-3-pyrrolidinyl)methyl]carbamate

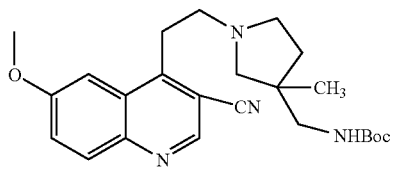

(±)-1,1-Dimethylethyl[(3-methyl-3-pyrrolidinyl)methyl]carbamate (407 mg, 1.9 mmol) and 4-ethenyl-6-(methyloxy)-3-quinolinecarbonitrile (400 mg, 1.9 mmol) were mixed in DMF (1 mL) and heated at 90° C. over 10 h. The solution was then concentrated and the residue was purified via column chromatography (silica, 0-5% MeOH in DCM) yielding the title compound (247 mg, 30%) as an off-white solid; LC/MS (ES) m/e 425 (M+H).

(b) (±)-4-{2-[3-(aminomethyl)-3-methyl-1-pyrrolidinyl]ethyl}-6-(methyloxy)-3-quinolinecarbonitrile

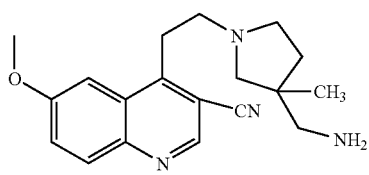

To a solution of (±)-1,1-dimethylethyl[(1-{2-[3-cyano-6-(methyloxy)-4-quinolinyl]ethyl}-3-methyl-3-pyrrolidinyl)methyl]carbamate (247 mg, 0.58 mmol) in DCM (5 mL) at 25° C. was added dropwise an HCl solution (0.6 mL, 2.4 mmol, 4M HCl in dioxane). After 24 h, the solution was concentrated to afford the HCl salt of the title compound (50 mg) which was used without further purification: LC/MS (ES) m/e 325 (M+H).

(c) (±)-4-{2-[3-methyl-3-({[(3-oxo-3,4-dihydro-2H-pyrido[3,2-b][1,4]thiazin-6-yl)methyl]amino}methyl)-1-pyrrolidinyl]ethyl}-6-(methyloxy)-3-quinolinecarbonitrile

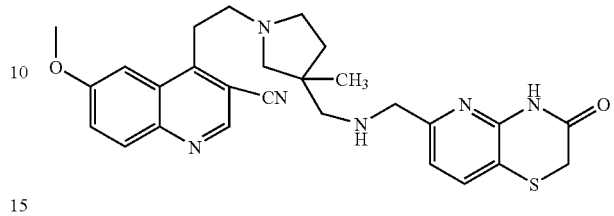

To a solution of the HCl salt of 4-{2-[3-(aminomethyl)-3-methyl-1-pyrrolidinyl]ethyl}-6-(methyloxy)-3-quinolinecarbonitrile (50 mg) in MeOH (2 mL) and DCM (2 mL) were added NaHCO (130 mg, 1.6 mmol) followed by 3-oxo-3,4-dihydro-2H-pyrido[3,2-b][1,4]thiazine-6-carbaldehyde (30 mg, 0.18 mmol). After 24 h at 25° C., NaBH (10 mg, 0.27 mmol) was added. After 1 h, the reaction was concentrated and the residue was partitioned between DCM-H O. The aqueous phase was extracted several times with DCM and the combined organic fractions were dried over MgSO, concentrated and purified via column chromatography (silica, 4% MeOH in DCM (1% NH OH)) yielding the title compound (20 mg) as a brown oil: LC/MS (ES) m/e 503 (M+H) $^1$H NMR (CDCl$_3$, 400 MHz) δ 8.85 (s, 1H), 8.22 (d, J=9.0 Hz, 1H), 7.58 (d, J=7.8 Hz, 1H), 7.55 (d, J=9.0 Hz, 1H), 7.35 (s, 1H), 6.95 (d, J=7.8 Hz, 1H), 4.12 (s, 3H), 3.83 (s, 2H), 3.51 (m, 3H), 2.9-2.5 (m, 6H), 2.3 (m, 1H), 1.85 (m, 1H), 1.55 (m, 1H), 1.1 (s, 3H).

This material, as a solution in MeOH, was treated with an excess of 4M HCl in dioxane and evaporated to dryness to provide the dihydrochloride salt of the title compound.

Example 77

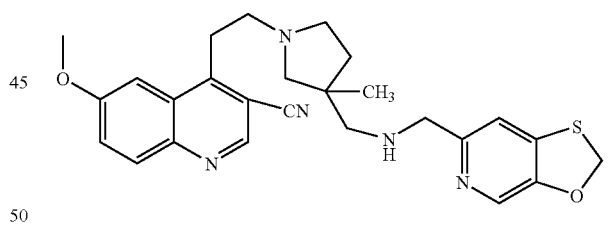

Preparation of (±)-4-[2-(3-methyl-3-{[([1,3]oxathiolo[5,4-c]pyridin-6-ylmethyl)amino]methyl}-1-pyrrolidinyl)ethyl]-6-(methyloxy)-3-quinolinecarbonitrile According to the procedure for Example 76, except substituting [1,3]oxathiolo[5,4-c]pyridine-6-carbaldehyde (26 mg, 0.15 mmol) for 3-oxo-3,4-dihydro-2H-pyrido[3,2-b][1,4]thiazine-6-carboxaldehyde. The title compound (24 mg, 34%) was obtained as an oil: LC/MS (ES) m/e 476 (M+H); $^1$H NMR (CDCl$_3$, 400 MHz) δ 8.8 (s, 1H), 8.22 (d, J=9.0 Hz, 1H), 8.5 (s, 1H), 7.5 (d, J=9.0 Hz, 1H), 7.35 (s, 1H), 7.20 (s, 1H), 5.7 (s, 2H), 4.05 (s, 3H), 3.8 (s, 2H), 3.50 (m, 2H), 2.8 (m, 4H), 2.5 (m, 3H), 2.3 (m, 1H), 1.85 (m, 1H), 1.55 (m, 1H), 1.1 (s, 3H).

This material, as a solution in MeOH, was treated with an excess of 4M HCl in dioxane and evaporated to dryness to provide the dihydrochloride salt of the title compound.

Example 78

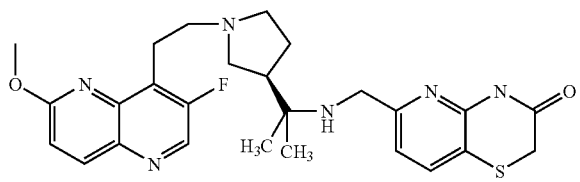

Preparation of 6-({[1-((3R)-1-{2-[3-fluoro-6-(methyloxy)-1,5-naphthyridin-4-yl]ethyl}-3-pyrrolidinyl)-1-methylethyl]amino}methyl)-2H-pyrido[3,2-b][1,4]thiazin-3(4H)-one (a) (3R)-1-(phenylmethyl)-3-pyrrolidinyl methanesulfonate

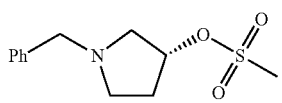

To a solution of (3R)-1-(phenylmethyl_3-pyrrolidinol (11 g, 60 mmol) in DCM (100 mL) with triethylamine (13.05 mL) at 0° C. was added methenesulfonyl chloride (5.8 mL) slowly. After stirring at 0° C. for 3 h, the mixture was concentrated. The resulting residue was diluted partitioned between diethyl ether and water. The aqueous solution was extracted several times with diethyl ether. The organic fractions were combined, washed with brine, drived over Mg SO and concentrated to afford the title compound as an oil (15.72 g, 99%) which was used without further purification: LC/MS (ES) m/e 256 (M+H)$^+$.

(b) (3S)-1-(phenylmethyl)-3-pyrrolidinecarbonitrile

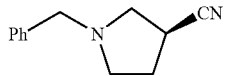

(3R)-1-(phenylmethyl)-3-pyrrolidinyl methanesulfonate (12.9 g, 50.6 mmol) and tertrabytulamonium cyanide (25 g, 93.3 mmol) was mixed in DCM (20 mL) and refluxed at 60° C. for 6 h. The resulting solution was cooled down to room temperature and diluted with saturated sodium bicarbonate solution in water. The aqueous phase was extracted several times with toluene. The organic fractions was combined, washed with brine and concentrated to provide the title compound as an oil (10.3 g, quantit.) which was used without further purification: LC/MS (ES) m/e 187 (M+H)$^+$.

(c) 2-[(3S)-1-(phenylmethyl)-3-pyrrolidinyl]-2-propanamine

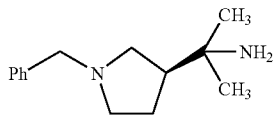

A solution of anhydrous trichlorocerium (41.6 g, 0.17 mol) in THF (520 mL), which was sounicated with stirring for 2.5 h, was cooled down to −70° C. and treated with a solution of Methyl Lithium (167 mL, 167 mmol, 1M in THF) followed with a solution of (3S)-1-(phenylmethyl)-3-pyrrolidinecarbonitrile (10.3 g, 55.4 mmol) in THF (20 mL). After stirring at −70° C. for 2.5 h, the resulting mixture was diluted with the aqueous solution of NH OH (26 mL). DCM (300 mL) was added to generate a suspension which was subsequently filtered. The filterate was concentrated and purified with column chromatography (silica, 10-20% MeOH in DCM) affording the title compound as an oil (6.75 g, 56%): LC/MS (ES) m/e 219 (M+H)$^+$.

(d) 1,1-dimethylethyl {1-methyl-1-[(3S)-1-(phenylmethyl)-3-pyrrolidinyl]ethyl}carbamate

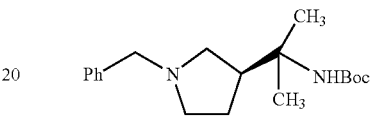

To a solution of 2-[(3S)-1-(phenylmethyl)-3-pyrrolidinyl]-2-propanamine (6.75 g, 31 mmol) in DCM (100 mL) was added bis(1,1-dimethylethyl)dicarbonate (6.78 g, 31 mmol) followed with triethylamine (4.8 g, 47.5 mmol). After stirring at room temperature for 24 h, the solution was partitioned between DCM and water. The aqueous solution was extracted several times with DCM. The organic fractions were pooled, concentrated and purified with column chromatography (silica, 30-50% ethyl acetate in hexane) providing the title compound as an oil (5.85 g, 59%): LC/MS (ES) m/e 319 (M+H)$^+$.

(e) 1,1-dimethylethyl {1-methyl-1-[(3S)-3-pyrrolidinyl]ethyl}carbamate

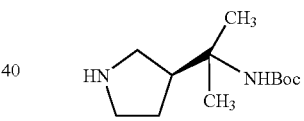

To a solution of 1,1-dimethylethyl {1-methyl-1-[(3S)-1-(phenylmethyl)-3-pyrrolidinyl]ethyl}carbamate (5.85 g, 18.4 mmol) in MeOH (100 mL) was added Pd/C (5 g, 10%). The suspension was hydrogenated at 50 psi of H using a Parr shaker. After 24 h, the mixture was filtered and washed several times with MeOH. The filtrate was concentrated to afford the title compound (4.8 g, quantit.) as an oil, which was used without further purification: LC/MS (ES) m/e 229 (M+H)$^+$.

(f) 1,1-dimethylethyl[1-((3S)-1-{2-[3-fluoro-6-(methyloxy)-1,5-naphthyridin-4-yl]ethyl}-3-pyrrolidinyl)-1-methylethyl]carbamate

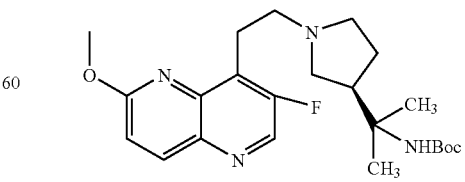

A solution of 8-ethenyl-7-fluoro-2-(methyloxy)-1,5-naphthyridine (600 mg, 2.95 mmol) in ethyl acetate (1 mL) and 1,1-dimethylethyl {1-methyl-1-[(3S)-3-pyrrolidinyl]ethyl}carbamate (670 mg, 2.94 mmol) were mixed in EtOH (3 mL) and heated at 90° C. for 24 h. DMF (2 mL) was added and the mixture was hearted at 90° C. for another 10 h. The solution was then concentrated and the residue was purified via column chromatography (silica, 1-10% MeOH in DCM) yielding the title compound (0.46 g, 36%) as an oil: LC/MS (ES) m/e 433 (M+H)$^+$.

(g) 2-((3R)-1-{2-[3-fluoro-6-(methyloxy)-1,5-naphthyridin-4-yl]ethyl}-3-pyrrolidinyl)-2-propanamine

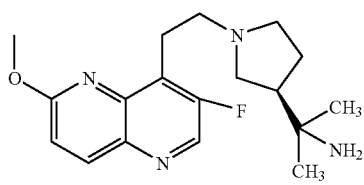

To a solution of 1,1-dimethylethyl[1-((3S)-1-{2-[3-fluoro-6-(methyloxy)-1,5-naphthyridin-4-yl]ethyl}-3-pyrrolidinyl)-1-methylethyl]carbamate (0.46 g, 1.06 mmol) in DCM (10 mL) at 25° C. was added dropwise an HCl solution (4.22 mL, 4.24 mmol, 1M HCl in dioxane). After 24 h, the solution was concentrated to afford the hydrochloride salt of the title compound as an off-white residue (0.43 g, quantit.), which was used without further purification: LC/MS (ES) m/e 333 (M+H)$^+$.

(h) 6-({[1-((3R)-1-{2-[3-fluoro-6-(methyloxy)-1,5-naphthyridin-4-yl]ethyl}-3-pyrrolidinyl)-1-methylethyl]amino}methyl)-2H-pyrido[3,2-b][1,4]thiazin-3(4H)-one

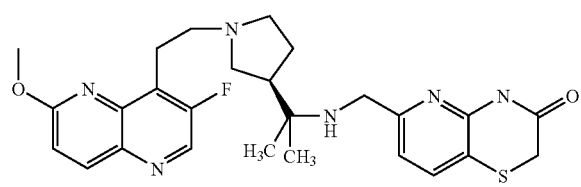

To a solution of the hydrochloride salt of 2-((3R)-1-{2-[3-fluoro-6-(methyloxy)-1,5-naphthyridin-4-yl]ethyl}-3-pyrrolidinyl)-2-propanamine (100 mg, 0.25 mmol) in DCM:EtOH (6 mL, 1:1) were added NaHCO (210 mg, 2.5 mmol) followed by 3-oxo-3,4-dihydro-2H-pyrido[3,2-b][1,4]thiazine-6-carbaldehyde (47 mg, 0.25 mmol). After 12 h at 25° C., NaBH (10 mg, 0.28 mmol) was added. After 1 h, the reaction was concentrated and the residue was partitioned between DCM and water. The aqueous phase was extracted several times with DCM and the combined organic fractions were dried over MgSO, concentrated and purified via column chromatography (silica, 0-1% MeOH in DCM (1% NH OH)) yielding the title compound (47 mg, 37%) as an off-white solid: LC/MS (ES) m/e 512 (M+H)$^+$; H NMR (CDCl, 400 Hz) δ 8.59 (s, 1H), 8.17 (d, J=9.1 Hz, 1H), 7.51 (d, J=7.8 Hz, 1H), 7.05 (d, J=9.0 Hz, 1H), 6.98 (d, J=7.8 Hz, 1H), 4.07 (s, 3H), 3.76 (s, 2H), 3.39-3.43 (m, 4H), 2.76-2.96 (m, 4H), 2.55-2.64 (m, 2H), 2.39-2.44 (m, 1H), 1.85-1.88 (m, 1H), 1.72-1.78 (m, 1H), 1.09 (s, 3H), 1.08 (s, 3H).

This material, as a solution in MeOH, was treated with 2 equivalents of 4M HCl in dioxane and evaporated to dryness to provide the dihydrochloride salt of the title compound.

Example 79

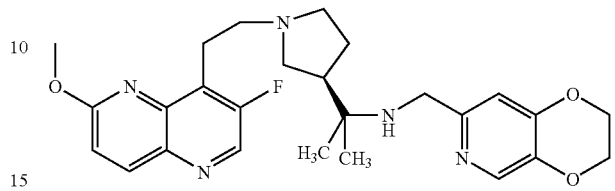

Preparation of N-(2,3-dihydro[1,4]dioxino[2,3-c]pyridin-7-ylmethyl)-2-((3R)-1-{2-[3-fluoro-6-(methyloxy)-1,5-naphthyridin-4-yl]ethyl}-3-pyrrolidinyl)-2-propanamine According to the procedure for Example 78, except 2,3-dihydro[1,4]dioxino[2,3-c]pyridine-7-carbaldehyde (40 mg, 0.25 mmol) for 3-oxo-3,4-dihydro-2H-pyrido[3,2-b][1,4]thiazine-6-carbaldehyde. The title compound (30 mg, 26%) was obtained as an off-white solid: LC/MS (ES) m/e 483 (M+H); $^1$H NMR (CDCl, 400 MHz) δ 8.60 (s, 1H), 8.16 (d, J=9.1 Hz, 1H), 8.07 (s, 1H), 7.06 (d, J=9.0 Hz, 1H), 6.86 (s, 1H), 4.31-4.33 (m, 2H), 4.25-4.27 (m, 2H), 4.08 (s, 3H), 3.74 (s, 2H), 3.41-3.45 (m, 2H), 2.85-2.91 (m, 3H), 2.75-2.80 (m, 1H), 2.52-2.57 (m, 2H), 2.42-2.46 (m, 1H), 1.84-1.89 (m, 1H), 1.72-1.76 (m, 1H), 1.09 (s, 6H).

This material, as a solution in MeOH, was treated with 2 equivalents of 4M HCl in dioxane and evaporated to dryness to provide the dihydrochloride salt of the title compound.

Example 80

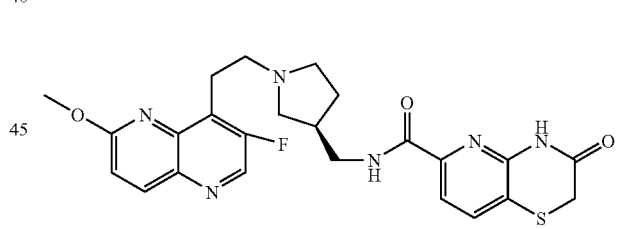

Preparation of N-[((3S)-1-{2-[3-fluoro-6-(methyloxy)-1,5-naphthyridin-4-yl]ethyl}-3-pyrrolidinyl)methyl]-3-oxo-3,4-dihydro-2H-pyrido[3,2-b][1,4]thiazine-6-carboxamide To a stirred solution of (3S,4S)-4-(aminomethyl)-1-{2-[3-fluoro-6-(methyloxy)-1,5-naphthyridin-4-yl]ethyl}-3-pyrrolidinol (105 mg, 0.34 mmole) in dry in DMF (25 mL) at RT was added diisopropylethylamine (0.18 mL, 1.02 mmole), 3-oxo-3,4-dihydro-2H-pyrido[3,2-b][1,4]thiazine-6-carboxylic acid (0.93 mg, 0.44 mmole), hydroxybenzotriazole hydrate (51 mg, 0.38 mmole) and EDC (73 mg, 0.38 mmole). After 18 h, the reaction contents were concentrated under high vacuum. Purification on silica (CHCl$_3$/MeOH, 9:1 containing 5% NH$_4$OH) afforded the title compound (30 mg, 17%) as a light yellow solid: $^1$H NMR (400 MHz, CD$_3$OD) δ

8.62 (m, 1H), 8.56 (s, 1H), 8.16 (d, J=9.04 Hz, 1H), 7.99 (m, 1H), 7.83 (d, J=7.91 Hz, 1H), 7.76 (d, J=7.92 Hz, 1H), 7.05 (d, J=9.04 Hz, 1H), 4.07 (s, 3H), 3.53 (d, 2H), 2.43-3.51 (br m, 11H), 2.06 (m, 1H), 1.58 (m, 1H). LC-MS (ES) m/e 497 (M+H)$^+$.

This material, as a solution in MeOH, was treated with an excess of 4M HCl in diethyl ether and evaporated to dryness to provide the dihydrochloride salt of the title compound.

Example 81

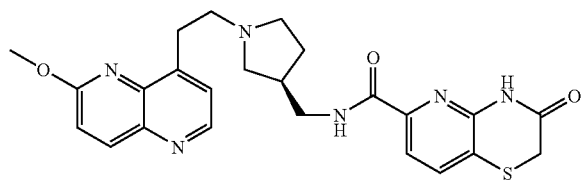

Preparation of N-[((3S)-1-{2-[6-(methyloxy)-1,5-naphthyridin-4-yl]ethyl}-3-pyrrolidinyl)methyl]-3-oxo-3,4-dihydro-2H-pyrido[3,2-b][1,4]thiazine-6-carboxamide To a stirred solution of [((3S)-1-{2-[6-(methyloxy)-1,5-naphthyridin-4-yl]ethyl}-3-pyrrolidinyl)methyl]amine (0.14 g, 0.49 mmole) in dry in DMF (25 mL) at RT was added diisopropylethylamine (0.10 mL, 0.54 mmole), 3-oxo-3,4-dihydro-2H-pyrido[3,2-b][1,4]thiazine-6-carboxylic acid (0.10 g, 0.49 mmole), hydroxybenzotriazole hydrate (0.73 g, 0.54 mmole) and EDC (0.10 g, 0.54 mmole). After 18 h, the reaction contents were concentrated under high vacuum. Purification on silica (CHCl$_3$/MeOH, 9:1 containing 5% NH$_4$OH) afforded the title compound (0.17 g, 75%) as a light yellow solid: $^1$H NMR (400 MHz, CD$_3$OD) δ 9.05 (m, 1H), 8.47 (d, J=9.2 Hz, 1H), 8.25 (m, 2H), 7.92 (m, 1H), 7.72 (m, 1H), 7.62 (d, J=9.2 Hz, 1H), 4.22 (s, 3H), 3.91 (m, 2H), 3.82 (m, 2H), 3.67 (s, 2H), 3.65 (m, 2H), 3.44 (m, 2H), 3.18 (m, 2H), 2.98 (m, 1H), 2.37 (m, 1H), 2.05 (m, 1H). LC-MS (ES) m/e 479 (M+H)$^+$.

This material, as a solution in MeOH, was treated with an excess of 4M HCl in diethyl ether and evaporated to dryness to provide the dihydrochloride salt of the title compound.

Example 82

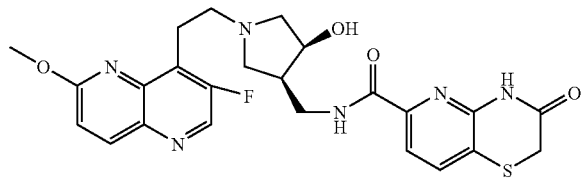

Preparation of N-[((3S,4S)-1-{2-[3-fluoro-6-(methyloxy)-1,5-naphthyridin-4-yl]ethyl}-3-hydroxy-3-pyrrolidinyl)methyl]-3-oxo-3,4-dihydro-2H-pyrido[3,2-b][1,4]thiazine-6-carboxamide To a stirred solution of (3S,4S)-4-(aminomethyl)-1-{2-[3-fluoro-6-(methyloxy)-1,5-naphthyridin-4-yl]ethyl}-3-pyrrolidinol (0.27 g, 0.84 mmole) in dry in DMF (25 mL) at RT was added diisopropylethylamine (0.44 mL, 2.52 mmole), 3-oxo-3,4-dihydro-2H-pyrido[3,2b][1,4]thiazine-6-carboxylic acid (0.18 g, 0.84 mmole), hydroxybenzotriazole hydrate (0.12 g, 0.92 mmole) and EDC (0.18 g, 0.92 mmole). After 18 h, the reaction contents were concentrated under high vacuum. Purification on silica (CHCl$_3$/MeOH, 9:1 containing 5% NH$_4$OH) afforded the title compound (0.49 g, 58%) as a light yellow solid: $^1$H NMR (400 MHz, CDCl$_3$) δ 8.56 (s, 1H), 8.15 (d, J=9.0 Hz, 1H), 7.78 (d, J=7.8 Hz, 1H), 7.72 (d, J=7.8 Hz, 1H), 7.02 (d, J=9.0 Hz, 1H), 4.34 (m, 1H), 4.07 (s, 3H), 3.69 (m, 2H), 3.54 (m, 2H), 3.39 (s, 2H), 3.14 (m, 1H), 2.98 (m, 2H), 2.77 (m, 2H), 2.45 (m, 2H). LC-MS (ES) m/e 479 (M+H)$^+$. LC-MS (ES) m/e 513 (M+H)$^+$.

This material, as a solution in MeOH, was treated with an excess of 4M HCl in diethyl ether and evaporated to dryness to provide the dihydrochloride salt of the title compound.

Example 83

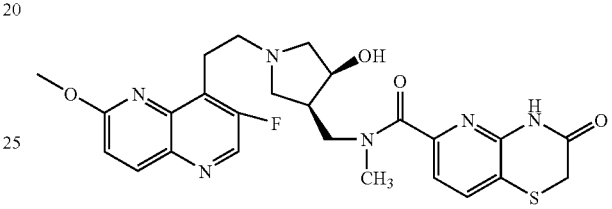

Preparation of (±)-N-[(cis-1-{2-[3-fluoro-6-(methyloxy)-1,5-naphthyridin-4-yl]ethyl}-4-hydroxy-3-pyrrolidinyl)methyl]-N-methyl-3-oxo-3,4-dihydro-2H-pyrido[3,2-b][1,4]thiazine-6-carboxamide To a stirred solution of (±)-1-{2-[3-fluoro-6-(methyloxy)-1,5-naphthyridin-4-yl]ethyl}-4-[(methylamino)methyl]-3-pyrrolidinol (1.5 g, 4.49 mmole) [from procedure 24] in dry in DMF (25 mL) at RT was added diisopropylethylamine (2.35 mL, 13.5 mmole), 3-oxo-3,4-dihydro-2H-pyrido[3,2b][1,4]thiazine-6-carboxylic acid (0.94 g, 4.49 mmole), hydroxybenzotriazole hydrate (0.67 g, 4.94 mmole) and EDC (0.95 g, 4.94 mmole). After 18 h, the reaction contents were concentrated under high vacuum. Purification on silica (CHCl$_3$/MeOH, 9:1 containing 5% NH$_4$OH) afforded the title compound (1.62 g, 69%) as a light yellow solid: $^1$H NMR (400 MHz, CDCl$_3$) δ 8.61 (s, 1H), 8.19 (d, J=9.0 Hz, 1H), 7.78 (d, J=7.8 Hz, 1H), 7.29 (d, J=7.8 Hz, 1H), 7.05 (d, J=9.0 Hz, 1H), 4.32 (m, 2H), 4.09 (s, 3H), 3.51 (s, 3H), 3.42 (m, 4H), 3.14 (m, 2H), 2.98 (m, 4H), 2.80 (m, 1H), 2.63 (m, 1H). LC-MS (ES) m/e 527 (M+H)$^+$.

This material, as a solution in MeOH, was treated with an excess of 4M HCl in diethyl ether and evaporated to dryness to provide the dihydrochloride salt of the title compound.

Example 84

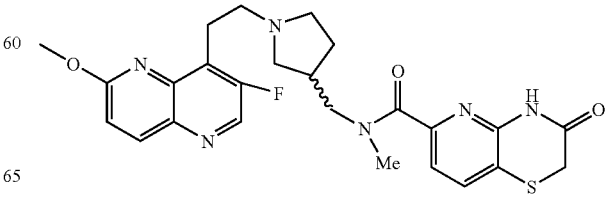

Preparation of (±)-N-[(1-{2-[3-fluoro-6-(methyloxy)-1,5-naphthyridin-4-yl]ethyl}-3-pyrrolidinyl)methyl]-N-methyl-3-oxo-3,4-dihydro-2H-pyrido[3,2-b][1,4]thiazine-6-carboxamide (a) (±)-1,1-Dimethylethyl 3-[(methylamino)methyl]-1-pyrrolidinecarboxylate

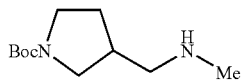

To a solution of 1,1-dimethylethyl 3-formyl-1-pyrrolidinecarboxylate (500 mg, 2.51 mmol) in MeOH/DCM (6 mL, 1:1) were added NaHCO (1.05 g, 12.6 mmol) followed by methylamine (2.51 mL, 5.02 mmol, 2.0 M in MeOH). After 12 h at 25° C., NaBH (1.05 g, 12.6 mmol) was added. After 1 h, the reaction was concentrated and the residue was partitioned between DCM and H O. The aqueous phase was extracted several times with DCM and the combined organic fractions were dried over MgSO₄, concentrated and purified via column chromatography (silica, 4% MeOH in DCM (1% NH OH)) yielding the title compound (512 mg, 95%) as a brown oil: LC/MS (ES) m/e 215 (M+H).

(b) (±)-1,1-Dimethylethyl 3-({methyl[(3-oxo-3,4-dihydro-2H-pyrido[3,2-b][1,4]thiazin-6-yl)carbonyl]amino}methyl)-1-pyrrolidinecarboxylate

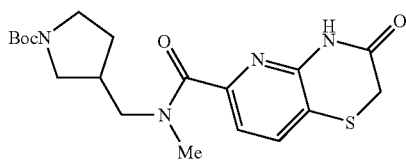

To a solution of 1,1-dimethylethyl 3-[(methylamino)methyl]-1-pyrrolidinecarboxylate (153 mg, 0714 mmol) in DMF (2 mL) were added triethylamine (0.1 mL, 0.714 mmol) followed by DPPA (0.154 mL, 0.714 mmol) and 3-oxo-3,4-dihydro-2H-pyrido[3,2-b][1,4]thiazine-6-carboxylic acid (150 mg, 0.714 mmol). After stirring at room temperature for 24 h, the solution was partitioned between ethyl acetate and K CO solution (5% in H O). The aqueous layer was extracted several times with ethyl acetate. The organic fractions were combined, dried over MgSO, concentrated and purified with column chromatography (silica, 0-5% MeOH in DCM) to provide the title compound as an off-white solid (240 mg, 83%): LC/MS (ES) m/e 407 (M+H).

(c) (±)-N-Methyl-3-oxo-N-(3-pyrrolidinylmethyl)-3,4-dihydro-2H-pyrido[3,2-b][1,4]thiazine-6-carboxamide

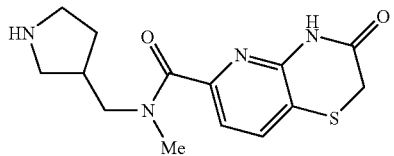

To a solution of 1,1-dimethylethyl 3-({methyl[(3-oxo-3,4-dihydro-2H-pyrido[3,2-b][1,4]thiazin-6-yl)carbonyl]amino}methyl)-1-pyrrolidinecarboxylate (240 mg, 0.59 mmol) in DCM (5 mL) at 25° C. was added dropwise an HCl solution (0.75 mL, 3.0 mmol, 4M HCl in dioxane). After 24 h, the solution was concentrated to afford the HCl salt of the title compound (238 mg, quantit.) as a yellow foam, which was used without further purification: LC/MS (ES) m/e 307 (M+H).

(d) (±)-N-[(1-{2-[3-Fluoro-6-(methyloxy)-1,5-naphthyridin-4-yl]ethyl}-3-pyrrolidinyl)methyl]-N-methyl-3-oxo-3,4-dihydro-2H-pyrido[3,2-b][1,4]thiazine-6-carboxamide

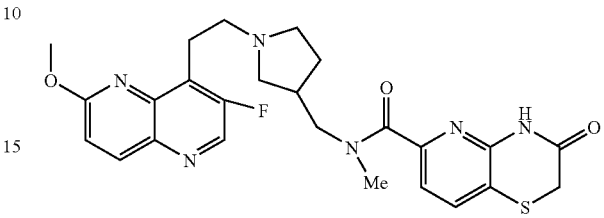

N-Methyl-3-oxo-N-(3-pyrrolidinylmethyl)-3,4-dihydro-2H-pyrido[3,2-b][1,4]thiazine-6-carboxamide (225 mg, 0.734 mmol), diisopropylethylamine (0.26 mL, 1.47 mmol) and 1-ethenyl-2-fluoro-7-(methyloxy)naphthalene (150 mg, 0.734 mmol) were mixed in DMF (1 mL) with catalytic amount of DMAP. The resulting mixture was heated at 94° C. over 24 h. The solution was then concentrated and the residue was purified via column chromatography (silica, 0-10% MeOH in DCM) yielding the title compound (82 mg, 22%) as an off-white foam; LC/MS (ES) m/e 511 (M+H); H NMR This material, as a solution in MeOH, was treated with an excess of 4M HCl in dioxane and evaporated to dryness to provide the dihydrochloride salt of the title compound.

Example 85

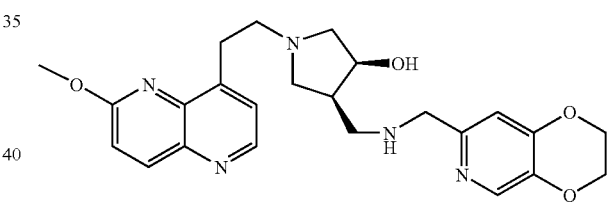

Preparation of (3S,4S)-4-{[(2,3-dihydro[1,4]dioxino[2,3-c]pyridin-7-ylmethyl)amino]methyl}1-{2-[6-(methyloxy)-1,5-naphthyridin-4-yl]ethyl}-3-pyrrolidinol a) phenylmethyl[((3S,4S)-4-hydroxy-1-{2-[6-(methyloxy)-1,5-naphthyridin-4-yl]ethyl}-3-pyrrolidinyl)methyl]carbamate

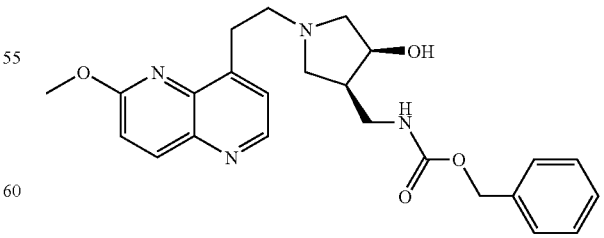

To a stirred solution of 8-ethenyl-2-(methyloxy)-1,5-naphthyridine (4.2 mmole) in EtOH (5 mL) was added phenylmethyl {[(3R,4S)-4-hydroxy-3-pyrrolidinyl]methyl}carbamate (1.05 g, 4.2 mmole). After 24 h at 80° C. the reaction contents were purified on silica (CHCl₃/MeOH, 9:1 containing 5% NH₄OH) affording the title compound (1.46 g, 80%) as a light yellow foam: LC-MS (ES) m/e 437 (M+H)⁺.

b) (3S,4S)-4-(aminomethyl)-1-{2-[6-(methyloxy)-1,5-naphthyridin-4-yl]ethyl}-3-pyrrolidinol

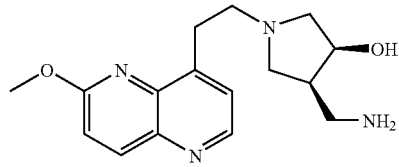

To a solution of phenylmethyl[((3S,4S)-4-hydroxy-1-{2-[6-(methyloxy)-1,5-naphthyridin-4-yl]ethyl}-3-pyrrolidinyl)methyl]carbamate (1.46 g, 3.34 mmole) in MeOH (100 mL) in a round bottom flask was added Pd(OH)₂ (~100 mg). The reaction contents were stirred under a balloon of H₂ overnight at RT. The reaction contents were filtered through Celite® (MeOH) and concentrated to give the title compound (x g, quant.) as a light yellow foam: LC-MS (ES) m/e 303 (M+H)⁺.

c) (3S,4S)-4-{[(2,3-dihydro[1,4]dioxino[2,3-c]pyridin-7-ylmethyl)amino]methyl}-1-{2-[6-(methyloxy)-1,5-naphthyridin-4-yl]ethyl}-3-pyrrolidinol To a stirred solution of (3S,4S)-4-(aminomethyl)-1-{2-[6-(methyloxy)-1,5-naphthyridin-4-yl]ethyl}-3-pyrrolidinol (0.30 g, 1.0 mmole) in dry CH₂Cl₂ (25 mL) and dry EtOH (10 mL) at RT was added 2,3-dihydro[1,4]dioxino[2,3-c]pyridine-7-carbaldehyde (0.165 g, 1.0 mmole). After 24 h, at RT was added NaBH(OAc)₃ (0.32 g, 1.5 mmole). After 2 h, the reaction solution was concentrated under vacuum and purified on silica (CHCl₃/MeOH, 9:1 containing 5% NH₄OH) to afford the title compound (0.12 g, 27%) as light yellow solid: ¹H NMR (400 MHz, CD₃OD) δ 8.67 (d, J=4.5 Hz, 1H), 8.19 (d, J=9.0 Hz, 1H), 7.68 (d, J=4.5 Hz, 1H), 7.25 (d, J=9.0 Hz, 1H), 7.02 (s, 1H), 4.61 (m, 1H), 4.38 (m, 4H), 4.20 (s, 2H), 4.15 (s, 3H), 3.60 (m, 8H), 3.42 (m, 1H), 3.25 (m, 1H), 2.82 (m, 1H). LC-MS (ES) m/e 452 (M+H)⁺.

This material, as a solution in MeOH, was treated with an excess of 4M HCl in diethyl ether and evaporated to dryness to provide the dihydrochloride salt of the title compound.

Example 86

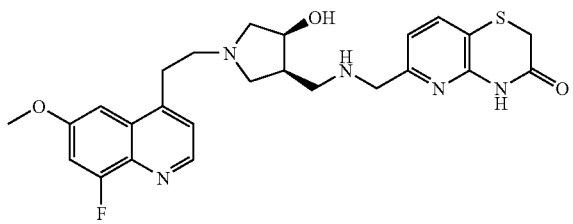

Preparation of 6-({[((3S,4S)-1-{2-[8-fluoro-6-(methyloxy)-4-quinolinyl]ethyl}-4-hydroxy-3-pyrrolidinyl)methyl]amino}methyl)-2H-pyrido[3,2-b][1,4]thiazin-3(4H)-one Prepared essentially according to the procedure of Example 85 except substituting (3S,4S)-4-(aminomethyl)-1-{2-[8-fluoro-6-(methyloxy)-4-quinolinyl]ethyl}-3-pyrrolidinol (98 mg, 0.307 mmol) for (3S,4S)-4-(aminomethyl)-1-{2-[6-(methyloxy)-1,5-naphthyridin-4-yl]ethyl}-3-pyrrolidinol, and substituting 3-oxo-3,4-dihydro-2H-pyrido[3,2-b][1,4]thiazine-6-carbaldehyde (54 mg, 0.278 mmol) for 2,3-dihydro[1,4]dioxino[2,3-c]pyridine-7-carbaldehyde, the title compound (84 mg, 55%) was prepared as an orange solid: LCMS (+ve ion electrospray) m/z 498 (M+H)⁺; H NMR (CHCl, 400 MHz) δ 8.67 (d, J=4.38 Hz, 1H), 7.55 (d, J=7.79 Hz, 1H), 7.27 (d, J=4.47 Hz, 1H), 7.10-7.06 (m, 2H), 6.89 (d, J=7.82 Hz, 1H), 4.58-4.45 (m, 1H), 3.93 (s, 3H), 3.87-3.77 (m, 2H), 3.45 (s, 2H), 3.28-3.17 (m, 2H), 3.08-2.99 (m, 1H), 2.98-2.74 (m, 6H), 2.67-2.54 (m, 1H), 2.52-2.40 (m, 1H).

This material, as a solution in MeOH, was treated with excess of 2M HCl in diethyl ether and evaporated to dryness to provide the dihydrochloride salt of the title compound.

Example 87

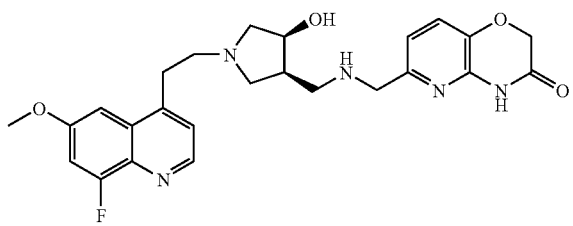

Preparation of 6-({[((3S,4S)-1-{2-[8-fluoro-6-(methyloxy)-4-quinolinyl]ethyl}-4-hydroxy-3-pyrrolidinyl)methyl]amino}methyl)-2H-pyrido[3,2-b][1,4]oxazin-3(4H)-one The title compound (61 mg, 41%) was prepared as a yellow solid prepared essentially according to Example 86, except substituting (3S,4S)-4-(aminomethyl)-1-{2-[8-fluoro-6-(methyloxy)-4-quinolinyl]ethyl}-3-pyrrolidinol (98 mg, 0.307 mmol) for (3S,4S)-4-(aminomethyl)-1-{2-[6-(methyloxy)-1,5-naphthyridin-4-yl]ethyl}-3-pyrrolidinol, and substituting 3-oxo-3,4-dihydro-2H-pyrido[3,2-b][1,4]oxazine-6-carbaldehyde (56 mg, 0.312 mmol) for 2,3-dihydro[1,4]dioxino[2,3-c]pyridine-7-carbaldehyde: LCMS (+ve ion electrospray) m/z 482 (M+H)⁺; H NMR (CHCl, 400 MHz) δ 8.65 (d, J=4.32 Hz, 1H), 7.26 (d, J=4.36 Hz, 1H), 7.17 (d, J=8.04 Hz, 1H), 7.11-7.01 (m, 2H), 6.84 (d, J=8.05 Hz, 1H), 4.59 (s, 2H), 4.56-4.42 (m, 1H), 3.92 (s, 3H), 3.89-3.71 (m, 2H), 3.48 (s, 2H), 3.29-3.12 (m, 2H), 3.09-2.98 (m, 1H), 2.97-2.71 (m, 5H), 2.66-2.53 (m, 1H), 2.53-2.41 (m, 1H).

This material, as a solution in MeOH, was treated with excess of 2M HCl in diethyl ether and evaporated to dryness to provide the dihydrochloride salt of the title compound.

Example 88

Preparation of 6-({[((3S,4S)-1-{2-[6-fluoro-5-(methyloxy)-4-quinolinyl]ethyl}-4-hydroxy-3-pyrrolidinyl)methyl]amino}methyl)-2H-pyrido[3,2-b][1,4]oxazin-3(4H)-one

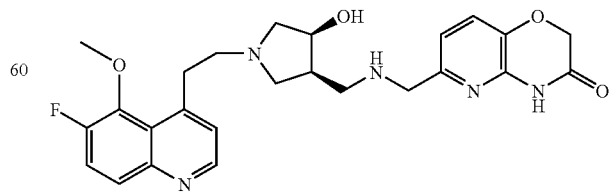

The title compound (83 mg, 42%) was prepared as a yellow solid essentially according to Example 85, except substituting (3S,4S)-4-(aminomethyl)-1-{2-[6-fluoro-5-(methyloxy)-4-quinolinyl]ethyl}-3-pyrrolidinol (130 mg, 0.407 mmol) for (3S,4S)-4-(aminomethyl)-1-{2-[6-(methyloxy)-1,5-naphthyridin-4-yl]ethyl}-3-pyrrolidinol and 3-oxo-3,4-dihydro-2H-pyrido[3,2-b][1,4]oxazine-6-carbaldehyde (78 mg, 0.438 mmol) for 2,3-dihydro[1,4]dioxino[2,3-c]pyridine-7-carbaldehyde: LCMS (+ve ion electrospray) m/z 482 (M+H)$^+$; H NMR (CHCl, 400 MHz) δ 8.70 (d, J=4.42 Hz, 1H), 7.91-7.84 (m, 1H), 7.58-7.46 (m, 1H), 7.24 (d, J=4.34 Hz, 1H), 7.19 (d, J=8.03 Hz, 1H), 6.85 (d, J=8.05 Hz, 1H), 4.63 (s, 2H), 4.57-4.48 (m, 1H), 4.07 (s, 3H), 3.90-3.72 (m, 2H), 3.57-3.34 (m, 2H), 3.04-2.92 (m, 1H), 2.91-2.70 (m, 5H), 2.61-2.50 (m, 1H), 2.49-2.39 (m, 1H).

This material, as a solution in MeOH, was treated with excess of 2M HCl in diethyl ether and evaporated to dryness to provide the dihydrochloride salt of the title compound.

Example 89

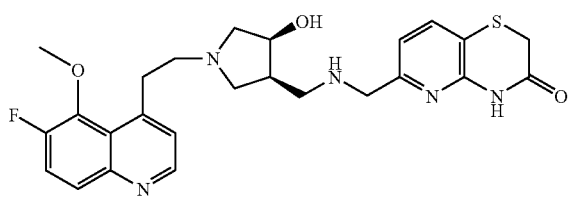

Preparation of 6-({[((3S,4S)-1-{2-[6-fluoro-5-(methyloxy)-4-quinolinyl]ethyl}-4-hydroxy-3-pyrrolidinyl)methyl]amino}methyl)-2H-pyrido[3,2-b][1,4]thiazin-3(4H)-one The title compound (45 mg, 22%) was prepared as a yellow solid essentially according to Example 85, except substituting (3S,4S)-4-(aminomethyl)-1-{2-[6-fluoro-5-(methyloxy)-4-quinolinyl]ethyl}-3-pyrrolidinol (130 mg, 0.407 mmol) for (3S,4S)-4-(aminomethyl)-1-{2-[6-(methyloxy)-1,5-naphthyridin-4-yl]ethyl}-3-pyrrolidinol, and substituting 3-oxo-3,4-dihydro-2H-pyrido[3,2-b][1,4]thiazine-6-carbaldehyde (94 mg, 0.484 mmol) for 2,3-dihydro[1,4]dioxino[2,3-c]pyridine-7-carbaldehyde: LCMS (+ve ion electrospray) m/z 498 (M+H)$^+$; H NMR (CHCl, 400 MHz) δ 8.69 (d, J=4.42 Hz, 1H), 7.93-7.82 (m, 1H), 7.56 (m, J=7.79 Hz, 1H), 7.52-7.44 (m, 1H), 7.22 (d, J=4.12 Hz, 1H), 6.89 (d, J=7.82 Hz, 1H), 4.56-4.45 (m, 1H), 4.06 (s, 3H), 3.90-3.74 (m, 2H), 3.57-3.31 (m, 5H), 3.09-2.94 (m, 1H), 2.93-2.73 (m, 5H), 2.62-2.52 (m, 1H), 2.51-2.39 (m, 1H).

This material, as a solution in MeOH, was treated with excess of 2M HCl in diethyl ether and evaporated to dryness to provide the dihydrochloride salt of the title compound.

Example 90

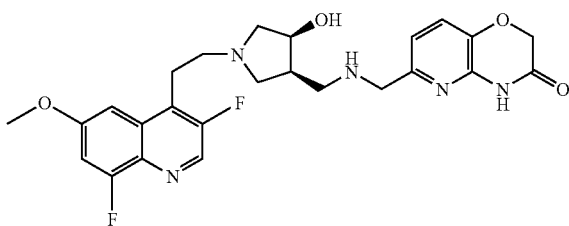

Preparation of 6-({[((3S,4S)-1-{2-[3,8-difluoro-6-(methyloxy)-4-quinolinyl]ethyl}-4-hydroxy-3-pyrrolidinyl)methyl]amino}methyl)-2H-pyrido[3,2-b][1,4]oxazin-3(4H)-one The title compound (182 mg, 65%) was prepared as a yellow solid essentially according to Example 85, except substituting (3S,4S)-4-(aminomethyl)-1-{2-[3,8-difluoro-6-(methyloxy)-4-quinolinyl]ethyl}-3-pyrrolidinol (190 mg, 0.563 mmol) for (3S,4S)-4-(aminomethyl)-1-{2-[6-(methyloxy)-1,5-naphthyridin-4-yl]ethyl}-3-pyrrolidinol and 3-oxo-3,4-dihydro-2H-pyrido[3,2-b][1,4]oxazine-6-carbaldehyde (114 mg, 0.640 mmol) for 2,3-dihydro[1,4]dioxino[2,3-c]pyridine-7-carbaldehyde: LCMS (+ve ion electrospray) m/z 500 (M+H)$^+$; H NMR (CHCl, 400 MHz) δ 8.54 (s, 1H), 7.15 (m, J=8.02 Hz, 1H), 7.08-6.94 (m, 2H), 6.83 (d, J=8.05 Hz, 1H), 4.55 (s, 2H), 4.52-4.41 (m, 1H), 3.91 (s, 3H), 3.85-3.73 (m, 2H), 3.30-3.13 (m, 2H), 3.09-2.96 (m, 1H), 2.94-2.70 (m, 6H), 2.69-2.52 (m, 1H), 2.51-2.39 (m, 1H).

This material, as a solution in MeOH, was treated with excess of 2M HCl in diethyl ether and evaporated to dryness to provide the dihydrochloride salt of the title compound.

Example 91

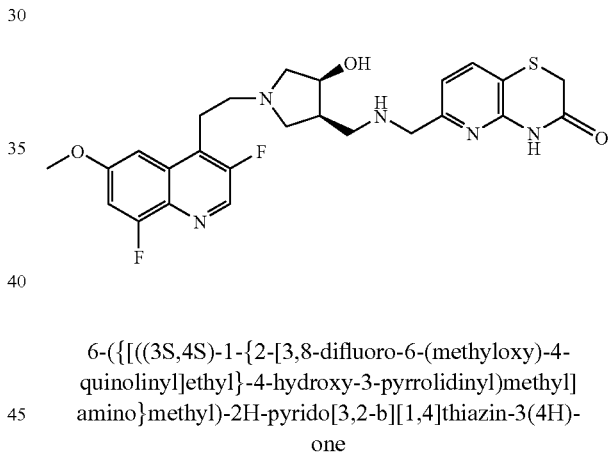

6-({[((3S,4S)-1-{2-[3,8-difluoro-6-(methyloxy)-4-quinolinyl]ethyl}-4-hydroxy-3-pyrrolidinyl)methyl]amino}methyl)-2H-pyrido[3,2-b][1,4]thiazin-3(4H)-one The title compound (162 mg, 63%) was prepared as a yellow solid essentially according to Example 85, except substituting (3S,4S)-4-(aminomethyl)-1-{2-[3,8-difluoro-6-(methyloxy)-4-quinolinyl]ethyl}-3-pyrrolidinol (190 mg, 0.563 mmol) for (3S,4S)-4-(aminomethyl)-1-{2-[6-(methyloxy)-1,5-naphthyridin-4-yl]ethyl}-3-pyrrolidinol and substituting 3-oxo-3,4-dihydro-2H-pyrido[3,2-b][1,4]thiazine-6-carbaldehyde (99 mg, 0.510 mmol) for 2,3-dihydro[1,4]dioxino[2,3-c]pyridine-7-carbaldehyde: LCMS (+ve ion electrospray) m/z 516 (M+H)$^+$; H NMR (CHCl, 400 MHz) δ 8.58 (s, 1H), 7.56 (m, J=8.02 Hz, 1H), 7.10-6.98 (m, 2H), 6.89 (d, J=7.82 Hz, 1H), 4.56-4.46 (m, 1H), 3.95 (s, 3H), 3.91-3.74 (m, 2H), 4.43 (s, 2H), 3.31-3.18 (m, 2H), 3.09-2.96 (m, 1H), 2.94-2.74 (m, 6H), 2.69-2.59 (m, 1H), 2.56-2.40 (m, 1H).

This material, as a solution in MeOH, was treated with excess of 2M HCl in diethyl ether and evaporated to dryness to provide the dihydrochloride salt of the title compound.

Example 92

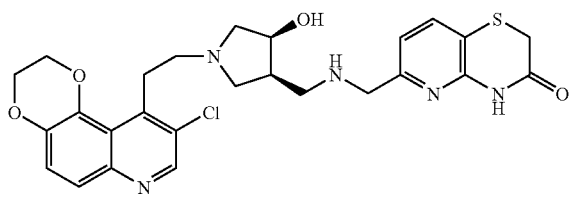

6-{[({(3S,4S)-1-[2-(9-chloro-2,3-dihydro[1,4]di-oxino[2,3-f]quinolin-10-yl)ethyl]-4-hydroxy-3-pyrrolidinyl}methyl)amino]methyl}-2H-pyrido[3,2-b][1,4]thiazin-3(4H)-one The title compound (25 mg, 26%) was prepared as a yellow solid essentially according to Example 85, except substituting (3S,4S)-4-(aminomethyl)-1-[2-(9-chloro-2,3-dihydro[1,4]dioxino[2,3-f]quinolin-10-yl)ethyl]-3-pyrrolidinol (190 mg, 0.563 mmol) for (3S,4S)-4-(aminomethyl)-1-{2-[6-(methyloxy)-1,5-naphthyridin-4-yl]ethyl}-3-pyrrolidinol and substituting 3-oxo-3,4-dihydro-2H-pyrido[3,2-b][1,4]thiazine-6-carbaldehyde (99 mg, 0.510 mmol) for 2,3-dihydro[1,4]dioxino[2,3-c]pyridine-7-carbaldehyde: LCMS (+ve ion electrospray) m/z 542 (M+H)$^+$; H NMR (CHCl, 400 MHz) δ 8.60 (s, 1H), 7.69-7.51 (m, 2H), 7.36-7.22 (m, 1H), 6.91 (d, J=7.82 Hz, 1H), 4.58-4.49 (m, 1H), 4.47-4.31 (m, 4H), 3.94-3.76 (m, 2H), 3.74-3.58 (m, 2H), 3.47 (s, 2H), 3.19-3.04 (m, 1H), 2.99-2.68 (m, 6H), 2.61-2.51 (m, 1H), 2.51-2.39 (m, 1H).

This material, as a solution in MeOH, was treated with excess of 2M HCl in diethyl ether and evaporated to dryness to provide the dihydrochloride salt of the title compound.

Example 93

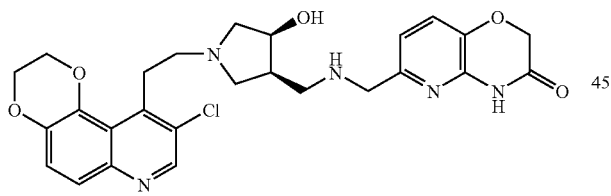

Preparation of 6-{[({(3S,4S)-1-[2-(9-chloro-2,3-dihydro[1,4]dioxino[2,3-f]quinolin-10-yl)ethyl]-4-hydroxy-3-pyrrolidinyl}methyl)amino]methyl}-2H-pyrido[3,2-b][1,4]oxazin-3(4H)-one The title compound (35 mg, 38%) was prepared as a yellow solid essentially according to Example 85, except substituting (3S,4S)-4-(aminomethyl)-1-[2-(9-chloro-2,3-dihydro[1,4]dioxino[2,3-f]quinolin-10-yl)ethyl]-3-pyrrolidinol (190 mg, 0.563 mmol) for (3S,4S)-4-(aminomethyl)-1-{2-[6-(methyloxy)-1,5-naphthyridin-4-yl]ethyl}-3-pyrrolidinol, and substituting 3-oxo-3,4-dihydro-2H-pyrido[3,2-b][1,4]oxazine-6-carbaldehyde (34 mg, 0.191 mmol) for 2,3-dihydro[1,4]dioxino[2,3-c]pyridine-7-carbaldehyde: LCMS (+ve ion electrospray) m/z 526 (M+H)$^+$; H NMR (CHCl, 400 MHz) δ 8.59 (s, 1H), 7.60 (d, J=9.10 Hz, 1H), 7.28 (d, J=9.11 Hz, 1H), 7.18 (d, J=8.01 Hz, 1H), 6.86 (d, J=8.04 Hz, 1H), 4.60 (s, 2H), 4.58-4.49 (m, 1H), 4.46-4.32 (m, 4H), 3.91-3.74 (m, 2H), 3.72-3.60 (m, 2H), 3.49 (s, 2H), 3.18-3.06 (m, 1H), 2.99-2.71 (m, 5H), 2.62-2.53 (m, 1H), 2.52-2.40 (m, 1H).

This material, as a solution in MeOH, was treated with excess of 2M HCl in diethyl ether and evaporated to dryness to provide the dihydrochloride salt of the title compound.

Example 94

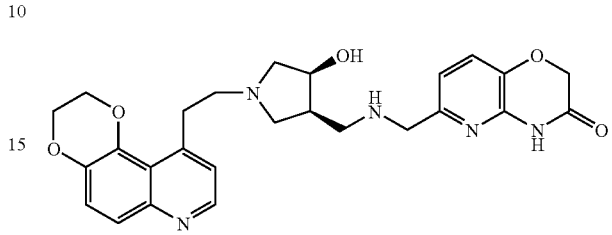

Preparation of 6-{[({(3S,4S)-1-[2-(2,3-dihydro[1,4]dioxino[2,3-f]quinolin-10-yl)ethyl]-4-hydroxy-3-pyrrolidinyl}methyl)amino]methyl}-2H-pyrido[3,2-b][1,4]oxazin-3(4H)-one Prepared essentially according to the procedure of Example 85 except substituting (3S,4S)-4-(aminomethyl)-1-[2-(2,3-dihydro[1,4]dioxino[2,3-f]quinolin-10-yl)ethyl]-3-pyrrolidinol for (3S,4S)-4-(aminomethyl)-1-{2-[6-(methyloxy)-1,5-naphthyridin-4-yl]ethyl}-3-pyrrolidinol and substituting 3-oxo-3,4-dihydro-2H-pyrido[3,2-b][1,4]oxazine-6-carbaldehyde for 2,3-dihydro[1,4]dioxino[2,3-c]pyridine-7-carbaldehyde, the title compound was prepared as a yellow solid: LCMS (+ve ion electrospray) m/z 492 (M+H)$^+$; H NMR (CHCl, 400 MHz) δ 8.54 (d, J=4.42 Hz, 1H), 7.64 (d, J=9.11 Hz, 1H), 7.27 (d, J=9.13 Hz, 1H), 7.14 (d, J=8.00 Hz, 1H), 7.09 (d, J=4.46 Hz, 1H), 6.82 (d, J=8.04 Hz, 1H), 4.56 (s, 2H), 4.52-4.44 (m, 1H), 4.42-4.29 (m, 4H), 3.90-3.70 (m, 2H), 3.51-3.32 (m, 2H), 3.09-2.99 (m, 1H), 2.92-2.68 (m, 6H), 2.59-2.37 (m, 2H).

This material, as a solution in MeOH, was treated with excess of 2M HCl in diethyl ether and evaporated to dryness to provide the dihydrochloride salt of the title compound.

Example 95

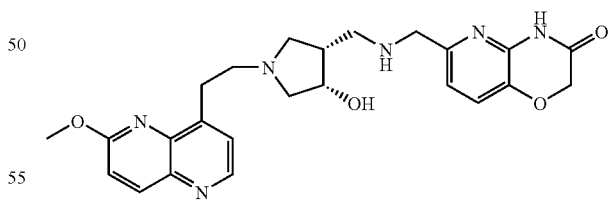

Preparation of 6-({[((3S,4S)-4-hydroxy-1-{2-[6-(methyloxy)-1,5-naphthyridin-4-yl]ethyl}-3-pyrrolidinyl)methyl]amino}methyl)-2H-pyrido[3,2-b][1,4]oxazin-3(4H)-one The title compound (56 mg, 45%) was prepared as a brown solid essentially according to Example 85, except substituting 3-oxo-3,4-dihydro-2H-pyrido[3,2-b][1,4]oxazine-6-carbaldehyde (49 mg, 0.272 mmol) for 2,3-dihydro[1,4]dioxino[2, 3-c]pyridine-7-carbaldehyde: LCMS (+ve ion electrospray) m/z 465 (M+H)+; H NMR (CHCl 400 MHz) δ 8.61 (d, J=4.48 Hz, 1H), 8.16 (d, J=9.01 Hz, 1H), 7.39 (d, J=4.50 Hz, 1H), 7.13 (d, J=8.01 Hz, 1H), 7.06 (d, J=9.03 Hz, 1H), 6.80 (d, J=8.05 Hz, 1H), 4.56 (s, 2H), 4.52-4.42 (m, 1H), 4.04 (s, 3H), 3.83-3.66 (m, 2H), 3.46 (s, 1H), 3.42-3.30 (m, 2H), 3.09-2.68 (m, 7H), 2.65-2.52 (m, 1H), 2.51-2.37 (m, 1H).

This material, as a solution in MeOH, was treated with excess of 2M HCl in diethyl ether and evaporated to dryness to provide the dihydrochloride salt of the title compound.

Example 96

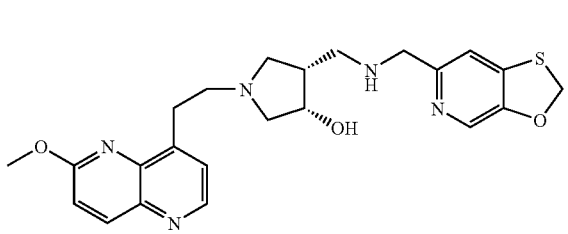

Preparation of (3S,4S)-1-{2-[6-(methyloxy)-1,5-naphthyridin-4-yl]ethyl}-4-{[([1,3]oxathiolo[5,4-c]pyridin-6-ylmethyl)amino]methyl}-3-pyrrolidinol The title compound (61 mg, 41%) was prepared as a yellow solid essentially according to Example 85, except substituting [1,3]oxathiolo[5,4-c]pyridine-6-carbaldehyde (37 mg, 0.22 mmol) for 2,3-dihydro[1,4]dioxino[2,3-c]pyridine-7-carbaldehyde: LCMS (+ve ion electrospray) m/z 454 (M+H)+; H NMR (CHCl, 400 MHz) δ 8.66 (d, J=4.47 Hz, 1H), 8.19 (d, J=9.04 Hz, 1H), 8.02 (s, 1H), 7.43 (d, J=4.47 Hz, 1H), 7.19-7.03 (m, 2H), 5.76 (s, 2H), 4.58-4.46 (m, 1H), 4.09 (s, 3H), 3.87-3.72 (m, 2H), 3.49-3.31 (m, 2H), 3.12-3.01 (m, 1H), 2.97-2.69 (m, 6H), 2.60-2.51 (m, 1H), 2.50-2.37 (m, 1H).

This material, as a solution in MeOH, was treated with excess of 2M HCl in diethyl ether and evaporated to dryness to provide the dihydrochloride salt of the title compound.

Example 97

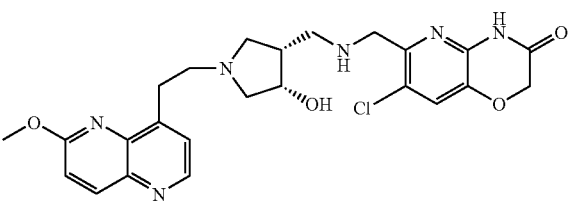

Preparation of 7-chloro-6-({[((3S,4S)-4-hydroxy-1-{2-[6-(methyloxy)-1,5-naphthyridin-4-yl]ethyl}-3-pyrrolidinyl)methyl]amino}methyl)-2H-pyrido[3,2-b][1,4]oxazin-3(4H)-one The title compound (21 mg, 11%) was prepared as a yellow solid essentially according to Example 85, except substituting 7-chloro-3-oxo-3,4-dihydro-2H-pyrido[3,2-b][1,4]oxazine-6-carbaldehyde (79 mg, 0.372 mmol) for 2,3-dihydro[1,4]dioxino[2,3-c]pyridine-7-carbaldehyde: LCMS (+ve ion electrospray) m/z 499 (M+H)+; H NMR (CHCl, 400 MHz) δ 8.66 (d, J=4.46 Hz, 1H), 8.19 (d, J=9.03 Hz, 1H), 7.43 (d, J=4.48 Hz, 1H), 7.20 (s, 1H), 7.10 (d, J=9.03 Hz, 1H), 4.59 (s, 2H), 4.57-4.48 (m, 1H), 4.07 (s, 3H), 4.01-3.81 (m, 2H), 3.49-3.38 (m, 2H), 3.24-2.81 (m, 8H), 2.80-2.69 (m, 1H), 2.63-2.50 (m, 1H).

This material, as a solution in MeOH, was treated with excess of 2M HCl in diethyl ether and evaporated to dryness to provide the dihydrochloride salt of the title compound.

Example 98

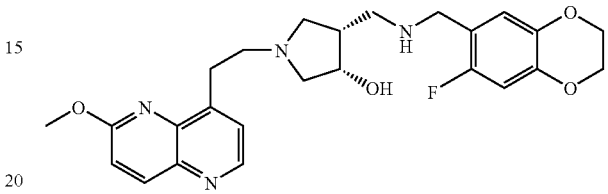

(3S,4S)-4-({[(7-fluoro-2,3-dihydro-1,4-benzodioxin-6-yl)methyl]amino}methyl)-1-{2-[6-(methyloxy)-1,5-naphthyridin-4-yl]ethyl}-3-pyrrolidinol (GSK713092A)

The title compound (77 mg, 47%) was prepared as a tan solid essentially according to Example 85, except substituting 7-fluoro-2,3-dihydro-1,4-benzodioxin-6-carbaldehyde (67 mg, 0.368 mmol) for 2,3-dihydro[1,4]dioxino[2,3-c]pyridine-7-carbaldehyde: LCMS (+ve ion electrospray) m/z 498 (M+H)+; H NMR (CHCl, 400 MHz) δ 8.62 (d, J=4.47 Hz, 1H), 8.16 (d, J=9.01 Hz, 1H), 7.40 (d, J=4.48 Hz, 1H), 7.09 (d, J=9.05 Hz, 1H), 6.98 (d, J=9.26 Hz, 1H), 6.84 (d, J=6.42 Hz, 1H), 4.54-4.41 (m, 1H), 4.06 (s, 3H), 3.73 (s, 2H), 3.49-3.29 (m, 4H), 3.04-2.73 (m, 7H), 2.71-2.61 (m, 1H), 2.53-2.39 (m, 1H).

This material, as a solution in MeOH, was treated with excess of 2M HCl in diethyl ether and evaporated to dryness to provide the dihydrochloride salt of the title compound.

Example 99

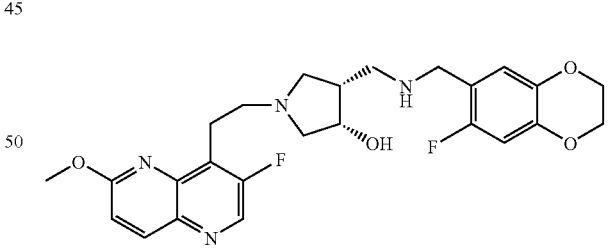

Preparation of (3S,4S)-4-({[(7-fluoro-2,3-dihydro-1,4-benzodioxin-6-yl)methyl]amino}methyl)-1-{2-[3-fluoro-6-(methyloxy)-1,5-naphthyridin-4-yl]ethyl}-3-pyrrolidinol The title compound (75 mg, 41%) was prepared as a yellow solid essentially according to Example 85, except substituting (3S,4S)-4-(aminomethyl)-1-{2-[3-fluoro-6-(methyloxy)-1,5-naphthyridin-4-yl]ethyl}-3-pyrrolidinol (120 mg, 0.375 mmol) for (3S,4S)-4-(aminomethyl)-1-{2-[6-(methyloxy)-1,5-naphthyridin-4-yl]ethyl}-3-pyrrolidinol and 7-fluoro-2,3- dihydro-1,4-benzodioxin-6-carbaldehyde for 2,3-dihydro-1,4-benzodioxin-6-carbaldehyde (69 mg, 0.378 mmol) for: LCMS (+ve ion electrospray) m/z 487 (M+H)+; H NMR (CHCl, 400 MHz) δ 8.57 (s, 1H), 8.13 (d, J=9.04 Hz, 1H), 7.04 (d, J=9.04 Hz, 1H), 6.71 (d, J=7.19 Hz, 1H), 6.57 (d, J=10.41 Hz, 1H), 4.99-4.39 (m, 1H), 4.28-4.16 (m, 4H), 4.06 (s, 3H), 3.67 (s, 2H), 3.42-3.30 (m, 2H), 3.02-2.92 (m, 1H), 2.88-2.63 (m, 6H), 2.58-2.46 (m, 1H), 2.43-2.32 (m, 1H).

This material, as a solution in MeOH, was treated with excess of 2M HCl in diethyl ether and evaporated to dryness to provide the dihydrochloride salt of the title compound.

Example 100

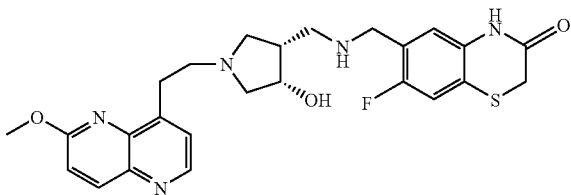

Preparation of 7-fluoro-6-({[((3S,4S)-4-hydroxy-1-{2-[6-(methyloxy)-1,5-naphthyridin-4-yl]ethyl}-3-pyrrolidinyl)methyl]amino}methyl)-2H-1,4-benzothiazin-3(4H)-one The title compound (67 mg, 36%) was prepared as a yellow solid essentially according to Example 85, except substituting 7-fluoro-3-oxo-3,4-dihydro-2H-1,4-benzothiazine-6-carbaldehyde (78 mg, 0.371 mmol) for 7-chloro-3-oxo-3,4-dihydro-2H-pyrido[3,2-b][1,4]oxazine-6-carbaldehyde: LCMS (+ve ion electrospray) m/z 498 (M+H)+; H NMR (CHCl, 400 MHz) δ 8.62 (d, J=4.47 Hz, 1H), 8.16 (d, J=9.01 Hz, 1H), 7.40 (d, J=4.48 Hz, 1H), 7.09 (d, J=9.05 Hz, 1H), 6.98 (d, J=9.26 Hz, 1H), 6.84 (d, J=6.42 Hz, 1H), 4.54-4.41 (m, 1H), 4.06 (s, 3H), 3.73 (s, 2H), 3.47-3.29 (m, 4H), 3.01-2.72 (m, 7H), 2.71-2.60 (m, 1H), 2.51-2.39 (m, 1H).

This material, as a solution in MeOH, was treated with excess of 2M HCl in diethyl ether and evaporated to dryness to provide the dihydrochloride salt of the title compound.

Example 101

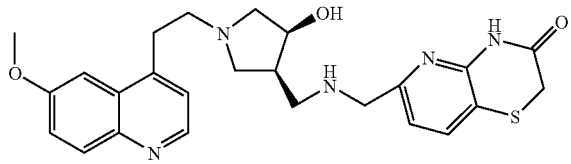

Preparation of 6-({[((3S,4S)-4-hydroxy-1-{2-[6-(methyloxy)-4-quinolinyl]ethyl}-3-pyrrolidinyl)methyl]amino}methyl)-2H-pyrido[3,2-b][1,4]thiazin-3(4H)-one The title compound (120 mg, 58%) was prepared as a yellow foam essentially according to Example 85, except substituting 4-ethenyl-6-(methyloxy)quinoline (740 mg, 4 mmol) for 8-ethenyl-2-(methyloxy)-1,5-naphthyridine and substituting 3-oxo-3,4-dihydro-2H-pyrido[3,2-b][1,4]thiazine-6-carbaldehyde for 2,3-dihydro[1,4]dioxino[2,3-c]pyridine-7-carbaldehyde: LC/MS (ES) m/e 480 (M+H); H NMR (CD OD, 400 Hz) δ 8.54 (s, 1H), 7.89 (d, J=8.7 Hz, 1H), 7.65 (d, J=7.8 Hz, 1H), 7.36-7.40 (m, 3H), 7.0 (d, J=8.8 Hz, 1H), 4.35-4.38 (m, 1H), 3.95 (s, 3H), 3.8 (d, J=3.2 Hz, 2H), 3.48 (s, 2H), 3.22-3.26 (m, 2H), 3.13-3.17 (m, 1H), 2.98-3.02 (m, 1H), 2.87-2.95 (m, 3H), 2.7-2.72 (m, 1H), 2.6-2.65 (m, 1H), 2.5-2.52 (m, 1H), 2.42-2.45 (m, 1H).

This material, as a solution in MeOH, was treated with an excess of 4M HCl in dioxane and evaporated to dryness to provide the dihydrochloride salt of the title compound as a yellow solid.

Example 102

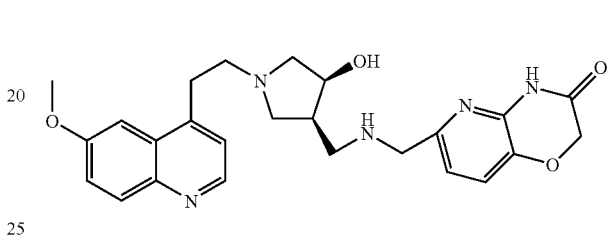

Preparation of 6-({[((3S,4S)-4-hydroxy-1-{2-[6-(methyloxy)-4-quinolinyl]ethyl}-3-pyrrolidinyl)methyl]amino}methyl)-2H-pyrido[3,2-b][1,4]oxazin-3(4H)-one The title compound (120 mg, 60%) was prepared as a white foam according to Example 85, except substituting 4-ethenyl-6-(methyloxy)quinoline (740 mg, 4 mmol) for 8-ethenyl-2-(methyloxy)-1,5-naphthyridine and 3-oxo-3,4-dihydro-2H-pyrido[3,2-b][1,4]oxazine-6-carbaldehyde (77 mg, 0.42 mmol) for 2,3-dihydro[1,4]dioxino[2,3-c]pyridine-7-carbaldehyde: LC/MS (ES) m/e 465 (M+H); H NMR (CD OD, 400 Hz) δ 8.53 (s, 1H), 7.89 (d, J=8.3 Hz, 1H), 7.36-7.44 (m, 3H), 7.24 (d, J=8.0 Hz, 1H), 6.94 (d, J=8.0 Hz, 1H), 4.62 (s, 2H), 4.37-4.39 (m, 1H), 3.95 (s, 3H), 3.77 (s, 2H), 3.22-3.24 (m, 2H), 3.15-3.17 (m, 1H), 2.97-3.02 (m, 1H), 2.86-2.93 (m, 3H), 2.66-2.7 (m, 1H), 2.58-2.6 (m, 1H), 2.5-2.54 (m, 1H), 2.4-2.44 (m, 1H).

This material, as a solution in MeOH, was treated with an excess of 4M HCl in dioxane and evaporated to dryness to provide the dihydrochloride salt of the title compound.

Example 103

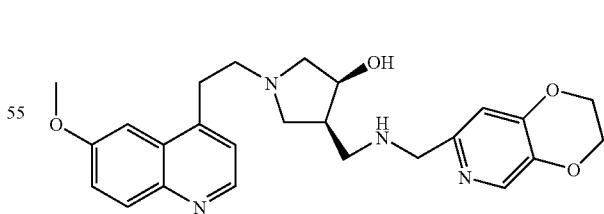

Preparation of (3S,4S)-4-{[(2,3-dihydro[1,4]dioxino[2,3-c]pyridin-7-ylmethyl)amino]methyl}-1-{2-[6-(methyloxy)-4-quinolinyl]ethyl}-3-pyrrolidinol The title compound (96 mg, 49%) was prepared as a clear oil essentially according to Example 85, except substituting 4-ethenyl-6-(methyloxy)quinoline (740 mg, 4 mmol) for 8-ethenyl-2-(methyloxy)-1,5-naphthyridine: LC/MS (ES) m/e 451 (M+H); H NMR (CD OD, 400 Hz) δ 8.55 (s, 1H), 8.0 (s, 1H), 7.91 (d, J=10.0 Hz, 1H), 7.36-7.40 (m, 3H), 6.95 (s, 1H), 4.29-4.41 (m, 5H), 3.97 (s, 3H), 3.76 (d, J=4.6 Hz, 2H), 3.16-3.28 (m, 3H), 2.98-3.01 (m, 1H), 2.85-2.89 (m, 3H), 2.67-2.7 (m, 1H), 2.6-2.63 (m, 1H), 2.5-2.54 (m, 1H), 2.42-2.47 (m, 1H).

This material, as a solution in MeOH, was treated with an excess of 4M HCl in dioxane and evaporated to dryness to provide the dihydrochloride salt of the title compound.

Example 104

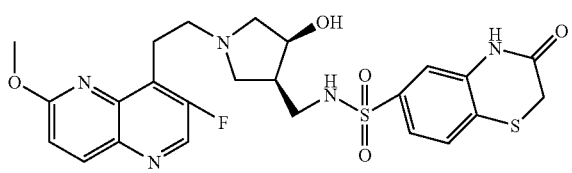

Preparation of N-[((3R,4S)-1-{2-[3-fluoro-6-(methyloxy)-1,5-naphthyridin-4-yl]ethyl}-4-hydroxy-3-pyrrolidinyl)methyl]-3-oxo-3,4-dihydro-2H-1,4-benzothiazine-6-sulfonamide To a solution of (3S,4S)-4-(aminomethyl)-1-{2-[3-fluoro-6-(methyloxy)-1,5-naphthyridin-4-yl]ethyl}-3-pyrrolidinol (225 mg, 0.703 mmol) in DIPEA (188 µL, 1.05 mmol) and DCM (7 mL) at 0° C. was added 3-oxo-3,4-dihydro-2H-1,4-benzothiazine-6-sulfonyl chloride (210 mg, 0.845 mmol) in one portion. The solution stirred for 0.5 h and was concentrated. The resulting residue was purified by column chromatography (silica, 2-4% MeOH in DCM (1% NH OH)) yielding the title compound (290 mg, 75%) as a white foam: LC/MS (ES) m/e 548 (M+H); H NMR (CD OD, 400 Hz) δ 8.65 (s, 1H), 8.22 (d, J=9.1 Hz, 1H), 7.53 (d, J=8.0 Hz, 1H), 7.45-7.48 (m, 2H), 7.20 (d, J=9.1 Hz, 1H), 4.28-4.31 (m, 1H), 4.14 (s, 3H), 3.55 (s, 2H), 3.42-3.46 (m, 2H), 3.21-3.23 (m, 1H), 3.05-3.15 (m, 1H), 2.91-3.05 (m, 2H), 2.86-2.90 (m, 2H), 2.51-2.62 (m, 2H), 2.33-2.4 (m, 1H).

This material, as a solution in MeOH, was treated with an excess of 4M HCl in dioxane and evaporated to dryness to provide the dihydrochloride salt of the title compound.

Example 105

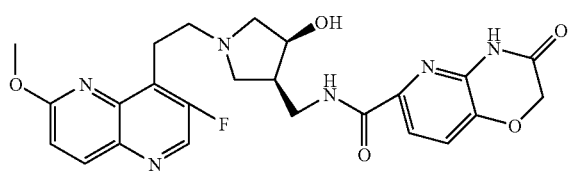

Preparation of N-[((3S,4S)-1-{2-[3-fluoro-6-(methyloxy)-1,5-naphthyridin-4-yl]ethyl}-4-hydroxy-3-pyrrolidinyl)methyl]-3-oxo-3,4-dihydro-2H-pyrido[3,2-b][1,4]oxazine-6-carboxamide To a solution of (3S,4S)-4-(aminomethyl)-1-{2-[3-fluoro-6-(methyloxy)-1,5-naphthyridin-4-yl]ethyl}-3-pyrrolidinol (230 mg, 0.719 mmol) in DCM-DMF (6:1, 7 mL) at 25° C. were added 3-oxo-3,4-dihydro-2H-pyrido[3,2-b][1,4]oxazine-6-carboxylic acid (140 mg, 0.719 mmol), EDC (134 mg, 0.836 mmol) and HOBT (117 mg, 0.863 mmol). After 12 h, the solution was concentrated and purified by column chromatography (silica, 2-3% MeOH in DCM (1% NH OH)) yielding the title compound (130 mg, 36%) as a yellow foam: LC/MS (ES) m/e 497 (M+H); H NMR (CD OD, 400 Hz) δ 8.4 (s, 1H), 7.95 (d, J=9.1 Hz, 1H), 7.53 (d, J=8.2 Hz, 1H), 7.19 (d, J=8.2 Hz, 1H), 6.93 (d, J=9.1 Hz, 1H), 4.63 (AB quart., 2H), 4.20-4.24 (m, 1H), 3.9 (s, 3H), 3.55-3.59 (m, 1H), 3.40-3.43 (m, 1H), 3.23-3.28 (m, 2H), 3.16-3.19 (m, 1H), 2.91-2.94 (m, 1H), 2.7-2.82 (m, 2H), 2.49-2.52 (m, 2H), 2.37-2.42 (m, 1H).

This material, as a solution in MeOH, was treated with an excess of 4M HCl in dioxane and evaporated to dryness to provide the dihydrochloride salt of the title compound.

Example 106

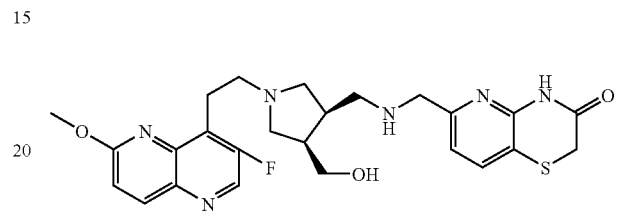

Preparation of (±)-6-[({[(3R,4R)/(3S,4S)-1-{2-[3-fluoro-6-(methyloxy)-1,5-naphthyridin-4-yl]ethyl}-4-(hydroxymethyl)-3-pyrrolidinyl]methyl}amino)methyl]-2H-pyrido[3,2-b][1,4]thiazin-3(4H)-one (8)

a) N-Benzyl-N-cyanomethyl-N-trimethylsilylmethylamine

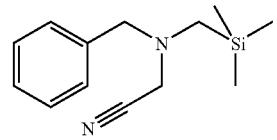

To trimethylsilylbenzyl amine (Aldrich; 10 g, 52 mmol) at room temperature was added HCl (1N, 51.6 mL) which caused formation of white precipitate. To the mixture were added THF (28 mL), KCN (4.2 g, 64 mmol) and formaldehyde (4.96 mL, 55 mmol, 37% solution in water). The resulting mixture was stirred overnight at room temperature. The resulting mixture was extracted with ether, washed with H O, NaCl, dried over Na SO4 and concentrated under reduce pressure to give desired product as liquid (12.7 g, 100%). LC/MS 233 (M+H).

b) (±)-Ethyl(3S,4R)/(3R,4S)-4-cyano-1-(phenylmethyl)-3-pyrrolidinecarboxylate

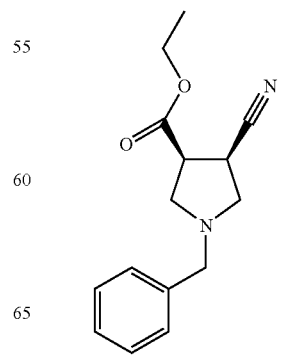

To a solution of N-benzyl-N-cyanomethyl-N-trimethylsilylmethylamine (11.7 g, 50 mmol) in CH CN (160 mL) was added ethyl-cis-beta-cyanoacrylate (Aldrich, 6.62 g, 53 mmol) followed by AgF (6.7 g, 53 mmol). The resulting mixture was stirred overnight at room temperature in the dark. The resulting mixture was diluted with CH Cl and filtered through the pad of celite. Chromatography on silica gel eluting with 80:20 CHCl-EtOAc gave desired product as oil (6.9 g, 54%). LC/MS 259 (M+H).

c) (±)-[(3S,4S)/(3R,4R)-4-(aminomethyl)-1-(phenylmethyl)-3-pyrrolidinyl]methanol

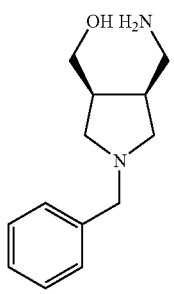

To a cooled solution of ethyl(3RS,4RS)-4-cyano-1-(phenylmethyl)-3-pyrrolidinecarboxylate (4 g, 15 mmol) in THF (80 mL) was added LiAlH (31 mL, 31 mmol, 1N solution in THF). The resulting mixture was stirred at 0° C. for 2 hour. The reaction mixture was quenched with 2 mL H O, 2.4 mL of NaOH (40%) followed by 5.4 mL of H 0. The resulting gel cake was filtered through the pad of celite. Organic layer concentrated under reduce pressure to give desired product as oil (3.26 g, 95%). LC/MS 221 (M+H).

d) (±)-1,1-dimethylethyl[(3S,4S)/(3R/4R)-4-[({[(1,1-dimethylethyl)oxy]carbonyl}amino)methyl]-1-(phenylmethyl)-3-pyrrolidinyl]methyl carbonate

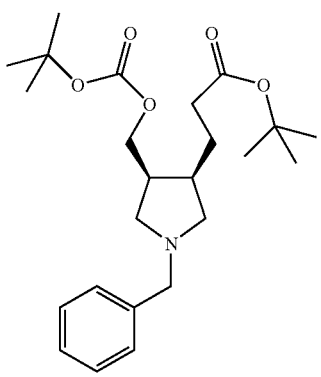

To a solution of [(3RS,4RS)-4-(aminomethyl)-1-(phenylmethyl)-3-pyrrolidinyl]methanol (3.26 g, 14.8 mmol) in CH Cl (50 mL) was added Boc-anydride (7.1 g, 32 mmol) followed by Triethylamine (10.3 mL, 75 mmol). The resulting mixture was stirred at room temperature for 24 hours. The resulting mixture was diluted with CH Cl, washed with H O, brine, dried over MgSO. Chromatography on silica gel eluting with 5:20 EtOAc-hexane gave desired product as oil (2.8 g, 45%). LC/MS 421 (M+H).

e) (±)-1,1-dimethylethyl[(3S,4R)/(3R,4S)-4-[({[(1,1-dimethylethyl)oxy]carbonyl}amino)methyl]-3-pyrrolidinyl]methyl carbonate

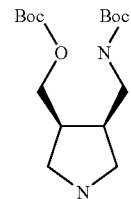

To a solution of 1,1-dimethylethyl[(3RS,4RS)-4-[({[(1,1-dimethylethyl)oxy]carbonyl}amino)methyl]-1-(phenylmethyl)-3-pyrrolidinyl]methyl carbonate (1.85 g, 4.4 mmol) in MeOH (50 mL) was added 10% Pd over carbon (1.5 g). The resulting mixture was shaken in the Parr Shaker at 50 psi of H at room temperature for 24 hours. The resulting mixture was diluted with MeOH and filtered through the pad of celite. The organic layer was concentrated under reduce pressure to give desired product as an oil (1.2 g, 82%). LC/MS 330 (M+H).

f) (±)-1,1-dimethylethyl((3R,4R)/(3S,4S)-4-[({[(1,1-dimethylethyl)oxy]carbonyl}amino)methyl]-1-{2-[3-fluoro-6-(methyloxy)-1,5-naphthyridin-4-yl]ethyl}-3-pyrrolidinyl)methyl carbonate

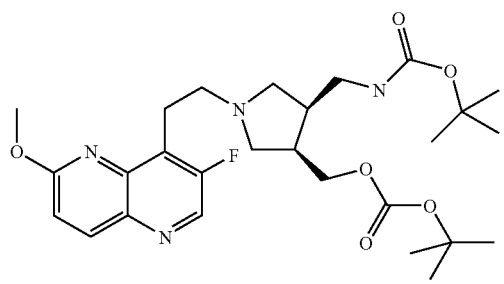

To a solution of 8-ethenyl-7-fluoro-2-(methyloxy)-1,5-naphthyridine (0.74 g, 3.6 mmol) in DMF (2 mL) was added 1,1-dimethylethyl[(3RS,4RS)-4-[({[(1,1-dimethylethyl)oxy]carbonyl}amino)methyl]-3-pyrrolidinyl]methyl carbonate (1.2 g, 3.6 mmol). After 24 h at 100° C., the reaction contents were concentrated under vacuum and purified on silica (CHCl₃/MeOH, 9:1 containing 5% NH₄OH) to give the title compound (1.43 g, 73%) as yellow oil: LC-MS (ES) m/e 535 (M+H)⁺.

g) (±)-((3R,4R)/(3S,4S)-4-(aminomethyl)-1-{2-[3-fluoro-6-(methyloxy)-1,5-naphthyridin-4-yl]ethyl}-3-pyrrolidinyl)methanol

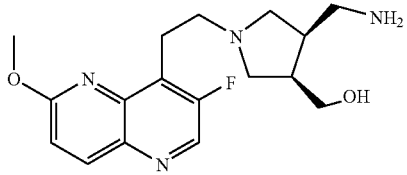

To a stirred solution of 1,1-dimethylethyl((3RS,4RS)-4-[({[(1,1-dimethylethyl)oxy]carbonyl}amino)methyl]-1-{2-

[3-fluoro-6-(methyloxy)-1,5-naphthyridin-4-yl]ethyl}-3-pyrrolidinyl)methyl carbonate (1.32 g, 2.4 mmol) in DCM (10 mL) was added 4M HCl (2.5 mL, 4M in dioxane). After 3 h at RT, the suspension was concentrated under vacuum and afforded the title compound (0.8 g, 100%) as light yellow solid: LC-MS (ES) m/e 335 (M+H)+.

h) (±)-6-[({[(3R,4R)/(3S,4S)-1-{2-[3-fluoro-6-(methyloxy)-1,5-naphthyridin-4-yl]ethyl}-4-(hydroxymethyl)-3-pyrrolidinyl]methyl}amino)methyl]-2H-pyrido[3,2-b][1,4]thiazin-3(4H)-one

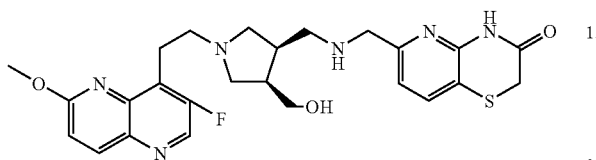

To a solution of ((3RS,4RS)-4-(aminomethyl)-1-{2-[3-fluoro-6-(methyloxy)-1,5-naphthyridin-4-yl]ethyl}-3-pyrrolidinyl)methanol (0.12 g, 0.27 mmole) in dry CH$_2$Cl$_2$ (3 mL) and dry MeOH (3 mL) at RT was added 3-oxo-3,4-dihydro-2H-pyrido[3,2-b][1,4]thiazine-6-carbaldehyde (60 mg, 0.27 mmole) followed by NaHCO3 (02 g, 2.7 mmol). After 24 h, at RT was added NaBH$_4$ (79 mg, 2.08 mmole). After 2 h, silica gel (5 g) was added to the reaction solution and the suspension was concentrated under vacuum to a dry solid. Purification on silica (CHCl$_3$/MeOH, 9:1 containing 5% NH$_4$OH) afforded the title compound (0.04 g, 28%) as light yellow solid: LC-MS (ES) m/e 513 (M+H)+. $^1$H NMR (400 MHz, CDCl) δ ppm 2.10-2.20 (2H, m) 2.49-2.60 (1H, m) 2.61-2.71 (1H, m) 2.71-2.91 (3H, m) 3.02-3.13 (2H, m) 3.37 (2H, t, J=7.33 Hz) 3.42-3.53 (4H, m) 3.69 (1H, dd, J=11.75, 9.47 Hz) 3.74-3.86 (2H, m) 3.97 (1H, s) 4.07 (3H, s) 6.90 (1H, d, J=7.83 Hz) 7.06 (1H, d, J=9.09 Hz) 7.57 (1H, d, J=7.83 Hz) 8.17 (1H, d, J=9.09 Hz) 8.60 (1H, s).

Example 107

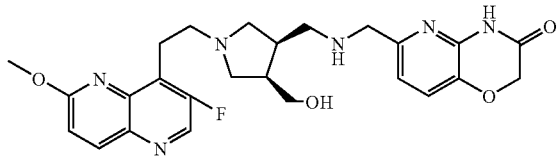

Preparation of (±)-6-[({[(3R,4R)/(3S,4S)-1-{2-[3-fluoro-6-(methyloxy)-1,5-naphthyridin-4-yl]ethyl}-4-(hydroxymethyl)-3-pyrrolidinyl]methyl}amino)methyl]-2H-pyrido[3,2-b][1,4]thiazin-3(4H)-one Prepared essentially according to the procedure for Example 106, except substituting 3-oxo-3,4-dihydro-2H-pyrido[3,2-b][1,4]oxazine-6-carbaldehyde for 3-oxo-3,4-dihydro-2H-pyrido[3,2-b][1,4]thiazine-6-carbaldehyde, the title compound (300 mg, 23%) was prepared as a light yellow solid: LC-MS (ES) m/e 497 (M+H)+. 1H NMR (400 MHz, CDCl) δ ppm 2.10-2.20 (2H, m) 2.49-2.60 (1H, m) 2.61-2.71 (1H, m) 2.71-2.91 (3H, m) 3.02-3.13 (2H, m) 3.37 (2H, t, J=7.33 Hz) 3.42-3.53 (4H, m) 3.69 (1H, dd, J=11.75, 9.47 Hz) 4.9 (2H, m) 3.97 (1H, s) 4.07 (3H, s) 6.90 (1H, d, J=7.83 Hz) 7.06 (1H, d, J=9.09 Hz) 7.57 (1H, d, J=7.83 Hz) 8.17 (1H, d, J=9.09 Hz) 8.60 (1H, s).

Enantiomers were separated on chiral prep HPLC (chiralpak AS-H) of 210 mg racemate to give E1 (85 mg; E1 retention time 3.78 min>98% ee), E2 (85 mg; E2 retention time 4.39 min>98.4% ee), Example 108

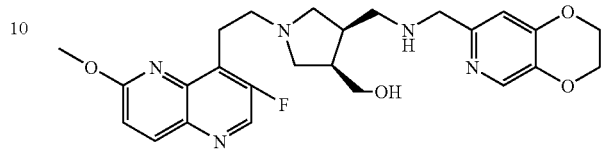

Preparation of (±)-((3R,4R)/(3S,4S)-4-{[(2,3-dihydro[1,4]dioxino[2,3-c]pyridin-7-ylmethyl)amino]methyl}-1-{2-[3-fluoro-6-(methyloxy)-1,5-naphthyridin-4-yl]ethyl}-3-pyrrolidinyl)methanol Prepared essentially according to the procedure of Example 106, except substituting 2,3-dihydro[1,4]dioxino[2,3-c]pyridine-7-carbaldehyde (126 mg, 0.76 mmole) for 3-oxo-3,4-dihydro-2H-pyrido[3,2-b][1,4]thiazine-6-carbaldehyde, the title compound (100 mg, 27%) was prepared as a light yellow solid: LC-MS (ES) m/e 484 (M+H)+. H NMR (400 MHz, CDCl) δ ppm 2.00-2.14 (1H, m) 2.55 (1H, d, J=6.82 Hz) 2.61-2.88 (4H, m) 3.01-3.18 (1H, m) 3.37 (1H, t, J=7.83 Hz) 3.47 (1H, dd, J=11.75, 3.16 Hz) 3.62-3.84 (3H, m) 4.07 (3H, s) 4.21-4.42 (6H, m) 6.75 (1H, s) 7.06 (1H, d, J=9.09 Hz) 7.25-7.33 (1H, m) 8.13-8.23 (1H, m) 8.60 (1H, s).

Example 109

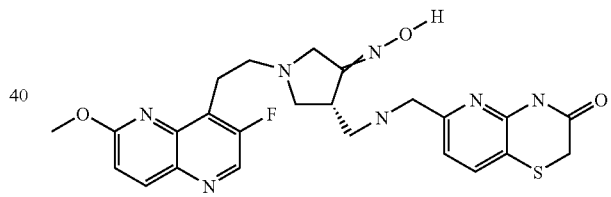

Preparation of 6-[({[(3R,4Z)-1-{2-[3-fluoro-6-(methyloxy)-1,5-naphthyridin-4-yl]ethyl}-4-(hydroxyimino)-3-pyrrolidinyl]methyl}amino)methyl]-2H-pyrido[3,2-b][1,4]thiazin-3(4H)-one a) 1,1-dimethylethyl(4R)-3-oxo-4-[({[(phenylmethyl)oxy]carbonyl}amino)methyl]-1-pyrrolidinecarboxylate

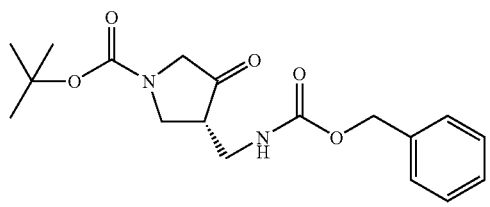

Dissolve 1,1-dimethylethyl(3R,4R)-3-hydroxy-4-[({[(phenylmethyl)oxy]carbonyl}amino)methyl]-1-pyrrolidinecarboxylate (1.0 g, 2.85 mmol) in methylene chloride (20 mL). Add PCC (1.23 g, 5.7 mmol) and Florisil (2.5 g) and stir at ambient temperature for 16 hours. Add 3 more equivalents of PCC (1.84 g, 8.55 mmol) and stir for 48 hours. Dilute solution with ether and filter through a pad of celite. The solvent was removed under reduced pressure yielding a crude oil. The crude mixture was purified on silica gel. (0.598 g, 60%). LCMS: m/z 349.4 (MH+).

b) 1,1-dimethylethyl(3Z,4R)-3-(hydroxyimino)-4-[({[(phenylmethyl)oxy]carbonyl}amino)methyl]-1-pyrrolidinecarboxylate

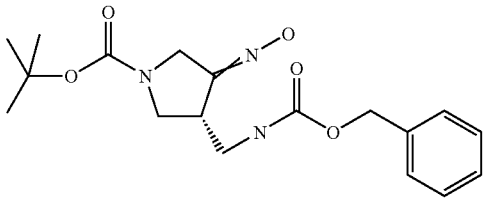

Dissolve 1,1-dimethylethyl(4R)-3-oxo-4-[({[(phenylmethyl)oxy]carbonyl}amino)methyl]-1-pyrrolidinecarboxylate (0.87 g, 2.49 mmol) in 5:1 MeOH/H O (10 mL). Add in hydroxylamine HCl (0.177 g, 2.54 mmol) and sodium acetate (2.04 g, 24.9 mmol). The mixture was heated to reflux and allowed to stir 3 hours. After the reaction was complete the solution was concentrated under reduced pressure and extracted with CHCl3 (3×). The organic layer was washed with 0.5 M HCl and brine. The solution was dried over $Na_2SO_4$, and evaporated to yield an oil. (0.90 g, quant). LCMS: m/z 364.6 (MH+).

c) Phenylmethyl {[(3S,4Z)-4-(hydroxyimino)-3-pyrrolidinyl]methyl}carbamate HCl salt

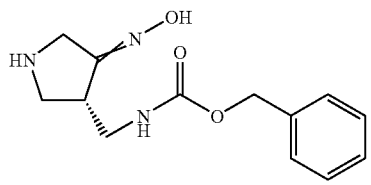

Dissolve 1,1-dimethylethyl(3Z,4R)-3-(hydroxyimino)-4-[({[(phenylmethyl)oxy]carbonyl}amino)methyl]-1-pyrrolidinecarboxylate (0.90 g, 2.53 mmol) in methylene chloride (10 mL). Add HCl/dioxane (excess) and stir at ambient temperature for 3 hours. Concentrate solution under reduced pressure. (0.66 g, quant). LCMS: m/z 254.4 (MH+).

d) Phenylmethyl {[(3R,4Z)-1-{2-[3-fluoro-6-(methyloxy)-1,5-naphthyridin-4-yl]ethyl}-4-(hydroxyimino)-3-pyrrolidinyl]methyl}carbamate

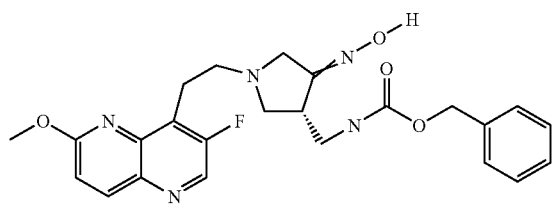

To 3-Fluoro-6-methoxy-4-vinyl-quinoline (0.554 g, 2.72 mmol) was added DMF (2.0 mL). Phenylmethyl {[(3S,4Z)-4-(hydroxyimino)-3-pyrrolidinyl]methyl}carbamate (0.66 g, 2.21 mmol) and TEA (0.76 mL, 5.44 mmol) were added to the mixture and the reaction was heated and stirred at 90 degrees C. for 18 hours. The solution was concentrated under reduced pressure and was chromatographed on silica gel to yield an oil (0.180 g, 18%). LCMS: m/z 468.4 (MH+).

e) (3Z,4R)-4-(aminomethyl)-1-{2-[3-fluoro-6-(methyloxy)-1,5-naphthyridin-4-yl]ethyl}-3-pyrrolidinone oxime

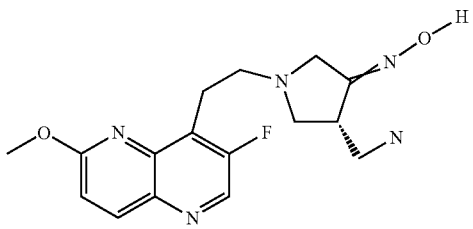

Phenylmethyl {[(3R,4Z)-1-{2-[3-fluoro-6-(methyloxy)-1,5-naphthyridin-4-yl]ethyl}-4-(hydroxyimino)-3-pyrrolidinyl]methyl}carbamate (0.180 g, 0.39 mmol) was dissolved in 1:1 (MeOH/THF) (10 mL). Catalytic 10% Palladium on carbon was added and the solution subjected to H at 55 PSI on a Parr shaker for 6 hours. The solution was filtered through a pad of celite and concentrated under reduced pressure. (0.174 g, quant.) LCMS: m/z 334.4 (MH+).

f) 6-[({[(3R,4Z)-1-{2-[3-fluoro-6-(methyloxy)-1,5-naphthyridin-4-yl]ethyl}-4-(hydroxyimino)-3-pyrrolidinyl]methyl}amino)methyl]-2H-pyrido[3,2-b][1,4]thiazin-3(4H)-one

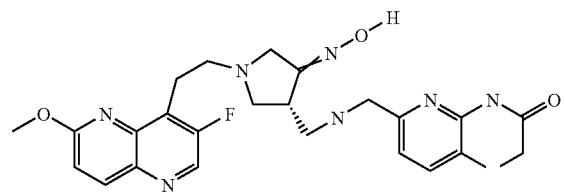

(3Z,4R)-4-(aminomethyl)-1-{2-[3-fluoro-6-(methyloxy)-1,5-naphthyridin-4-yl]ethyl}-3-pyrrolidinone oxime (0.087 g, 0.261 mmol) was dissolved in a 1:1 mixture of $CH_2Cl_2$/MeOH (10 mL). 3-Oxo-3,4-dihydro-2H-pyrido[3,2-b][1,4]thiazine-6-carbaldehyde (0.048 g, 0.261 mmol) was added followed by $NaHCO_3$ (0.109 g, 1.30 mmol). The solution was allowed to stir at ambient temperature for 17 hours. It was then cooled to 0 degrees C., excess sodium borohydride was added (0.010 g, 0.261 mmol) and it was allowed to stir at ambient temperature for 1 hour. The reaction mixture was poured into a saturated solution of $NaHCO_3$ and extracted with $CHCl_3$. (3×). The organic layer was washed with water (2×) and brine, dried over $Na_2SO_4$, and evaporated to yield a yellow oil. This was chromatographed on silica gel (90:10:1 $CHCl_3$/MeOH/$NH_4OH$) to yield an off-white solid (0.047 g, 35%). The di-HCl salt was then prepared by dissolving the product in chloroform and adding 2 equivalents of HCl/ether. The solution was stirred for 15 minutes and the solvent removed under reduced pressure yielding an off white solid (0.042 g). LCMS: m/z 512.4 (MH+). 1H NMR (400 MHz, CHLOROFORM-d) δ ppm 2.52 (1H, s) 2.82 (1H, s) 2.85 (2H, d, J=6.82 Hz) 3.00 (2H, s) 3.07-3.19 (2H, m) 3.34-3.46 (6H, m) 3.72-3.83 (2H, m) 3.83-3.93 (1H, m) 4.03-4.10 (3H, m)

6.86 (1H, d, J=7.83 Hz) 6.99-7.08 (1H, m) 7.49 (1H, d, J=7.83 Hz) 8.11-8.20 (1H, m) 8.54-8.63 (1H, m).

Example 110

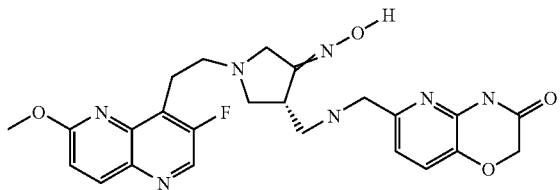

Preparation of 6-[({[(3R,4Z)-1-{2-[3-fluoro-6-(methyloxy)-1,5-naphthyridin-4-yl]ethyl}-4-(hydroxyimino)-3-pyrrolidinyl]methyl}amino)methyl]-2H-pyrido[3,2-b][1,4]oxazin-3(4H)-one (3Z,4R)-4-(aminomethyl)-1-{2-[3-fluoro-6-(methyloxy)-1,5-naphthyridin-4-yl]ethyl}-3-pyrrolidinone oxime (0.098 g, 0.294 mmol) was dissolved in a 1:1 mixture of CH₂Cl₂/MeOH (10 mL). 3-oxo-3,4-dihydro-2H-pyrido[3,2-b][1,4]oxazine-6-carbaldehyde (0.052 g, 0.294 mmol) was added followed by NaHCO₃ (0.123 g, 1.47 mmol). The solution was allowed to stir at ambient temperature for 17 hours. It was then cooled to 0 degrees C., excess sodium borohydride was added (0.011 g, 0.294 mmol) and it was allowed to stir at ambient temperature for 1 hour. The reaction mixture was poured into a saturated solution of NaHCO₃ and extracted with CHCl₃. (3×). The organic layer was washed with water (2×) and brine, dried over Na₂SO₄, and evaporated to yield a yellow oil. This was chromatographed on silica gel (90:10:1 CHCl₃/MeOH/NH₄OH) to yield an off-white solid (0.110 g, 75%). The di-HCl salt was then prepared by dissolving the product in chloroform and adding 2 equivalents of HCl/ether. The solution was stirred for 15 minutes and the solvent removed under reduced pressure yielding an off white solid (0.12 g). LCMS: m/z 496.4 (MH+). H NMR (400 MHz, CHLOROFORM-d) δ ppm 2.51 (1H, t, J=8.21 Hz) 2.79-2.91 (3H, m) 2.94-3.05 (1H, m) 3.05-3.13 (1H, m) 3.19 (1H, t, J=7.96 Hz) 3.33-3.44 (3H, m) 3.71 (1H, d, J=13.89 Hz) 3.86 (2H, d, J=13.39 Hz) 4.02-4.13 (3H, s) 4.52-4.63 (2H, s) 6.80 (1H, d, J=8.08 Hz) 7.00 (1H, d) 7.10 (1H, d, J=7.83 Hz) 8.12 (1H, d, J=9.09 Hz) 8.56-8.64 (1H, s).

Example 111

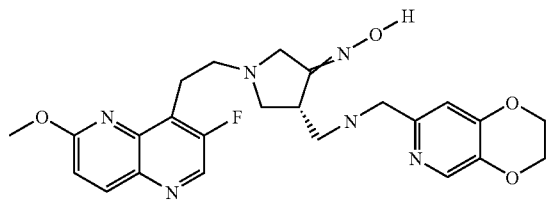

Preparation of (3Z,4R)-4-{[(2,3-dihydro[1,4]dioxino[2,3-c]pyridin-7-ylmethyl)amino]methyl}-1-{2-[3-fluoro-6-(methyloxy)-1,5-naphthyridin-4-yl]ethyl}-3-pyrrolidinone oxime (3Z,4R)-4-(aminomethyl)-1-{2-[3-fluoro-6-(methyloxy)-1,5-naphthyridin-4-yl]ethyl}-3-pyrrolidinone oxime (0.087 g, 0.261 mmol) was dissolved in a 1:1 mixture of CH₂Cl₂/MeOH (10 mL). 2,3-dihydro[1,4]dioxino[2,3-c]pyridine-7-carbaldehyde (0.043 g, 0.261 mmol) was added followed by NaHCO₃ (0.109 g, 1.30 mmol). The solution was allowed to stir at ambient temperature for 17 hours. It was then cooled to 0 degrees C., excess sodium borohydride was added (0.011 g, 0.294 mmol) and it was allowed to stir at ambient temperature for 1 hour. The reaction mixture was poured into a saturated solution of NaHCO₃ and extracted with CHCl₃. (3×). The organic layer was washed with water (2×) and brine, dried over Na₂SO₄, and evaporated to yield a yellow oil. This was chromatographed on silica gel (90:10:1 CHCl₃/MeOH/NH₄OH) to yield an off-white solid (0.083 g, 66%). The di-HCl salt was then prepared by dissolving the product in chloroform and adding 2 equivalents of HCl/ether. The solution was stirred for 15 minutes and the solvent removed under reduced pressure yielding an off white solid (0.085 g). LCMS: m/z 483.4 (MH+). 1H NMR (400 MHz, CHLOROFORM-d) δ ppm 2.50-2.58 (1H, m) 2.76-2.81 (1H, m) 2.82-2.94 (3H, m) 3.01-3.09 (1H, m) 3.12 (1H, m) 3.34-3.45 (3H, m) 3.73 (1H, m) 3.77-3.86 (2H, m) 4.05-4.15 (3H, m) 4.20-4.30 (2H, m) 4.32 (2H, dd, J=5.68, 2.40 Hz) 6.81-6.90 (1H, m) 7.07 (1H, d, J=9.09 Hz) 8.04-8.12 (1H, m) 8.18 (1H, d, J=8.84 Hz) 8.61 (1H, s).

Example 112

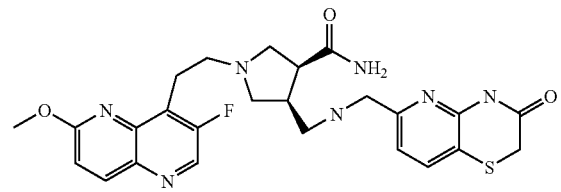

Preparation of (±)-(3S,4S)/(3R,4R)-1-{2-[3-fluoro-6-(methyloxy)-1,5-naphthyridin-4-yl]ethyl}-4-({[(3-oxo-3,4-dihydro-2H-pyrido[3,2-b][1,4]thiazin-6-yl)methyl]amino}methyl)-3-pyrrolidinecarboxamide a) (±)-(3S,4R)/(3R,4S)-4-cyano-1-(phenylmethyl)-3-pyrrolidinecarboxylic acid

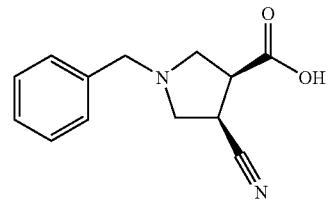

Dissolve ethyl(3S,4R)-4-cyano-1-(phenylmethyl)-3-pyrrolidinecarboxylate (2.0 g, 7.72 mmol) in 4:1 methanol/water (50 mL). The solution was cooled to 0 degrees C. and potassium hydroxide (0.867 g, 15.4 m, mol) was added. The reaction was allowed to stir at 0 degrees C. for 1 hour. 1 N HCl was added with cooling and the solution brought to pH=7. The solvent was removed under reduced pressure yielding a crude solid (3.244 g) which was taken on to the next step. LCMS: m/z 231.4 (MH+).

b) (±)-(3S,4R)/(3R,4S)-4-cyano-1-(phenylmethyl)-3-pyrrolidinecarboxamide

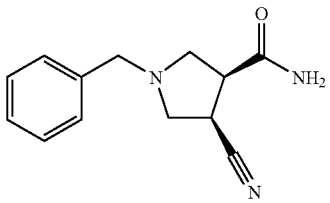

Crude (3S,4R)-4-cyano-1-(phenylmethyl)-3-pyrrolidinecarboxylic acid (3.24 g) was dissolved in THF (50 mL). N-methyl morpholine (0.93 mL, 8.49 mmol) was added and the solution allowed to stir overnight. A bit of solid remains undissolved. The solution was cooled to −15 degrees C. in an ethylene glycol/dry ice bath. Isobutyl chloroformate (1.1 mL, 8.49 mL) was added and the reaction stirred at −15 degrees C. for 1 hour. Ammonia was then bubbled through the solution for 20 minutes. The solution was allowed to warm to ambient temperature and the solvent removed under reduced pressure. The crude material was chromatographed on silica gel to yield a solid (1.56 g, 88% over 2 steps). LCMS: m/z 230.4 (MH+).

c) (±)-(3S,4S)/(3R,4R)-4-(aminomethyl)-1-(phenylmethyl)-3-pyrrolidinecarboxamide

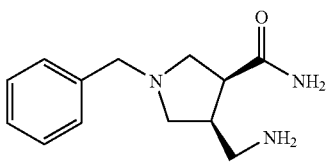

Dissolve (3S,4R)-4-cyano-1-(phenylmethyl)-3-pyrrolidinecarboxamide (1.50 g, 6.55 mmol) in methanol (10 mL). Add NiCl 6H O (3.11 g, 13.1 mmol) followed by NaBH (0.99 g, 26.2 mmol) portionwise. The reaction was stirred for 2 hours, but it was not complete. Additional NaBH (0.5 g) was added and the reaction stirred another 1 hour. The solution was filtered through a plug of celite and washed with methanol. The solvent was evaporated under reduced pressure yielding a crude oil (1.51 g). LCMS: m/z 234.4 (MH+).

d) (±)-1,1-dimethylethyl {[(3S,4S)/(3R,4R)-4-(aminocarbonyl)-1-(phenylmethyl)-3-pyrrolidinyl]methyl}carbamate

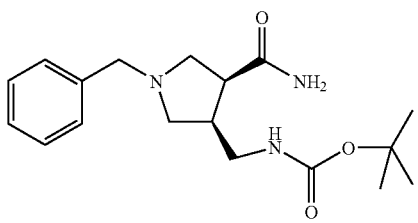

Crude (3S,4S)-4-(aminomethyl)-1-(phenylmethyl)-3-pyrrolidinecarboxamide (1.51 g, 6.55 mmol) was dissolved in CH Cl (20 mL). Triethylamine (1.0 mL, 7.21 mmol) was added followed by di-t-butyl dicarbonate (1.57 g, 7.21 mmol). The solution was stirred at ambient temperature for 4 hours. The solution was diluted with water and extracted 2 times with methylene chloride, washed with brine, dried over Na$_2$SO$_4$, and evaporated. This was chromatographed on silica gel to yield an off-white solid (0.49 g, 22%). LCMS: m/z 334.4 (MH+).

e) (±)-1,1-dimethylethyl {[(3R,4S)/(3S,4R)-4-(aminocarbonyl)-3-pyrrolidinyl]methyl}carbamate

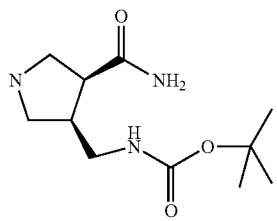

1,1-dimethylethyl {[(3S,4S)-4-(aminocarbonyl)-1-(phenylmethyl)-3-pyrrolidinyl]methyl}carbamate (0.49 g, 1.47 mmol) was dissolved in methanol (5.0 mL). Catalytic 20% palladium hydroxide was added and the solution subjected to H using a balloon. The reaction was allowed to stir 4 hours and then filtered through a plug of celite. The solution was concentrated under reduced pressure yielding an oil (0.34 g, 100%). LCMS: m/z 244.4 (MH+).

f) (±)-1,1-dimethylethyl[((3S,4S)/(3R,4R)-4-(aminocarbonyl)-1-{2-[3-fluoro-6-(methyloxy)-1,5-naphthyridin-4-yl]ethyl}-3-pyrrolidinyl)methyl]carbamate

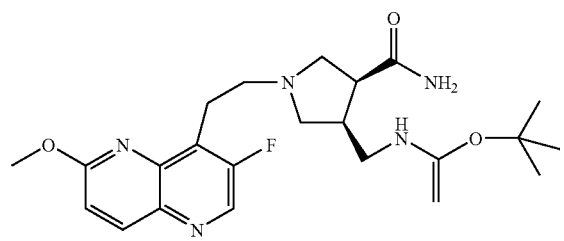

To 1,1-dimethylethyl {[(3R,4S)-4-(aminocarbonyl)-3-pyrrolidinyl]methyl}carbamate (0.34 g, 1.47 mmol) was added DMF (2.0 mL). 8-ethenyl-7-fluoro-2-(methyloxy)-1,5-naphthyridine (0.31 g, 1.52 mmol) was added to the mixture and the reaction was heated and stirred at 90 degrees C. for 18 hours. The solution was concentrated under reduced pressure and was chromatographed on silica gel to yield an oil (0.512 g, 78%). LCMS: m/z 448.4 (MH+).

g) (±)-(3S,4S)/(3R,4R)-4-(aminomethyl)-1-{2-[3-fluoro-6-(methyloxy)-1,5-naphthyridin-4-yl]ethyl}-3-pyrrolidinecarboxamide

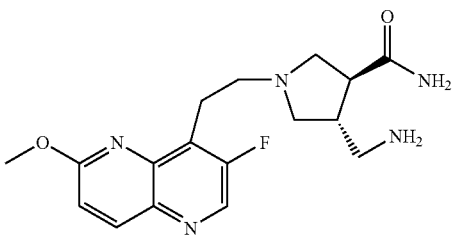

1,1-dimethylethyl[((3S,4S)-4-(aminocarbonyl)-1-{2-[3-fluoro-6-(methyloxy)-1,5-naphthyridin-4-yl]ethyl}-3-pyrrolidinyl)methyl]carbamate (0.51 g, 1.14 mmol) was dissolved in methylene chloride (5 mL). HCl in dioxane (2.87 mL, 11.14 mmol) was added and the solution stirred at ambient temperature for 2 hours. The solvent was removed under reduced pressure. (0.534 g, quant.) LCMS: m/z 348.4 (MH+).

h) (±)-(3S,4S)/(3R,4R)-1-{2-[3-fluoro-6-(methyloxy)-1,5-naphthyridin-4-yl]ethyl}-4-({[(3-oxo-3,4-dihydro-2H-pyrido[3,2-b][1,4]thiazin-6-yl)methyl]amino}methyl)-3-pyrrolidinecarboxamide

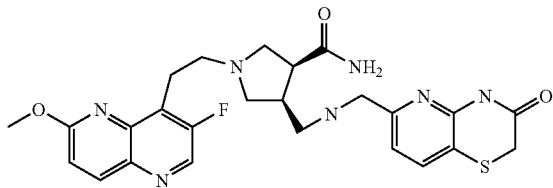

(±)-(3S,4S)/(3R,4R)-4-(aminomethyl)-1-{2-[3-fluoro-6-(methyloxy)-1,5-naphthyridin-4-yl]ethyl}-3-pyrrolidinecarboxamide (0.085 g, 0.246 mmol) was dissolved in a 1:1 mixture of $CH_2Cl_2$/MeOH (10 mL). 3-Oxo-3,4-dihydro-2H-pyrido[3,2-b][1,4]thiazine-6-carbaldehyde (0.045 g, 0.246 mmol) was added followed by $NaHCO_3$ (0.103 g, 1.23 mmol). The solution was allowed to stir at ambient temperature for 17 hours. It was then cooled to 0 degrees C., excess sodium borohydride was added (0.009 g, 0.246 mmol) and it was allowed to stir at ambient temperature for 1 hour. The reaction mixture was poured into a saturated solution of $NaHCO_3$ and extracted with $CHCl_3$. (3×). The organic layer was washed with water (2×) and brine, dried over $Na_2SO_4$, and evaporated to yield a yellow oil. This was chromatographed on silica gel (90:10:1 $CHCl_3$/MeOH/$NH_4OH$) to yield an off-white solid (0.106 g, 82%). The di-HCl salt was then prepared by dissolving the product in chloroform and adding 2 equivalents of HCl/ether. The solution was stirred for 15 minutes and the solvent removed under reduced pressure yielding an off white solid (0.113 g). LCMS: m/z 526.6 (MH+). 1H NMR (400 MHz, CDCl3) δ ppm 2.34 (1H, dd, J=8.97, 6.19 Hz) 2.51 (1H, d, J=4.04 Hz) 2.64-2.85 (5H, m) 2.85-2.95 (2H, m) 2.99 (1H, t, J=8.59 Hz) 3.07-3.17 (1H, m) 3.39 (2H, t, J=7.45 Hz) 3.47 (3H, d, J=1.01 Hz) 3.81 (2H, q, J=14.15 Hz) 4.07 (3H, s) 6.19 (1H, d, J=2.02 Hz) 6.91 (1H, d, J=7.83 Hz) 7.06 (1H, d, J=9.09 Hz) 7.55 (1H, d, J=7.83 Hz) 7.63 (1H, d, J=2.53 Hz) 8.17 (1H, d, J=8.84 Hz) 8.60 (1H, s).

Example 113

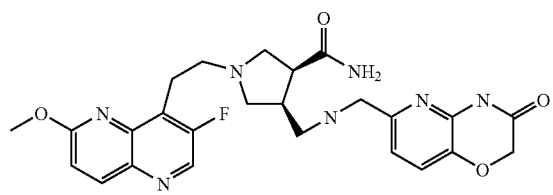

Preparation of (±)-(3S,4S)/(3R,4R)-1-{2-[3-fluoro-6-(methyloxy)-1,5-naphthyridin-4-yl]ethyl}-4-({[(3-oxo-3,4-dihydro-2H-pyrido[3,2-b][1,4]oxazin-6-yl)methyl]-amino}methyl)-3-pyrrolidinecarboxamide (±)-(3S,4S)/(3R,4R)-4-(aminomethyl)-1-{2-[3-fluoro-6-(methyloxy)-1,5-naphthyridin-4-yl]ethyl}-3-pyrrolidinecarboxamide (0.085 g, 0.246 mmol) was dissolved in a 1:1 mixture of $CH_2Cl_2$/MeOH (10 mL). 3-oxo-3,4-dihydro-2H-pyrido[3,2-b][1,4]oxazine-6-carbaldehyde (0.044 g, 0.246 mmol) was added followed by $NaHCO_3$ (0.103 g, 1.23 mmol). The solution was allowed to stir at ambient temperature for 17 hours. It was then cooled to 0 degrees C., excess sodium borohydride was added (0.009 g, 0.246 mmol) and it was allowed to stir at ambient temperature for 1 hour. The reaction mixture was poured into a saturated solution of $NaHCO_3$ and extracted with $CHCl_3$. (3×). The organic layer was washed with water (2×) and brine, dried over $Na_2SO_4$, and evaporated to yield a yellow oil. This was chromatographed on silica gel (90:10:1 $CHCl_3$/MeOH/$NH_4OH$) to yield an off-white solid (0.115 g, 92%). The di-HCl salt was then prepared by dissolving the product in chloroform and adding 2 equivalents of HCl/ether. The solution was stirred for 15 minutes and the solvent removed under reduced pressure yielding an off white solid (0.12 g). LCMS: m/z 510.6 (MH+). 1H NMR (400 MHz, CHLOROFORM-d) δ ppm 2.34 (1H, dd, J=9.09, 6.06 Hz) 2.45-2.59 (1H, m) 2.63-2.73 (1H, m) 2.73-2.83 (4H, m) 2.89-2.94 (1H, m) 2.99 (1H, t, J=8.59 Hz) 3.08-3.23 (1H, m) 3.39 (2H, t, J=7.45 Hz) 3.78 (2H, dd) 4.06 (13H, s) 4.60 (2H, s) 6.45 (1H, d, J=1.77 Hz) 6.85 (1H, d, J=8.08 Hz) 7.05 (1H, d, J=8.84 Hz) 7.15 (1H, d, J=8.08 Hz) 7.78 (1H, d, J=2.27 Hz) 8.16 (1H, d, J=9.09 Hz) 8.59 (1H, s)

Example 114

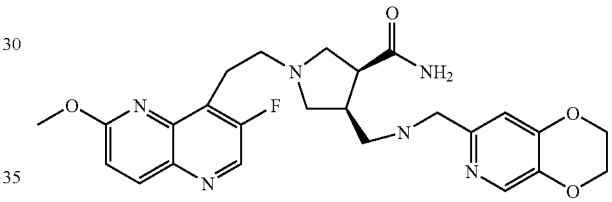

Preparation of (±)-(3S,4S)/(3R,4R)-4-{[(2,3-dihydro[1,4]dioxino[2,3-c]pyridin-7-ylmethyl)amino]methyl}-1-{2-[3-fluoro-6-(methyloxy)-1,5-naphthyridin-4-yl]ethyl}-3-pyrrolidinecarboxamide (±)-(3S,4S)/(3R,4R)-4-(aminomethyl)-1-{2-[3-fluoro-6-(methyloxy)-1,5-naphthyridin-4-yl]ethyl}-3-pyrrolidinecarboxamide (0.146 g, 0.380 mmol) was dissolved in a 1:1 mixture of $CH_2Cl_2$/MeOH (10 mL). 2,3-dihydro[1,4]dioxino[2,3-c]pyridine-7-carbaldehyde (0.380 g, 0.380 mmol) was added followed by $NaHCO_3$ (0.160 g, 1.90 mmol). The solution was allowed to stir at ambient temperature for 17 hours. It was then cooled to 0 degrees C., excess sodium borohydride was added (0.029 g, 0.760 mmol) and it was allowed to stir at ambient temperature for 1 hour. The reaction mixture was poured into a saturated solution of $NaHCO_3$ and extracted with $CHCl_3$. (3×). The organic layer was washed with water (2×) and brine, dried over $Na_2SO_4$, and evaporated to yield a yellow oil. This was chromatographed on silica gel (90:10:1 $CHCl_3$/MeOH/$NH_4OH$) to yield an off-white solid (0.130 g, 69%). The di-HCl salt was then prepared by dissolving the product in chloroform and adding 2 equivalents of HCl/ether. The solution was stirred for 15 minutes and the solvent removed under reduced pressure yielding an off white solid (0.141 g). LCMS: m/z 497.6 (MH+). 1H NMR (400 MHz, CHLOROFORM-d) δ ppm 2.36 (1H, dd, J=8.97, 5.94 Hz) 2.44 (1H, dd, J=7.96, 4.42 Hz) 2.57-2.67 (3H, m) 2.71-2.82 (3H, m) 2.84 (2H, d) 2.92-2.97 (1H, m) 3.11 (1H, dd, J=8.72, 4.93 Hz) 3.40 (2H, t, J=7.33 Hz) 3.71-3.82 (2H, m) 4.08 (3H, s) 4.26-4.35 (14H, m) 5.35 (1H, d, J=2.78 Hz) 6.75 (1H, s) 7.06 (1H, d, J=9.09 Hz) 7.70 (1H, d, J=2.78 Hz) 8.09 (1H, s) 8.16 (1H, d, J=9.09 Hz) 8.60 (1H, s).

Example 115

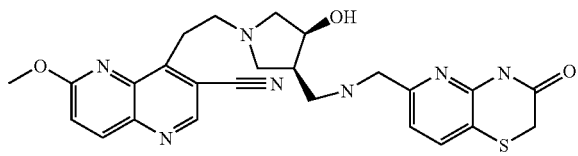

Preparation of 4-{2-[(3S,4S)-3-hydroxy-4-({[(3-oxo-3,4-dihydro-2H-pyrido[3,2-b][1,4]thiazin-6-yl)methyl]amino}methyl)-1-pyrrolidinyl]ethyl}-6-(methyloxy)-1,5-naphthyridine-3-carbonitrile a) 1,1-dimethylethyl(3S,4S)-3-(aminomethyl)-4-hydroxy-1-pyrrolidinecarboxylate

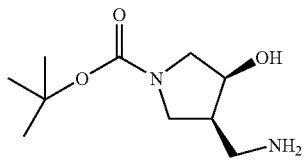

Dissolve 1,1-dimethylethyl(3S,4S)-3-hydroxy-4-[({[(phenylmethyl)oxy]carbonyl}amino)methyl]-1-pyrrolidinecarboxylate (0.75 g, 2.14 mmol) in methanol (10 mL). Add 20% PdOH (catalytic) and subject to H at 55 PSI on a Parr hydrogenation apparatus. The solution was filtered through a plug of celite and concentrated under reduced pressure to yield an oil. (0.712 g, quantitative) LCMS: m/z 133.2 (MH+).

b) (1,1-dimethylethyl(3S,4S)-3-hydroxy-4-{[(trifluoroacetyl)amino]methyl}-1-pyrrolidinecarboxylate

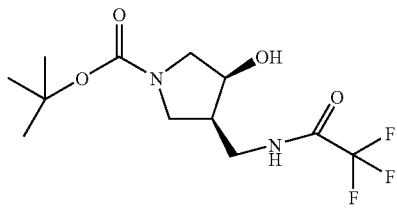

1,1-dimethylethyl(3S,4S)-3-(aminomethyl)-4-hydroxy-1-pyrrolidinecarboxylate (0.238 g, 1.10 mmol) was dissolved in methylene chloride (10 mL). Triethylamine (0.322 mL, 2.31 mmol), trifluoroacetic anhydride (0.163 mL, 1.16 mmol), and DMAP (0.013 g, 0.11 mmol) were added and the reaction stirred at ambient temperature for 5 hours. The reaction was quenched with water and extracted 3× with methylene chloride. The solution was dried over Na₂SO₄, and evaporated. This was chromatographed on silica gel to yield a white solid (0.193 g, 56%). LCMS: m/z 313.4 (MH+).

c) 2,2,2-trifluoro-N-{[(3R,4S)-4-hydroxy-3-pyrrolidinyl]methyl}acetamide

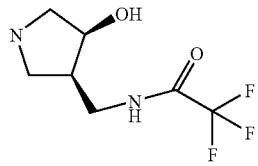

(1,1-dimethylethyl(3S,4S)-3-hydroxy-4-{[(trifluoroacetyl)amino]methyl}-1-pyrrolidinecarboxylate (0.192 g, 0.615 mmol) was dissolved in methylene chloride (5 mL). HCl in dioxane (1.0 mL, 4.0 mmol) was added and the solution stirred at ambient temperature for 2 hours. The solvent was removed under reduced pressure. (0.137 g, quant.) LCMS: m/z 213.2 (MH+).

d) N-[((3S,4S)-1-{2-[3-cyano-6-(methyloxy)-1,5-naphthyridin-4-yl]ethyl}-4-hydroxy-3-pyrrolidinyl)methyl]-2,2,2-trifluoroacetamide

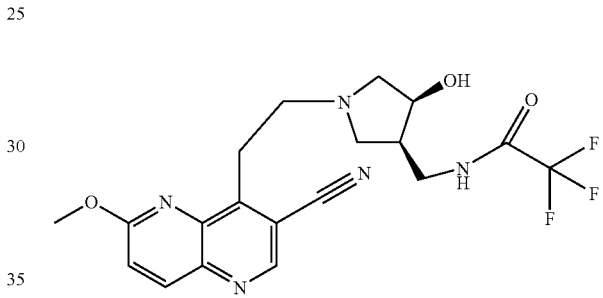

To 2,2,2-trifluoro-N-{[(3R,4S)-4-hydroxy-3-pyrrolidinyl]methyl}acetamide HCl (0.137 g, 0.552 mmol) was added EtOH (2.0 mL). 4-ethenyl-6-(methyloxy)-1,5-naphthyridine-3-carbonitrile (0.117 g, 0.552 mmol) was added to the mixture along with TEA (0.231 mL, 1.66 mmol) and the reaction was heated and stirred at 95 degrees C. for 18 hours, allowing the ethanol to evaporate. The solution was concentrated under reduced pressure and was chromatographed on silica gel to yield an oil (0.110 g, 47%). LCMS: m/z 424.4 (MH+).

e) 4-{2-[(3S,4S)-3-(aminomethyl)-4-hydroxy-1-pyrrolidinyl]ethyl}-6-(methyloxy)-1,5-naphthyridine-3-carbonitrile

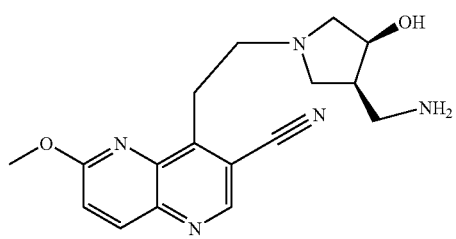

N-[((3S,4S)-1-{2-[3-cyano-6-(methyloxy)-1,5-naphthyridin-4-yl]ethyl}-4-hydroxy-3-pyrrolidinyl)methyl]-2,2,2-trifluoroacetamide (0.110 g, 0.26 mmol) was dissolved in methanol (5 mL). 10% aqueous K CO was added to the original solution and it was stirred at ambient temperature for 2 hours. The solution was extracted 3× with chloroform and washed with brine. The solvent was removed under reduced pressure. (0.076 g, 89%) LCMS: m/z 328.6 (MH+).

f) 4-{2-[(3S,4S)-3-hydroxy-4-({[(3-oxo-3,4-dihydro-2H-pyrido[3,2-b][1,4]thiazin-6-yl)methyl]amino}methyl)-1-pyrrolidinyl]ethyl}-6-(methyloxy)-1,5-naphthyridine-3-carbonitrile

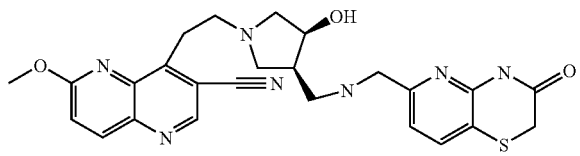

4-{2-[(3S,4S)-3-(aminomethyl)-4-hydroxy-1-pyrrolidinyl]ethyl}-6-(methyloxy)-1,5-naphthyridine-3-carbonitrile (0.070 g, 0.214 mmol) was dissolved in a 1:1 mixture of $CH_2Cl_2$/MeOH (10 mL). 3-Oxo-3,4-dihydro-2H-pyrido[3,2-b][1,4]thiazin-6-carbaldehyde (0.039 g, 0.214 mmol) was added followed by $NaHCO_3$ (0.090 g, 1.07 mmol). The solution was allowed to stir at ambient temperature for 17 hours. It was then cooled to 0 degrees C., excess sodium borohydride was added (0.024 g, 0.642 mmol) and it was allowed to stir at ambient temperature for 1 hour. The reaction mixture was poured into a saturated solution of $NaHCO_3$ and extracted with $CHCl_3$. (3×). The organic layer was washed with water (2×) and brine, dried over $Na_2SO_4$, and evaporated to yield a yellow oil. This was chromatographed on silica gel (90:10:1 $CHCl_3$/MeOH/$NH_4OH$) to yield an off-white solid (0.015 g, 14%). The di-HCl salt was then prepared by dissolving the product in chloroform and adding 2 equivalents of HCl/ether. The solution was stirred for 15 minutes and the solvent removed under reduced pressure yielding an off white solid (0.019 g). LCMS: m/z 506.4 (MH+). 1H NMR (400 MHz, CDCl3) δ ppm 2.42 (1H, d, J=5.05 Hz) 2.64 (1H, dd, J=9.22, 6.44 Hz) 2.76-2.88 (4H, m) 2.90-2.99 (3H, m) 3.40-3.51 (3H, m) 3.54-3.65 (2H, m) 3.74-3.84 (2H, m) 3.87-3.91 (1H, m) 4.04-4.14 (4H, m) 4.45 (1H, td, J=6.44, 3.28 Hz) 6.88 (1H, d, J=7.83 Hz) 7.22 (1H, d, J=9.09 Hz) 7.52-7.61 (1H, m) 8.22 (1H, d, J=9.09 Hz) 8.79-8.86 (1H, m).

Example 116

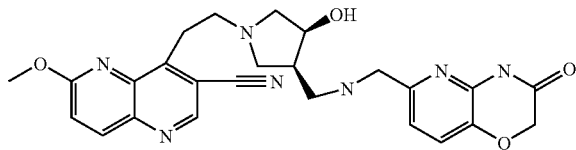

Preparation of 4-{2-[(3S,4S)-3-hydroxy-4-({[(3-oxo-3,4-dihydro-2H-pyrido[3,2-b][1,4]oxazin-6-yl)methyl]amino}methyl)-1-pyrrolidinyl]ethyl}-6-(methyloxy)-1,5-naphthyridine-3-carbonitrile 4-{2-[(3S,4S)-3-(aminomethyl)-4-hydroxy-1-pyrrolidinyl]ethyl}-6-(methyloxy)-1,5-naphthyridine-3-carbonitrile (0.070 g, 0.214 mmol) was dissolved in a 1:1 mixture of $CH_2Cl_2$/MeOH (10 mL). 3-oxo-3,4-dihydro-2H-pyrido[3,2-b][1,4]oxazine-6-carbaldehyde (0.038 g, 0.214 mmol) was added followed by $NaHCO_3$ (0.090 g, 1.07 mmol). The solution was allowed to stir at ambient temperature for 17 hours. It was then cooled to 0 degrees C., excess sodium borohydride was added (0.024 g, 0.642 mmol) and it was allowed to stir at ambient temperature for 1 hour. The reation mixture was poured into a saturated solution of $NaHCO_3$ and extracted with $CHCl_3$. (3×). The organic layer was washed with water (2×) and brine, dried over $Na_2SO_4$, and evaporated to yield a yellow oil. This was chromatographed on silica gel (90:10:1 $CHCl_3$/MeOH/$NH_4OH$) to yield an off-white solid (0.037 g, 35%). The di-HCl salt was then prepared by dissolving the product in chloroform and adding 2 equivalents of HCl/ether. The solution was stirred for 15 minutes and the solvent removed under reduced pressure yielding an off white solid (0.041 g). LCMS: m/z 490.4 (MH+). 1H NMR (400 MHz, CHLOROFORM-d) δ ppm 1.38 (1H, t, J=7.33 Hz) 2.59-2.69 (1H, m) 2.77 (1H, s) 2.80-2.88 (1H, m) 2.95 (3H, t, J=7.58 Hz) 3.00-3.14 (2H, m) 3.48 (2H, s) 3.53-3.62 (2H, m) 3.85-3.95 (1H, m) 4.09 (3H, s) 4.51-4.59 (3H, m) 6.89 (1H, d, J=8.08 Hz) 7.18 (1H, d, J=7.83 Hz) 7.21 (1H, d, J=9.09 Hz) 7.27 (1H, s) 8.19 (1H, d, J=9.09 Hz) 8.78 (1H, s).

Example 117

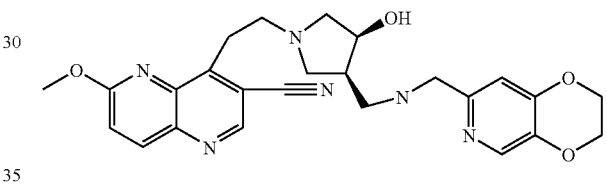

Preparation of 4-[2-((3S,4S)-3-{[(2,3-dihydro[1,4]dioxino[2,3-c]pyridin-7-ylmethyl)amino]methyl}-4-hydroxy-1-pyrrolidinyl)ethyl]-6-(methyloxy)-1,5-naphthyridine-3-carbonitrile 4-{2-[(3S,4S)-3-(aminomethyl)-4-hydroxy-1-pyrrolidinyl]ethyl}-6-(methyloxy)-1,5-naphthyridine-3-carbonitrile (0.070 g, 0.214 mmol) was dissolved in a 1:1 mixture of $CH_2Cl_2$/MeOH (10 mL). 2,3-dihydro[1,4]dioxino[2,3-c]pyridine-7-carbaldehyde (0.035 g, 0.214 mmol) was added followed by $NaHCO_3$ (0.090 g, 1.04 mmol). The solution was allowed to stir at ambient temperature for 17 hours. It was then cooled to 0 degrees C., excess sodium borohydride was added (0.024 g, 0.642 mmol) and it was allowed to stir at ambient temperature for 1 hour. The reaction mixture was poured into a saturated solution of $NaHCO_3$ and extracted with $CHCl_3$. (3×). The organic layer was washed with water (2×) and brine, dried over $Na_2SO_4$, and evaporated to yield a yellow oil. This was chromatographed on silica gel (90:10:1 $CHCl_3$/MeOH/$NH_4OH$) to yield an off-white solid (0.033 g, 32%). The di-HCl salt was then prepared by dissolving the product in chloroform and adding 2 equivalents of HCl/ether. The solution was stirred for 15 minutes and the solvent removed under reduced pressure yielding an off white solid (0.035 g). LCMS: m/z 497.6 (MH+). $^1$H NMR (400 MHz, CHLOROFORM-D) δ ppm 2.33-2.46 (1H, m) 2.55 (1H, dd, J=9.09, 7.07 Hz) 2.71 (1H, dd, J=9.85, 3.54 Hz) 2.80-2.87 (3H, m) 2.90 (2H, td, J=7.64, 4.42 Hz) 3.04 (1H, dd, J=9.98, 5.94 Hz) 3.60 (2H, t, J=7.71 Hz) 3.76 (2H, d, J=6.06 Hz) 4.08-4.16 (3H, m) 4.25-4.35 (5H, m) 4.47 (1H, td, J=6.44, 3.79 Hz) 6.73 (1H, s) 7.22 (1H, d, J=9.09 Hz) 8.10 (1H, s) 8.20 (1H, d, J=9.09 Hz) 8.82 (1H, s).

Example 118

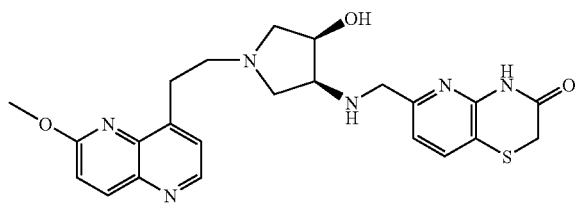

Preparation of (±)-6-{[((3S,4R)/(3R,4S)-4-hydroxy-1-{2-[6-(methyloxy)-1,5-naphthyridin-4-yl]ethyl}-3-pyrrolidinyl)amino]methyl}-2H-pyrido[3,2-b][1,4]thiazin-3(4H)-one a) phenylmethyl 2,5-dihydro-1H-pyrrole-1-carboxylate

To a solution of 2,5-dihydro-1H-pyrrole (3.3 mL, 43.4 mmol) and Et N (9 mL, 65.1 mmol) in DCM (200 mL) at 0° C. was added dropwise benzyl chloroformate (7.3 mL, 52 mmol). After 1 h, the solution was partitioned between H O-DCM. The organic phase was back extracted several times with DCM and the combined organic fractions were dried (Na SO), concentrated and purified via column chromatography (silica, DCM) yielding the title compound (6 g, 68%) as a yellow oil: LCMS ES (m/e) 204 (M+H).

b) phenylmethyl(±)-(3S,4R)/(3R,4S)-3-({[(1,1-dimethylethyl)oxy]carbonyl}amino)-4-hydroxy-1-pyrrolidinecarboxylate

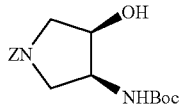

To a solution of Boc-carbamate (3.57 g, 30.54 mmol) in nPrOH (93 mL) at 25° C. was added an NaOH solution (44 mL, prepared from 1.2 g of NaOH in 49 mL H O) followed by tBuOCl (3.45 mL, 30.05 mmol). After 15 min, phenylmethyl 2,5-dihydro-1H-pyrrole-1-carboxylate (2 g, 9.85 mmol) in nPrOH (5 mL) was added followed by K OsO (OH) (145 mg, 0.394 mmol) dissolved in the remaining NaOH solution prepared above (5 mL). After 1 h, the solution was extracted with EtOAc, concentrated and purified via column chromatography (2% MeOH in DCM (1% NH OH)) yielding the title compound (1 g, contaminated with residual Boc-carbamate) as a clear oil: LCMS (ES) m/e 281 (M+H).

c) (±)-1,1-dimethylethyl[(3S,4R)/(3R,4S)-4-hydroxy-3-pyrrolidinyl]carbamate

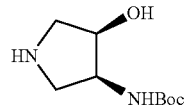

To a solution of phenylmethyl(3S,4R)-3-({[(1,1-dimethylethyl)oxy]carbonyl}amino)-4-hydroxy-1-pyrrolidinecarboxylate (~1 g, 2.98 mmol) in EtOH (30 mL) was added Pd(OH) (600 mg, 60 wt. %). The reaction stirred under 1 atm of H for 12 h, was filtered through Celite, concentrated and purified via column chromatography (silica, 3-10% MeOH in DCM (1% NH OH)) yielding the title compound (400 mg, 20%-2 steps) as a white solid: LCMS (ES) m/e 147 (M-tBu).

d) (±)-1,1-dimethylethyl((3S,4R)/(3R,4S)-4-hydroxy-1-{2-[6-(methyloxy)-1,5-naphthyridin-4-yl]ethyl}-3-pyrrolidinyl)carbamate

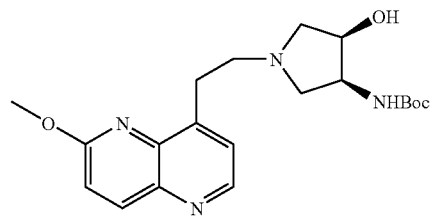

A solution of 1,1-dimethylethyl[(3S,4R)-4-hydroxy-3-pyrrolidinyl]carbamate (200 mg, 0.990 mmol) and 8-ethenyl-2-(methyloxy)-1,5-naphthyridine (184 mg, 0.990 mmol) in EtOH (1 mL) was stirred at 85° C. over 12 h. The slurry was concentrated and the residue purified via column chromatography (silica, 2.5% MeOH in DCM (1% NH OH)) yielding the title compound (327 mg, 85%) as a yellow foam: LCMS (ES) m/e 389 (M+H).

e) (±)-(3R,4S)/(3S,4R)-4-amino-1-{2-[6-(methyloxy)-1,5-naphthyridin-4-yl]ethyl}-3-pyrrolidinol

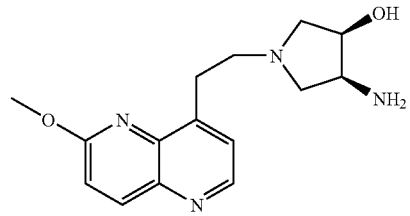

To a solution of 1,1-dimethylethyl((3S,4R)-4-hydroxy-1-{2-[6-(methyloxy)-1,5-naphthyridin-4-yl]ethyl}-3-pyrrolidinyl)carbamate (327 mg, 0.843 mmol) in MeOH (4 mL) at 25° C. was added dropwise a 4M HCl in dioxane solution (1.5 mL, 5.9 mmol). After 12 h, the solution was concentrated and the residue neutralized with excess MP carbonate resin in DCM to afford the title compound (242 mg, quant.) as a yellow oil: LCMS (ES) m/e 289 (M+H).

f) (±)-6-{[((3S,4R)/(3R,4S)-4-hydroxy-1-{2-[6-(methyloxy)-1,5-naphthyridin-4-yl]ethyl}-3-pyrrolidinyl)amino]methyl}-2H-pyrido[3,2-b][1,4]thiazin-3(4H)-one (GSK675294)

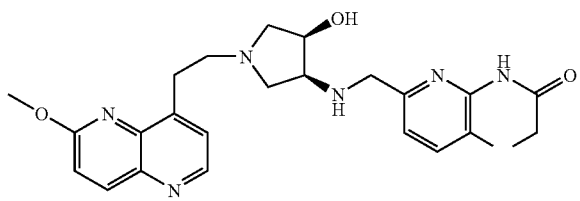

A solution of (3R,4S)-4-amino-1-{2-[6-(methyloxy)-1,5-naphthyridin-4-yl]ethyl}-3-pyrrolidinol (120 mg, 0.417 mmol), 3-oxo-3,4-dihydro-2H-pyrido[3,2-b][1,4]thiazine-6-carbaldehyde (81 mg, 0.417 mmol) and Na SO (89 mg, 0.625 mmol) in DCM-MeOH (2 mL, 5:1) was stirred at 25° C. over 12 h. NaBH(OAc) (132 mg, 0.626 mmol) was then added in one portion. After an additional 2 h, the solution was partitioned between NaHCO (sat)-DCM. The aqueous phase was back extracted several times with DCM and the combined organic fractions were dried (Na SO), concentrated and purified via column chromatography (silica, 2% MeOH in DCM (1% NH OH)) yielding the title compound (89 mg, 46%) as a yellow solid: LCMS (ES) m/e 467 (M+H); H NMR (CD OD, 400 MHz) δ 8.63 (d, J=4.5 Hz, 1H), 8.19 (d, J=9.0 Hz, 1H), 7.70 (d, J=7.8 Hz, 1H), 7.60 (d, J=4.5 Hz, 1H), 7.23 (d, J=9.0 Hz, 1H), 7.05 (d, J=7.8 Hz, 1H), 4.25-4.27 (m, 1H), 4.12 (s, 3H), 3.85 (AB quart., 2H), 3.52 (s, 2H), 3.35-3.45 (m, 2H), 3.22-3.30 (m, 2H), 3.11-3.16 (m, 1H), 2.98-3.02 (m, 2H), 2.72-2.75 (m, 1H), 2.57-2.61 (m, 1H).

Example 119

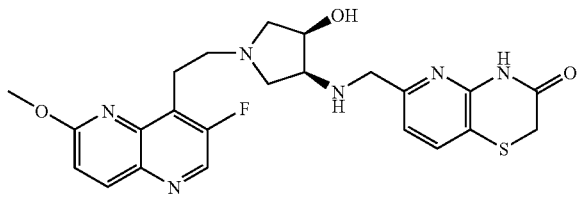

Preparation of (±)-6-{[((3S,4R)/(3R,4S)-1-{2-[3-fluoro-6-(methyloxy)-1,5-naphthyridin-4-yl]ethyl}-4-hydroxy-3-pyrrolidinyl)amino]methyl}-2H-pyrido[3,2-b][1,4]thiazin-3(4H)-one The title compound (65 mg, 31%) was prepared as a yellow solid essentially according to Example 118, except substituting 8-ethenyl-7-fluoro-2-(methyloxy)-1,5-naphthyridine (202 mg, 0.990 mmol) for 8-ethenyl-2-(methyloxy)-1,5-naphthyridine: LCMS (ES) m/e 485 (M+H); H NMR (CD OD, 400 MHz) δ 8.65 (s, 1H), 8.21 (d, J=9.0 Hz, 1H), 7.70 (d, J=7.8 Hz, 1H), 7.19 (d, J=9.0 Hz, 1H), 7.05 (d, J=7.8 Hz, 1H), 4.23-4.26 (m, 1H), 4.13 (s, 3H), 3.85 (AB quart., 2H), 3.52 (s, 2H), 3.42-3.48 (m, 2H), 3.23-3.29 (m, 2H), 3.12-3.16 (m, 1H), 2.93-2.97 (m, 2H), 2.70-2.74 (m, 1H), 2.56-2.60 (m, 1H).

Example 120

Antimicrobial Activity Assay

Whole-cell antimicrobial activity was determined by broth microdilution using the National Committee for Clinical Laboratory Standards (NCCLS) recommended procedure, Document M7-A6, "Methods for Dilution Susceptibility Tests for Bacteria that Grow Aerobically". The compounds were tested in serial two-fold dilutions ranging from 0.016 to 16 mcg/mL.

Compounds were evaluated against a panel of Gram-positive organisms, including *Staphylococcus aureus, Streptococcus pneumoniae, Streptococcus pyogenes, Enterococcus faecalis* and *Enterococcus faecium*.

In addition, compounds were evaluated against a panel of Gram-negative strains including *Haemophilus influenzae, Moraxella catarrhalis, Escherichia coli, Pseudomonas aeruginosa, Proteus mirabilis, Enterobacter cloacae, Enterobacter aerogenes, Klebsiella pneumoniae* and *Stenotrophomonas maltophilia*.

The minimum inhibitory concentration (MIC) was determined as the lowest concentration of compound that inhibited visible growth. A mirror reader was used to assist in determining the MIC endpoint.

One skilled in the art would consider any compound with a MIC of less than 20 mg/mL to be a potential lead compound. For instance, each of the listed Examples (1 to 119), as identified in the present application, had a MIC≦20 mg/ml against at least one of the organisms listed above.

Example 121

Rat Infection Model

Certain compounds of this invention were tested in the rat infection model. Specific pathogen-free male Sprague-Dawley CD rats were used for all bacterial strains. Each therapy group consists of 5 animals. Infection was carried out by intrabronchial instillation of 100 ml bacterial suspension for *H. influenzae* H128, and 50 ml of bacterial suspension for *S. pneumoniae* 1629 via non-surgical intubation. All compounds were administered at 1, 7, 24 and 31 hour post infection via oral gavage. In each experiment, an additional group of animals was included and served as untreated infected controls. Approximately 17 hour after the end of therapy, the animals were killed and their lungs excised and enumeration of the viable bacteria was conducted by standard methods. The lower limit of detection was 1.7 log 10 CFU/lungs.

In vivo, activity was observed in infection models in rats versus *S. pneumoniae* 1629 at doses ranging from 25-100 mg/Kg with oral dosing and for some compounds versus *H. influenzae* H128 at doses from 25-100 mg/Kg with oral dosing. Certain formula (I) compounds showed a greater than 2 log drop in viable counts in the lungs compared to non-treated controls versus *S. pneumoniae* 1629. Certain compounds of formula (I) showed greater than a 4 log drop in viable counts in the lungs compared to non-treated controls versus *H. influenzae* H 128. At least some of the compounds of this invention are particularly interesting due to their low toxicity with no toxicity being observed in rats with dosing twice daily for 2 days at 50 mg/Kg.

It is to be understood that the invention is not limited to the embodiments illustrated hereinabove and the right is reserved to the illustrated embodiments and all modifications coming within the scope of the following claims.

Table of Examples

| Example # | Structure | Formula |
|---|---|---|
| 1 | 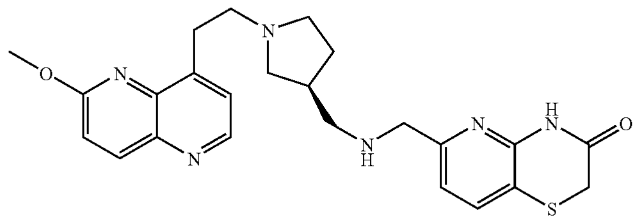 | 6-({[((3S)-1-{2-[6-(methyloxy)-1,5-naphthyridin-4-yl]ethyl}-3-pyrrolidinyl)methyl]amino}methyl)-2H-pyrido[3,2-b][1,4]thiazin-3(4H)-one |
| 2 | 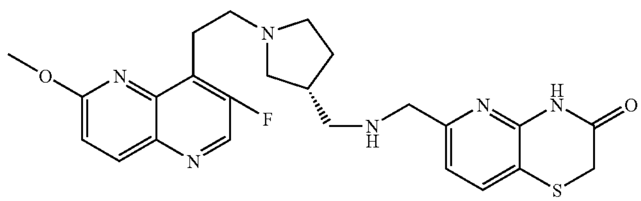 | 6-({[((3R)-1-{2-[3-fluoro-6-(methyloxy)-1,5-naphthyridin-4-yl]ethyl}-3-pyrrolidinyl)methyl]amino}methyl)-2H-pyrido[3,2-b][1,4]thiazin-3(4H)-one |
| 3 | 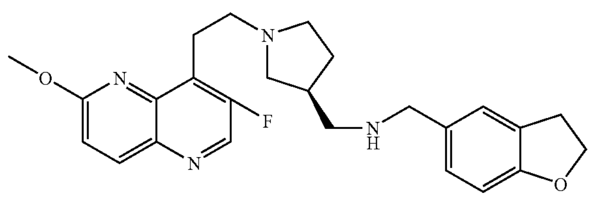 | (2,3-dihydro-1-benzofuran-5-ylmethyl)[((3S)-1-{2-[3-fluoro-6-(methyloxy)-1,5-naphthyridin-4-yl]ethyl}-3-pyrrolidinyl)methyl]amine |
| 4 | 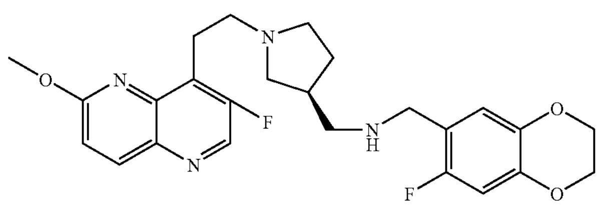 | [(7-fluoro-2,3-dihydro-1,4-benzodioxin-6-yl)methyl][((3S)-1-{2-[3-fluoro-6-(methyloxy)-1,5-naphthyridin-4-yl]ethyl}-3-pyrrolidinyl)methyl]amine |
| 5 | 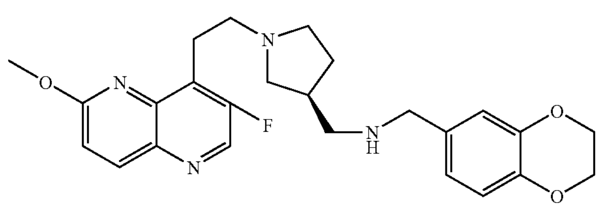 | (2,3-dihydro-1,4-benzodioxin-6-ylmethyl)[((3S)-1-{2-[3-fluoro-6-(methyloxy)-1,5-naphthyridin-4-yl]ethyl}-3-pyrrolidinyl)methyl]amine |
| 6 | 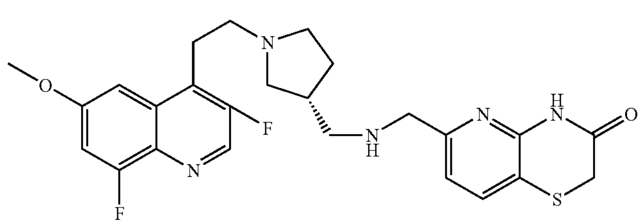 | 6-({[((3R)-1-{2-[3,8-difluoro-6-(methyloxy)-4-quinolinyl]ethyl}-3-pyrrolidinyl)methy]amino}methyl)-2H-pyrido[3,2-b][1,4]thiazin-3(4H)-one |
| 7 | 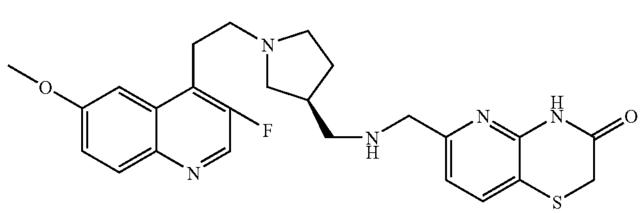 | 6-({[((3S)-1-{2-[3-fluoro-6-(methyloxy)-4-quinolinyl]ethyl}-3-pyrrolidinyl)methyl]amino}methyl)-2H-pyrido[3,2-b][1,4]thiazin-3(4H)-one |

| Example # | Structure | Formula |
|---|---|---|
| 8 | 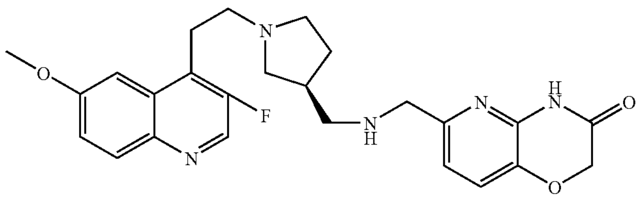 | 6-({[((3S)-1-{2-[3-fluoro-6-(methyloxy)-4-quinolinyl]ethyl}-3-pyrrolidinyl)methyl]amino}methyl)-2H-pyrido[3,2-b][1,4]oxazin-3(4H)-one |
| 9 | 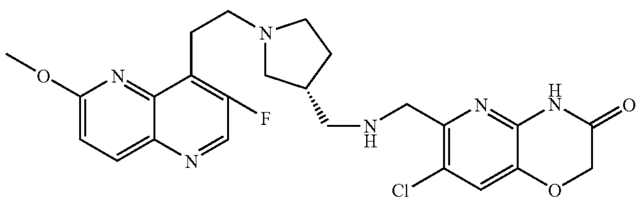 | 7-chloro-6-({[((3R)-1-{2-[3-fluoro-6-(methyloxy)-1,5-naphthyridin-4-yl]ethyl}-3-pyrrolidinyl)methyl]amino}methyl)-2H-pyrido[3,2-b][1,4]oxazin-3(4H)-one |
| 10 | 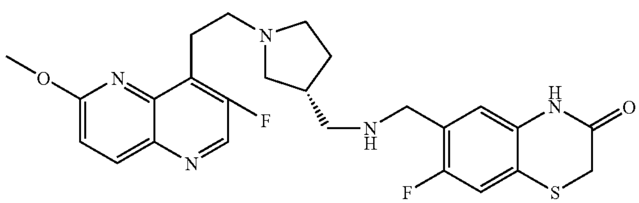 | 7-fluoro-6-({[((3R)-1-{2-[3-fluoro-6-(methyloxy)-1,5-naphthyridin-4-yl]ethyl}-3-pyrrolidinyl)methyl]amino}methyl)-2H-1,4-benzothiazin-3(4H)-one |
| 11 | 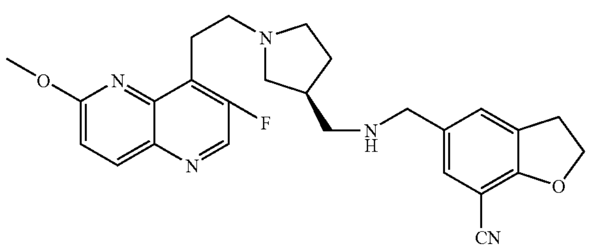 | 5-({[((3S)-1-{2-[3-fluoro-6-(methyloxy)-1,5-naphthyridin-4-yl]ethyl}-3-pyrrolidinyl)methyl]amino}methyl)-2,3-dihydro-1-benzofuran-7-carbonitrile |
| 12 | 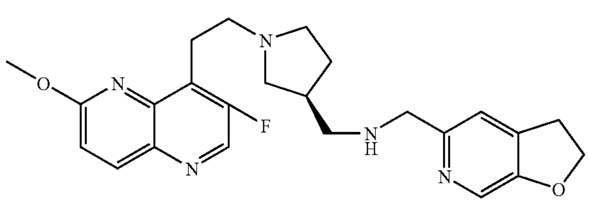 | (2,3-dihydrofuro[2,3-c]pyridin-5-ylmethyl)[((3S)-1-{2-[3-fluoro-6-(methyloxy)-1,5-naphthyridin-4-yl]ethyl}-3-pyrrolidinyl)methyl]amine |
| 13 | 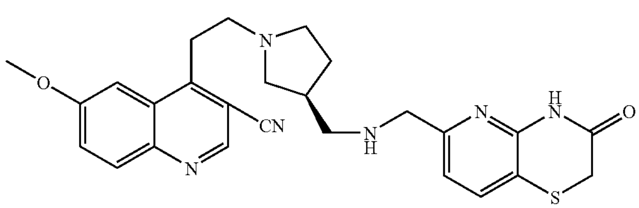 | 6-(methyloxy)-4-{2-[(3S)-3-({[(3-oxo-3,4-dihydro-2H-pyrido[3,2-b][1,4]thiazin-6-yl)methyl]amino}methyl)-1-pyrrolidinyl]ethyl}-3-quinolinecarbonitrile |
| 14 | 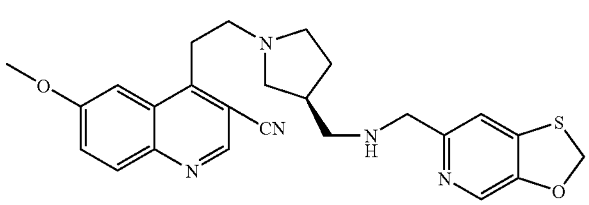 | 6-(methyloxy)-4-[2-((3S)-3-{[([1,3]oxathiolo[5,4-c]pyridin-6-ylmethyl)amino]methyl}-1-pyrrolidinyl)ethyl]-3-quinolinecarbonitrile |

-continued

Table of Examples

| Example # | Structure | Formula |
|---|---|---|
| 15 | 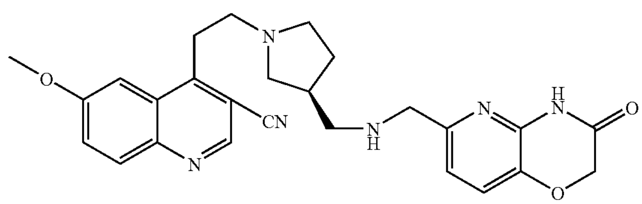 | 6-(methyloxy)-4-{2-[(3S)-3-({[(3-oxo-3,4-dihydro-2H-pyrido[3,2-b][1,4]oxazin-6-yl)methyl]amino}methyl)-1-pyrrolidinyl]ethyl}-3-quinolinecarbonitrile |
| 16 | 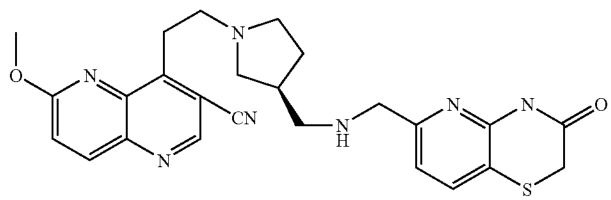 | 6-(methyloxy)-4-{2-[(3S)-3-({[(3-oxo-3,4-dihydro-2H-pyrido[3,2-b][1,4]thiazin-6-yl)methyl]amino}methyl)-1-pyrrolidinyl]ethyl}-1,5-naphthyridine-3-carbonitrile |
| 17 | 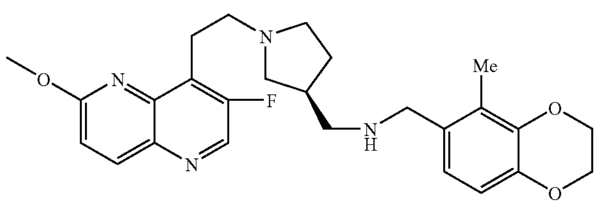 | 1-[((3S)-1-{2-[3-fluoro-6-(methyloxy)-1,5-naphthyridin-4-yl]ethyl}-3-pyrrolidinyl)methyl][(5-methyl-2,3-dihydro-1,4-benzodioxin-6-yl)methyl]amine |
| 18 | 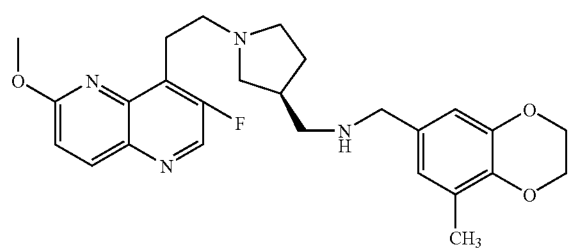 | 1-((3S)-1-{2-[3-fluoro-6-(methyloxy)-1,5-naphthyridin-4-yl]ethyl}-3-pyrrolidinyl)-N-[(8-methyl-2,3-dihydro-1,4-benzodioxin-6-yl)methyl]methanamine |
| 19 | 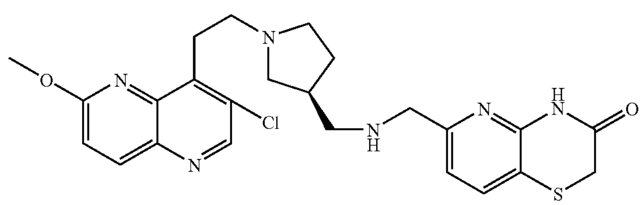 | 6-({[((3S)-1-{2-[3-chloro-6-(methyloxy)-1,5-naphthyridin-4-yl]ethyl}-3-pyrrolidinyl)methyl]amino}methyl)-2H-pyrido[3,2-b][1,4]thiazin-3(4H)-one |
| 20 | 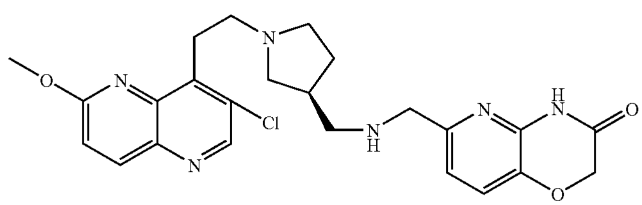 | 6-({[((3S)-1-{2-[3-chloro-6-(methyloxy)-1,5-naphthyridin-4-yl]ethyl}-3-pyrrolidinyl)methyl]amino}methyl)-2H-pyrido[3,2-b][1,4]oxazin-3(4H)-one |
| 21 | 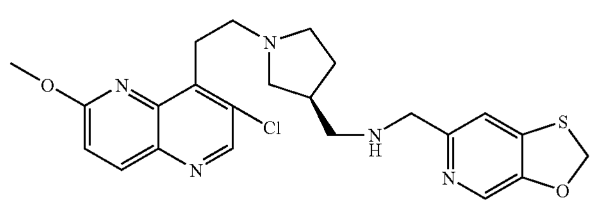 | [((3S)-1-{2-[3-chloro-6-(methyloxy)-1,5-naphthyridin-4-yl]ethyl}-3-pyrrolidinyl)methyl]([1,3]oxathiolo[5,4-c]pyridin-6-ylmethyl)amine |

-continued

Table of Examples

| Example # | Structure | Formula |
|---|---|---|
| 22 | 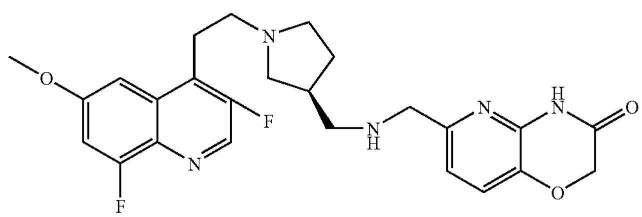 | 6-({[((3S)-1-{2-[3,8-difluoro-6-(methyloxy)-4-quinolinyl]ethyl}-3-pyrrolidinyl)methyl]amino}methyl)-2H-pyrido[3,2-b][1,4]oxazin-3(4H)-one |
| 23 | 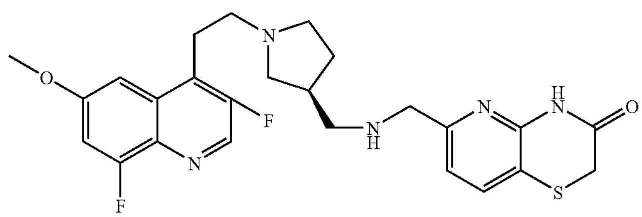 | 6-({[((3S)-1-{2-[3,8-difluoro-6-(methyloxy)-4-quinolinyl]ethyl}-3-pyrrolidinyl)methyl]amino}methyl)-2H-pyrido[3,2-b][1,4]thiazin-3(4H)-one |
| 24 | 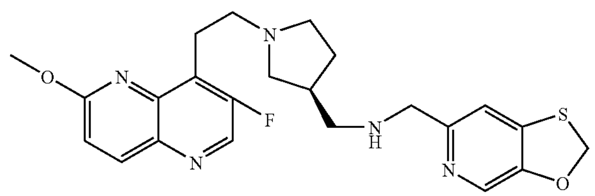 | [((3S)-1-{2-[3-fluoro-6-(methyloxy)-1,5-naphthyridin-4-yl]ethyl}-3-pyrrolidinyl)methyl]([1,3]oxathiolo[5,4-c]pyridin-6-ylmethyl)amine |
| 25 | 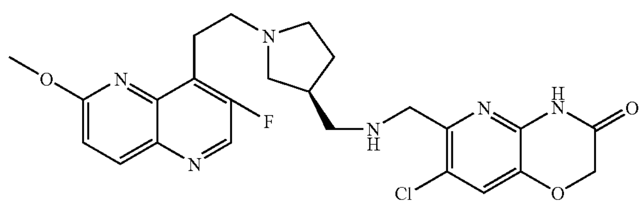 | 7-chloro-6-({[((3S)-1-{2-[3-fluoro-6-(methyloxy)-1,5-naphthyridin-4-yl]ethyl}-3-pyrrolidinyl)methyl]amino}methyl)-2H-pyrido[3,2-b][1,4]oxazin-3(4H)-one |
| 26 | 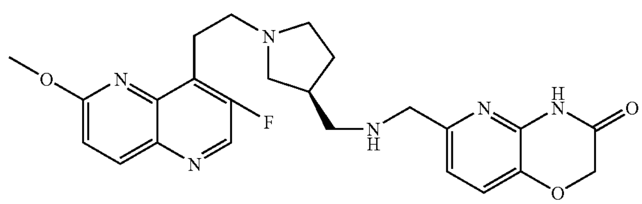 | 6-({[((3S)-1-{2-[3-fluoro-6-(methyloxy)-1,5-naphthyridin-4-yl]ethyl}-3-pyrrolidinyl)methyl]amino}methyl)-2H-pyrido[3,2-b][1,4]oxazin-3(4H)-one |
| 27 | 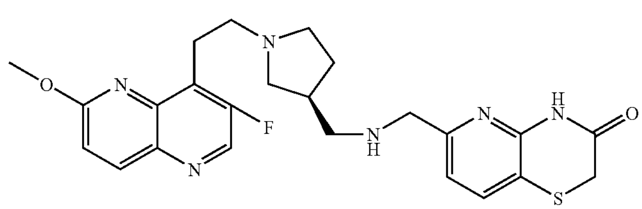 | 6-({[((3S)-1-{2-[3-fluoro-6-(methyloxy)-1,5-naphthyridin-4-yl]ethyl}-3-pyrrolidinyl)methyl]amino}methyl)-2H-pyrido[3,2-b][1,4]thiazin-3(4H)-one |
| 28 | 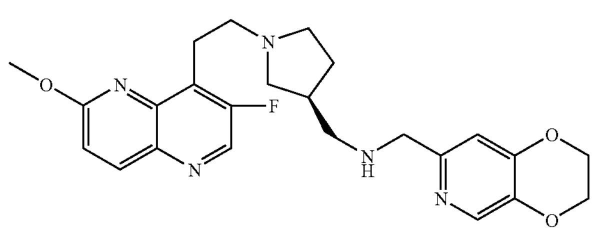 | (2,3-dihydro[1,4]dioxino[2,3-c]pyridin-7-ylmethyl)[((3S)-1-{2-[3-fluoro-6-(methyloxy)-1,5-naphthyridin-4-yl]ethyl}-3-pyrrolidinyl)methyl]amine |

-continued

Table of Examples

| Example # | Structure | Formula |
|---|---|---|
| 29 | 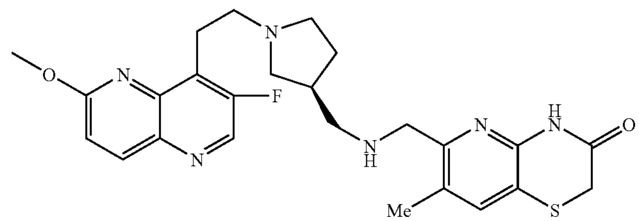 | 6-({[((3S)-1-{2-[3-fluoro-6-(methyloxy)-1,5-naphthyridin-4-yl]ethyl}-3-pyrrolidinyl)methyl]amino}methyl)-7-methyl-2H-pyrido[3,2-b][1,4]thiazin-3(4H)-one |
| 30 | 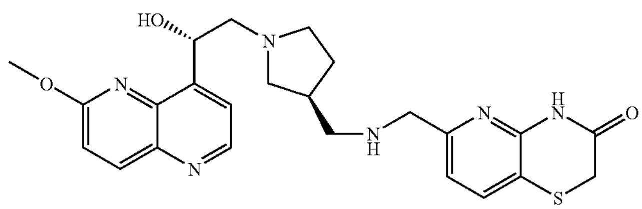 | 6-({[((3S)-1-{(2S)-2-hydroxy-2-[6-(methyloxy)-1,5-naphthyridin-4-yl]ethyl}-3-pyrrolidinyl)methyl]amino}methyl)-2H-pyrido[3,2-b][1,4]thiazin-3(4H)-one |
| 31 | 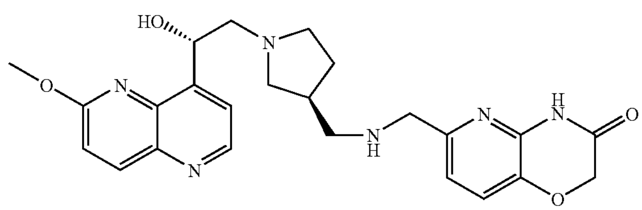 | 6-({[((3S)-1-{(2S)-2-hydroxy-2-[6-(methyloxy)-1,5-naphthyridin-4-yl]ethyl}-3-pyrrolidinyl)methyl]amino}methyl)-2H-pyrido[3,2-b][1,4]oxazin-3(4H)-one |
| 32 | 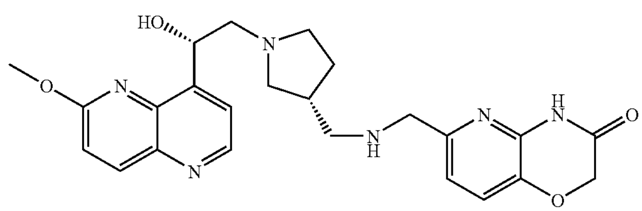 | 6-({[((3R)-1-{(2S)-2-hydroxy-2-[6-(methyloxy)-1,5-naphthyridin-4-yl]ethyl}-3-pyrrolidinyl)methyl]amino}methyl)-2H-pyrido[3,2-b][1,4]oxazin-3(4H)-one |
| 33 | 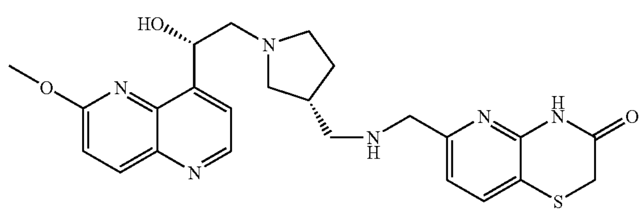 | 6-({[((3R)-1-{(2S)-2-hydroxy-2-[6-(methyloxy)-1,5-naphthyridin-4-yl]ethyl}-3-pyrrolidinyl)methyl]amino}methyl)-2H-pyrido[3,2-b][1,4]thiazin-3(4H)-one |
| 34 | 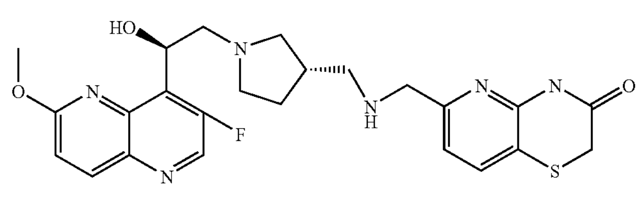 | 6-{[((3S)-1-{(2R)-2-[3-fluoro-6-(methyloxy)-1,5-naphthyridin-4-yl]-2-hydroxyethyl}-3-pyrrolidinyl)methyl]amino}methyl)-2H-pyrido[3,2-b][1,4]thiazin-3(4H)-one |
| 35 | 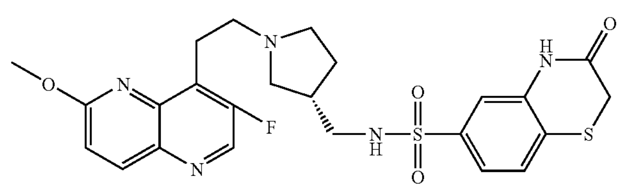 | N-[((3S)-1-{2-[3-fluoro-6-(methyloxy)-1,5-naphthyridin-4-yl]ethyl}-3-pyrrolidinyl)methyl]-3-oxo-3,4-dihydro-2H-1,4-benzothiazine-6-sulfonamide |

-continued

Table of Examples

| Example # | Structure | Formula |
|---|---|---|
| 36 | 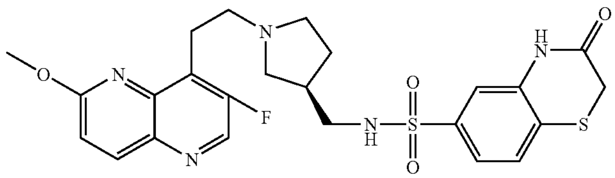 | N-[((3R)-1-{2-[3-fluoro-6-(methyloxy)-1,5-naphthyridin-4-yl]ethyl}-3-pyrrolidinyl)methyl]-3-oxo-3,4-dihydro-2H-1,4-benzothiazine-6-sulfonamide |
| 37 | 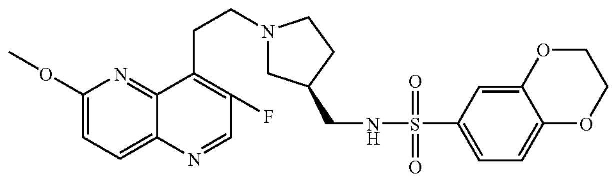 | N-[((3R)-1-{2-[3-fluoro-6-(methyloxy)-1,5-naphthyridin-4-yl]ethyl}-3-pyrrolidinyl)methyl]-2,3-dihydro-1,4-benzodioxin-6-sulfonamide |
| 38 | 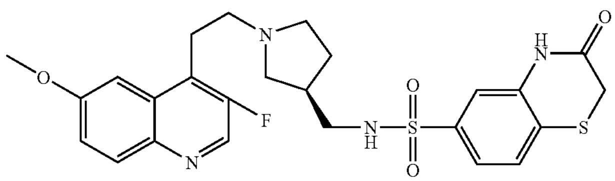 | N-[((3R)-1-{2-[3-fluoro-6-(methyloxy)-4-quinolinyl]ethyl}-3-pyrrolidinyl)methyl]-3-oxo-3,4-dihydro-2H-1,4-benzothiazine-6-sulfonamide |
| 39 | 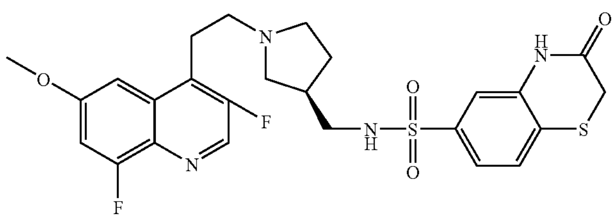 | N-[((3R)-1-{2-[3,8-difluoro-6-(methyloxy)-4-quinolinyl]ethyl}-3-pyrrolidinyl)methyl]-3-oxo-3,4-dihydro-2H-1,4-benzothiazine-6-sulfonamide |
| 40 | 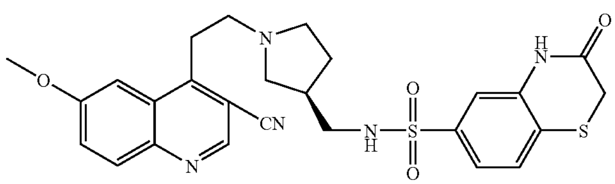 | N-[((3R)-1-{2-[3-cyano-6-(methyloxy)-4-quinolinyl]ethyl}-3-pyrrolidinyl)methyl]-3-oxo-3,4-dihydro-2H-1,4-benzothiazine-6-sulfonamide |
| 41 | 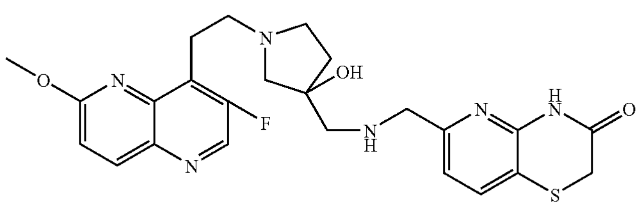 | (±)-6-({[(1-{2-[3-fluoro-6-(methyloxy)-1,5-naphthyridin-4-yl]ethyl}-3-hydroxy-3-pyrrolidinyl)methyl]amino}methyl)-2H-pyrido[3,2-b][1,4]thiazin-3(4H)-one |
| 42 | 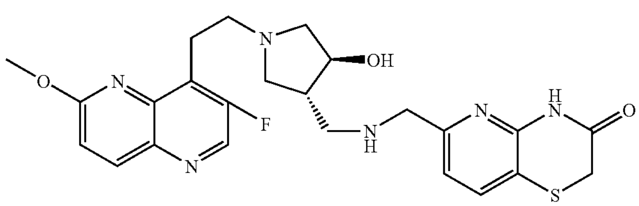 | (±)-6-({[[(trans-3,4)-1-{2-[3-fluoro-6-(methyloxy)-1,5-naphthyridin-4-yl]ethyl}-4-hydroxy-3-pyrrolidinyl]methyl]amino}methyl)-2H-pyrido[3,2-b][1,4]thiazin-3(4H)-one |

-continued

Table of Examples

| Example # | Structure | Formula |
|---|---|---|
| 42 E1 | 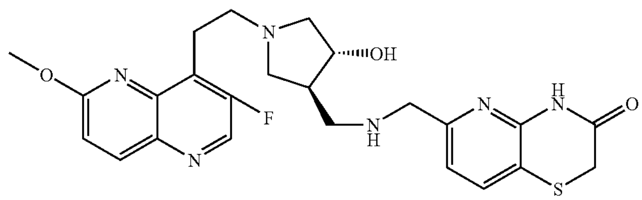 | 6-({[(trans-3,4)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]thiazin-3(4H)-one |
| 42 E2 | 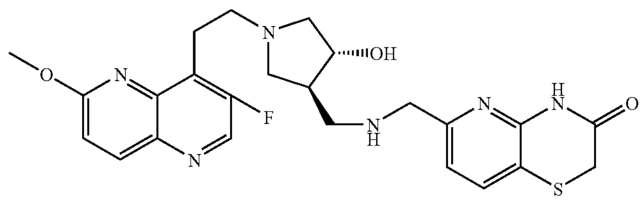 | 6-({[(trans-3,4)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]thiazin-3(4H)-one |
| 43 | 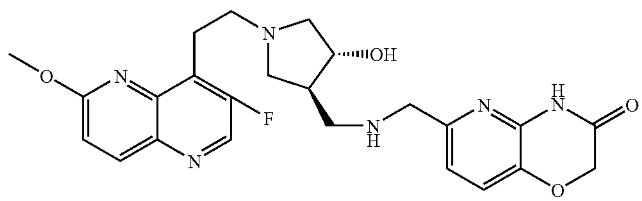 | (±)-6-({[(trans-3,4)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]oxazin-3(4H)-one |
| 43 E1 | 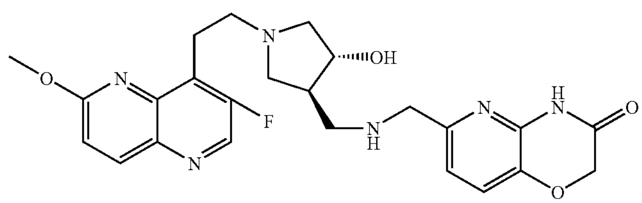 | 6-({[(trans-3,4)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]oxazin-3(4H)-one |
| 43 E2 | 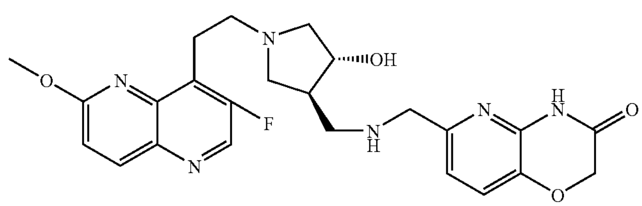 | 6-({[(trans-3,4)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]oxazin-3(4H)-one |
| 44 | 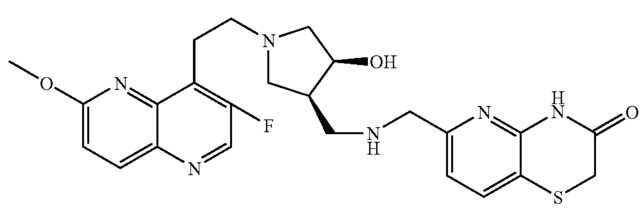 | (±)-6-({[((cis-3,4)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]thiazin-3(4H)-one |
| 45 | 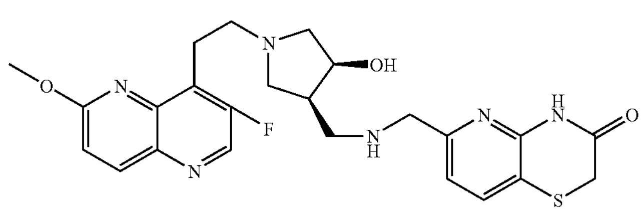 | 6-({[((3S,4S)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]thiazin-3(4H)-one |

-continued

Table of Examples

| Example # | Structure | Formula |
|---|---|---|
| 46 | 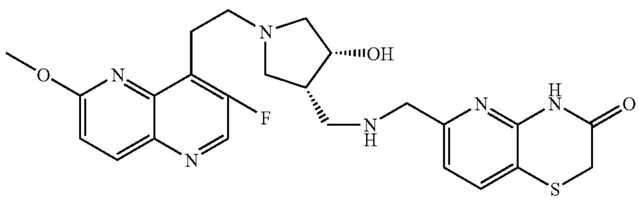 | 6-({[((3R,4R)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]thiazin-3(4H)-one |
| 47 | 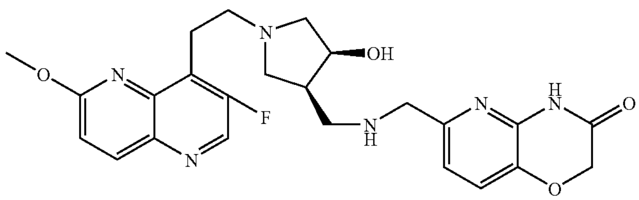 | 6-({[((3S,4S)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]oxazin-3(4H)-one |
| 48 | 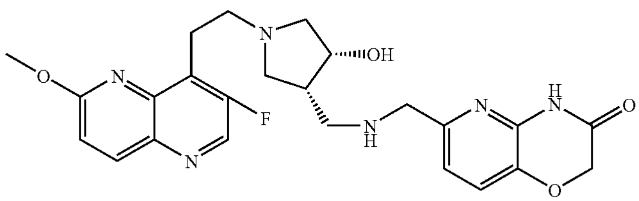 | 6-({[((3R,4R)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]oxazin-3(4H)-one |
| 49 | 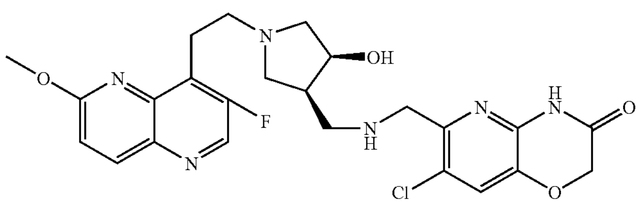 | (±)-7-chloro-6-({[((cis-3,4)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]oxazin-3(4H)-one |
| 50 | 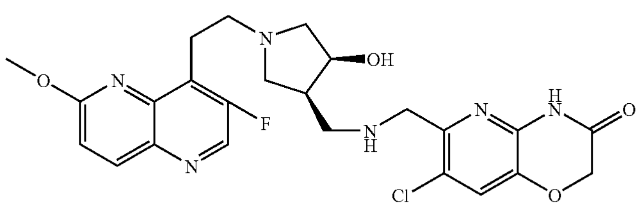 | 7-chloro-6-({[((3S,4S)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]oxazin-3(4H)-one |
| 51 | 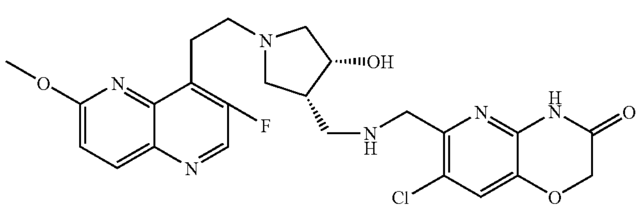 | 7-chloro-6-({[((3R,4R)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]oxazin-3(4H)-one |
| 52 | 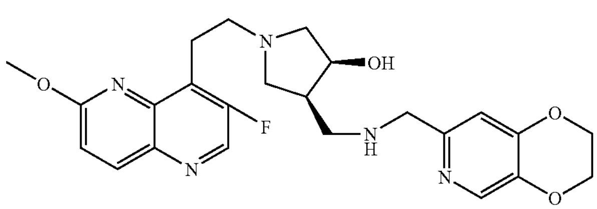 | (±)-(cis-3,4)-4-{[(2,3-dihydro[1,4]dioxino[2,3-c]pyridin-7-ylmethyl)amino]methyl}-1-{2-[3-fluoro-6-(methyloxy)-1,5-naphthyridin-4-yl]ethyl}-3-pyrrolidinol |

-continued

Table of Examples

| Example # | Structure | Formula |
|---|---|---|
| 53 | 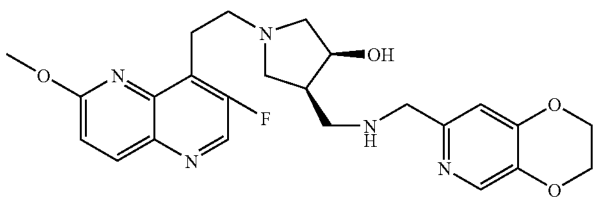 | (3S,4S)-4-{[(2,3-dihydro[1,4]dioxino[2,3-c]pyridin-7-ylmethyl)amino]methyl}-1-{2-[3-fluoro-6-(methyloxy)-1,5-naphthyridin-4-yl]ethyl}-3-pyrrolidinol |
| 54 | 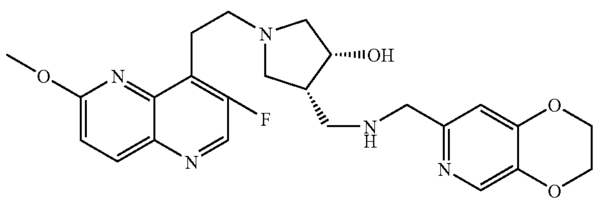 | (3R,4R)-4-{[(2,3-dihydro[1,4]dioxino[2,3-c]pyridin-7-ylmethyl)amino]methyl}-1-{2-[3-fluoro-6-(methyloxy)-1,5-naphthyridin-4-yl]ethyl}-3-pyrrolidinol |
| 55 | 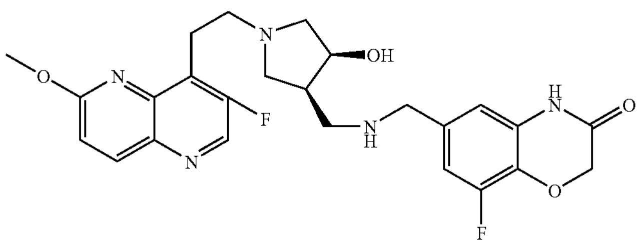 | 8-fluoro-6-({[((3S,4S)-1-{2-[3-fluoro-6-(methyloxy)-1,5-naphthyridin-4-yl]ethyl}-4-hydroxy-3-pyrrolidinyl)methyl]amino}methyl)-2H-1,4-benzoxazin-3(4H)-one |
| 56 | 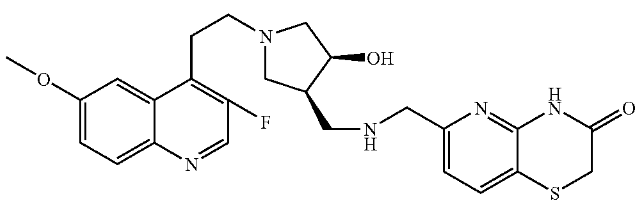 | 6-({[((3S,4S)-1-{2-[3-fluoro-6-(methyloxy)-4-quinolinyl]ethyl}-4-hydroxy-3-pyrrolidinyl)methyl]amino}methyl)-2H-pyrido[3,2-b][1,4]thiazin-3(4H)-one |
| 57 | 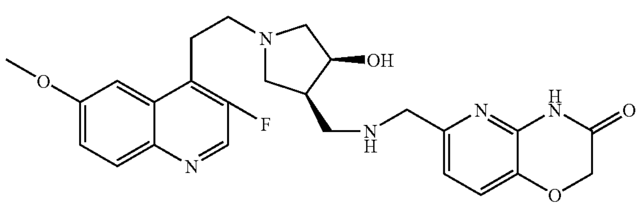 | 6-({[((3S,4S)-1-{2-[3-fluoro-6-(methyloxy)-4-quinolinyl]ethyl}-4-hydroxy-3-pyrrolidinyl)methyl]amino}methyl)-2H-pyrido[3,2-b][1,4]oxazin-3(4H)-one |
| 58 | 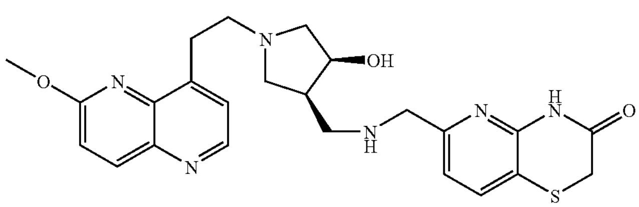 | (±)-6-({[((cis-3,4)-4-hydroxy-1-{2-[6-(methyloxy)-1,5-naphthyridin-4-yl]ethyl}-3-pyrrolidinyl)methyl]amino}methyl)-2H-pyrido[3,2-b][1,4]thiazin-3(4H)-one |
| 59 | 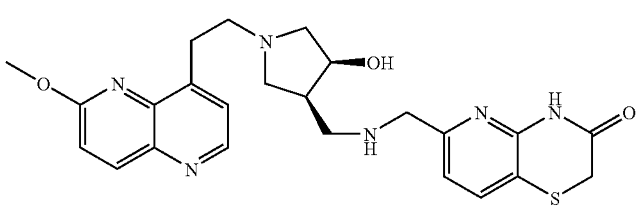 | 6-({[((3S,4S)-4-hydroxy-1-{2-[6-(methyloxy)-1,5-naphthyridin-4-yl]ethyl}-3-pyrrolidinyl)methyl]amino}methyl)-2H-pyrido[3,2-b][1,4]thiazin-3(4H)-one |

-continued

Table of Examples

| Example # | Structure | Formula |
|---|---|---|
| 60 | 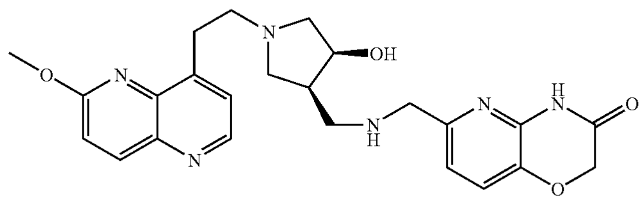 | (±)-6-({[((cis-3,4)-4-hydroxy-1-{2-[6-(methyloxy)-1,5-naphthyridin-4-yl]ethyl}-3-pyrrolidinyl)methyl]amino}methyl)-2H-pyrido[3,2-b][1,4]oxazin-3(4H)-one |
| 61 | 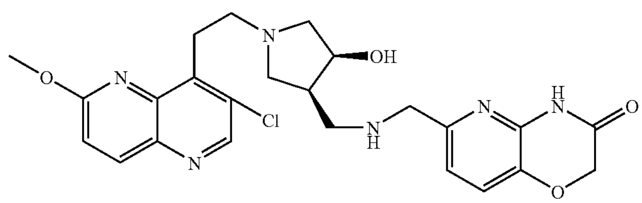 | 6-({[((3S,4S)-1-{2-[3-chloro-6-(methyloxy)-1,5-naphthyridin-4-yl]ethyl}-4-hydroxy-3-pyrrolidinyl)methyl]amino}methyl)-2H-pyrido[3,2-b][1,4]oxazin-3(4H)-one |
| 62 | 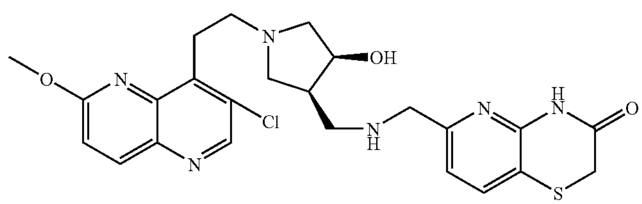 | 6-({[((3S,4S)-1-{2-[3-chloro-6-(methyloxy)-1,5-naphthyridin-4-yl]ethyl}-4-hydroxy-3-pyrrolidinyl)methyl]amino}methyl)-2H-pyrido[3,2-b][1,4]thiazin-3(4H)-one |
| 63 | 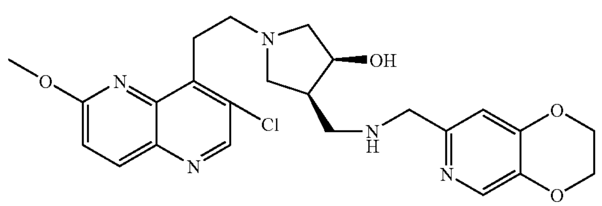 | (3S,4S)-1-{2-[3-chloro-6-(methyloxy)-1,5-naphthyridin-4-yl]ethyl}-4-{[(2,3-dihydro[1,4]dioxino[2,3-c]pyridin-7-ylmethyl)amino]methyl}-3-pyrrolidinol |
| 64 | 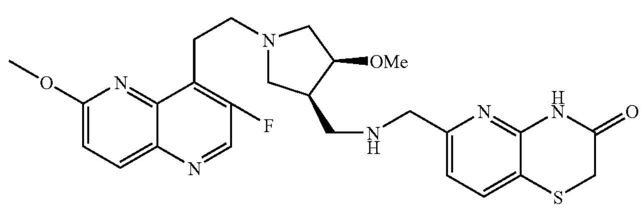 | (±)-6-[({[(cis-3,4)-1-{2-[3-fluoro-6-(methyloxy)-1,5-naphthyridin-4-yl]ethyl}-4-(methyloxy)-3-pyrrolidinyl]methyl}amino)methyl]-2H-pyrido[3,2-b][1,4]thiazin-3(4H)-one |
| 65 | 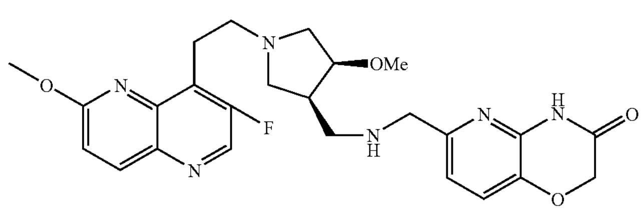 | (±)-6-[({[(cis-3,4)-1-{2-[3-fluoro-6-(methyloxy)-1,5-naphthyridin-4-yl]ethyl}-4-(methyloxy)-3-pyrrolidinyl]methyl}amino)methyl]-2H-pyrido[3,2-b][1,4]oxazin-3(4H)-one |
| 66 | 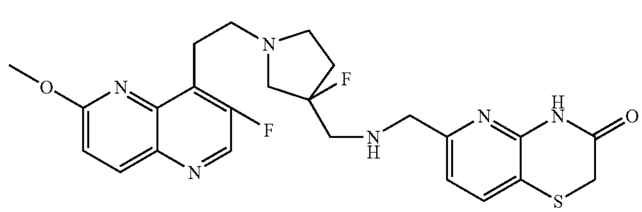 | (±)-6-({[(3-fluoro-1-{2-[3-fluoro-6-(methyloxy)-1,5-naphthyridin-4-yl]ethyl}-3-pyrrolidinyl)methyl]amino}methyl)-2H-pyrido[3,2-b][1,4]thiazin-3(4H)-one |

-continued

Table of Examples

| Example # | Structure | Formula |
|---|---|---|
| 67 | 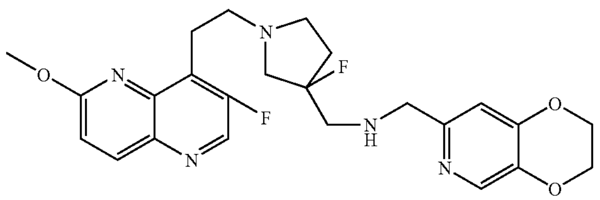 | (±)-(2,3-dihydro[1,4]dioxino[2,3-c]pyridin-7-ylmethyl)[(3-fluoro-1-{2-[3-fluoro-6-(methyloxy)-1,5-naphthyridin-4-yl]ethyl}-3-pyrrolidinyl)methyl]amine |
| 68 | 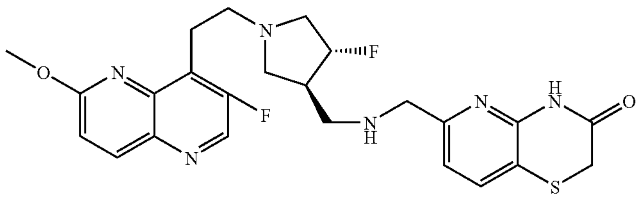 | (±)-6-({[((3S,4R)-4-fluoro-1-{2-[3-fluoro-6-(methyloxy)-1,5-naphthyridin-4-yl]ethyl}-3-pyrrolidinyl)methyl]amino}methyl)-2H-pyrido[3,2-b][1,4]thiazin-3(4H)-one |
| 69 | 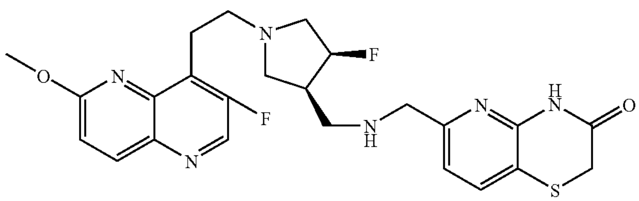 | (±)-6-({[((3S,4S)-4-fluoro-1-{2-[3-fluoro-6-(methyloxy)-1,5-naphthyridin-4-yl]ethyl}-3-pyrrolidinyl)methyl]amino}methyl)-2H-pyrido[3,2-b][1,4]thiazin-3(4H)-one |
| 70 D1 | 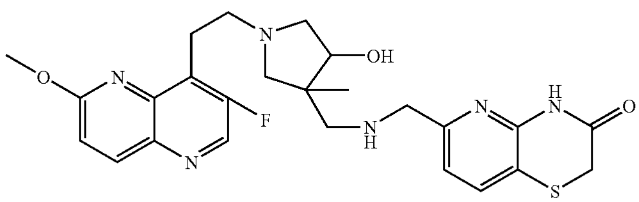 | (±)-6-({[(1-{2-[3-fluoro-6-(methyloxy)-1,5-naphthyridin-4-yl]ethyl}-4-hydroxy-3-methyl-3-pyrrolidinyl)methyl]amino}methyl)-2H-pyrido[3,2-b][1,4]thiazin-3(4H)-one |
| 70 D2 | 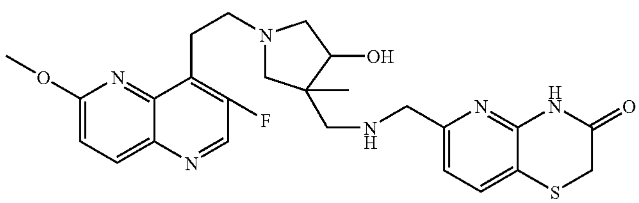 | (±)-6-({[(1-{2-[3-fluoro-6-(methyloxy)-1,5-naphthyridin-4-yl]ethyl}-4-hydroxy-3-methyl-3-pyrrolidinyl)methyl]amino}methyl)-2H-pyrido[3,2-b][1,4]thiazin-3(4H)-one |
| 71 D1 | 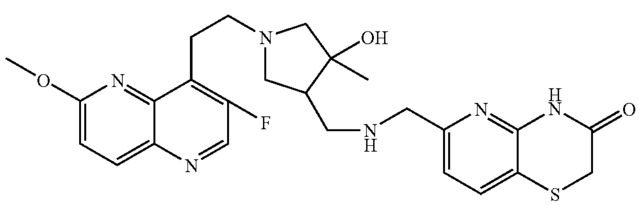 | (±)-6-({[(1-{2-[3-fluoro-6-(methyloxy)-1,5-naphthyridin-4-yl]ethyl}-4-hydroxy-4-methyl-3-pyrrolidinyl)methyl]amino}methyl)-2H-pyrido[3,2-b][1,4]thiazin-3(4H)-one |
| 71 D2 | 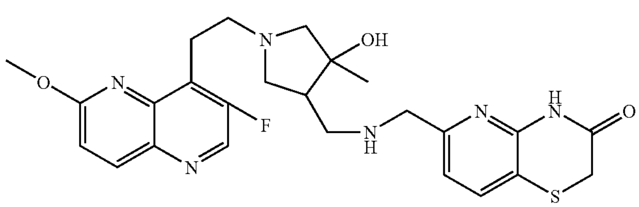 | (±)-6-({[(1-{2-[3-fluoro-6-(methyloxy)-1,5-naphthyridin-4-yl]ethyl}-4-hydroxy-4-methyl-3-pyrrolidinyl)methyl]amino}methyl)-2H-pyrido[3,2-b][1,4]thiazin-3(4H)-one |

-continued

Table of Examples

| Example # | Structure | Formula |
|---|---|---|
| 72 | 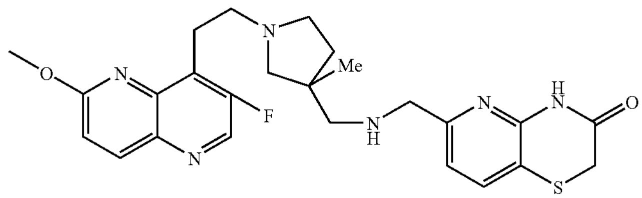 | (±)-6-({[(1-{2-[3-fluoro-6-(methyloxy)-1,5-naphthyridin-4-yl]ethyl}-3-methyl-3-pyrrolidinyl)methyl]amino}methyl)-2H-pyrido[3,2-b][1,4]thiazin-3(4H)-one |
| 73 | 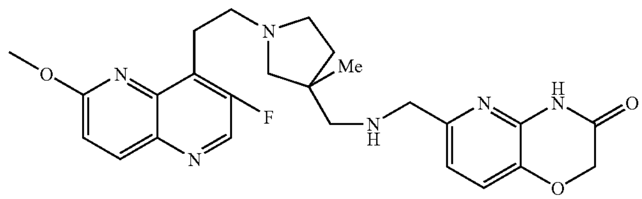 | (±)-6-({[(1-{2-[3-fluoro-6-(methyloxy)-1,5-naphthyridin-4-yl]ethyl}-3-methyl-3-pyrrolidinyl)methyl]amino}methyl)-2H-pyrido[3,2-b][1,4]oxazin-3(4H)-one |
| 74 | 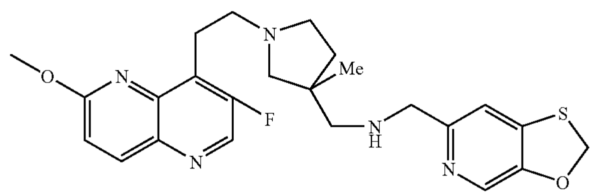 | (±)-[(1-{2-[3-fluoro-6-(methyloxy)-1,5-naphthyridin-4-yl]ethyl}-3-methyl-3-pyrrolidinyl)methyl]([1,3]oxathiolo[5,4-c]pyridin-6-ylmethyl)amine |
| 75 | 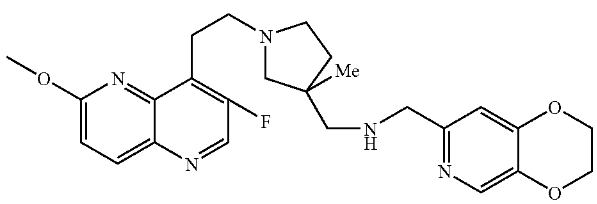 | (±)-(2,3-dihydro[1,4]dioxino[2,3-c]pyridin-7-ylmethyl)[(1-{2-[3-fluoro-6-(methyloxy)-1,5-naphthyridin-4-yl]ethyl}-3-methyl-3-pyrrolidinyl)methyl]amine |
| 76 | 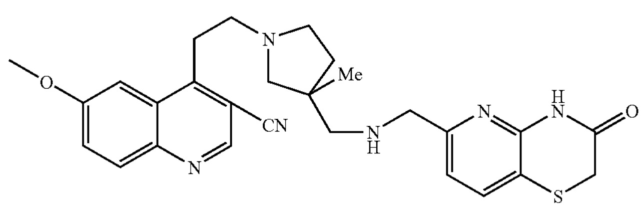 | (±)-4-{2-[3-methyl-3-({[(3-oxo-3,4-dihydro-2H-pyrido[3,2-b][1,4]thiazin-6-yl)methyl]amino}methyl)-1-pyrrolidinyl]ethyl}-6-(methyloxy)-3-quinolinecarbonitrile |
| 77 | 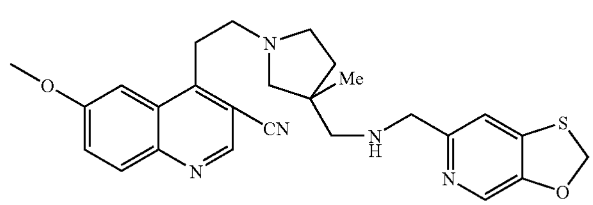 | (±)-4-[2-(3-methyl-3-{[([1,3]oxathiolo[5,4-c]pyridin-6-ylmethyl)amino]methyl}-1-pyrrolidinyl)ethyl]-6-(methyloxy)-3-quinolinecarbonitrile |
| 78 | 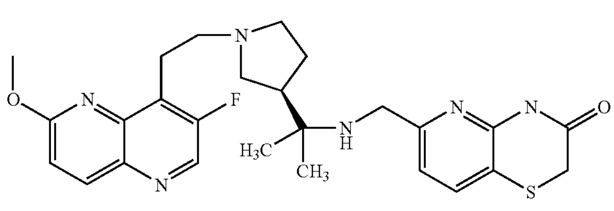 | 6-({[1-((3R)-1-{2-[3-fluoro-6-(methyloxy)-1,5-naphthyridin-4-yl]ethyl}-3-pyrrolidinyl)-1-methylethyl]amino}methyl)-2H-pyrido[3,2-b][1,4]thiazin-3(4H)-one |

Table of Examples

| Example # | Formula |
|---|---|
| 79 | N-(2,3-dihydro[1,4]dioxino[2,3-c]pyridin-7-ylmethyl)-2-((3R)-1-{2-[3-fluoro-6-(methyloxy)-1,5-naphthyridin-4-yl]ethyl}-3-pyrrolidinyl)-2-propanamine |
| 80 | N-[((3S)-1-{2-[3-fluoro-6-(methyloxy)-1,5-naphthyridin-4-yl]ethyl}-3-pyrrolidinyl)methyl]-3-oxo-3,4-dihydro-2H-pyrido[3,2-b][1,4]thiazine-6-carboxamide |
| 81 | N-[((3S)-1-{2-[6-(methyloxy)-1,5-naphthyridin-4-yl]ethyl}-3-pyrrolidinyl)methyl]-3-oxo-3,4-dihydro-2H-pyrido[3,2-b][1,4]thiazine-6-carboxamide |
| 82 | N-[((3S,4S)-1-{2-[3-fluoro-6-(methyloxy)-1,5-naphthyridin-4-yl]ethyl}-4-hydroxy-3-pyrrolidinyl)methyl]-3-oxo-3,4-dihydro-2H-pyrido[3,2-b][1,4]thiazine-6-carboxamide |
| 83 | (±)-N-[((cis-3,4)-1-{2-[3-fluoro-6-(methyloxy)-1,5-naphthyridin-4-yl]ethyl}-4-hydroxy-3-pyrrolidinyl)methyl]-N-methyl-3-oxo-3,4-dihydro-2H-pyrido[3,2-b][1,4]thiazine-6-carboxamide |
| 84 | (±)-N-[(1-{2-[3-fluoro-6-(methyloxy)-1,5-naphthyridin-4-yl]ethyl}-3-pyrrolidinyl)methyl]-N-methyl-3-oxo-3,4-dihydro-2H-pyrido[3,2-b][1,4]thiazine-6-carboxamide |
| 85 | (3S,4S)-4-{[(2,3-dihydro[1,4]dioxino[2,3-c]pyridin-7-ylmethyl)amino]methyl}-1-{2-[6-(methyloxy)-1,5-naphthyridin-4-yl]ethyl}-3-pyrrolidinyl |

-continued

Table of Examples

| Example # | Structure | Formula |
|---|---|---|
| 86 | 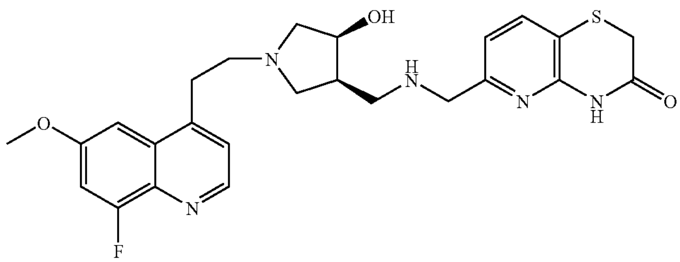 | 6-({[((3S,4S)-1-{2-[8-fluoro-6-(methyloxy)-4-quinolinyl]ethyl}-4-hydroxy-3-pyrrolidinyl)methyl]amino}methyl)-2H-pyrido[3,2-b][1,4]thiazin-3(4H)-one |
| 87 | 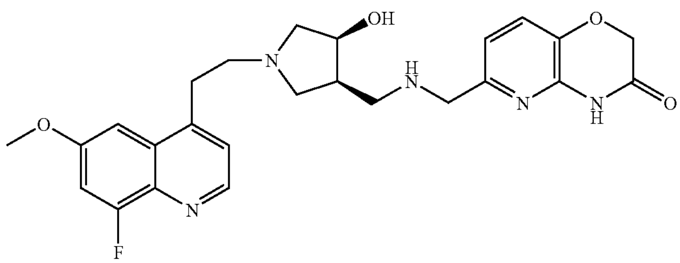 | 6-({[((3S,4S)-1-{2-[8-fluoro-6-(methyloxy)-4-quinolinyl]ethyl}-4-hydroxy-3-pyrrolidinyl)methyl]amino}methyl)-2H-pyrido[3,2-b][1,4]oxazin-3(4H)-one |
| 88 | 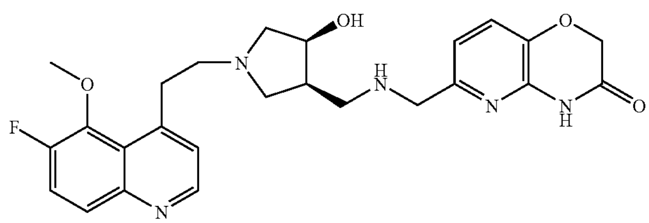 | 6-({[((3S,4S)-1-{2-[6-fluoro-5-(methyloxy)-4-quinolinyl]ethyl}-4-hydroxy-3-pyrrolidinyl)methyl]amino}methyl)-2H-pyrido[3,2-b][1,4]oxazin-3(4H)-one |
| 89 | 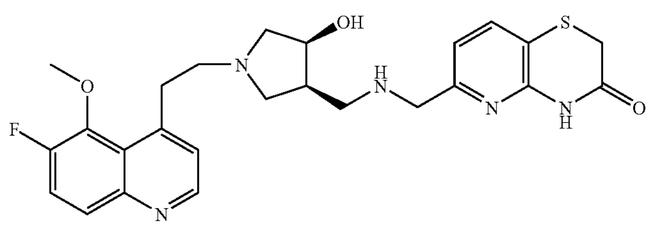 | 6-({[((3S,4S)-1-{2-[6-fluoro-5-(methyloxy)-4-quinolinyl]ethyl}-4-hydroxy-3-pyrrolidinyl)methyl]amino}methyl)-2H-pyrido[3,2-b][1,4]thiazin-3(4H)-one |
| 90 | 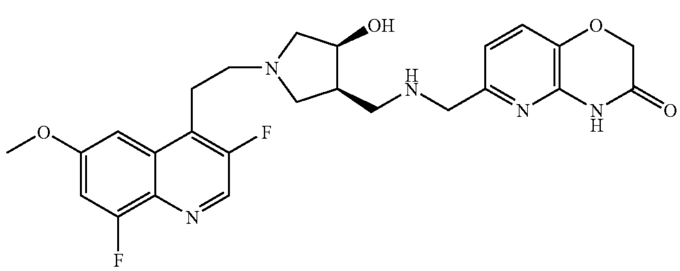 | 6-({[((3S,4S)-1-{2-[3,8-difluoro-6-(methyloxy)-4-quinolinyl]ethyl}-4-hydroxy-3-pyrrolidinyl)methyl]amino}methyl)-2H-pyrido[3,2-b][1,4]oxazin-3(4H)-one |
| 91 | 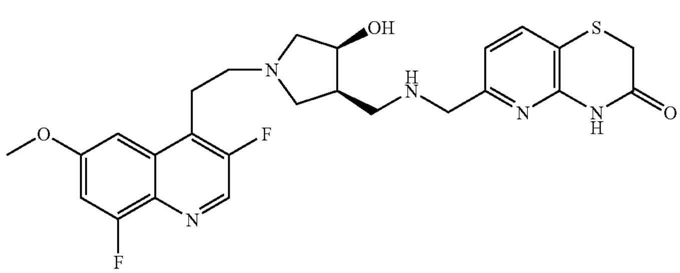 | 6-({[((3S,4S)-1-{2-[3,8-difluoro-6-(methyloxy)-4-quinolinyl]ethyl}-4-hydroxy-3-pyrrolidinyl)methyl]amino}methyl)-2H-pyrido[3,2-b][1,4]thiazin-3(4H)-one |

-continued

Table of Examples

| Example # | Structure | Formula |
|---|---|---|
| 92 | 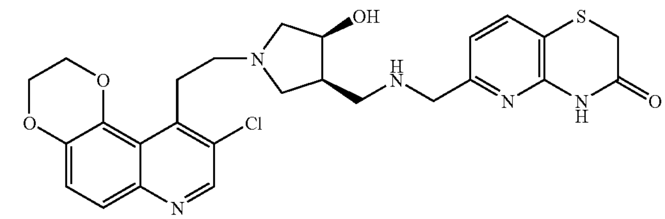 | 6-{[({(3S,4S)-1-[2-(9-chloro-2,3-dihydro[1,4]dioxino[2,3-f]quinolin-10-yl)ethyl]-4-hydroxy-3-pyrrolidinyl}methyl)amino]methyl}-2H-pyrido[3,2-b][1,4]thiazin-3(4H)-one |
| 93 | 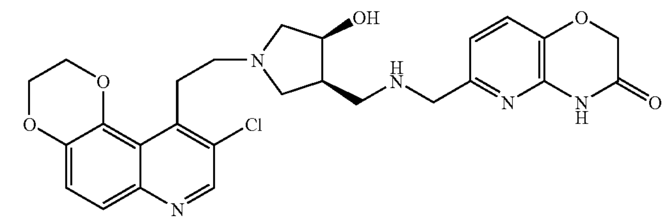 | 6-{[({(3S,4S)-1-[2-(9-chloro-2,3-dihydro[1,4]dioxino[2,3-f]quinolin-10-yl)ethyl]-4-hydroxy-3-pyrrolidinyl}methyl)amino]methyl}-2H-pyrido[3,2-b][1,4]oxazin-3(4H)-one |
| 94 | 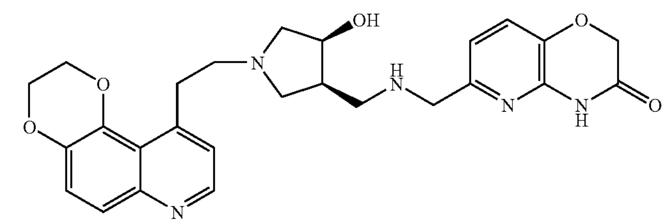 | 6-{[({(3S,4S)-1-[2-(2,3-dihydro[1,4]dioxino[2,3-f]quinolin-10-yl)ethyl]-4-hydroxy-3-pyrrolidinyl}methyl)amino]methyl}-2H-pyrido[3,2-b][1,4]oxazin-3(4H)-one |
| 95 | 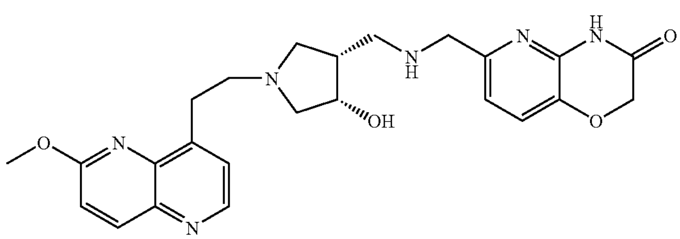 | 6-({[((3S,4S)-4-hydroxy-1-{2-[6-(methyloxy)-1,5-naphthyridin-4-yl]ethyl}-3-pyrrolidinyl)methyl]amino}methyl)-2H-pyrido[3,2-b][1,4]oxazin-3(4H)-one |
| 96 | 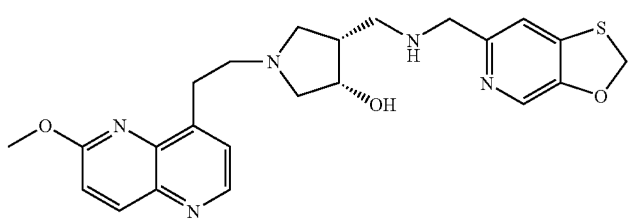 | (3S,4S)-1-{2-[6-(methyloxy)-1,5-naphthyridin-4-yl]ethyl}-4-{[([1,3]oxathiolo[5,4-c]pyridin-6-ylmethyl)amino]methyl}-3-pyrrolidinol |
| 97 | 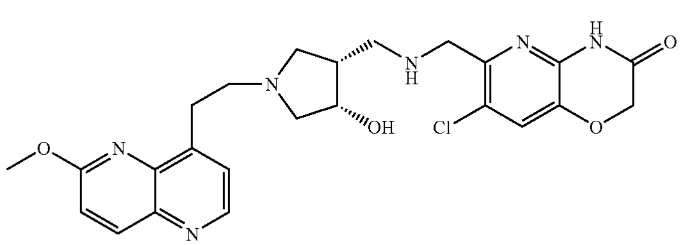 | 7-chloro-6-({[((3S,4S)-4-hydroxy-1-{2-[6-(methyloxy)-1,5-naphthyridin-4-yl]ethyl}-3-pyrrolidinyl)methyl]amino}methyl)-2H-pyrido[3,2-b][1,4]oxazin-3(4H)-one |

Table of Examples

| Example # | Structure | Formula |
|---|---|---|
| 98 | 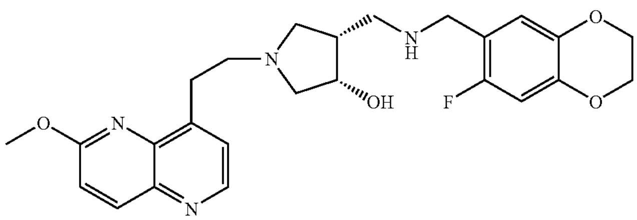 | (3S,4S)-4-({[(7-fluoro-2,3-dihydro-1,4-benzodioxin-6-yl)methyl]amino}methyl)-1-{2-[6-(methyloxy)-1,5-naphthyridin-4-yl]ethyl}-3-pyrrolidinol |
| 99 | 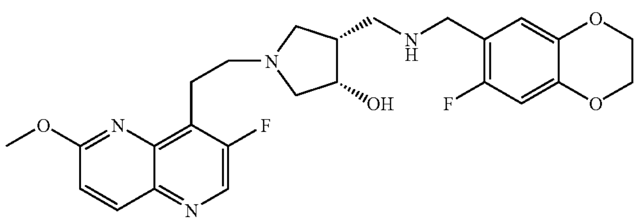 | (3S,4S)-4-({[(7-fluoro-2,3-dihydro-1,4-benzodioxin-6-yl)methyl]amino}methyl)-1-{2-[3-fluoro-6-(methyloxy)-1,5-naphthyridin-4-yl]ethyl}-3-pyrrolidinol |
| 100 | 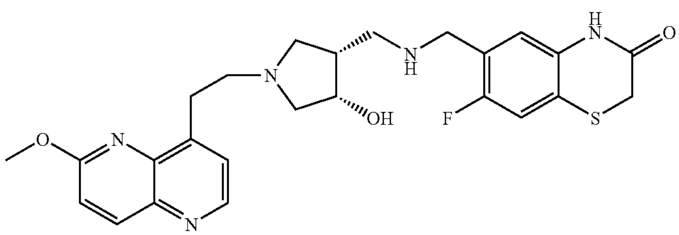 | 7-fluoro-6-({[((3S,4S)-4-hydroxy-1-{2-[6-(methyloxy)-1,5-naphthyridin-4-yl]ethyl}-3-pyrrolidinyl)methyl]amino}methyl)-2H-1,4-benzothiazin-3(4H)-one |
| 101 | 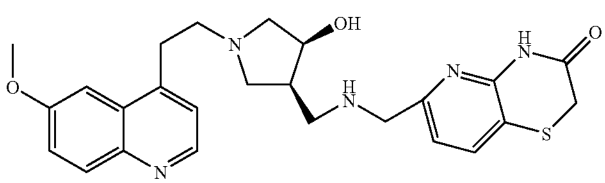 | 6-({[((3S,4S)-4-hydroxy-1-{2-[6-(methyloxy)-4-quinolinyl]ethyl}-3-pyrrolidinyl)methyl]amino}methyl)-2H-pyrido[3,2-b][1,4]thiazin-3(4H)-one |
| 102 | 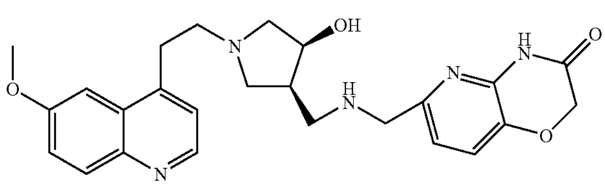 | 6-({[((3S,4S)-4-hydroxy-1-{2-[6-(methyloxy)-4-quinolinyl]ethyl}-3-pyrrolidinyl)methyl]amino}methyl)-2H-pyrido[3,2-b][1,4]oxazin-3(4H)-one |
| 103 | 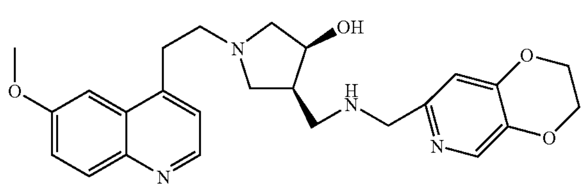 | (3S,4S)-4-{[(2,3-dihydro[1,4]dioxino[2,3-c]pyridin-7-ylmethyl)amino]methyl}-1-{2-[6-(methyloxy)-4-quinolinyl]ethyl}-3-pyrrolidinyl |
| 104 | 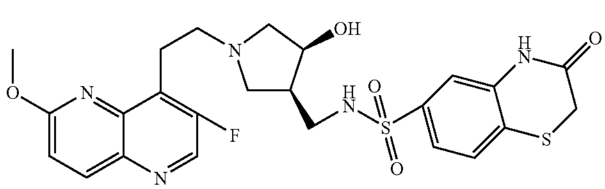 | N-[((3R,4S)-1-{2-[3-fluoro-6-(methyloxy)-1,5-naphthyridin-4-yl]ethyl}-4-hydroxy-3-pyrrolidinyl)methyl]-3-oxo-3,4-dihydro-2H-1,4-benzothiazine-6-sulfonamide |

-continued

Table of Examples

| Example # | Structure | Formula |
|---|---|---|
| 105 | 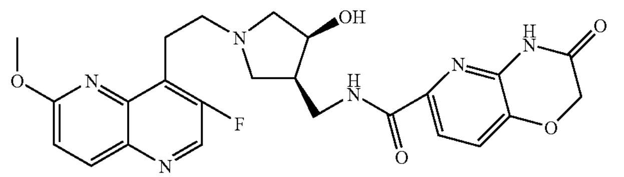 | N-[((3S,4S)-1-{2-[3-fluoro-6-(methyloxy)-1,5-naphthyridin-4-yl]ethyl}-4-hydroxy-3-pyrrolidinyl)methyl]-3-oxo-3,4-dihydro-2H-pyrido[3,2-b][1,4]oxazine-6-carboxamide |
| 106 | 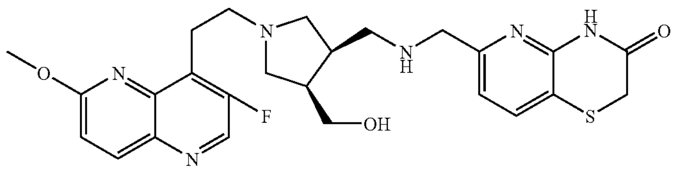 | (±)-6-[({[(3R,4S)/(3S,4R)-1-{2-[3-fluoro-6-(methyloxy)-1,5-naphthyridin-4-yl]ethyl}-4-(hydroxymethyl)-3-pyrrolidinyl]methyl}amino)methyl]-2H-pyrido[3,2-b][1,4]thiazin-3(4H)-one |
| 107 | 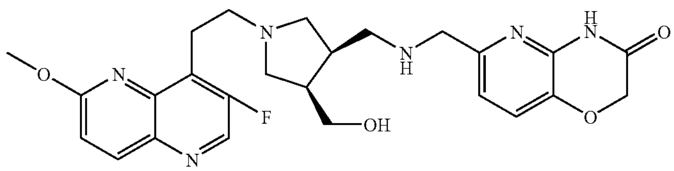 | (±)-6-[({[(3R,4S)/(3S,4R)-1-{2-[3-fluoro-6-(methyloxy)-1,5-naphthyridin-4-yl]ethyl}-4-(hydroxymethyl)-3-pyrrolidinyl]methyl}amino)methyl]-2H-pyrido[3,2-b][1,4]thiazin-3(4H)-one |
| 107E1 and 107 E2 (Structures separated but not assigned) | | 6-[({[(3R,4S)--1-{2-[3-fluoro-6-(methyloxy)-1,5-naphthyridin-4-yl]ethyl}-4-(hydroxymethyl)-3-pyrrolidinyl]methyl}amino)methyl]-2H-pyrido[3,2-b][1,4]thiazin-3(4H)-one and (±)-6-[({[(3S,4R)/(3S,4R)--1-{2-[3-fluoro-6-(methyloxy)-1,5-naphthyridin-4-yl]ethyl}-4-(hydroxymethyl)-3-pyrrolidinyl]methyl}amino)methyl]-2H-pyrido[3,2-b][1,4]thiazin-3(4H)-one |
| 108 | 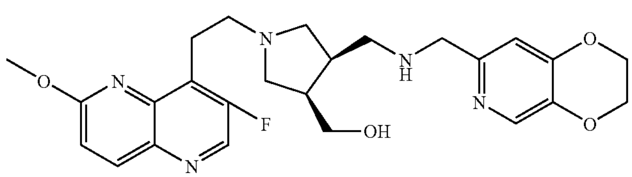 | (±)-((3R,4S)/(3S,4R)--4-{[(2,3-dihydro[1,4]dioxino[2,3-c]pyridin-7-ylmethyl)amino]methyl}-1-{2-[3-fluoro-6-(methyloxy)-1,5-naphthyridin-4-yl]ethyl}-3-pyrrolidinyl)methanol |
| 109 | 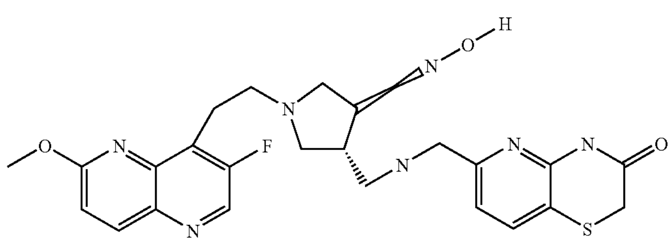 | 6-[({[(3R,4Z)-1-{2-[3-fluoro-6-(methyloxy)-1,5-naphthyridin-4-yl]ethyl}-4-(hydroxyimino)-3-pyrrolidinyl]methyl}amino)methyl]-2H-pyrido[3,2-b][1,4]thiazin-3(4H)-one |
| 110 | 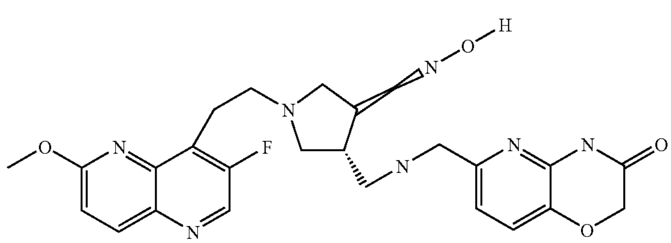 | 6-[({[(3R,4Z)-1-{2-[3-fluoro-6-(methyloxy)-1,5-naphthyridin-4-yl]ethyl}-4-(hydroxyimino)-3-pyrrolidinyl]methyl}amino)methyl]-2H-pyrido[3,2-b][1,4]oxazin-3(4H)-one |

-continued

Table of Examples

| Example # | Structure | Formula |
|---|---|---|
| 111 | 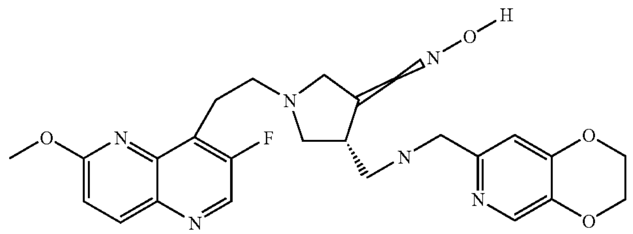 | (3Z,4R)-4-{[(2,3-dihydro[1,4]dioxino[2,3-c]pyridin-7-ylmethyl)amino]methyl}-1-{2-[3-fluoro-6-(methyloxy)-1,5-naphthyridin-4-yl]ethyl}-3-pyrrolidinone oxime |
| 112 | 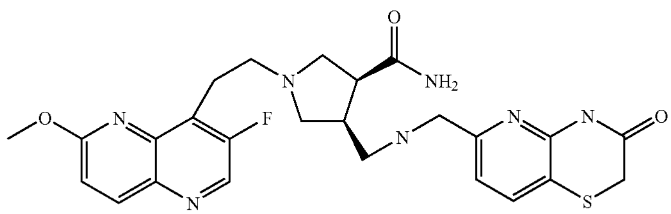 | (±)-(3S,4S)/(3R,4R)-1-{2-[3-fluoro-6-(methyloxy)-1,5-naphthyridin-4-yl]ethyl}-4-({[(3-oxo-3,4-dihydro-2H-pyrido[3,2-b][1,4]thiazin-6-yl)methyl]amino}methyl)-3-pyrrolidinecarboxamide |
| 113 | 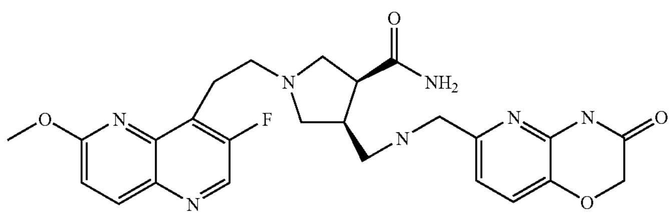 | (±)-(3S,4S)/(3R,4R)-1-{2-[3-fluoro-6-(methyloxy)-1,5-naphthyridin-4-yl]ethyl}-4-({[(3-oxo-3,4-dihydro-2H-pyrido[3,2-b][1,4]oxazin-6-yl)methyl]amino}methyl)-3-pyrrolidinecarboxamide |
| 114 | 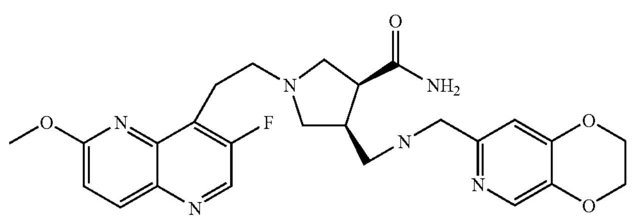 | (±)-(3S,4S)/(3R,4R)-4-{[(2,3-dihydro[1,4]dioxino[2,3-c]pyridin-7-ylmethyl)amino]methyl}-1-{2-[3-fluoro-6-(methyloxy)-1,5-naphthyridin-4-yl]ethyl}-3-pyrrolidinecarboxamide |
| 115 | 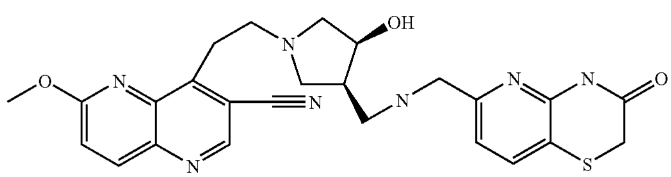 | 4-{2-[(3S,4S)-3-hydroxy-4-({[(3-oxo-3,4-dihydro-2H-pyrido[3,2-b][1,4]thiazin-6-yl)methyl]amino}methyl)-1-pyrrolidinyl]ethyl}-6-(methyloxy)-1,5-naphthyridine-3-carbonitrile |
| 116 | 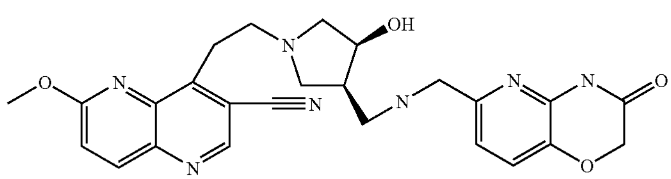 | 4-{2-[(3S,4S)-3-hydroxy-4-({[(3-oxo-3,4-dihydro-2H-pyrido[3,2-b][1,4]oxazin-6-yl)methyl]amino}methyl)-1-pyrrolidinyl]ethyl}-6-(methyloxy)-1,5-naphthyridine-3-carbonitrile |
| 117 | 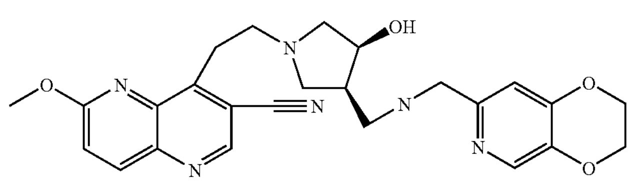 | 4-[2-((3S,4S)-3{[(2,3-dihydro[1,4]dioxino[2,3-c]pyridin-7-ylmethyl)amino]methyl}-4-hydroxy-1-pyrrolidinyl)ethyl]-6-(methyloxy)-1,5-naphthyridine-3-carbonitrile |

Table of Examples

| Example # | Structure | Formula |
|---|---|---|
| 118 | 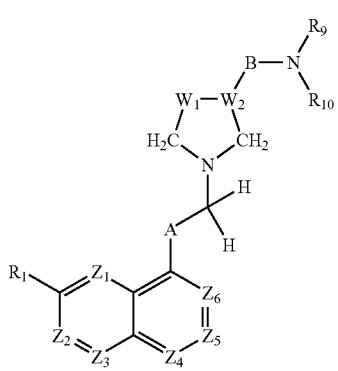 | (±)-6-{[((3S,4R)/(3R,4S)-4-hydroxy-1-{2-[6-(methyloxy)-1,5-naphthyridin-4-yl]ethyl}-3-pyrrolidinyl)amino]methyl}-2H-pyrido[3,2-b][1,4]thiazin-3(4H)-one |
| 119 | 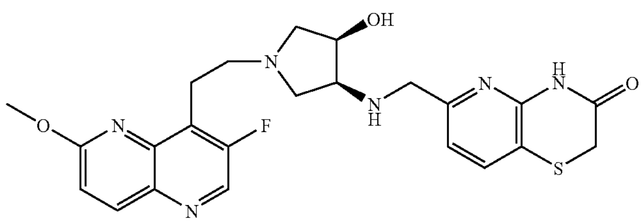 | (±)-6-{[((3S,4R)/(3R,4S)-1-{2-[3-fluoro-6-(methyloxy)-1,5-naphthyridin-4-yl]ethyl}-4-hydroxy-3-pyrrolidinyl)amino]methyl}-2H-pyrido[3,2-b][1,4]thiazin-3(4H)-one |

What is claimed is:

1. A compound of formula (I) or a pharmaceutically acceptable salt thereof:

(I)

wherein:

$Z_1$, $Z_3$, and $Z_4$ are each independently N or $CR^{1a}$;

$Z_2$, $Z_5$ and $Z_6$ are each $CR^{1a}$;

$R_1$ and $R^{1a}$ are independently at each occurrence hydrogen; cyano; halogen; hydroxy; $(C_{1-6})$alkoxy unsubstituted or substituted by $(C_{1-6})$alkoxy, hydroxy, amino, piperidyl, guanidino or amidino any of which is unsubstituted or N-substituted by one or two $(C_{1-6})$alkyl, acyl, $(C_{1-6})$alkylsulphonyl, $CONH_2$, hydroxy, $(C_{1-6})$alkylthio, heterocyclylthio, heterocyclyloxy, arylthio, aryloxy, acylthio, acyloxy or $(C_{1-6})$alkylsulphonyloxy; $(C_{1-6})$alkyl; $(C_{1-6})$alkylthio; trifluoromethyl; trifluoromethoxy; nitro; azido; acyl; acyloxy; acylthio; $(C_{1-6})$alkylsulphonyl; $(C_{1-6})$alkylsulphoxide; arylsulphonyl; arylsulphoxide; or an amino, piperidyl, guanidino or amidino group unsubstituted or N-substituted by one or two $(C_{1-6})$alkyl, acyl or $(C_{1-6})$alkylsulphonyl groups;

or $R_1$ and $R^{1a}$ of $Z_2$, or $R_1$ and $R^{1a}$ of $Z_1$ together form ethylenedioxy;

A is $CR_2R_3$;

$R_2$ is hydrogen; halogen; hydroxy; acyloxy; or $(C_{1-6})$alkoxy; and $R_3$ is hydrogen;

$W_1$ is $CR_4R_5$;

$R_4$ is hydrogen; halogen; hydroxy; $(C_{1-6})$alkyl; $(C_{1-6})$hydroxyalkyl; $C(=O)-NR^{1d}R^{1d'}$; $(C_{1-6})$alkoxy; $NR^{1b}R^{1b'}$ or acyloxy; and $R_5$ is hydrogen or $(C_{1-6})$alkyl;

or $R_4$ and $R_5$ together are $=N-OH$;

$R^{1b}$ and $R^{1b'}$ are each independently hydrogen; $(C_{1-6})$alkyl; aryl; heteroaryl; or together with the nitrogen to which they are attached form an aziridine, azetidine, pyrrolidine, piperidine or hexamethyleneimine ring (wherein said aziridine, azetidine, pyrrolidine, piperidine or hexamethyleneimine ring is optionally substituted with 1 to 3 substitutents selected from halogen, $(C_{1-6})$alkyl, hydroxy and aryl);

$R^{1d}$ and $R^{1d'}$ are each independently hydrogen or $(C_{1-6})$alkyl;

$W_2$ is $CR_6$;

$R_6$ is hydrogen; halogen; hydroxy; $(C_{1-6})$alkyl; $NR^{1c}R^{1c'}$; acyloxy; or $(C_{1-6})$alkoxy;

$R^{1c}$ and $R^{1c'}$ are each independently hydrogen; $(C_{1-6})$alkyl; aryl; heteroaryl; or together with nitrogen to which they are attached form an aziridine, azetidine, pyrrolidine, piperidine or hexamethyleneimine ring (wherein said azidirine, azetidine, pyrrolidine, piperidine or hexamethyleneimine ring is optionally substituted with 1 to 3 substituents selected from halogen, $(C_{1-6})$alkyl, hydroxy and aryl);

B is $CR_7R_8$ or a bond;

$R_7$ and $R_8$ are each independently hydrogen or $(C_{1-6})$alkyl;

$R_9$ is hydrogen; aryl; heteroaryl; $(C_{1-6})$alkyl unsubstituted or substituted by one or two $(C_{1-6})$alkoxy, acyloxy, carboxy, hydroxy, amino, piperidyl, piperazinyl, morpholino, guanidino, or amidino, any of which is unsubstituted or N-substituted by one or two aryl, heteroaryl, halogen, unsubstituted $(C_{1-6})$alkyl, acyl, $(C_{1-6})$alkylsulphonyl, arylsulphonyl, hydroxy, $(C_{1-6})$alkylthio, heterocyclylthio, heterocyclyloxy, arylthio, aryloxy, acylthio, acyloxy, or $(C_{1-6})$alkylsulphonyloxy; $(C_{1-6})$alkylcarbonyl; or $(C_{2-6})$alkenylcarbonyl;

$R_{10}$ is a group —U—$R_{11}$ where:
$R_{11}$ is:

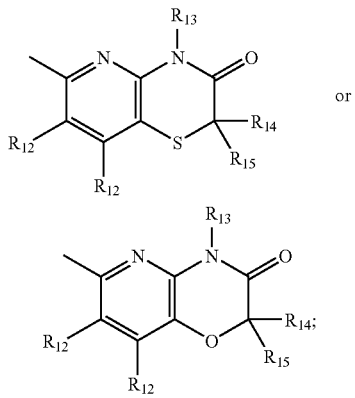

$R_{12}$, $R_{14}$ and $R_{15}$ are at each occurrence independently selected from: H; $(C_{1-4})$alkylthio; halo; $(C_{1-4})$alkyl; $(C_{2-4})$alkenyl; hydroxy; hydroxy$(C_{1-4})$alkyl; mercapto$(C_{1-4})$alkyl; $(C_{1-4})$alkoxy; trifluoromethoxy; nitro; cyano; carboxy; and amino or aminocarbonyl unsubstituted or substituted by $(C_{1-4})$alkyl;

$R_{13}$ is at each occurrence independently hydrogen; trifluoromethyl; $(C_{1-4})$alkyl unsubstituted or substituted by hydroxy, carboxy, $(C_{1-4})$alkoxy, $(C_{1-6})$alkylthio, halo or trifluoromethyl; $(C_{2-4})$alkenyl; or aminocarbonyl wherein the amino group is optionally substituted with $(C_{1-4})$alkyl;

U is C(=O); $SO_2$; or $CR_{16}R_{17}$; and $R_{16}$ and $R_{17}$ are independently selected from H; aryl; heteroaryl; $(C_{1-6})$alkyl; $(C_{1-6})$alkyl substituted by $(C_{1-6})$alkoxy, hydroxy, amino, piperidyl, piperazinyl, morpholino, guanidino, or amidino, any of which is substituted or N-substituted by one or two H, aryl, heteroaryl, halogen, cyano, $CF_3$, $(C_{1-6})$alkyl, acyl, $(C_{1-6})$alkylsulphonyl, arylsulphonyl, hydroxy, $(C_{1-6})$alkylthio, heterocyclylthio, heterocyclyloxy, arylthio, aryloxy, acylthio, acyloxy, or $(C_{1-6})$alkylsulphonyloxy; $(C_{1-6})$alkoxy-substituted $(C_{1-6})$alkyl; hydroxy-substituted$(C_{1-6})$alkyl; amino-substituted$(C_{1-6})$alkyl, which is N-substituted by one or two $(C_{1-6})$alkyl, acyl, $(C_{1-6})$alkylsulphonyl, or arylsulphonyl; $(C_{1-6})$alkylcarbonyl; $(C_{2-6})$alkenylcarbonyl; $(C_{1-6})$alkoxycarbonyl; $CO_2H$; and $CF_3$.

2. The compound according to claim 1, wherein $Z_1$ and $Z_4$ are N and $Z_3$ is $CR^{1a}$.

3. The compound according to claim 1, wherein $R_1$ is $OCH_3$.

4. The compound according to claim 1, wherein $R^{1a}$ is at each occurrence independently hydrogen, halogen or cyano.

5. The compound according to claim 2, wherein $R^{1a}$ of $Z_2$, $Z_3$ and $Z_5$ are each hydrogen; $R^{1a}$ of $Z_6$ is hydrogen, halogen or cyano; and $R_1$ is $OCH_3$.

6. The compound according to claim 1, wherein $R_2$ is hydrogen or hydroxy.

7. The compound according to claim 1, wherein B is $CH_2$.

8. The compound according to claim 1, wherein $R_4$ is hydroxyl and $R_5$ is hydrogen.

9. The compound according to claim 1, wherein $R_9$ is hydrogen.

10. The compound according to claim 1, wherein U is $CH_2$.

11. The compound according to claim 1, wherein $R_{11}$ is:
4H-Pyrido[3,2-b][1,4]thiazin-3-oxo-6-yl;
4H-Pyrido[3,2-b][1,4]oxazin-3-oxo-6-yl;
7-Chloro-4H-pyrido[3,2-b]oxazin-3-oxo-6-yl; or
7-Methyl-4H-pyrido[3,2-b][1,4]thiazin-3-oxo-6-yl.

12. The compound according to claim 1, wherein the compound of formula (I) is:

a) 6-({[((3S)-1-{2-[6-(methyloxy)-1,5-naphthyridin-4-yl]ethyl}-3-pyrrolidinyl)methyl]amino}methyl)-2H-pyrido[3,2-b][1,4]thiazin-3(4H)-one;

b) 6-({[((3R)-1-{2-[3-fluoro-6-(methyloxy)-1,5-naphthyridin-4-yl]ethyl}-3-pyrrolidinyl)methyl]amino}methyl)-2H-pyrido[3,2-b][1,4]thiazin-3(4H)-one;

f) 6-({[((3R)-1-{2-[3,8-difluoro-6-(methyloxy)-4-quinolinyl]ethyl}-3-pyrrolidinyl)methyl]amino}methyl)-2H-pyrido[3,2-b][1,4]thiazin-3(4H)-one;

g) 6-({[((3S)-1-{2-[3-fluoro-6-(methyloxy)-4-quinolinyl]ethyl}-3-pyrrolidinyl)methyl]amino}methyl)-2H-pyrido[3,2-b][1,4]thiazin-3(4H)-one;

h) 6-({[((3S)-1-{2-[3-fluoro-6-(methyloxy)-4-quinolinyl]ethyl}-3-pyrrolidinyl)methyl]amino}methyl)-2H-pyrido[3,2-b][1,4]oxazin-3(4H)-one;

j) 7-chloro-6-({[((3R)-1-{2-[3-fluoro-6-(methyloxy)-1,5-naphthyridin-4-yl]ethyl}-3-pyrrolidinyl)methyl]amino}methyl)-2H-pyrido[3,2-b][1,4]oxazin-3(4H)-one;

m) 6-(methyloxy)-4-{2-[(3S)-3-({[(3-oxo-3,4-dihydro-2H-pyrido[3,2-b][1,4]thiazin-6-yl)methyl]amino}methyl)-1-pyrrolidinyl]ethyl}-3-quinolinecarbonitrile;

o) 6-(methyloxy)-4-{2-[(3S)-3-({[(3-oxo-3,4-dihydro-2H-pyrido[3,2-b][1,4]oxazin-6-yl)methyl]amino}methyl)-1-pyrrolidinyl]ethyl}-3-quinolinecarbonitrile;

p) 6-(methyloxy)-4-{2-[(3S)-3-({[(3-oxo-3,4-dihydro-2H-pyrido[3,2-b][1,4]thiazin-6-yl)methyl]amino}methyl)-1-pyrrolidinyl]ethyl}-1,5-naphthyridine-3-carbonitrile;

s) 6-({[((3S)-1-{2-[3-chloro-6-(methyloxy)-1,5-naphthyridin-4-yl]ethyl}-3-pyrrolidinyl)methyl]amino}methyl)-2H-pyrido[3,2-b][1,4]thiazin-3(4H)-one;

t) 6-({[((3S)-1-{2-[3-chloro-6-(methyloxy)-1,5-naphthyridin-4-yl]ethyl}-3-pyrrolidinyl)methyl]amino}methyl)-2H-pyrido[3,2-b][1,4]oxazin-3(4H)-one;

v) 6-({[((3S)-1-{2-[3,8-difluoro-6-(methyloxy)-4-quinolinyl]ethyt}-3-pyrrolidinyl)methyl]amino}methyl)-2H-pyrido[3,2-b][1,4]oxazin-3(4H)-one;

w) 6-({[((3S)-1-{2-[3,8-difluoro-6-(methyloxy)-4-quinolinyl]ethyl}-3-pyrrolidinyl)methyl]amino}methyl)-2H-pyrido[3,2-b][1,4]thiazin-3(4H)-one;

y) 7-chloro-6-({[((3S)-1-{2-[3-fluoro-6-(methyloxy)-1,5-naphthyridin-4-y]ethyl}-3-pyrrolidinyl)methyl]amino}methyl)-2H-pyrido[3,2-b][1,4]oxazin-3(4H)-one;

z) 6-({[((3S)-1-{2-[3-fluoro-6-(methyloxy)-1,5-naphthyridin-4-y]ethyl}-3-pyrrolidinyl)methyl]amino}methyl)-2H-pyrido[3,2-b][1,4]oxazin-3(4H)-one;

aa) 6-({[((3S)-1-{2-[3-fluoro-6-(methyloxy)-1,5-naphthyridin-4-yl]ethyl}-3-pyrrolidinyl)methyl]amino}methyl)-2H-pyrido[3,2-b][1,4]thiazin-3(4H)-one;

ac) 6-({[((3S)-1-{2-[3-fluoro-6-(methyloxy)-1,5-naphthyridin-4-yl]ethyl}-3-pyrrolidinyl)methyl]amino}methyl)-7-methyl-2H-pyrido[3,2-b][1,4]thiazin-3(4H)-one;

ad) 6-({[((3S)-1-{(2S)-2-hydroxy-2-[6-(methyloxy)-1,5-naphthyridin-4-yl]ethyl}-3-pyrrolidinyl)methyl]amino}methyl)-2H-pyrido[3,2-b][1,4]thiazin-3(4H)-one;

ae) 6-({[((3S)-1-{(2S)-2-hydroxy-2-[6-(methyloxy)-1,5-naphthyridin-4-yl]ethyl}-3-pyrrolidinyl)9methyl]amino}methyl)-2H-pyrido[3,2-b][1,4]oxazin-3(4H)-one;

af) 6-({[((3R)-1-{(2S)-2-hydroxy-2-[6-(methyloxy)-1,5-naphthyridin-4-yl]ethyl}-3-pyrrolidinyl)methyl]amino}methyl)-2H-pyrido[3,2-b][1,4]oxazin-3(4H)-one;

ag) 6-({[((3R)-1-{(2S)-2-hydroxy-2-[6-(methyloxy)-1,5-naphthyridin-4-yl]ethyl}-3-pyrrolidinyl)methyl]amino}methyl)-2H-pyrido[3,2-b][1,4]thiazin-3(4H)-one;

ah) 6-({[((3S)-1-{(2R)-2-[3-fluoro-6-(methyloxy)-1,5-naphthyridin-4-yl]-2-hydroxyethyl}-3-pyrrolidinyl)methyl]amino}methyl)-2H-pyrido[3,2-b][1,4]thiazin-3(4H)-one;

ao) (±)-6-({[(1-{2-[3-fluoro-6-(methyloxy)-1,5-naphthyridin-4-yl]ethyl}-3-hydroxy-3-pyrrolidinyl)methyl]amino}methyl)-2H-pyrido[3,2-b][1,4]thiazin-3(4H)-one;

ap) (±)-6-({[(trans-3,4)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]thiazin-3(4H)-one;

aq) 6-({[(trans-3,4)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]thiazin-3(4H)-one;

ar) 6-({[(trans-3,4)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]thiazin-3(4H)-one;

as) (±)-6-({[(trans-3,4)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]oxazin-3(4H)-one;

at) 6-({[(trans-3,4)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]oxazin-3(4H)-one;

au) 6-({[(trans-3,4)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]oxazin-3(4H)-one;

av) (±)-6-({[((cis-3,4)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]thiazin-3(4H)-one;

aw) 6-({[((3S,4S)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]thiazin-3(4H)-one;

ax) 6-({[((3R,4R)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]thiazin-3(4H)-one;

ay) 6-({[((3S,4S)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]oxazin-3(4H)-one;

az) 6-({[((3R,4R)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]oxazin-3(4H)-one;

ba) (±)-7-chloro-6-({[((cis-3,4)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]oxazin-3(4H)-one;

bb) 7-chloro-6-({[((3S,4S)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]oxazin-3(4H)-one;

bc) 7-chloro-6-({[((3R,4R)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]oxazin-3(4H)-one;

bh) 6-({[((3S,4S)-1-{2-[3-fluoro-6-(methyloxy)-4-quinolinyl]ethyl}-4-hydroxy-3-pyrrolidinyl)methyl]amino}methyl)-2H-pyrido[3,2-b][1,4]thiazin-3(4H)-one;

bi) 6-({[((3S,4S)-1-{2-[3-fluoro-6-(methyloxy)-4-quinolinyl]ethyl}-4-hydroxy-3-pyrrolidinyl)methyl]amino}methyl)-2H-pyrido[3,2-b][1,4]oxazin-3(4H)-one;

bj) (±)-6-({[((cis-3,4)-4-hydroxy-1-{2-[6-(methyloxy)-1,5-naphthyridin-4-yl]ethyl}-3-pyrrolidinyl)methyl]amino}methyl)-2H-pyrido[3,2-b][1,4]oxazin-3(4H)-one;

bk) 6-({[((3S,4S)-4-hydroxy-1-{2-[6-(methyloxy)-1,5-naphthyridin-4-yl]ethyl}-3-pyrrolidinyl)methyl]amino}methyl)-2H-pyrido[3,2-b][1,4]thiazin-3(4H)-one;

bl) (±)-6-({[((cis-3,4)-4-hydroxy-1-{2-[6-(methyloxy)-1,5-naphthyridin-4-yl]ethyl}-3-pyrrolidinyl)methyl]amino}methyl)-2H-pyrido[3,2-b][1,4]oxazin-3(4H)-one;

bm) 6-({[((3S,4S)-1-{2-[3-chloro-6-(methyloxy)-1,5-naphthyridin-4-yl]ethyl}-4-hydroxy-3-pyrrolidinyl)methyl]amino}methyl)-2H-pyrido[3,2-b][1,4]oxazin-3(4H)-one;

bn) 6-({[((3S,4S)-1-{2-[3-chloro-6-(methyloxy)-1,5-naphthyridin-4-yl]ethyl}-4-hydroxy-3-pyrrolidinyl)methyl]amino}methyl)-2H-pyrido[3,2-b][1,4]thiazin-3(4H)-one;

bp) (±)-6-[({[(cis-3,4)-1-{2-[3-fluoro-6-(methyloxy)-1,5-naphthyridin-4-yl]ethyl}-4-(methyloxy)-3-pyrrolidinyl]methyl}amino)methyl]-2H-pyrido[3,2-b][1,4]thiazin-3(4H)-one;

bq) (±)-6-[({[(cis-3,4)-1-{2-[3-fluoro-6-(methyloxy)-1,5-naphthyridin-4-yl]ethyl}-4-(methyloxy)-3-pyrrolidinyl]methyl}amino)methyl]-2H-pyrido[3,2-b][1,4]oxazin-3(4H)-one;

br) (±)-6-({[(3-fluoro-1-{2-[3-fluoro-6-(methyloxy)-1,5-naphthyridin-4-yl]ethyl}-3-pyrrolidinyl)methyl]amino}methyl)-2H-pyrido[3,2-b][1,4]thiazin-3(4H)-one;

bt) (±)-6-({[((3S,4R)-4-fluoro-1-{2-[3-fluoro-6-(methyloxy)-1,5-naphthyridin-4-yl]ethyl}-3-pyrrolidinyl)methyl]amino}methyl)-2H-pyrido[3,2-b][1,4]thiazin-3(4H)-one;

bu) (±)-6-({[((3S,4S)-4-fluoro-1-{2-[3-fluoro-6-(methyloxy)-1,5-naphthyridin-4-yl]ethyl}-3-pyrrolidinyl)methyl]amino}methyl)-2H-pyrido[3,2-b][1,4]thiazin-3(4H)-one;

bv) (±)-6-({[(1-{2-[3-fluoro-6-(methyloxy)-1,5-naphthyridin-4-yl]ethyl}-4-hydroxy-3-methyl-3-pyrrolidinyl)methyl]amino}methyl)-2H-pyrido[3,2-b][1,4]thiazin-3(4H)-one;

bw) (±)-6-({[(1-{2-[3-fluoro-6-(methyloxy)-1,5-naphthyridin-4-yl]ethyl}-4-hydroxy-3-methyl-3-pyrrolidinyl)methyl]amino}methyl)-2H-pyrido[3,2-b][1,4]thiazin-3(4H)-one;

bx) (±)-6-({[(1-{2-[3-fluoro-6-(methyloxy)-1,5-naphthyridin-4-yl]ethyl}-4-hydroxy-4-methyl-3-pyrrolidinyl)methyl]amino}methyl)-2H-pyrido[3,2-b][1,4]thiazin-3(4H)-one;

by) (±)-6-({[(1-{2-[3-fluoro-6-(methyloxy)-1,5-naphthyridin-4-yl]ethyl}-4-hydroxy-4-methyl-3-pyrrolidinyl)methyl]amino}methyl)-2H-pyrido[3,2-b][1,4]thiazin-3(4H)-one;

bz) (±)-6-({[(1-{2-[3-fluoro-6-(methyloxy)-1,5-naphthyridin-4-yl]ethyl}-3-methyl-3-pyrrolidinyl)methyl]amino}methyl)-2H-pyrido[3,2-b][1,4]thiazin-3(4H)-one;

ca) (±)-6-({[(1-{2-[3-fluoro-6-(methyloxy)-1,5-naphthyridin-4-yl]ethyl}-3-methyl-3-pyrrolidinyl)methyl]amino}methyl)-2H-pyrido[3,2-b][1,4]oxazin-3(4H)-one;

cd) (±)-4-{2-[3-methyl-3-({[(3-oxo-3,4-dihydro-2H-pyrido[3,2-b][1,4]thiazin-6-yl)methyl]amino}methyl)-1-pyrrolidinyl]ethyl}-6-(methyloxy)-3-quinolinecarbonitrile;

cf) 6-({[1-((3R)-1-{2-[3-fluoro-6-(methyloxy)-1,5-naphthyridin-4-yl]ethyl}-3-pyrrolidinyl)-1-methylethyl]amino}methyl)-2H-pyrido[3,2-b][1,4]thiazin-3(4H)-one;

ch) N-[((3S)-1-{2-[3-fluoro-6-(methyloxy)-1,5-naphthyridin-4-yl]ethyl}-3-pyrrolidinyl)methyl]-3-oxo-3,4-dihydro-2H-pyrido[3,2-b][1,4]thiazine-6-carboxamide;

ci) N-[((3S)-1-{2-[6-(methyloxy)-1,5-naphthyridin-4-yl]ethyl}-3-pyrrolidinyl)methyl]-3-oxo-3,4-dihydro-2H-pyrido[3,2-b][1,4]thiazine-6-carboxamide;

cj) N-[((3S,4S)-1-{2-[3-fluoro-6-(methyloxy)-1,5-naphthyridin-4-yl]ethyl}-4-hydroxy-3-pyrrolidinyl)methyl]-3-oxo-3,4-dihydro-2H-pyrido[3,2-b][1,4]thiazine-6-carboxamide;

ck) (±)-N-[((cis-3,4)-1-{2-[3-fluoro-6-(methyloxy)-1,5-naphthyridin-4-yl]ethyl}-4-hydroxy-3-pyrrolidinyl)methyl]-N-methyl-3-oxo-3,4-dihydro-2H-pyrido[3,2-b][1,4]thiazine-6-carboxamide;

cl) (±)-N-[(1-{2-[3-fluoro-6-(methyloxy)-1,5-naphthyridin-4-yl]ethyl}-3-pyrrolidinyl)methyl]-N-methyl-3-oxo-3,4-dihydro-2H-pyrido[3,2-b][1,4]thiazine-6-carboxamide;

cn) 6-({[((3S,4S)-1-{2-[8-fluoro-6-(methyloxy)-4-quinolinyl]ethyl}-4-hydroxy-3-pyrrolidinyl)methyl]amino}methyl)-2H-pyrido[3,2-b][1,4]thiazin-3(4H)-one;

co) 6-({[((3S,4S)-1-{2-[8-fluoro-6-(methyloxy)-4-quinolinyl]ethyl}-4-hydroxy-3-pyrrolidinyl)methyl]amino}methyl)-2H-pyrido[3,2-b][1,4]oxazin-3(4H)-one;

cp) 6-({[((3S,4S)-1-{2-[6-fluoro-5-(methyloxy)-4-quinolinyl]ethyl}-4-hydroxy-3-pyrrolidinyl)methyl]amino}methyl)-2H-pyrido[3,2-b][1,4]oxazin-3(4H)-one;

cq) 6-({[((3S,4S)-1-{2-[6-fluoro-5-(methyloxy)-4-quinolinyl]ethyl}-4-hydroxy-3-pyrrolidinyl)methyl]amino}methyl)-2H-pyrido[3,2-b][1,4]thiazin-3(4H)-one;

cr) 6-({[((3S,4S)-1-{2-[3,8-difluoro-6-(methyloxy)-4-quinolinyl]ethyl}-4-hydroxy-3-pyrrolidinyl)methyl]amino}methyl)-2H-pyrido[3,2-b][1,4]oxazin-3(4H)-one;

cs) 6-({[((3S,4S)-1-{2-[3,8-difluoro-6-(methyloxy)-4-quinolinyl]ethyl}-4-hydroxy-3-pyrrolidinyl)methyl]amino}methyl)-2H-pyrido[3,2-b][1,4]thiazin-3(4H)-one;

ct) 6-{[({(3S,4S)-1-[2-(9-chloro-2,3-dihydro[1,4]dioxino[2,3-f]quinolin-10-yl)ethyl]-4-hydroxy-3-pyrrolidinyl}methyl)amino]methyl}-2H-pyrido[3,2-b][1,4]thiazin-3(4H)-one;

cu) 6-{[({(3S,4S )-1-[2-(9-chloro-2,3-dihydro[1,4]dioxino[2,3-f]quinolin-10-yl)ethyl]-4-hydroxy-3-pyrrolidinyl}methyl)amino]methyl}-2H-pyrido[3,2-b][1,4]oxazin-3(4H)-one;

cv) 6-{[({(3S,4S)-1-[2-(2,3-dihydro[1,4]dioxino[2,3-f]quinolin-10-yl)ethyl]-4-hydroxy-3-pyrrolidinyl}methyl)amino]methyl}-2H-pyrido[3,2-b][1,4]oxazin-3(4H)-one;

cw) 6-({[((3S,4S)-4-hydroxy-1-{2-[6-(methyloxy)-1,5-naphthyridin-4-yl]ethyl}-3-pyrrolidinyl)methyl]amino}methyl)-2H-pyrido[3,2-b][1,4]oxazin-3(4H)-one;

cy) 7-chloro-6-({[((3S,4S)-4-hydroxy-1-{2-[6-(methyloxy)-1,5-naphthyridin-4-yl]ethyl}-3-pyrrolidinyl)methyl]amino}methyl)-2H-pyrido[3,2-b][1,4]oxazin-3(4H)-one;

dc) 6-({[((3S,4S)-4-hydroxy-1-{2-[6-(methyloxy)-4-quinolinyl]ethyl}-3-pyrrolidinyl)methyl]amino}methyl)-2H-pyrido[3,2-b][1,4]thiazin-3(4H)-one;

dd) 6-({[((3S,4S)-4-hydroxy-1-{2-[6-(methyloxy)-4-quinolinyl]ethyl}-3-pyrrolidinyl)methyl]amino}methyl)-2H-pyrido[3,2-b][1,4]oxazin-3(4H)-one;

dg) N-[((3S,4S)-1-{2-[3-fluoro-6-(methyloxy)-1,5-naphthyridin-4-yl]ethyl}-4-hydroxy-3-pyrrolidinyl)methyl]-3-oxo-3,4-dihydro-2H-pyrido[3,2-b][1,4]oxazine-6-carboxamide;

dh) (±)-6-[({[(3R,4S)/(3S,4R)-1-{2-[3-fluoro-6-(methyloxy)-1,5-naphthyridin-4-yl]ethyl}-4-(hydroxymethyl)-3-pyrrolidinyl]methyl}amino)methyl]-2H-pyrido[3,2-b][1,4]thiazin-3(4H)-one;

di) (±)-6-[({[(3R,4S)/(3S,4R)-1-{2-[3-fluoro-6-(methyloxy)-1,5-naphthyridin-4-yl]ethyl}-4-(hydroxymethyl)-3-pyrrolidinyl]methyl}amino)methyl]-2H-pyrido[3,2-b][1,4]thiazin-3(4H)-one;

dj) 6-[({[(3R,4S)-1-{2-[3-fluoro-6-(methyloxy)-1,5-naphthyridin-4-yl]ethyl}-4-(hydroxymethyl)-3-pyrrolidinyl]methyl}amino)methyl]-2H-pyrido[3,2-b][1,4]thiazin-3(4H)-one;

dk) (±)-6-[({[(3S,4R)/(3S,4R)-1-{2-[3-fluoro-6-(methyloxy)-1,5-naphthyridin-4-yl]ethyl}-4-(hydroxymethyl)-3-pyrrolidinyl]methyl}amino)methyl]-2H-pyrido[3,2-b][1,4]thiazin-3(4H)-one;

dm) 6-[({[(3R,4Z)-1-{2-[3-fluoro-6-(methyloxy)-1,5-naphthyridin-4-yl]ethyl}-4-(hydroxyimino)-3-pyrrolidinyl]methyl}amino)methyl]-2H-pyrido[3,2-b][1,4]thiazin-3(4H)-one;

dn) 6-[({[(3R,4Z)-1-{2-[3-fluoro-6-(methyloxy)-1,5-naphthyridin-4-yl]ethyl}-4-(hydroxyimino)-3-pyrrolidinyl]methyl}amino)methyl]-2H-pyrido[3,2-b][1,4]oxazin-3(4H)-one;

dp) (±)-(3S,4S)/(3R,4R)-1-{2-[3-fluoro-6-(methyloxy)-1,5-naphthyridin-4-yl]ethyl}-4-({[(3-oxo-3,4-dihydro-2H-pyrido[3,2-b][1,4]thiazin-6-yl)methyl]amino}methyl)-3-pyrrolidinecarboxamide;

dq) (±)-(3S,4S)/(3R,4R)-1-{2-[3-fluoro-6-(methyloxy)-1,5-naphthyridin-4-yl]ethyl}-4-({[(3-oxo-3,4-dihydro-2H-pyrido[3,2-b][1,4]oxazin-6-yl)methyl]amino}methyl)-3-pyrrolidinecarboxamide;

ds) 4-{2-[(3S,4S)-3-hydroxy-4-({[(3-oxo-3,4-dihydro-2H-pyrido[3,2-b][1,4]thiazin-6-yl)methyl]amino}methyl)-1-pyrrolidinyl]ethyl}-6-(methyloxy)-1,5-naphthyridine-3-carbonitrile;

dt) 4-{2-[(3S,4S)-3-hydroxy-4-({[(3-oxo-3,4-dihydro-2H-pyrido[3,2-b][1,4]oxazin-6-yl)methyl]amino}methyl)-1-pyrrolidinyl]ethyl}-6-(methyloxy)-1,5-naphthyridine-3-carbonitrile;

dv) (±)-6-{[((3S,4R)/(3R,4S)-4-hydroxy-1-{2-[6-(methyloxy)-1,5-naphthyridin-4-yl]ethyl}-3-pyrrolidinyl)amino]methyl}-2H-pyrido[3,2-b][1,4]thiazin-3(4H)-one; or dw) (±)-6-{[((3S,4R)/(3R,4S)-1-{2-[3-fluoro-6-(methyloxy)-1,5-naphthyridin-4-yl]ethyl}-4-hydroxy-3-pyrrolidinyl)amino]methyl}-2H-pyrido[3,2-b][1,4]thiazin-3(4H)-one.

13. A pharmaceutical composition comprising the compound according to claim 1 and at least one pharmaceutically acceptable excipient.

14. The compound according to claim 1, wherein:
$Z_1$ and $Z_4$ are N;
$Z_3$ is $CR^{1a}$;
$R_1$ is OMe;
$R^{1a}$ of $Z_2$, $Z_3$, and $Z_5$ are hydrogen;
$R^{1a}$ of $Z_6$ is hydrogen, fluoro, chloro, or cyano;
$R_2$ is hydrogen or hydroxy;
$R_4$ is hydrogen, hydroxy, fluoro, methyl, or methoxy;
$R_5$ is hydrogen or methyl;
$R_6$ is hydrogen; hydroxy; fluoro; or methyl;
$R_7$ and $R_8$ are independently hydrogen or methyl;
$R_9$ is hydrogen or methyl; and
U is $CH_2$; $SO_2$ or C(=O).

15. The compound according to claim 14, wherein $R_{11}$ is 4H-Pyrido[3,2-b][1,4]thiazin-3-oxo-6-yl, 4H-Pyrydo[3,2-b]oxazin-3-oxo-6-yl, 7-Chloro-4H-pyrido[3,2-b]oxaxin-3-6-yl, or 7-Methyl-4H-pyrido[3,2-b][1,4]thiazin-3-oxo-6-yl.

16. The compound according to claim 1, wherein the compound of formula (I) is selected from:

6-({[((3S)-1-{2-[6-(methyloxy)-1,5-naphthyridin-4-yl]ethyl}-3-pyrrolidinyl)methyl]amino}methyl)-2H-pyrido[3,2-b][1,4]thiazin-3(4H)-one;

6-({[((3R)-1-{2-[3-fluoro-6-(methyloxy)-1,5-naphthyridin-4-yl]ethyl}-3-pyrrolidinyl)methyl]amino}methyl)-2H-pyrido[3,2-b][1,4]thiazin-3(4H)-one;

6-({[((3R)-1-{2-[3,8-difluoro-6-(methyloxy)-4-quinolinyl]ethyl}-3-pyrrolidinyl)methyl]amino}methyl)-2H-pyrido[3,2-b][1,4]thiazin-3(4H)-one;

6-({[((3S)-1-{2-[3-fluoro-6-(methyloxy)-4-quinolinyl]ethyl}-3-pyrrolidinyl)methyl]amino}methyl)-2H-pyrido[3,2-b][1,4]thiazin-3(4H)-one;

6-({[((3S)-1-{2-[3-fluoro-6-(methyloxy)-4-quinolinyl]ethyl}-3-pyrrotidinyl)methyl]amino}methyl)-2H-pyrido[3,2-b][1,4]oxazin-3(4H)-one;

7-chloro-6-({[((3R)-1-{2-[3-fluoro-6-(methyloxy)-1,5-naphthyridin-4-yl]ethyl}-3-pyrrolidinyl)methyl]amino}methyl)-2H-pyrido[3,2-b][1,4]oxazin-3(4H)-one;

6-(methyloxy)-4-{2-[(3S)-3-({[(3-oxo-3,4-dihydro-2H-pyrido[3,2-b1][1,4]thiazin-6-yl)methyl]amino}methyl)-1-pyrrolidinyl]ethyl}-3-quinolinecarbonitrile;

6-(methyloxy)-4-{2-[(3S)-3-({[(3-oxo-3,4-dihydro-2H-pyrido[3,2-b][1,4]oxazin-6-yl)methyl]amino}methyl)-1-pyrrolidinyl]ethyl}-1,5-naphthyridine-3-carbonitrile;

6-(methyloxy)-4-{2-[(3S)-3-({[(3-oxo-3,4-dihydro-2H-pyrido[3,2-b][1,4]thiazin-6-yl)methyl]amino}methyl)-1-pyrrolidinyl]ethyl}-1,5-naphthyridine-3-carbonitrile;

6-({[((3S)-1-{2-[3-chloro-6-(methyloxy)-1,5-naphthyridin-4-yl]ethyl}-3-pyrrolidinyl)methyl]amino}methyl)-2H-pyrido[3,2-b][1,4]thiazin-3(4H)-one;

6-({[((3S)-1-{2-[3-chloro-6-(methyloxy)-1,5-naphthyridin-4-yl]ethyl}-3-pyrrolidinyl)methyl]amino}methyl)-2H-pyrido[3,2-b][1,4]oxazin-3(4H)-one;

6-({[((3S)-1-{2-[3,8-difluoro-6-(methyloxy)-4-quinolinyl]ethyl}-3-pyrrolidinyl)methyl]amino}methyl)-2H-pyrido[3,2-b][1,4]oxazin-3(4H)-one;

6-({[((3S)-1-{2-[3,8-difluoro-6-(methyloxy)-4-quinolinyl]ethyl}-3-pyrrolidinyl)methyl]amino}methyl)-2H-pyrido[3,2-b][1,4]thiazin-3(4H)-one;

7-chloro-6-({[((3S)-1-{2-[3-fluoro-6-(methyloxy)-1,5-naphthyridin-4-yl]ethyl}-3-pyrrolidinyl)methyl]amino}methyl)-2H-pyrido[3,2-b][1,4]oxazin-3(4H)-one;

6-({[((3S)-1-{2-[3-fluoro-6-(methyloxy)-1,5-naphthyridin-4-yl]ethyl}-3-pyrrolidinyl)methyl]amino}methyl)-2H-pyrido[3,2-b][1,4]oxazin-3(4H)-one;

6-({[((3S)-1-{2-[3-fluoro-6-(methyloxy)-1,5-naphthyridin-4-yl]ethyl}-3-pyrrolidinyl)methyl]amino}methyl)-2H-pyrido[3,2-b][1,4]oxazin-3(4H)-one;

6-({[((3S)-1-{2-[3-fluoro-6-(methyloxy)-1,5-naphthyridin-4-yl]ethyl}-3-pyrrolidinyl)methyl]amino}methyl)2H-pyrido[3,2-b][1,4]thiazin-3(4H)-one;

6-({[((3S)-1-{(2S)-2-hydroxy-2-[6-(methyloxy)-1,5-naphthyridin-4-yl]ethyl}-3-pyrrolidinyl)methyl]amino}methyl)-2H-pyrido[3,2-b][1,4]oxazin-3(4H)-one;

6-({[((3R)-1-{(2S)-2-hydroxy-2-[6-(methyloxy)-1,5-naphthyridin-4-yl]ethyl}-3-pyrrolidinyl)methyl]amino}methyl)-2H-pyrido[3,2-b][1,4]thiazin-3(4H)-one;

6-({[((3R)-1-{(2S)-2-hydroxy-2-[6-(methyloxy)-1,5-naphthyridin-4-yl]ethyl}-3-pyrrolidinyl)methyl]amino}methyl)-2H-pyrido[3,2-b][1,4]oxazin-3(4H)-one;

6-({[((3R)-1-{(2S)-2-hydroxy-2-[6-(methyloxy)-1,5-naphthyridin-4-yl]ethyl}-3-pyrrolidinyl)methyl]amino}methyl)-2H-pyrido[3,2-b][1,4]oxazin-3(4H)-one;

6-({[((3S)-1-{(2R)-2-[3-fluoro-6-(methyloxy)-1,5-naphthyridin-4-yl]-2-hydroxyethyl}-3-pyrrolidinyl)methyl]amino}methyl)-2H-pyrido[3,2-b][1,4]thiazin-3(4H)-one;

(±)-6-({[(trans-3,4)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]thiazin-3(4H)-one;

6-({[(trans-3,4)-1-{2-[3-fluoro-6-(methyloxy)-1,5-naphthyridin-4-yl]ethyl}-4-hydroxy-3-pyrrolidinyl )methyl]amino}methyl)-2H-pyrido[3,2-b][1,4]thiazin-3(4H)-one (Enantiomer 1);

6-({[[(trans-3,4)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]thiazin-3(4H)-one (Enantiomer 2);

(±)-6-({[[(trans-3,4)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]oxazin-3(4H)-one;

6-({[[(trans-3,4)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]oxazin-3(4H)-one (Enantiomer 1);

6-({[[(trans-3,4)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]oxazin-3(4H)-one (Enantiomer 2);

(±)-6-({[((cis-3,4)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-][1,4]thiazin-3(4H)-one;

6-({[((3S,4S)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]thiazin-3(4H)-one;

6-({[((3R,4R)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]thiazin-3(4H)-one;

6-({[((3S,4S)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]oxazin-3(4H)-one;

6-({[((3R,4R)-1-{2-[3-fluoro-6-(methyloxy)-1,5-naphthyridin-4-yl]ethyl}-4-hydroxy-3-pyrrotidinyl)methyl]amino}methyl)-2H-pyrido[3,2-b][1,4]oxazin-3(4H)-one;

(±)-7-chloro-6-({[((cis-3,4)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]oxazin-3(4H)-one;

7-chloro-6-({[((3S,4S)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]oxazin-3(4H)-one;

7-chloro-6-({[((3R,4R)-1-{2-[3-fluoro-6-(methyloxy)-1,5-naphthyridin-4-yl]ethyl}-4-hydroxy-3-pyrrolidinyl)methyl]amino}methyl)-2H-pyrido[3,2-b][1,4]oxazin-3(4H)-one;

6-({[((3S,4S)-1-{2-[3-fluoro-6-(methyloxy)-4-quinolinyl]ethyl}-4-hydroxy-3-pyrrolidinyl)methyl]amino}methyl)-2H-pyrido[3,2-b][1,4]thiazin-3(4H)-one;

6-({[((3S,4S)-1-{2-[3-fluoro-6-(methyloxy)-4-quinolinyl]ethyl}-4-hydroxy-3-pyrrolidinyl)methyl]amino}methyl)-2H-pyrido[3,2-b][1,4]oxazin-3(4H)-one;

(±)-6-({[((cis-3,4)-4-hydroxy-1-{2-[6-(methyloxy)-1,5-naphthyridin-4-yl]lethyl}-3-pyrrolidinyl)methyl]amino}methyl)-2H-pyrido[3,2-b][1,4]thiazin-3(4H)-one;

6-({[((3S,4S)-4-hydroxy-1-{2-[6-(methyloxy)-1,5-naphthyridin-4-yl]ethyl}-3-pyrrolidinyl)methyl]amino}methyl)-2H-pyrido[3,2-b][1,4]thiazin-3(4H)-one;

(±)-6-({[((cis-3,4)-4-hydroxy-1-{2-[6-(methyloxy)-1,5-naphthyridin-4-yl]ethyl}-3-pyrrotidinyl)methyl]amino}methyl)-2H-pyrido[3,2-b][1,4]oxazin-3(4H)-one;

6-({[((3S,4S)-1-{2-[3-chloro-6-(methyloxy)-1,5-naphthyridin-4-yl]ethyl}-4-hydroxy-3-pyrrolidinyl)methyl]amino}methyl)-2H-pyrido[3,2-b][1,4]oxazin-3(4H)-one;

6-({[((3S,4S)-1-{2-[3-chloro-6-(methyloxy)-1,5-naphthyridin-4-yl]ethyl}-4-hydroxy-3-pyrrolidinyl)methyl]amino}methyl)-2H-pyrido[3,2-b][1,4]thiazin-3(4H)-one;

6-({[((3S,4S)-1-{2-[8-fluoro-6-(methyloxy)-4-quinoliny]ethyl}-4-hydroxy-3-pyrrolidinyl)methyl]amino}methyl)-2H-pyrido[3,2-b][1,4]thiazin-3(4H)-one;

6-({[((3S,4S)-1-{2-[8-fluoro-6(methyloxy)-4-quinoliny]ethyl}-4-hydroxy-3-pyrrolidinyl)methyl]amino}methyl)-2H-pyrido[3,2-b][1,4]oxazin-3(4H)-one;

6-({[((3S,4S)-1-{2-[3,8-difluoro-6-(methyloxy)-4-quinolinyl]ethyl}-4-hydroxy-3-pyrroidinyl)methyl]amino}methyl)-2H-pyrido[3,2-b][1,4]oxazin-3(4H)-one;

6-({[((3S,4S)-1-{2-[3,8-difluoro-6-(methyloxy)-4-quinolinyl]ethyl}-4-hydroxy-3-pyrrolidinyl)methyl]amino}methyl)-2H-pyrido[3,2-b][1,4]thiazin-3(4H)-one;

6-({[((3S,4S)-4-hydroxy-1-{2-[6-(methyloxy)-1,5-naphthyridin-4-yl]ethyl}-3-pyrrolidinyl)methyl]amino}methyl)-2H-pyrido[3,2-b][1,4]oxazin-3(4H)-one;

7-chloro-6-({[((3,S4S)-4-hydroxy-1-{2-[6-(methyloxy)-1,5-naphthyridin-4-yl]ethyl}-3-pyrrolidinyl)methyl]amino}methyl)-2H-pyrido[3,2-b][1,4]oxazin-3(4H)-one;

6-({[((3S,4S)-4-hydroxy-1-{2-[6-(methyloxy)-4-quinolinyl]ethyl}-3-pyrrolidinyl)methyl]amino}methyl)-2H-pyrido[3,2-b][1,4]thiazin-3(4H)-one;

6-({[((3S,4S)-4-hydroxy-1-{2-[6-(methyloxy)-4-quinolinyl]ethyl}-3-pyrrolidinyl)methyl]amino}methyl)-2H-pyrido[3,2-b][1,4]oxazin-3(4H)-one;

4-{2-[(3S,4S)-3-hydroxy-4-({[(3-oxo-3,4-dihydro-2H-pyrido[3,2-b][1,4]thiazin-6-yl)methyl]amino}methyl)-1-pyrrolidinyl]ethyl}-6-(methyloxy)-1,5-naphthyridine-3-carbonitrile; and 4-{2-[(3S,4S)-3-hydroxy-4-({[(3-oxo-3,4-dihydro-2H-pyrido[3,2-b][1,4]oxazin-6-yl)methyl]amino}methyl)-1-pyrrolidinyl]ethyl}-6-(methyloxy)-1,5-naphthyridine-3-carbonitrile.

17. A pharmaceutical composition comprising the compound according to claim 16 and at least one pharmaceutically acceptable excipient.

* * * * *